United States Patent
Hishiya et al.

(10) Patent No.: US 9,758,807 B2
(45) Date of Patent: Sep. 12, 2017

(54) PROTEIN EXPRESSION ENHANCING POLYPEPTIDES

(71) Applicant: Strategia Therapeutics, Inc., Boston, MA (US)

(72) Inventors: Akinori Hishiya, Belmont, MA (US); Keizo Koya, Chestnut Hill, MA (US); Luca Rastelli, Norwell, MA (US)

(73) Assignee: SOLA Biosciences, LLC, Boston, MA (US)

( * ) Notice: Subject to any disclaimer, the term of this patent is extended or adjusted under 35 U.S.C. 154(b) by 0 days.

(21) Appl. No.: 14/649,187

(22) PCT Filed: Dec. 5, 2013

(86) PCT No.: PCT/US2013/073442
§ 371 (c)(1),
(2) Date: Jun. 2, 2015

(87) PCT Pub. No.: WO2014/089375
PCT Pub. Date: Jun. 12, 2014

(65) Prior Publication Data
US 2015/0299756 A1 Oct. 22, 2015

Related U.S. Application Data

(60) Provisional application No. 61/733,743, filed on Dec. 5, 2012, provisional application No. 61/733,884, filed on Dec. 5, 2012.

(51) Int. Cl.
| | | |
|---|---|---|
| *A01B 9/00* | (2006.01) |
| *C07K 14/31* | (2006.01) |
| *C12P 21/02* | (2006.01) |
| *C07K 14/54* | (2006.01) |
| *C07K 14/315* | (2006.01) |
| *C07K 14/47* | (2006.01) |
| *C07K 14/715* | (2006.01) |
| *C07K 14/755* | (2006.01) |
| *C07K 14/81* | (2006.01) |
| *C07K 16/22* | (2006.01) |
| *C07K 16/24* | (2006.01) |
| *C12N 9/64* | (2006.01) |
| *A61K 48/00* | (2006.01) |

(52) U.S. Cl.
CPC .............. *C12P 21/02* (2013.01); *C07K 14/31* (2013.01); *C07K 14/315* (2013.01); *C07K 14/47* (2013.01); *C07K 14/5437* (2013.01); *C07K 14/7155* (2013.01); *C07K 14/755* (2013.01); *C07K 14/8125* (2013.01); *C07K 16/22* (2013.01); *C07K 16/241* (2013.01); *C07K 16/244* (2013.01); *C12N 9/644* (2013.01); *C12N 9/6437* (2013.01); *A61K 48/00* (2013.01); *C07K 2317/14* (2013.01); *C07K 2319/00* (2013.01); *C07K 2319/30* (2013.01); *C07K 2319/35* (2013.01); *C07K 2319/43* (2013.01); *C07K 2319/70* (2013.01); *C07K 2319/705* (2013.01)

(58) Field of Classification Search
None
See application file for complete search history.

(56) References Cited

U.S. PATENT DOCUMENTS

| | | |
|---|---|---|
| 6,747,137 B1 | 6/2004 | Weinstock et al. |
| 2004/0064844 A1 | 4/2004 | Sudhof et al. |
| 2004/0172684 A1 | 9/2004 | Kovalic et al. |
| 2004/0214272 A1 | 10/2004 | La Rosa et al. |
| 2008/0274508 A1 | 11/2008 | Chen et al. |
| 2011/0020865 A1 | 1/2011 | Payne et al. |

FOREIGN PATENT DOCUMENTS

| | | |
|---|---|---|
| CA | 2343602 A1 | 10/2001 |
| EP | 1 077 262 B1 | 7/2005 |
| EP | 2 154 251 A1 | 2/2010 |
| JP | 2008-161185 A | 7/2008 |
| JP | 2008-543323 A | 12/2008 |
| WO | WO 00/20606 A1 | 4/2000 |
| WO | WO 01/36440 A1 | 5/2001 |
| WO | WO 02/19965 A2 | 3/2002 |
| WO | WO 2006/136831 A | 12/2006 |
| WO | WO 2008/043245 A1 | 4/2008 |
| WO | WO 2012/087835 A2 | 6/2012 |

OTHER PUBLICATIONS

Chuang, C.K., et al., "A dual-functional *E coli* vector for expressing recombinant protein with high solubility and antigen presentation ability," *Protein Expr. Purif.*, 65: 51-56 (2009).
Kelley, W.L., "The J-domain family and the recruitment of chaperone power," *Trends Biochem. Sci.*, 23: 222-227 (1998).
Reimann and Schirmbeck, "DNA vaccines expressing antigens with a stress protein-capturing domain display enhanced immunogenicity," *Immunol. Rev.*, 199: 54-67 (2004).
Chan et al., "Therapeutic antibodies for autoimmunity and inflammation," *Nature Rev*, 10: 301-316 (2010)
Cruz et al., "In vivo post-transcriptional gene silencing of α-1 antitrypsin by adeno-associated virus vectors expressing siRNA," *Laboratory Investigation*, 87: 893-902 (2007).
Davies et al., "Gene Therapy for Cystic Fibrosis," *Proc. Am. Thorac. Soc.*, 7: 408-414 (2010).
DeLANO et al., "Convergent Solutions to Binding at a Protein-Protein Interface," *Science*, 287:1279-1283 (2000).
George et al., "An analysis of protein domain linkers: their classification and role in protein folding," *Protein Eng.*, 15(11): 871-879 (2003).

(Continued)

*Primary Examiner* — Jeanette Lieb
(74) *Attorney, Agent, or Firm* — Thomas R. Berka; Leon R. Yankwich; Yankwich & Associates, P.C.

(57) ABSTRACT

Fusion proteins comprising a protein expression enhancing polypeptide linked to a target protein binding domain and nucleic acid molecules encoding such fusion proteins are described for use in enhancing expression and/or location of a targeted protein of interest, for restoring lost functions in cells, and for treating disease. Additional fusion proteins comprising a target protein of interest modified with a fusion partner comprising a protein expression enhancing polypeptide are also disclosed.

27 Claims, 27 Drawing Sheets

(56) References Cited

OTHER PUBLICATIONS

Graille et al., "Complex between *Peptostreptococcus magnus* Protein L and a Human Antibody Reveals Structural Convergence in the Interaction Modes of Fab Binding Proteins," *Structure*, 9: 679-687 (2001).
Guggino, W.B., "The Cystic Fibrosis Transmembrane Regulator Forms Macromolecular Complexes with PDZ Domain Scaffold Proteins," *Proc. Am. Thorac. Soc.*, 1: 28-32 (2004).
Haggie et al., "Increased Diffusional Mobility of CFTR at the Plasma Membrane after Deletion of Its C-terminal PDZ Binding Motif," *J. Biol. Chem.*, 279(7): 5494-5500 (2004).
Hedner, Ulla, "Mechanism of Action of Recombinant Activated Factor VII: An Update," *Semin. Hematol.*, 43 (suppl 1): S105-S107 (2006).
Hennessy et al., "Not all J domains are created equal: Implications for the specificity of Hsp40-Hsp70 interactions," *Protein Science*, 14:1697-1709 (2005).
Kampinga et al., "The HSP70 chaperone machinery: J proteins as drivers of functional specificity," *Nature Rev. Mol. Cell Biol.*, 11:579-592 (2010).
Kawakami et al., "Identification of Distinct Roles for a Dileucine and a Tyrosine Internalization Motif in the Interleukin (IL)-13 Binding Component IL13 Receptor α2 Chain," *J. Biol. Chem.*, 276(27): 25114-25120 (2001).
Knoell et al., "Alpha 1-antitrypsin and Protease Complexation Is Induced by Lipopolysaccharide, Interleukin-1β, and Tumor Necrosis Factor-α in Monocytes," *Am. J. Respir. Crit. Care Med.*, 157(1): 246-255 (1998).
Kontermann, Roland E.: "Recombinant bispecific antibodies for cancer therapy," *Acta Pharmacologica Sinica*, 26(1): 1-9 (Jan. 2005).
Kufer et al., "A revival of bispecific antibodies," *Trends Biotechnol.*, 22(5): 238-244 (2004).
Kyratsous et al., "Chaperone-fusion expression plasmid vectors for improved solubility of recombinant proteins in *Escherichia coli,*" *Gene*, 440: 9-15 (Jul. 2009).
Lee, Gene W., et al., "Improving the Expression of a Soluble Receptor:Fc fusion Protein in CHO Cells by Coexpression with the Receptor Ligand," *In Cell Technolnology for Cell Products (Proceedings of the 19$^{19}$ ESACT Meeting: Harrowgate, UK, Jun. 5-8, 2005)*, (R. Smith, ed.) (Springer Netherlands, 2007) pp. 29-39.
Lee, Gene W., "Stabilizing Protein-Folding Conformations—New Methodology Takes the Development of Soluble Receptor:Fc Fusion Proteins Forward," *Genetic Engineering & Biotechnology News*, 28(5): 1-4 (2008).
Loetscher et al., "Recombinant 55-kDa Tumor Necrosis Factor (TNF) Receptor—Stoichiometry of Binding to TNF α and TNF β and Inhibition of TNF Activity," *J. Biol. Chem.*, 266(27): 18324-18329 (1991).
Marvin et al.: "Recombinant approaches to IgG-like bispecific antibodies," *Acta Pharmacologica Sinica*, 26(6): 649-658 (Jun. 2005).
Muyldermans et al., "Sequence and structure of $V_H$ domain from naturally occurring camel heavy chain immunoglobulins lacking light chains," *Protein Eng.*, 7: 1129-1135 (1994).
Muyldermans et al., "Recognition of antigens by single-domain antibody fragments: the superfluous luxury of paired domains," *Trends Biochem. Sci.*, 26: 230-235 (2001).
Nguyen et al., "Heavy-chain antibodies in *Camelidae*; a case of evolutionary innovation," *Immunogenetics*, 54: 39-47 (2002).
O'Sullivan et al., "Cystic Fibrosis," *Lancet*, 373: 1891-1904 (2009) (online publication date Apr. 28, 2008, http://www.thelancet.com ).
Powell et al., "Safety and prolonged activity of recombinant factor VIII Fc fusion protein in hemophilia A patients," *Blood*, 119(13): 3031-3037 (2012).
Robinson et al., "Optimizing the stability of single-chain proteins by linker length and composition mutagenesis," *Proc. Natl. Acad. Sci. USA*, 95: 5929-5934 (1998).
Schultz et al., "Pharmacology of CFTR Chloride Channel Activity," *Physiol. Rev.*, 79 (1 Suppl.): S109-S144 (1999).
Singh et al., "Differential roles of NHERF1, NHERF2, and PDZK1 in regulating CFTR-mediated intestinal anion secretion in mice," *J. Clin. Investig.*, 119(3): 540-550 (2009).
Takayama et al., "Molecular chaperone targeting and regulation by BAG family proteins," *Nature Cell Biol.*, 3: E237-E241 (2001).
Tang et al., "Expression and characterization of recombinant canine IL-13 receptor α2 protein and its biological activity in vitro," *Molec. Immunol.* 39: 719-727 (2003).
Tettelin et al., Genbank Accession No. P63969; Chaperone Protein DnaJ, Oct. 11, 2004, polypeptide sequence, residues 21-29.
Turpin et al., "Influenza Virus Infection Increases p53 Activity: Role of p53 in Cell Death and Viral Replication," *J. Virol.*, 79(14): 8802-8811 (2005).
Voisine et al., "Chaperone networks: Tipping the balance in protein folding diseases," *Neurobiol. Dis.*, 40: 12-20 (2010).
Vu et al., "Comparison of llama $V_H$ sequences from conventional and heavy chain antibodies," *Mol. Immunol.*, 34: 1121-1131 (1997).
Ward et al., "Binding activities of a repertoire of single immunoglobulin variable domains secreted from *Escherichia coli,*" *Nature*, 341: 544-546 (1989).
Yang et al., "Hexamer peptide affinity resins that bind the Fc region of human immunoglobulin G," *J. Peptide Res.*, 66(Suppl. 1): 120-137 (2006).
Young et al.,"Pathways of Chaperone-Mediated Protein Folding in the Cytosol," *Nature Rev. Mol. Cell Biol.*, 5:781-791 (2004).
Zhang, et al., "Identification, Purification, and Characterization of a Soluble Interleukin (IL)-13-binding Protein," *J. Biol. Chem.*, 272(14): 9474-9480 (1997).
International Search Report and Written Opinion ("ISR & WO") dated Apr. 28, 2014, issued in PCT/US2013/0073442.
International Preliminary Report on Patentability ("IPRP") dated Apr. 8, 2015, issued in PCT/US2013/0073442.
Document related to U.S. Pat. No. 6,747,137 B1 CAS RN 696924-86-4—Sequence from patent.
Document related to US 2004/0172684 A1 excerpt from Seq. Listing: Seq. ID No. 56129.
Document related to US 2004/0214272 A1 excerpt from Seq. Listing: Seq. ID No. 294867.
Document related to US 2004/0214272 A1 excerpt from Seq. Listing: Seq. ID No. Seq. ID No. 204377.
Document related to WO 2001/036440 A1 excerpt from Seq. Listing contained in published application: Seq. ID No. 138.
Document related to CA 2,343,602 A1 excerpt from Seq. Listing: Seq. ID No. 13998.
Document related to CA 2,343,602 A1 excerpt from Seq. Listing: Seq. ID No. 18106.
GenBank Accession No. AAA23247, Apr. 26, 1993.
Narberhaus, F. et al., "Molecular Characterization of the dnaK Gene Region of Clostridium acetobutylicum, Including grpE, dnaJ, and a new heat shock gene", *J. Bacteriology.*, 174(10): 3290-3299 (1992) (document related to GenBank Accession No. AAA23247, Apr. 26, 1993).
GenBank Accession No. ABA38820, Sep. 26, 2005.
Laport, M.S. et al., "Organization of heat shock dnaK and groE operons of the nosocomial pathogen Enterococcus faecium", *Research in Microbiology*, 157(2):162-168 (2006) (document related to GenBank Accession No. ABA38820, Sep. 26, 2005).
GenBank Accession No. CAA74628, Apr. 18, 2005.
Chakrabarti, S. et al., "Role of DnaK in In vitro and In vivo expression of virulence factors of Vibrio Cholerae", *Infection and Immunity*, 67(3): 1025-1033 (1999) (document related to GenBank Accession No. CAA74628, Apr. 18, 2005).
GenBank Accession No. GU591873, Mar. 2, 2011.
Fernández-Taboada, et al., "A proteomics approach to decipher the molecular nature of planarian stem cells", *BMC Genomics*, 12(133): 1-13 (2011) (document related to GenBank Accession No. GU591873, Mar. 2, 2011).
Welsh et al., Abstracts of Papers, 236th ACS National Meeting, Philadelphia, PA, United States, 2008, [abstract] Chemical Abstracts [online], Accession No. 2008:950319, entitled "Enhancing production of complex mammalian proteins using *E. coli* based cell-free protein synthesis.".

(56) References Cited

OTHER PUBLICATIONS

Australian Patent Examination Report No. 1, dated Oct. 25, 2016, in counterpart Australian patent application No. 2013355120.
Arai et al., "Design of the linkers which effectively separate domains of a bifunctional fusion protein," Protein Eng., 14(8): 529-532 (2001).
Crasto et al., "LINKER: a program to generate linker sequences for fusion proteins," Protein Eng., 13(5): 309-314 (2000).
Walsh et al., "The J-protein family: modulating protein assembly, disassembly and translocation," EMBO reports, 5: 567-571 (2004).

Secreted IL13Rα2
(Truncated Form)

Target Fc-Fusion Protein

Bifunctional Fusion Protein
(Invention)

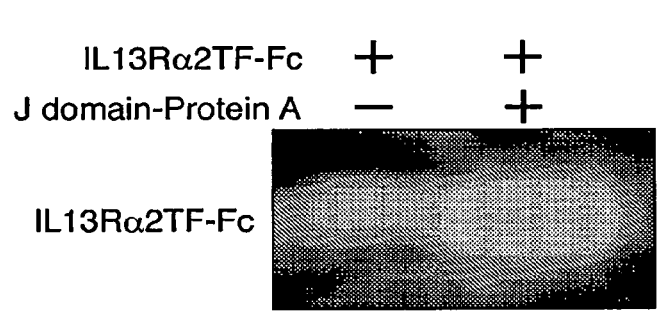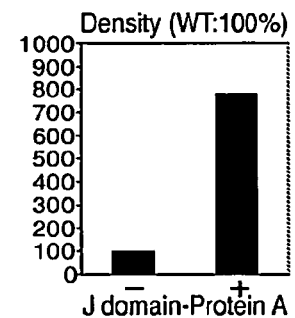
Fig. 13A-1    Fig. 13A-2
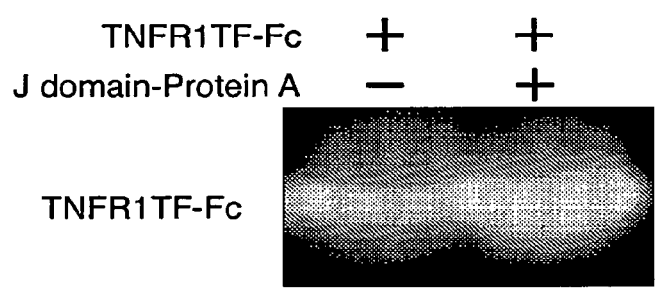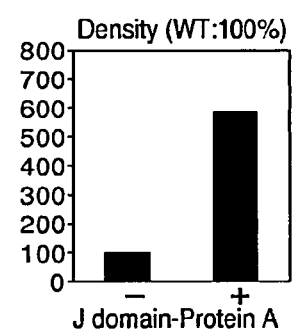
Fig. 13B-1    Fig. 13B-2
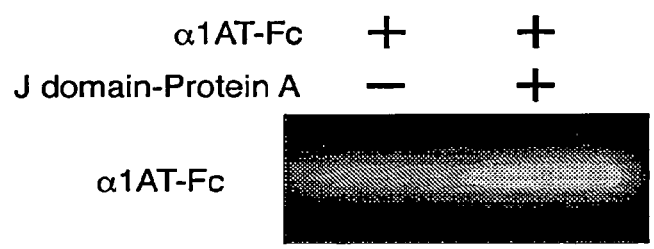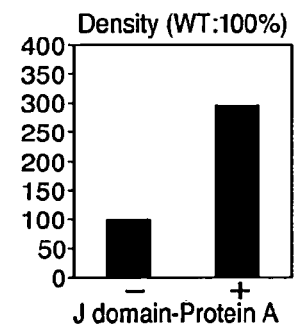
Fig. 13C-1    Fig. 13C-2

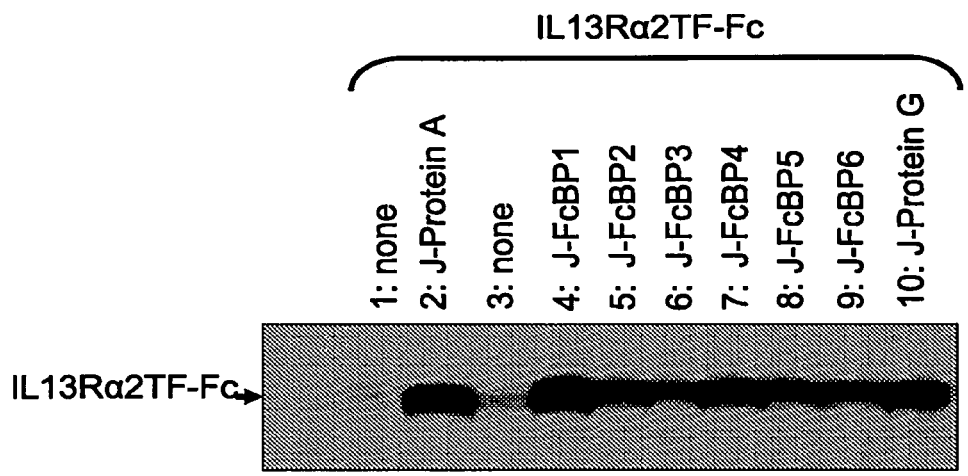
Fig. 17A-1
| FcBP1: | DCAWHLGELVWCT | (SEQ ID NO:240) |
| FcBP2: | HWRGWV | (SEQ ID NO:241) |
| FcBP3: | HVHYYW | (SEQ ID NO:242) |
| FcBP4: | YYWLHH | (SEQ ID NO:243) |
| FcBP5: | HVHYY | (SEQ ID NO:244) |
| FcBP6: | YYWL | (SEQ ID NO:245) |
Fig. 17A-2
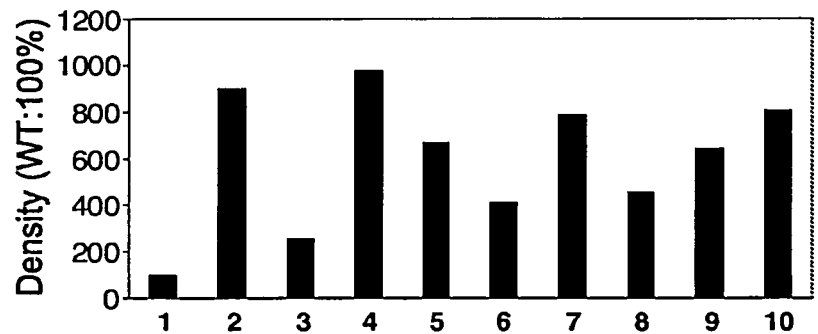
Fig. 17B anti-VEGF Ab
(bevacizumab)

1: no anti-VEGF antibody

2: antibody without BSC1-Protein A

3: antibody with BSC1-Protein A

Fig. 26C anti-TNFα Ab
(adalimumab)

1: no anti-TNFα antibody

2: antibody without BSC1-Protein A

3: antibody with BSC1-Protein A

PROTEIN EXPRESSION ENHANCING POLYPEPTIDES

CROSS-REFERENCE TO RELATED APPLICATIONS

This application is a United States national stage filing under 35 U.S.C. §371 of international application No. PCT/US2013/073442, filed Dec. 5, 2013, designating the U.S., which claims priority to U.S. Provisional Application No. 61/733,743, filed Dec. 5, 2012, and U.S. Provisional Application No. 61/733,884, filed Dec. 5, 2012.

FIELD OF THE INVENTION

This invention is in the field of engineered proteins. In particular, the invention is directed to polypeptides for enhancing expression of proteins and nucleic acid molecules encoding such protein expression enhancing polypeptides. Methods of increasing production levels of a protein of interest are also provided.

BACKGROUND OF THE INVENTION

Expressing a protein of interest in a culture of genetically engineered cells at levels that permit easy isolation in quantities sufficient for research, development, or commercial use requires the optimization of a variety of recombinant techniques and cell culture methodologies. Such techniques include in vitro methods of isolating and recombining nucleic acid molecules to encode a desired protein molecule, operably linking the desired coding sequences with appropriate transcriptional and translational elements, inserting the engineered genetic material into an appropriate expression vector, introducing the resulting recombinant expression vector into compatible host cells, and culturing the host cells containing the recombinant expression vector under conditions that permit expression of the desired recombinant protein. Proper selection and optimization of such methods has permitted expression and use of a variety of recombinant proteins from a wide variety of host cells, including bacterial, fungal, insect, plant, and mammalian host cells.

Despite many advances in recombinant and cell culture methodologies, the problem of ensuring proper protein folding can still thwart the most extensive efforts to produce useful amounts of a desired recombinant protein. All proteins must achieve a proper two- and three-dimensional conformation in order to function properly at their intended location. Proper conformation ensures that a protein will provide a cell or multi-cell organism with its intended function (for example, enzymatic activity, signal transduction, or structural feature) at its intended location (for example, cytoplasm, nucleus, intracellular structure, organelle, cell membrane, or extracellular (secreted) location). Although the information for the proper structure and conformation resides in a protein's amino acid sequence, the general intracellular environment and a variety of stimuli and environmental stresses, including oxidative stress, nutrient deprivation, and high temperature, can make proper folding of even endogenously produced proteins more difficult to the point that many protein molecules take on an undesired structure and thus fail to provide a cell with their intended function. To deal with the continual risk of not attaining or maintaining proper functional conformations, cells possess a system of proteins that serve as molecular chaperones to assist in the folding and refolding of nascent and mature proteins into their proper conformations. The heat shock 70 kDa proteins (referred herein as "Hsp70s") constitute one of the most ubiquitous classes of chaperone proteins in the cells of a wide variety of species. The Hsp70 machinery includes the participation of co-factor (or co-chaperone) proteins, such as J proteins, and nucleotide exchange factors (NEFs).

In a current model of the Hsp70 chaperone machinery for folding proteins, Hsp70 cycles between ATP- and ADP-bound states. In this model, a J protein binds to a protein in need of folding or refolding (referred to as a "client protein") and interacts with an ATP-bound state of Hsp70 (Hsp70-ATP). Binding by the J protein-client complex to Hsp70-ATP stimulates ATP hydrolysis, which causes a conformational change in the Hsp70 protein that closes a helical lid, thereby stabilizing the interaction between the client protein with the Hsp70-ADP, and release of the J protein, which is then free to bind another client protein. While bound to the Hsp70-ADP, the client protein is provided with an environment that permits folding or refolding into a proper conformation. Next, a nucleotide exchange factor (NEF) binds to Hsp70-ADP resulting in release of ADP and binding of ATP. The client protein is then released because of its low affinity (in the absence of J protein) for Hsp70-ATP. If the client protein has not achieved a proper conformation, it may be rebound by a J protein and enter the cycle again. See, Kampinga et al., *Nat. Rev.*, 11: 579-592 (2010). Thus, according to this model, J proteins play a critical role in the Hsp70 machinery by associating with individual client proteins and also with the Hsp70 chaperone protein to provide a bridging function that facilitates the capture and submission of a wide variety of client proteins into the Hsp70 machinery to promote folding or refolding into proper conformations. When attempts by the Hsp70 chaperone machinery fail to fold or refold a protein into proper functional conformations, the Hsp70 chaperone machinery also can facilitate the transfer of the improperly folded protein to the cell's proteolytic system (e.g., the proteasome) for degradation and recycling of amino acids. For a review of the Hsp70 chaperone machinery, including the critical role of J proteins, see, Kampinga et al, *Nature Rev.*, 11: 579-592 (2010) and Voisine et al., *Neurobiol. Dis.*, 40: 12-20 (2010).

Expressed proteins are thus subjected to a strict quality control system of the Hsp70 machinery for maintaining proper conformations. The problem of proper protein folding is of particular concern in the case of producing useful quantities of functional exogenous (recombinant) proteins expressed in various recombinant host cells. The problem can arise in both eukaryotic and prokaryotic host cells. The failure to properly fold exogenous proteins expressed in bacterial host cells frequently can result in the formation within the cells of large, potentially toxic, aggregates of inactive molecules of the exogenous protein. Such aggregates are referred to as "inclusion bodies" and are considered to be the result of ineffective protein folding that leads to non-functional conformations with exposed hydrophobic domains that in turn promote association and aggregation with other improperly folded protein molecules.

When a wild-type gene encoding a protein undergoes a mutation, the encoded mutant form of the protein may still be expressed in the cell. Such expressed mutant proteins usually fail to achieve a proper functional conformation of the wild-type protein and may form inactive aggregates. Such improperly folded mutant protein species are typically ushered by the Hsp70 machinery into the cells proteolytic system for degradation and recycling of amino acids Elimination of the improperly folded mutant protein still, of course, leaves the cell with a loss of functional protein and the consequence of such loss of function can be debilitating or even fatal to the cell. In fact, loss of properly folded functional protein species has been demonstrated or is implicated in a number of diseases, including prion-associated diseases (transmissible spongiform encephalopathies), Alzheimer's disease, Parkinson's disease, Huntington's disease, and cystic fibrosis.

Members of the BAG family of proteins found in eukaryotes are nucleotide exchange factors (NEFs) that possess diverse N-terminal domains and a conserved C-terminal Hsp70-binding domain (the BAG domain) that can interact with the ATPase domain of Hsp70. See, for example, Kampinga et al., *Nat. Rev. Biol.*, 11:579-592 (2010). Thus, BAG proteins have a topology, binding domains, and binding specificities that are consistent with a protein designed to participate in recruiting the Hsp70 chaperone machinery. Although a BAG protein might participate as a NEF in the Hsp70 machinery, many studies suggest that BAG proteins may predominantly be involved in regulatory mechanisms to control a variety of activities, including promoting cell growth, quiescence, or apoptosis; regulating transcription complex formation; and modulating signal transduction. See, for example, the review by Takayama et al., *Nat. Cell Biol.*, 3: E237-E241 (2001). Recently, it has been reported that when desired recombinant proteins are linked to a BAG domain, the resulting fusion proteins are expressed at levels that are greater than those of the protein alone. See, International Publication No. WO 2012/087835 A2.

In general, with an increasing level of expression of a protein in a cell (as can easily occur in recombinant gene expression systems), there is an increasing risk that such proteins may fail to fold or refold into proper functional conformations. Accordingly, along with a constant desire for increasing expression of desired exogenous or endogenous proteins, needs remain for means for enhancing the proper folding of exogenous and endogenous proteins expressed in cells, i.e., to increase the yield of properly conformed, functional proteins.

SUMMARY OF THE INVENTION

The present invention provides compositions and methods for enhancing the level of expression of a target protein of interest produced by a cell. In particular, the invention provides protein expression enhancing polypeptides that can be incorporated into genetically engineered fusion proteins, which when expressed by a host cell are able to enhance the level of expression of a specific target protein of interest at its intended location.

In one embodiment, a protein expression enhancing polypeptide of the invention is selected from the group consisting of:

(a) an isolated J domain of a J protein;
(b) an isolated protein expression enhancing polypeptide fragment of a J domain;
(c) an isolated protein expression enhancing polypeptide analog of a J domain, said J domain analog polypeptide comprises the amino acid sequence of formula I:

(SEQ ID NO: 47)
(I) X1-X2-X3-X4-X5-X6-X7-X8-X9,

X1 is isoleucine (I), leucine (L), valine (V), alanine (A), or methionine (M);
X2 and X3 are each independently any amino acid with the proviso that one or both are K or R;
X4 is any amino acid or X4 may be absent when X1 through X3 are present and X5 through X9 are present;
X5 is tyrosine (Y), tryptophan (W), or phenylalanine (F);
X6 and X7 are each independently any amino acid with the proviso that one or both are lysine (K) or arginine (R); or either one of X6 and X7 may be absent when the other is K or R and when X1 through X5 are present and X8 and X9 are present; and
X8 and X9 are any amino acid with the proviso that one or both are leucine (L) or alanine (A); or one of X8 and X9 may be absent when the other is L or A and when X1 through X7 are present; and (d) an isolated protein expression enhancing polypeptide selected from the group of decapeptides consisting of:

```
                            (SEQ ID NO: 49)
        IKKAYKLALQ, (SEQ ID NO: 50)
        IKKAYRLALQ, (SEQ ID NO: 51)
        IKKAYRKALQ,
        or (SEQ ID NO: 52)
        IKKAYRKLLQ.
```

In accordance with the invention, a protein expression enhancing polypeptide enhances the level of expression of a target protein of interest expressed in a host cell as compared to the level of expression of the target protein of interest in the absence of the protein expression enhancing polypeptide. Use of the polypeptides of the present invention provides a means for increasing the amount of a desired recombinant protein in the desired location (compartment) with respect to the producing cell.

In a particular embodiment, a protein expression enhancing polypeptide of the invention is an isolated J domain that has an amino acid sequence selected from any of the J domain sequences set forth in Table 1, infra.

Preferably, a protein expressing enhancing polypeptide of the invention is an isolated J domain of an Erdj protein, a large T antigen of SV40, or a mammalian cysteine string protein alpha (CSP-α). A preferred isolated J domain of an Erdj protein of the invention is an isolated J domain of Erdj1, Erdj2, Erdj3, Erdj4, Erdj5, Erdj6 or Erdj7. Particularly preferred is an isolated J domain of Erdj3.

In another embodiment, a protein expression enhancing polypeptide of the invention is a polypeptide fragment of a J domain that has an amino acid sequence that is selected from any of the following:

```
                            (SEQ ID NO: 48)
        I-K-K-A-Y-R-K-L-A, (SEQ ID NO: 83)
        I-R-K-A-Y-R-K-L-S-L-T-L, (SEQ ID NO: 84)
        I-K-K-Q-Y-R-L-L-S-L-K-Y, (SEQ ID NO: 85)
        I-K-K-A-F-H-K-L-A-M-K-Y, (SEQ ID NO: 86)
        I-R-Q-A-F-K-K-L-A-L-K-L,
```

```
                                          (SEQ ID NO: 87)
I-I-K-A-Y-R-K-L-A-L-Q-W, (SEQ ID NO: 88)
I-A-R-A-Y-R-Q-L-A-R-R-Y, (SEQ ID NO: 89)
I-K-R-A-Y-R-R-Q-A-L-R-Y, (SEQ ID NO: 90)
I-K-K-S-Y-R-K-L-A-L-K-Y,
and (SEQ ID NO: 91)
I-K-K-A-Y-K-R-L-A-M-K-Y.
```

In another embodiment, a protein expression enhancing polypeptide is a J domain analog polypeptide having the amino acid sequence of formula I, supra. In particular embodiments, a protein enhancing polypeptide of the invention comprises a polypeptide having the sequence: X1-X2-X3-X4-X5-X6-X7-X8-X9 (SEQ ID NO:326), wherein:

X1 is I, L, V, A, or M;

the dipeptide X2-X3 is selected from the group consisting of: KR, KK, RK, RR, AK, AR, KA, IK, NK, KQ, RQ, and RD;

X4 is A, S, T, R, S, Q, E, F, C, or I;

X5 is Y or F;

the dipeptide X6-X7 is selected from the group consisting of: KR, KK, RK, RR, RQ, FR, RL, KL, HK, LK, QK, and KV; and the dipeptide X8-X9 is selected from the group consisting of: LA, LL, AL, AA, LC, LV, QA, KA, LS, LI, LY, and RA.

In particular embodiments, a J domain analog polypeptide of the invention comprises one of the following amino acid sequences:

| Sequence Identifier | Amino Acid Sequence 123456789012345 |
| --- | --- |
| SEQ ID NO: 48 | IKKAYRKLA |
| SEQ ID NO: 49 | IKKAYKLALQ |
| SEQ ID NO: 50 | IKKAYRLALQ |
| SEQ ID NO: 51 | IKKAYRKALQ |
| SEQ ID NO: 52 | IKKAYRKLLQ |
| SEQ ID NO: 53 | IKKYRKLA |
| SEQ ID NO: 54 | IKKAYKLA |
| SEQ ID NO: 55 | IKKAYRLA |
| SEQ ID NO: 56 | IKKAYRKA |
| SEQ ID NO: 57 | LKKAYRKLA |
| SEQ ID NO: 58 | VKKAYRKLA |
| SEQ ID NO: 59 | MKKAYRKLA |
| SEQ ID NO: 60 | AKKAYRKLA |
| SEQ ID NO: 61 | IAKAYRKLA |
| SEQ ID NO: 62 | IKAAYRKLA |
| SEQ ID NO: 63 | IKKRYRKLA |
| SEQ ID NO: 64 | IKKSYRKLA |
| SEQ ID NO: 65 | IKKQYRKLA |
| SEQ ID NO: 66 | IKKEYRKLA |
| SEQ ID NO: 67 | IKKFYRKLA |
| SEQ ID NO: 68 | IKKCYRKLA |
| SEQ ID NO: 69 | IKKAFRKLA |
| SEQ ID NO: 70 | IKKAWRKLA |
| SEQ ID NO: 71 | IKKAYRKQA |
| SEQ ID NO: 72 | IKKAYRKMA |
| SEQ ID NO: 73 | IKKAYRKIA |
| SEQ ID NO: 74 | IKKAYRKAA |
| SEQ ID NO: 75 | IKKAYRKVA |
| SEQ ID NO: 76 | IKKAYRKRA |
| SEQ ID NO: 77 | IKKAYRKLM |
| SEQ ID NO: 78 | IKKAYRKLI |
| SEQ ID NO: 79 | IKKAYRKLV |
| SEQ ID NO: 80 | IKKAYRKLC |
| SEQ ID NO: 81 | IKKAYRKLS |
| SEQ ID NO: 82 | IKKAYRKLY |
| SEQ ID NO: 83 | IRKAYRKLSLTL |
| SEQ ID NO: 84 | IKKQYRLLSLKY |
| SEQ ID NO: 85 | IKKAFHKLAMKY |
| SEQ ID NO: 86 | IRQAFKKLALKL |
| SEQ ID NO: 87 | IIKAYRKLALQW |
| SEQ ID NO: 88 | IARAYRQLARRY |
| SEQ ID NO: 89 | IKRAYRRQALRY |
| SEQ ID NO: 90 | IKKSYRKLALKY |
| SEQ ID NO: 91 | IKKAYKRLAMKY |

In a further embodiment, the invention provides a fusion protein comprising a protein expression enhancing polypeptide fused to a target protein of interest, wherein the protein expression enhancing polypeptide fusion partner is a J domain of a J protein, a J domain fragment having the ability to enhance expression of the protein of interest fusion partner, or a J domain analog polypeptide having the amino acid sequence of formula I (SEQ ID NO:47) as described above. Expression of this fusion protein leads to increased expression of the fused target protein of interest, as compared with expression of the target protein of interest without the use of the protein expression enhancing polypeptide fusion partner. Removal of the protein expression enhancing polypeptide portion of the fusion protein by standard methods results in increased recovery of the target protein of interest.

A fusion protein of the invention comprising a protein expression enhancing polypeptide described herein linked to a target protein of interest may be used in a method to restore a protein function in cells of a mammalian subject that are deficient in the secretion of a native secreted protein that provides the protein function comprising the steps of inserting into cells of the mammalian subject (such as a human, non-human primate, rodent, or livestock) an exogenous nucleic acid molecule encoding a fusion protein comprising a protein expression enhancing polypeptide as described above linked to the secreted protein, wherein expression of the fusion protein provides the function of the native secreted protein whose secretion is deficient in cells of the subject in the absence of the exogenous nucleic acid.

In a preferred embodiment, the above method for restoring a protein function in cells of a mammalian subject is used to treat a subject that has a disease associated with the deficient secretion of a native secreted protein in the subject. Such diseases include, but are not limited to, prion-associated disease, Alzheimer's disease, Parkinson's disease, Huntington's disease, cystic fibrosis (CF), and α1-antitrypsin deficiency. In a particularly preferred embodiment, a method for restoring a protein function is used to treat a human subject deficient in the secretion of cystic fibrosis transmembrane conductance regulator protein (CFTR) and the disease is cystic fibrosis. In this embodiment, an exogenous nucleic acid molecule that is inserted into cells of the human subject encodes a fusion protein comprising a protein expression enhancing polypeptide described above linked to CFTR. Expression of the fusion protein in the cells of the human subject restores the deficiency of CFTR function.

In a further embodiment, the invention provides a fusion protein comprising a protein expression enhancing polypeptide linked to a target protein binding domain, wherein the protein expression enhancing polypeptide element is a J domain of a J protein, a J domain fragment having the ability to enhance expression of the protein of interest fusion partner, or a J domain analog polypeptide having the amino acid sequence of formula I (SEQ ID NO:47) as described above, and the target protein binding domain is a polypeptide capable of binding to a target protein of interest when the fusion protein and the target protein of interest are co-expressed in the same host cell. A fusion protein that binds a target protein of interest enhances the level of expression of the target protein and/or enhances the level of the target protein at its proper cellular or extracellular location. Accordingly, fusion proteins described herein may be used to enhance the level of expression of a target protein of interest that is not expressed in adequate amounts or at the proper cellular or extracellular location for a given purpose. Such situations in which a fusion protein described herein is useful include, without limitation, failure to express desired quantities of an endogenous or heterologous (recombinant) protein of interest in cell culture and failure to express sufficient levels of a protein in vivo where inadequate expression of one or more functional proteins leads to a pathological state (such as, without limitation, a prion-associated disease (a transmissible spongiform encephalopathy); Alzheimer's disease; Parkinson's disease; Huntington's disease; cystic fibrosis; α1-antitrypsin deficiency).

A protein that is targeted by a fusion protein of the invention for an enhanced level of expression and/or enhanced expression at a desired cellular or extracellular location may be a soluble protein, a membrane-associated protein, or a secreted protein.

A target protein binding domain of a fusion protein of the invention is a polypeptide that binds a target protein. Preferably, the target binding domain has a binding affinity for a target protein that is sufficiently specific as to exclude other proteins from interfering with the enhancement in the level of expression of the target protein. Examples of polypeptides that may be used as a target binding domain of the invention include, but are not limited to, an antibody or antigen binding portion thereof that binds a target protein, an immunoglobulin-specific binding protein (such as Protein A, Protein L, and Protein G) that binds a target immunoglobulin or fragment thereof, an Fc binding protein (such as Protein A and Protein G) that binds an Fc domain of a target protein, an Fc binding peptide that binds an Fc domain of a target protein, a ligand binding domain of a receptor protein that binds the target protein of interest, a protein ligand of the target protein (such as a protein ligand of a receptor), a PDZ domain of a PDZ protein that binds a PDZ binding domain of a target protein, and the like.

In an embodiment of the invention, when the target protein is a cytokine, the target binding domain of a fusion protein of the invention may comprise a ligand binding domain of a cytokine receptor protein that binds the target cytokine protein.

In another embodiment, when the target protein is a receptor protein or ligand binding portion thereof, then the target binding domain of a fusion protein of the invention may comprise a protein ligand which is bound by the receptor or the ligand binding portion thereof. In a preferred embodiment, when the target protein is a cytokine receptor protein or cytokine binding portion thereof, the target binding domain comprises the cytokine that is bound by the cytokine receptor or cytokine binding portion of such receptor.

In an embodiment wherein the target protein, such as the cystic fibrosis transmembrane conductance regulator (CFTR) protein, possesses a PDZ-binding domain, then the target binding domain of a fusion protein of the invention may comprise a PDZ domain from any of a variety of proteins that possess a PDZ domain. In a preferred embodiment, when a target protein possesses a PDZ-binding domain, a target binding domain of a fusion protein of the invention comprises a PDZ domain from any of the members of the NHERF family of PDZ adapter proteins including, but not limited to, of NHERF1 (also known as NHERF, EBP50, or SLC9A3R1), NHERF2 (also known as E3KARP or SLC9A3R2), and PDZK1 (also known as CAP70 or NHERF3).

Particular embodiments of a target protein-binding fusion protein of the invention comprise a J domain of a J protein, or an active (expression enhancing) fragment thereof, or a protein expression enhancing polypeptide of formula I, fused to a target protein binding domain with or without a linker peptide. When a linker peptide is present in a target protein-binding fusion protein of the invention, the linker may be one or more amino acids, including 1 to 10 amino acids, 1 to 20 amino acids, and even 1 to 50 amino acids. Typically, a linker will not be more than 20 amino acids and will be selected or designed so that linker does not interfere with (and hopefully enhances) the function of either the target protein binding domain or the protein expression enhancement polypeptide. The linker, if present, preferably is selected to optimize the contribution of both elements of the fusion protein and thereby increase the level of expression and/or proper location of a target protein of interest. The linker may be omitted if direct attachment of a protein expression enhancement polypeptide to a target protein binding domain does not unacceptably diminish the function of either element or does not unacceptably diminish the desired enhancement in the level of expression and/or location of the target protein.

A linker useful in a fusion protein of the invention may include an enzymatically cleavable peptide, i.e., a cleavage site for an enzyme such as an enterokinase, the light chain of enterokinase, thrombin, urokinase, tobacco etch virus protease (TEV), tissue plasminogen activator, a zinc-dependent endopeptidase, a matrix metalloproteinase (MMP), a serralysin, an astacin, an adamalysin, a disintegrin, an ADAM, a caspase, a cathespsin, a calpain, and the like. Use of a cleavable linker in a fusion protein described herein may be advantageous to halt or slow the function of the fusion protein or to eliminate its presence in a cell or presence in a population of target protein molecules. Some cells possess one or more intracellular proteases that can cleave polypeptide linker molecules that contain a corresponding proteolytic recognition site. Accordingly, a cleavable linker used in a fusion protein of the invention may be selected that permits an intracellular protease to cleave the fusion protein after expression in the cell.

A fusion protein of the invention may further comprise an epitope tag to assist in detecting or isolating the fusion protein. An epitope tag useful in the invention includes, but is not limited to; a polyhistidine tag (such as hexaHis, SEQ ID NO:112), a V5 epitope tag, a Myc epitope tag, a Flag epitope tag, and an HA (human influenza hemagglutinin) epitope tag.

Fusion proteins of the present invention are demonstrated to enhance the level of expression of target proteins compared to the level of expression of the target proteins alone, i.e., in the absence of a fusion protein. The level of expression of a target protein of interest can be increased at least about 1.5-fold and up to 2-fold, 4-fold, 6-fold, 8-fold, 10-fold, 25-fold or more by following the methods described herein. Moreover, fusion proteins of the invention also enhance the level of target proteins at their proper cellular or extracellular locations.

In another embodiment, the invention provides compositions comprising a fusion protein useful for providing the fusion protein to an individual to enhance expression of a target protein. Compositions of the invention also include pharmaceutical compositions comprising a fusion protein and a pharmaceutically acceptable carrier for use in treating a disease or disorder in an individual, including in a human individual. Pharmaceutical compositions comprising a fusion protein as described herein may further comprise one or more other therapeutically active compounds. Examples of such additional therapeutically active compounds that may be incorporated into a pharmaceutical composition of the invention include, but are not limited to, an antibiotic, an anti-viral compound, an anti-cancer compound, a sedative, a stimulant, a local anesthetic, a corticosteroid, an analgesic, an anti-histamine, a non-steroid anti-inflammatory drug (NSAID), and appropriate combinations thereof.

The invention also provides methods of treating a human or animal subject for a disease state characterized by a loss or diminution of a function or property that can be provided by a target protein of interest whose expression is enhanced by one of the types of fusion proteins described herein. Such methods may include administering a fusion protein as described herein to a patient in need of treatment.

The invention also provides isolated nucleic acids encoding a protein expression enhancing polypeptide selected from the group consisting of an isolated J domain of a J protein, an isolated J domain fragment having the ability to enhance expression of a target protein of interest, or an isolated J domain analog polypeptide having the amino acid sequence of formula I (SEQ ID NO:47) as described above.

The invention also provides nucleic acid vectors comprising an isolated nucleic acid described above.

In another embodiment, the invention comprises a host cell comprising an isolated nucleic acid or a nucleic acid vector described above.

The invention provides isolated nucleic acid molecules encoding a fusion protein described herein. Also provided are recombinant vector molecules into which has been inserted an isolated nucleic acid molecule encoding a fusion protein of the invention. Such recombinant vector molecules include cloning vectors to replicate the inserted nucleic acid in a transfected host cell and also expression vectors for expressing the encoded fusion protein in a compatible transfected host cell. Any of a variety of expression vectors available in the art may be used to produce a fusion protein of the invention. Examples of expression vectors useful for expressing a fusion of the invention include, but are not limited to, plasmid pcDNA, pcDNA3.3 TOPO (Life Technologies, New York), plasmid pTT3, plasmid pEF-BOS, and the like.

The invention also provides expression vector molecules into which has been inserted an isolated nucleic acid encoding an isolated J domain, an active J domain fragment, or a J domain analog of formula I, for use in expressing a fusion protein of the invention in vitro in a compatible host cell.

Expression vectors of the invention also include gene therapy vectors for expressing a fusion protein of the invention in vivo in a gene therapy to restore a lost or deficient target protein function in a plant or animal (including mammals, such as humans, non-human primates, rodents, and livestock).

In another aspect, the invention provides a host cell comprising an expression vector for expressing a protein expression enhancing polypeptide described here or a fusion protein described herein. Host cells useful in the invention include, without limitation, eukaryotic host cells. Preferred eukaryotic host cells include, without limitation, a mammalian host cell, an insect host cell, a plant host cell, a fungal host cell, a eukaryotic algal host cell, a nematode host cell, a protozoan host cell, and a fish host cell. Preferably, a mammalian host cell is a Chinese Hamster Ovary (CHO) cell, a COS cell, a Vero cell, an SP2/0 cell, an NS/0 myeloma cell, a human embryonic kidney (HEK293) cell, a baby hamster kidney (BHK) cell, a HeLa cell, a human B cell, a CV-1/EBNA cell, an L cell, a 3T3 cell, an HEPG2 cell, a PerC6 cell, or an MDCK cell. Preferred fungal host cells include *Aspergillus, Neurospora, Saccharomyces, Pichia, Hansenula, Schizosaccharomyces, Kluyveromyces, Yarrowia,* and *Candida*. More preferably, a *Saccharomyces* host cell is a *Saccharomyces cerevisiae* cell.

The invention provides a method of expressing a fusion protein comprising a J domain of a J protein, a protein expression enhancing fragment thereof, or a J domain analog of formula I linked to a target protein of interest comprising culturing a host cell comprising a vector molecule comprising an isolated nucleic acid molecule encoding the fusion protein under conditions sufficient to produce the fusion protein.

In another embodiment, the invention provides a method of expressing a fusion protein comprising a J domain of a J protein, a protein expression enhancing fragment thereof, or a J domain analog of formula I as described above linked to a target protein of interest comprising transfecting a host cell with an expression vector comprising a structural gene encoding the fusion protein and culturing the transfected host cell under conditions causing the expression of the fusion protein.

The invention also provides a method of expressing a fusion protein comprising a protein expression enhancing polypeptide described herein linked to a target protein of interest comprising the steps of:
1) constructing a recombinant gene sequence encoding the fusion protein;
2) inserting the recombinant gene sequence into an expression vector to form a recombinant expression vector wherein said recombinant gene sequence is operably linked to a transcriptional promoter sequence;
3) transfecting said recombinant expression vector into host cells that are compatible with said promoter sequence; and
4) culturing said transfected host cells under conditions that permit expression said fusion protein.

The invention also provides a method of expressing a fusion protein comprising an isolated expression enhancing polypeptide described herein linked to a target protein binding domain comprising culturing a host cell comprising a vector comprising an isolated nucleic acid encoding the fusion protein under conditions sufficient to produce the fusion protein.

In another embodiment, the invention provides a method of enhancing the expression of a target protein of interest expressed by a host cell comprising transfecting the host cell with an expression vector comprising a structural gene encoding a fusion protein comprising an isolated J domain of a J protein, an isolated J domain fragment having the ability to enhance expression of a target protein of interest, or an isolated J domain analog polypeptide having the amino acid sequence of formula I (SEQ ID NO:47) as described above linked to the target protein binding domain, and culturing said transfected host cell under conditions causing the co-expression of said fusion protein encoded by said structural gene and of said target protein of interest.

The invention provides a method of enhancing the expression of a target protein of interest comprising (a) transfecting a host cell with an expression vector comprising a structural gene encoding a fusion protein, wherein the fusion protein comprises a J domain of a J protein, an active fragment thereof, or a J domain analog of formula I linked to a target protein binding domain and wherein the fusion protein binds the target protein of interest, and (b) culturing said transfected host cell under conditions causing the expression of the fusion protein encoded on the structural gene. Said structural gene may also include optional segments encoding a linker peptide connecting the J domain/J domain fragment/J domain analog element and the target protein binding domain element, and may also include segments encoding epitope tags, enzyme cleavage sites, and the like. The method may advantageously be carried out by following the steps:
1) constructing a recombinant gene sequence encoding a fusion protein comprising a protein expression enhancing polypeptide linked to a target binding domain;
2) inserting the recombinant gene sequence into an expression vector to form a recombinant expression vector wherein said recombinant gene sequence is operably linked to a transcriptional promoter sequence;
3) transfecting suitable host cells that are compatible with said promoter sequence with said recombinant expression vector; and
4) culturing said transfected host cells under conditions that lead to expression of said fusion protein.

In an embodiment of the invention, a nucleic acid encoding a fusion protein of the invention is inserted into the cells of a plant or non-human animal to express the fusion protein and enhance the level of expression of a target protein to provide a missing or desired function to the plant or non-human animal. Such methods include producing transgenic plants and transgenic non-human animals in which a nucleic acid encoding a fusion protein is permanently incorporated into the genome as a functional gene (transgene) such that the plant or non-human animal not only expresses the fusion protein, but also passes a copy of the expressible transgene on to progeny.

In another embodiment, the invention provides a method of restoring a function provided by a target protein in cells of a subject that are deficient in the expression of the target protein comprising inserting into cells of the subject an exogenous nucleic acid molecule encoding a fusion protein according to the invention, wherein after inserting the exogenous nucleic acid molecule into the cells, the fusion protein is expressed and enhances the level expression of the target protein (which enhancement may be the result of stabilizing the endogenous target protein, increasing the amount of properly folded target protein, improving the localization of the target protein to the desired cellular or extracellular compartment (e.g., improving secretion of a secreted protein), etc.), to provide the function of the target protein whose expression is deficient in the cells of the subject in the absence of the exogenous nucleic acid. Such a method is particularly useful in treating a subject that has a disease associated with the deficient expression of a protein in the subject. Such diseases include, but are not limited to, a prion-associated disease (a transmissible spongiform encephalopathy), Alzheimer's disease, Parkinson's disease, Huntington's disease, cystic fibrosis, and α1-antitrypsin (AAT) deficiency. Particularly preferred, are embodiments of the method wherein the subject is a human subject that is deficient in the expression of cystic fibrosis transmembrane conductance regulator (CFTR) protein and the disease is cystic fibrosis or wherein the subject is a human subject that is deficient in α1-antitrypsin and the disease is α1-antitrypsin (AAT) deficiency.

BRIEF DESCRIPTION OF THE DRAWINGS

FIG. 1A depicts diagrams of the structural genes for insertion into an expression vector plasmid used to transfect host cells. A cDNA encoding an IL13Rα2 protein (wild-type protein, "WT") was augmented with a segment encoding a V5 epitope tag at the 3' end for the "IL13Rα2WT" expression product. For BAG domain fusion proteins, a cDNA encoding IL13Rα2 was linked in frame to a segment encoding a BAG domain, which was linked in turn to a segment encoding a V5 epitope tag to provide BAG domain fusion protein expression products. For J domain fusion proteins of the invention, a cDNA encoding IL13Rα2 was linked in frame to a segment encoding a J domain, which was linked in turn to a segment encoding a V5 epitope tag to provide J domain fusion protein expression products. FIG. 1B shows x-ray film images of chemiluminescent signals of a Western blot (immunoblot) analysis of cell lysates indicating relative levels of expression of the tagged IL13Rα2 wild-type (WT) protein or fusion protein counterparts in transfected cells. It can be seen that employing a J domain of J proteins Hsp40, SV40, or CSP as a fusion partner for the IL13Rα2 protein of interest resulted in significantly greater protein expression compared to the wild-type IL13Rα2 protein (WT) or any of the BAG domain fusion counterparts comprising a BAG domain of BAG proteins BAG3, BAG4, BAG5, or BAG6. All transfectants were co-transfected with a reporter plasmid expressing green fluorescent protein (GFP) to show successful transfection and operability of the transfectants. See, lower panel of FIG. 1B. FIG. 1C provides the results of a densitometry analysis of the chemiluminescent signals in the immunoblot of FIG. 1B using the ImageJ image processing program. The bar graphs in FIG. 1C clearly show a significantly higher level of expression of all three secreted IL13Rα2-J domain fusion proteins compared to that for any of the four IL13Rα2-BAG domain fusion proteins or the wild-type IL13Rα2 protein (IL13α2WT expression=100%).

FIG. 2A depicts diagrams of the structural gene constructs for insertion into an expression vector plasmid used to transfect host cells. A cDNA encoding IL13Rα2TF was augmented with a segment encoding a V5 epitope tag at the 3' end for the IL13Rα2TF expression product. A cDNA encoding IL13Rα2TF was augmented at the 3' end with a segment encoding a V5 epitope tag and linked at the 5' end with a segment encoding a J domain (from J protein Erdj3) for a J domain fusion protein expression product of the invention (J-IL13Rα2TF). FIG. 2B shows x-ray film images of chemiluminescent signals in a Western blot indicating relative levels of expression in cells (cell lysates) and secreted into culture medium (medium) of the V5-tagged IL13Rα2TF protein and J domain fusion protein counterpart. It can be seen that employing a J domain as a fusion partner for the IL13Rα2TF protein of interest resulted in significantly greater level of protein expression compared to IL13Rα2TF protein without a J domain. All transfectants were co-transfected with a reporter plasmid expressing green fluorescent protein (GFP) to show successful transfection and operability of the transfectants. See, lower panel of FIG. 2B. Mock cultures contained cells transfected with an "empty" vector, i.e., an expression vector lacking a structural gene for expressing any protein.

FIGS. 3A and 3B show results of an experiment an experiment described in Example 2 comparing relative levels of expression of protein secreted into the culture medium of host cells transfected with an expression vector for expressing a truncated receptor protein (IL13Rα2TF), a BAG domain-IL13Rα2TF fusion protein (BAG-IL13Rα2TF), and a J domain-IL13Rα2TF fusion protein (J-IL13Rα2TF). FIG. 3A shows x-ray film images of chemiluminescent signals of a dot blot analysis of IL13Rα2TF, BAG domain-IL13Rα2TF fusion protein, and J domain-IL13Rα2TF fusion protein secreted into culture medium of transfected cells. All proteins carried a V5 epitope tag for innnunodetection with anti-V5 antibody. FIG. 3B provides the results of a densitometry analysis of the chemiluminescent signals in FIG. 3A using the NIH ImageJ image processing program. The bar graphs in FIG. 3B clearly show the significantly higher level of expression of secreted J domain-IL13Rα2TF fusion protein (bar graph 4) compared to either the IL13Rα2TF (bar graph 2) or the BAG domain-IL13Rα2TF fusion protein (bar graph 3). Mock cultures (bar graph 1) contained cells transfected with expression vector lacking a structural gene for expressing any protein.

FIGS. 4A-4C show results of an experiment described in Example 2 to examine improvement in the level of expression of a secreted α1 anti-trypsin (α1AT) in a modified arrangement in which α1AT is linked to (fused with) a J domain fusion partner in comparison to the protein alone or expressed as a fusion with a BAG domain. FIG. 4A depicts diagrams of the structural gene constructs for insertion into an expression vector plasmid used to transfect host cells. A cDNA encoding α1AT was augmented with a segment encoding a V5 epitope tag at the 3' end for the α1AT expression product. A cDNA encoding α1AT was linked in frame to a segment encoding a BAG domain, which was linked in turn to a segment encoding a V5 epitope tag for a BAG domain fusion protein (α1AT-BAG) expression product. A cDNA encoding α1AT was linked in frame to a segment encoding a J domain, which was linked in turn to a segment encoding a V5 epitope tag for a J domain fusion protein (α1AT-J) expression product of the invention. FIG. 4B shows x-ray film images of chemiluminescent signals of a dot blot analysis indicating relative levels of expression of secreted α1AT protein or secreted fusion protein counterparts secreted into culture media. It can be seen that employing a J domain as a fusion partner for the α1AT protein of interest (α1AT-J) resulted in significantly greater expression of the secreted protein (α1AT-J) compared to the α1AT protein alone or BAG domain fusion counterpart (α1AT-BAG). Mock cultures contained cells transfected with expression vector lacking a structural gene for expressing any protein. FIG. 4C provides the results of a densitometry analysis of the chemiluminescent signals in FIG. 4B using the NIH ImageJ image processing program. The bar graphs in FIG. 4C clearly show the significantly higher level of expression of secreted α1AT-J fusion protein (bar graph 4) compared to either the (unfused) α1AT (bar graph 2) or the BAG domain-α1AT fusion protein (bar graph 3).

FIGS. 5A-5C show results of an experiment described in Example 2 that demonstrate improvement in the level of expression of a secreted truncated form of a TNF-α receptor1 protein (TNFR1TF) in a modified arrangement in which TNFR1TF is linked to a J domain fusion partner in comparison to the protein alone (TNFR1TF). FIG. 5A depicts diagrams of the structural gene constructs for insertion into an expression vector plasmid used to transfect host cells. A cDNA encoding TNFR1TF was augmented with a segment encoding a V5 epitope tag at the 3' end for the TNFR1TF expression product. A cDNA encoding TNFR1TF was linked in frame to a segment encoding a J domain, which was linked in turn to a segment encoding a V5 epitope tag to provide a J domain fusion protein expression product of the invention. FIG. 5B shows x-ray film images of chemiluminescent signals of dot blots indicating relative levels of TNFR1TF and TNFR1TF-J domain fusion protein secreted into culture media. It can be seen that employing a J domain as a fusion partner for the TNFR1TF protein of interest (TNFR1TF-J) resulted in significantly greater expression of the secreted protein than for the (unfused) TNFR1TF protein. FIG. 5C provides the results of a densitometry analysis of the chemiluminescent signals in the dot blots of FIG. 5B using the NIH ImageJ image processing program. The bar graphs in FIG. 5C clearly show the significantly higher level of expression of secreted TNFR1TF-J domain fusion protein (bar graph 3) compared to TNFR1TF (bar graph 2). Mock cultures contained cells transfected with expression vector lacking a structural gene for expressing any protein.

FIG. 6A depicts diagrams of structural gene constructs used in this example. For the Fc fusion proteins, a cDNA encoding each protein of interest (TNFR1TF, IL13Rα2TF, or α1AT) was augmented with a segment encoding a V5 epitope tag at the 3' end, which was linked in turn to a segment ("Fc") encoding constant domains of an immunoglobulin Fc region. For J domain fusions, a cDNA encoding a J domain was linked in frame between the cDNA encoding each protein of interest and the segment encoding a V5 epitope tag. See, FIG. 6A. FIGS. 6B-1-6B-3 show dot blot analysis for secreted proteins in media from cultures of transfected cells. Each of the Fc fusion proteins (TNFR1-V5-Fc, IL13Rα2TF-Fc, and α1AT-Fc) were expressed in culture media as shown in the dot blots in the middle lane of each panel in FIGS. 6B-1-6B-3. This level of expression of the Fc fusion proteins was greater than that for each of the proteins of interest alone (i.e., without fusion to an Fc domain; data not shown). Significantly higher levels of expression were obtained in each case when a J domain was linked to the protein of interest segment within the Fc fusion proteins as shown in the dot blots in the right lane of each panel in FIGS. 6B-1-6B-3. The results of a densitometry analysis of the chemiluminescent signals of the dot blots in FIGS. 6B-1-6B-3 are shown in the corresponding panels of FIGS. 6C-1-6C-3, where the significantly higher level of expression of the J domain fusion proteins is clearly evident by comparing bar graph 2 (protein of interest-Fc fusion proteins) with bar graph 3 (protein of interest-J domain-Fc fusion proteins) in each of the panels of FIGS. 6C-1-6C-3. Mock cultures contained cells transfected with expression vector lacking a structural gene for expressing any protein.

FIG. 7A depicts diagrams of the constructs used in this experiment. A cDNA encoding p53 was augmented at its 5' end with a segment encoding a V5 epitope tag for the p53 expression product. A cDNA encoding p53 was linked in frame at its 5' end to a segment encoding a J domain of an SV40 J protein, which was in turn linked at its 5' end to a segment encoding a V5 epitope tag for a J domain fusion protein (J-p53) expression product of the invention. FIG. 7B shows x-ray film images of chemiluminescent signals of a Western blot of cell lysates indicating relative levels of expression in cells of the tagged p53 protein and the J domain fusion protein counterpart (J-p53). It can be seen that employing a J domain as a fusion partner for the p53 protein of interest (J-p53) resulted in a significantly greater level of expression in transfected cells compared to the level of expression in transfected cells of the p53 protein without a J domain (p53). Mock cultures contained cells transfected with expression vector lacking a structural gene for expressing any protein.

FIG. 8A depicts diagrams of constructs for insertion into an expression vector plasmid used to transfect host cells. A cDNA encoding each protein of interest, i.e., the wild-type CFTR protein (CFTR WT) or the CFTR Δ508F mutant protein (Δ508F), was augmented at the 5' end with a segment encoding a V5 epitope tag. For BAG domain fusions, a cDNA encoding a BAG domain was linked in frame between the cDNA encoding each protein of interest and the 5' segment encoding a V5 epitope tag. For J domain fusion protein expression products of the invention, a cDNA encoding an SV40 J domain was linked in frame between the cDNA encoding each protein of interest and a 5' segment encoding a V5 epitope tag for the J domain. See, FIG. 8A. FIG. 8B shows x-ray film images of chemiluminescent signals of a Western blot analysis of cell lysates indicating relative levels of expression in cells of the tagged proteins of interest (CFTR WT and CFTR Δ508F), BAG domain fusion proteins (BAG-CFTR WT and BAG-CFTR Δ508F), and J domain fusion proteins (J-CFTR WT and J-CFTR Δ508F). It can be seen that employing a J domain as a fusion partner for both CFTR WT and CFTR Δ508F proteins resulted in a significantly greater level of expression in transfected cells as compared to the levels of expression of (unfused) CFTR WT and mutant CFTR Δ508F proteins or of the BAG domain fusion counterparts. All transfectants were co-transfected with a reporter plasmid expressing green fluorescent protein (GFP) to show successful transfection and operability of the transfectants (lower panel of FIG. 8B).

FIG. 11A depicts a DNA construct encoding an Fc fusion protein (target protein) comprising a cDNA encoding a protein of interest augmented at its 3' end with a segment encoding a V5 epitope tag, which in turn was linked to a segment encoding the constant domains of an immunoglobulin Fc domain. For Example 5 below, the Fc fusion protein target comprised a truncated form of the IL13Rα2 receptor protein (IL13Rα2TF), which was linked to a V5 epitope tag, which in turn was linked to an Fc domain to yield the desired IL13Rα2TF-Fc fusion protein. FIG. 11B depicts a DNA construct encoding a fusion protein of the invention in which a protein expression enhancing polypeptide (PEEP) domain (such as a J domain of a J protein) is linked to a target protein binding domain (such as Protein A, which is known to bind Fc domains). The construct was further augmented at the 3' end with a coding segment for a Flag epitope tag for easy identification and isolation with a standard anti-Flag antibody.

FIG. 12A shows x-ray film images of chemiluminescent signals of a Western blot analysis of media from cultures of transfected cells expressing the IL13Rα2TF-Fc fusion protein (target protein) when expressed alone (lane 2, none), when co-expressed with Protein A alone (lane 3, Protein A Only), when co-expressed with an Erdj3 J domain-Protein A fusion protein (lane 4, J-Protein A), and when co-expressed with an Erdj5 J domain-Protein A fusion protein (lane 5, J2-Protein A), as described in Example 5. Mock cultures contained cells transfected with expression vector lacking a structural gene for expressing any protein (lane 1 from the left). It can be seen that co-expression of the IL13Rα2TF-Fc fusion target protein and either J domain-Protein A fusion protein (lanes 4 and 5 from the left) resulted in a significantly greater level of expression of the IL13Rα2TF-Fc fusion target protein secreted into culture medium as compared to the level of expression in transfectant cells expressing the IL13Rα2TF-Fc fusion target protein alone (lane 2 from the left) or co-expressing the IL13Rα2TF-Fc fusion target protein with unfused Protein A (lane 3 from the left).

FIG. 12B shows results of a densitometry analysis of the chemiluminescent signals in FIG. 12A using the NIH ImageJ image processing program. Bar graphs 1-5 of FIG. 12B correspond to signals in lanes 1-5 in FIG. 12A. The bar graphs in FIG. 12B clearly show that co-expression of the IL13Rα2TF-Fc target protein with either J domain-Protein A fusion protein (bar graphs 4 and 5) significantly enhanced the level of expression of secreted IL13Rα2TF-Fc as compared to expression of IL13Rα2TF-Fc alone (bar graph 2) or co-expression of IL13Rα2TF-Fc with (unfused) Protein A alone (bar graph 3).

FIG. 12C shows x-ray film images of chemiluminescent signals of a Western blot analysis of media from cultures of transfected cells expressing the IL13Rα2TF (no Fc domain) protein alone (lane 1, none), when co-expressed with an Erdj3 J domain-Protein A fusion protein (lane 2, J-Protein A), and when co-expressed with Protein A alone (lane 3, Protein A Only), as described in Example 5. The results show that little if any expression of secreted IL13Rα2TF protein was observed, as expected if the enhanced level of the secreted IL13Rα2TF-Fc fusion target protein in FIGS. 12A and 12B was dependent on the specificity of the target protein binding domain of the J domain-Protein A fusion protein for the Fc domain of IL13Rα2TF-Fc target protein. FIG. 12D provides the results of a densitometry analysis of the chemiluminescent signals in FIG. 12C using the NIH ImageJ image processing program: FIGS. 12C and 12D thus show a control experimental result in that the IL13Rα2TF protein was not recognized by the J domain-Protein A fusion (the Fc ligand for the target binding domain (Protein A) being absent), and thus the enhancement in the level of expression that could be provided by the J domain (a protein expression enhancing polypeptide domain) was not targeted to the IL13Rα2TF, as the results indicate.

FIGS. 13A-1-13C-2 provide results of a series of experiments that demonstrate significant enhancement of the level of expression of three different Fc fusion target proteins when co-expressed with a corresponding fusion protein of the invention as described in Example 6 below. FIG. 13A-1 shows x-ray film images of chemiluminescent signals of a Western blot assay for expression of an IL13Rα2TF-Fc fusion protein (target protein) secreted into the media of cultures of transfected cells expressing the IL13Rα2TF-Fc fusion protein alone (lane 1 from the left) and of transfected cells co-expressing the IL13Rα2TF-Fc fusion protein and the J domain-Protein A fusion protein (lane 2 from the left) as described in Example 6.1 below and similar to the experiment described in Example 5. FIG. 13A-2 provides the results of a densitometry analysis of the chemiluminescent signals in FIG. 13A-1 using the NIH ImageJ image processing program. Bar graphs 1 and 2 (from left to right) in FIG. 13A-2 correspond to the signals in lanes 1 and 2

Figure 6A:
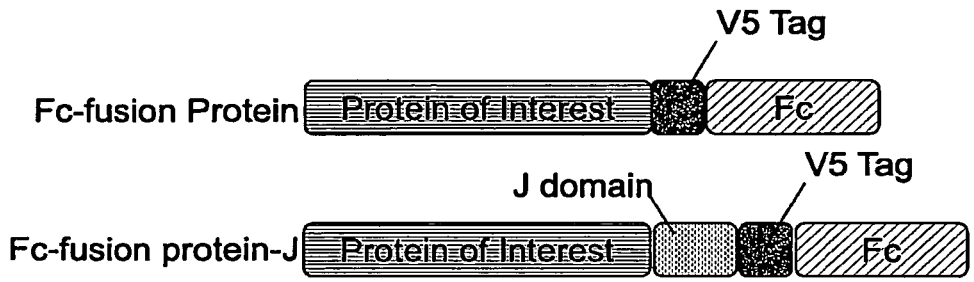
Figures 1, 6B:
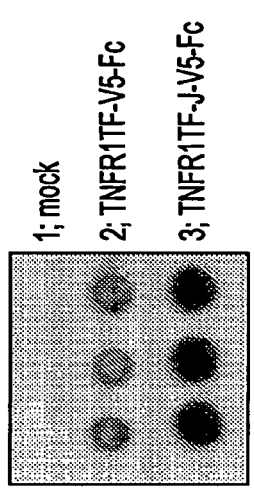
Figure 12A:
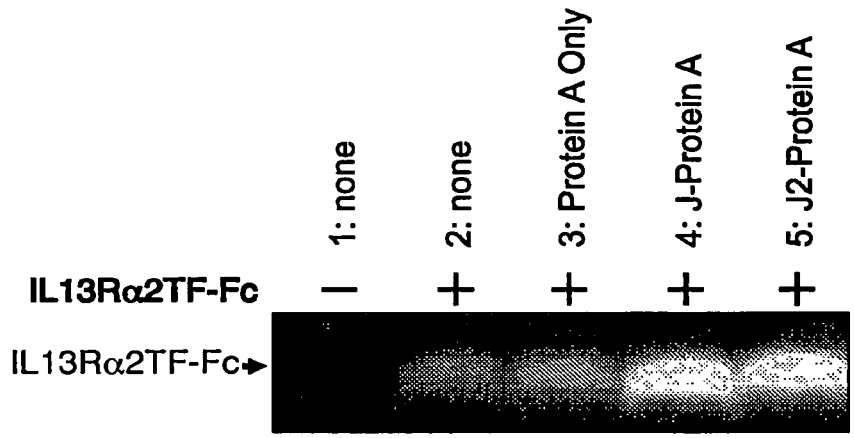
FIGS. 12A-12D show results of an experiment described in Example 5 that demonstrate significant enhancement in the expression of an IL13Rα2TF-Fc fusion protein (target protein) in an unmodified arrangement in which the target protein is co-expressed with a J domain-Protein A fusion protein but not when the target protein is co-expressed with Protein A alone.
Figure 12B:
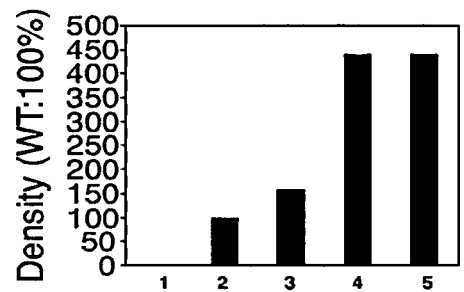
Figures 12C, 12D:
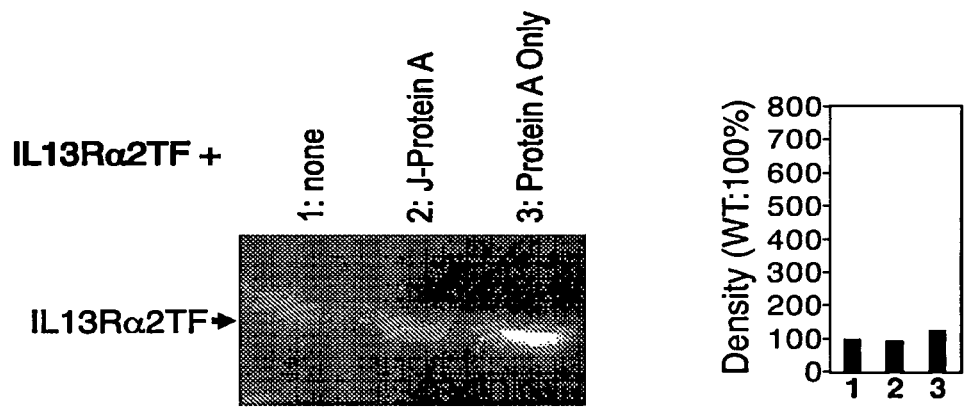

(from left to right) in FIG. 13A-1. The results show that co-expression of the J domain-Protein A fusion protein of the invention significantly elevated (8-fold) the level of expression of the IL13Rα2TF-Fc target protein secreted into the culture medium as compared to the level of expression of the target protein in the absence of the J domain-Protein A fusion protein. Results are consistent with those described in Example 5 and FIG. 12.

Figures 2, 6B:
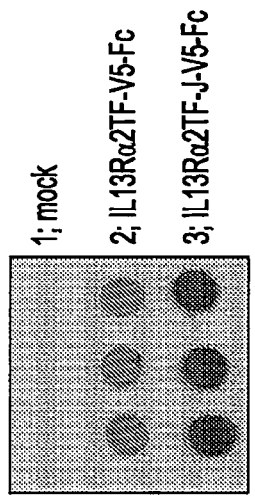
Figures 3, 6B:
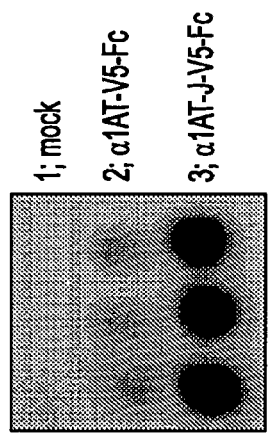

FIG. 13B-1 shows x-ray film images of chemiluminescent signals of a Western blot assay for expression of a TNFR1TF-Fc fusion protein (target protein) secreted into the media of cultures of transfected cells expressing the TNFR1TF-Fc fusion target protein alone (lane 1 from the left) and of transfected cells co-expressing the TNFR1TF-Fc fusion protein and the J domain-Protein A fusion (lane 2 from the left) as described in Example 6.2 below. FIG. 13B-2 provides the results of a densitometry analysis of the chemiluminescent signals in FIG. 13B-1 using the NIH ImageJ image processing program. Bar graphs 1 and 2 (from left to right) in FIG. 13B-2 correspond to the signals in lanes 1 and 2 (from left to right) in FIG. 13B-1. The results show that co-expression of J domain-Protein A fusion protein significantly elevated (6-fold) the level of expression of the TNFR1TF-Fc target protein secreted into the culture medium as compared to the level of expression of the target protein in the absence of the J domain-Protein A fusion protein.

FIG. 13C-1 shows x-ray film images of chemiluminescent signals of a Western blot assay for expression of an α1 anti-trypsin (α1AT)-Fc fusion protein (target protein) secreted into the media of cultures of transfected cells expressing the α1AT-Fc fusion target protein alone (lane 1 from the left) and of transfected cells co-expressing the α1AT-Fc fusion target protein and the J domain-Protein A fusion protein (lane 2 from the left) as described in Example 6.3. FIG. 13C-2 provides the results of a densitometry analysis of the chemiluminescent signals in FIG. 13C-1 using the NIH ImageJ image processing program. Bar graphs 1 and 2 (from left to right) in FIG. 13C-2 correspond to the signals in lanes 1 and 2 (from left to right) in FIG. 13C-1. The results show that co-expression of J domain-Protein A fusion protein significantly elevated (3-fold) the level of expression of the OAT-Fc fusion target protein secreted into the culture medium as compared to the level of expression of the target protein in the absence of the J domain-Protein A fusion protein.

Figure 14A:
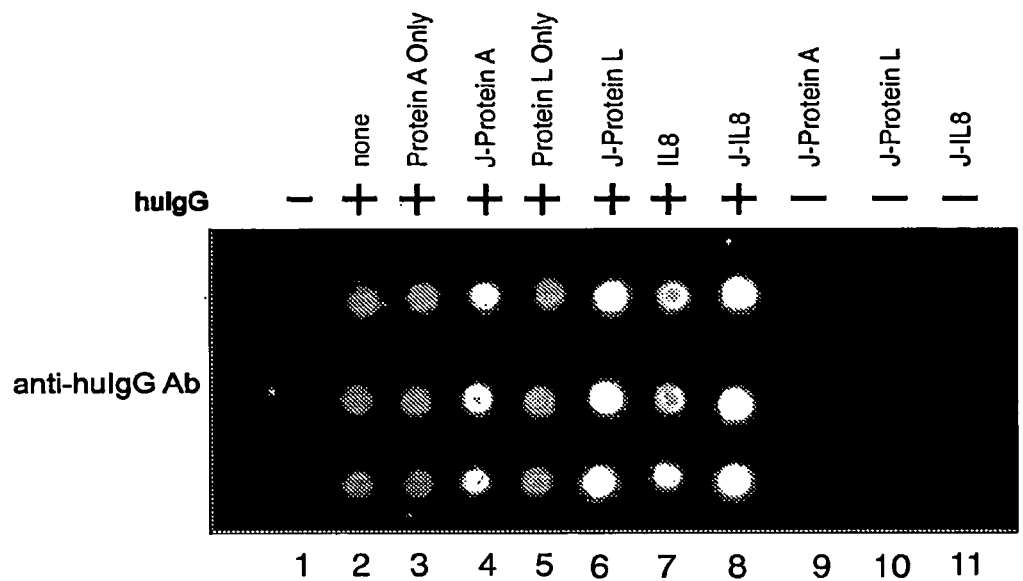
Figure 14B:
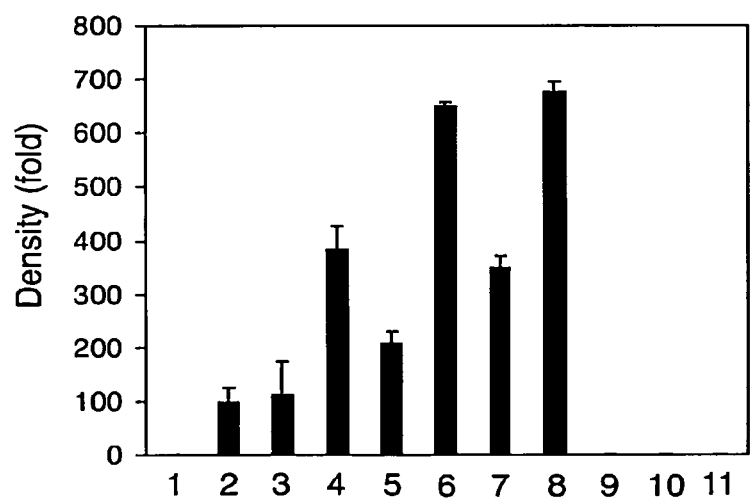

FIGS. 14A and 14B provide results from a series of experiments that test the enhancement in the level of expression of a secreted humanized anti-IL8 IgG1 antibody in an unmodified arrangement described in Example 7 below. FIG. 14A shows x-ray film images of chemiluminescent signals of a dot blot assay for expression of the anti-IL8 antibody (target protein) secreted into the media of cultures of transfected cells expressing the anti-IL8 antibody alone (lane 2), co-expressing anti-IL8 antibody and Protein A (lane 3, Protein A Only), co-expressing anti-IL8 antibody and an Erdj3 J domain-Protein A fusion protein of the invention (lane 4, J-Protein A), co-expressing anti-IL8 antibody and Protein L (lane 5, Protein L Only), co-expressing anti-IL8 antibody and an Erdj3 J domain-Protein L fusion protein of the invention (lane 6, J-Protein L), co-expressing anti-IL8 antibody and its IL8 ligand (lane 7, IL8), co-expressing an Erdj3 J domain-IL8 ligand fusion protein of the invention (lane 8, J-IL8), expressing the Erdj3 J-Protein A fusion protein alone (lane 9, J-Protein A), expressing the Erdj3 J domain-Protein L fusion protein alone (lane 10, J-Protein L), and expressing the Erdj3 J domain-IL8 ligand fusion protein (lane 11, J-IL8). Mock cultures contained cells transfected with expression vector lacking a structural gene for expressing any protein (no anti-IL8 antibody, lane 1). Expression of the anti-IL8 antibody in culture media was analyzed in the dot blot assay using an anti-human IgG antibody ("anti-huIgG Ab") (catalog no. AP112P, Millipore). It can be seen that co-expression in transfected cells of the anti-IL8 antibody with a J domain-Protein A fusion protein (lane 4), with a J domain-Protein L fusion protein (lane 6), or with a J domain-IL8 fusion protein (lane 8) significantly enhanced the level of expression of anti-IL8 antibody secreted into the culture medium as compared to the level of the antibody expressed in transfected cells expressing the anti-IL8 antibody alone (lane 2), co-expressing with Protein A alone (lane 3, Protein A Only), co-expressing Protein L alone (lane 5, Protein L Only), or co-expressing IL8 ligand protein alone (lane 7). No signal was detected in culture media of transfected cells expressing the J domain-Protein A fusion protein alone (lane 9, J-Protein A), of transfected cells expressing the J domain-Protein L fusion protein alone (lane 10, J-Protein L), or of transfected cells expressing the J domain-IL8 fusion protein alone (lane 10, J-IL8), indicating that all three fusion proteins specifically targeted and enhanced expression of the co-expressed anti-IL8 antibody target protein.

FIG. 14B shows the results of a densitometry analysis of the chemiluminescent signals in each of the lanes in FIG. 14A using the NIH ImageJ image processing program. The bar graphs of FIG. 14B are numbered to correspond to the lane numbers of FIG. 14A. The results of this series of experiments clearly show that co-expression of the targeted anti-IL8 antibody with a fusion protein of the invention comprising a protein expression enhancing polypeptide (here, an Erdj3 J domain) linked to a target protein binding domain (here, Protein A, Protein L, or IL8) significantly enhanced the expression of secreted anti-IL8 antibody as compared to co-expression of the antibody with the unfused target protein binding domain protein alone (Protein G only, Protein L only, or IL8 only).

Figure 15A:
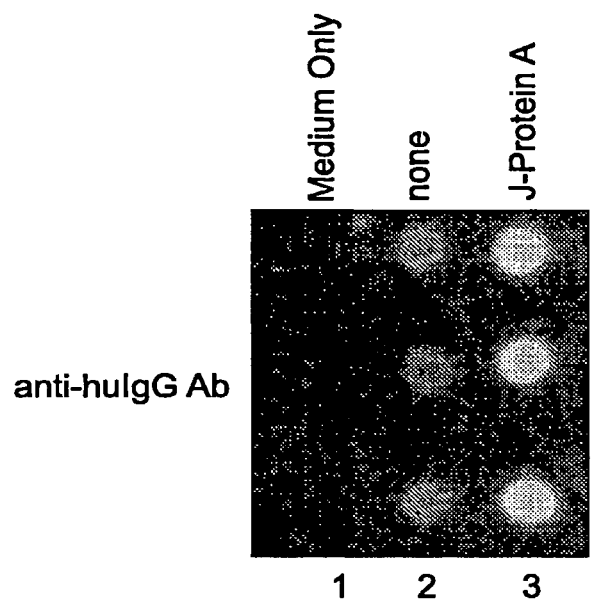
Figure 15B:
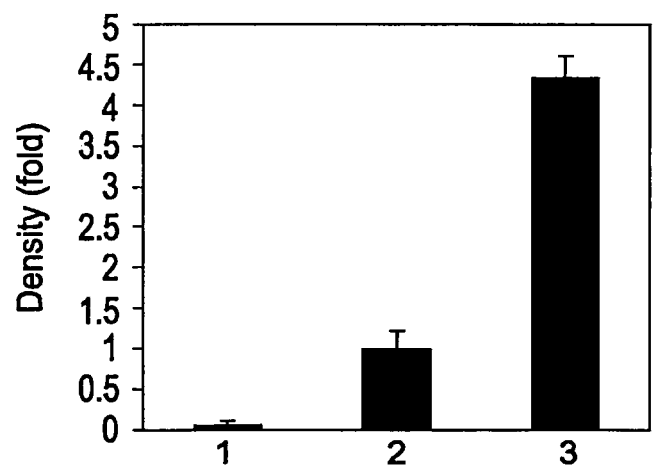

FIGS. 15A and 15B provide results that demonstrate that a fusion protein according to the invention can be used to enhance the level of expression of a target protein that is already stably produced in an established commercially relevant cell line as described in Example 8 below. FIG. 15A shows x-ray film images of chemiluminescent signals of a dot blot assay for expression of the anti-IL8 antibody (target protein) secreted into the media of cultures of cells of a CHO-DP12 cell line (accession no. CRL-124444, American Type Culture Collection, Manassas, Va.) expressing the anti-IL8 antibody alone (lane 2) and in transfected cells co-expressing anti-IL8 antibody and an Erdj3 J domain-Protein A fusion protein (lane 3, J-Protein A). Expression of the anti-IL8 antibody in culture media was analyzed in the dot blot assay using an anti-human IgG antibody ("anti-huIgG Ab"). It can be seen that co-expression of the anti-body with the J domain-Protein A fusion protein significantly enhanced the level of expression of the antibody secreted into the culture medium (lane 3) as compared to the level of the antibody expressed in the absence of the J domain-Protein A fusion protein (lane 2, none). Lane 1 is control (Medium Only). FIG. 15B shows the results of a densitometry analysis of the chemiluminescent signals in the dot blots in the lanes in FIG. 15A using the ImageJ image processing program is shown in the respective bar graphs in FIG. 15B. The results indicate that co-expression of the antibody with the J domain-Protein A fusion protein (bar graph 3) significantly enhanced expression of the secreted antibody, providing an approximately four- to five-fold greater enhancement in the level of expression, as compared to that obtained when the antibody was expressed in the absence of the J domain-Protein A fusion protein (bar graph 2). The results indicate that a fusion protein of the invention can be employed to significantly enhance the level of production of a target protein that is already stably expressed in an established production cell line.

Figure 16A:
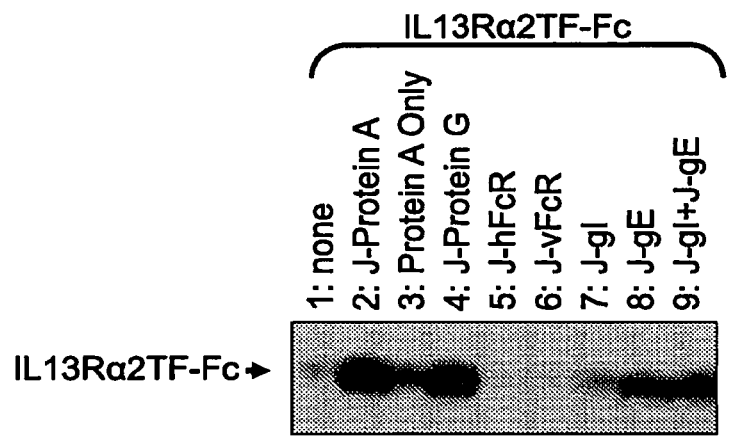
Figure 16B:
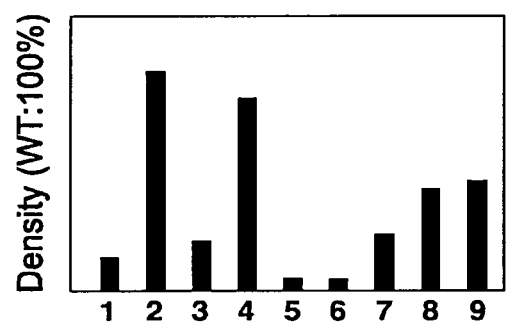

FIGS. 16A and 16B provide results from a series of experiments that tested various fusion proteins comprising a J domain (as a protein expression enhancing polypeptide domain) of a J protein linked to any of a variety of proteins, as described in Example 9.1 below. The various J domain fusion proteins and other proteins were then tested and compared for their ability to enhance levels of expression of the IL13Rα2TF-Fc fusion protein (target protein) secreted into media of cultures of transfected HEK293 cells. FIG. 16A shows x-ray film images of chemiluminescent signals of a Western blot analysis of samples of media from cultures of transfected cells expressing the IL13Rα2TF-Fc fusion protein (target protein) alone (lane 1), co-expressing IL13Rα2TF-Fc with a J domain-Protein A fusion protein (lane 2), co-expressing IL13Rα2TF-Fc with Protein A alone (lane 3, Protein A Only), co-expressing IL13Rα2TF-Fc with a J domain-Protein G fusion protein (lane 4), co-expressing IL13Rα2TF-Fc with a J domain-hFcR fusion protein (lane 5, J-hFcR), co-expressing IL13Rα2TF-Fc with a J domain-vFcR fusion protein (lane 6, J-vFcR), co-expressing IL13Rα2TF-Fc with a J domain-gI fusion protein (lane 7, J-gI), co-expressing IL13Rα2TF-Fc with a J domain-gE fusion protein (lane 8, J-gE), and co-expressing IL13Rα2TF-Fc with both J domain-gI fusion protein and J domain-gE fusion protein (lane 9, J-gI+J-gE). The results of a densitometry analysis of the chemiluminescent signals in the Western blot in FIG. 16A using the NIH ImageJ image processing program are shown in the respective bar graphs in FIG. 16B. See, Example 9.1 for details.

FIGS. 17A-1 and 17B provide results from a series of experiments that tested various fusion proteins comprising a J domain (as a protein expression enhancing polypeptide domain) of a J protein linked to each of six Fc-binding peptides (FcBP1 through FcBP6) for use in enhancing the level of expression of proteins that possess an Fc domain as described in Example 9.2 below. The amino acid sequences of the Fc binding peptides are given in FIG. 17A-2 (SEQ ID NOS:240-245, respectively). FIG. 17A-1 shows x-ray film images of chemiluminescent signals of a Western blot assay of samples of media of cultures of transfected cells expressing the IL13Rα2TF-Fc fusion protein (target protein) alone (lanes 1 and 3), co-expressing IL13Rα2TF-Fc with a J domain-Protein A fusion protein (lane 2, J-Protein A), co-expressing IL13Rα2TF-Fc with a J domain-FcBP1 fusion protein (lane 4, J-FcBP1), co-expressing IL13Rα2TF-Fc with a J domain-FcBP2 fusion protein (lane 5, J-FcBP2), co-expressing IL13Rα2TF-Fc with a J domain-FcBP3 fusion protein (lane 6, J-FcBP3), co-expressing IL13Rα2TF-Fc with a J domain-FcBP4 fusion protein (lane 7, J-FcBP4), co-expressing IL13Rα2TF-Fc with a J domain-FcBP5 fusion protein (lane 8, J-FcBP5), co-expressing IL13Rα2TF-Fc with a J domain-FcBP6 fusion protein (lane 9, J-FcBP6), and co-expressing IL13Rα2TF-Fc with a J domain-Protein G fusion protein (lane 10, J-Protein G). As shown in FIG. 17A-1, co-expression of the IL13Rα2TF-Fc fusion protein with each of the six J domain-peptide fusion proteins in HEK293 transfectants significantly enhanced the level of expression of secreted IL13Rα2TF-Fc fusion protein (lanes 4-9) as compared to the level of expression of IL13Rα2TF-Fc fusion protein alone (lanes 1 and 3). The experiment also included for comparison the effect of co-expression of IL13Rα2TF-Fc fusion protein with a J domain-Protein A fusion protein (lane 2) or with a J domain-Protein G fusion protein (lane 10) on the expression of secreted IL13Rα2TF-Fc fusion protein. As shown in FIG. 17A-1, co-expression of IL13Rα2TF-Fc fusion protein with either J domain-Protein A fusion protein (lane 2) or the J domain-Protein G fusion protein (lane 10) significantly enhanced the level of expression of secreted the IL13Rα2TF-Fc fusion protein as also observed in Examples 5 (FIGS. 12A and 12B), 6.1 (FIGS. 13A-1 and 13A-2), and 9.1 (FIGS. 16A and 16B). The results of a densitometry analysis of the chemiluminescent signals in the Western blot in FIG. 17A-1 using the NIH ImageJ image processing program are shown in the respective bar graphs in FIG. 17B.

Figure 18:
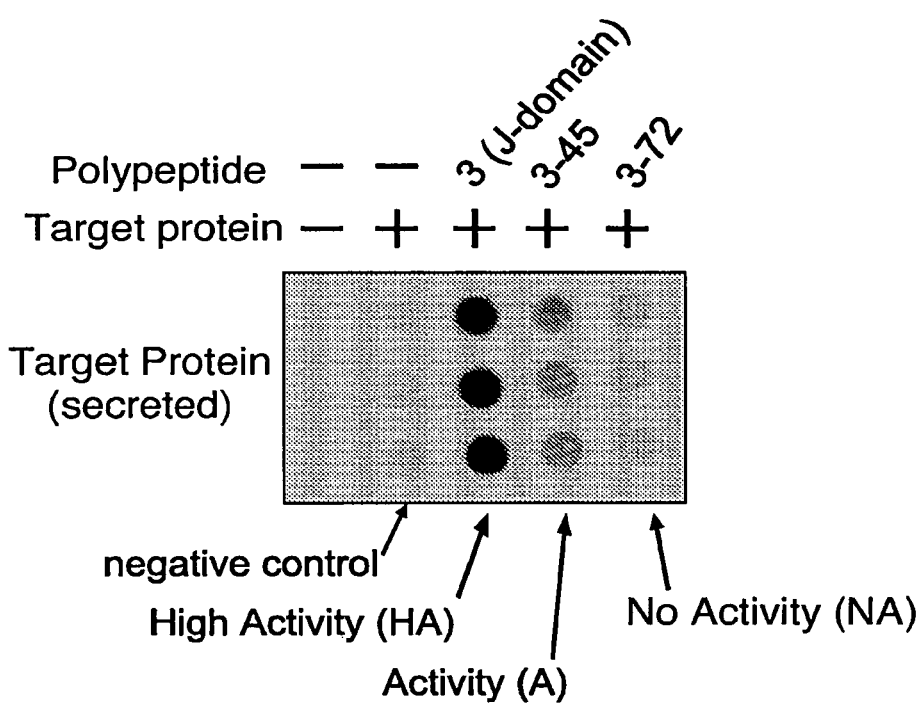

FIG. 18 shows x-ray film images of chemiluminescent signals of a dot blot assay showing examples of relative levels of target protein expression enhancing activity of three polypeptides used in an unmodified arrangement described in Example 10. The levels of expression indicated in the dot blot, i.e., High Activity (HA), Activity (A), and No Activity (NA), were determined for polypeptides designated "3 (J domain)", "3-45", and "3-72" (see Table 58, infra.). Each polypeptide was linked to Protein A to form a fusion protein that was co-expressed with a V5-tagged IL13Rα2-Fc target protein in transfected cells. The level of expression of the V5-tagged IL13Rα2-Fc target protein in culture media was determined in the dot blot using an anti-V5 antibody. The dot blot shows expression of the V5-tagged IL13Rα2-Fc target protein in the media of cultures of transfected cells expressing the target protein alone (lane 2 from left), of transfected cells co-expressing the target protein and the polypeptide 3-Protein A fusion protein (lane 3 from left), of transfected cells co-expressing the target protein and the polypeptide 3-45-Protein A fusion protein (lane 4 from left), and of transfected cells co-expressing the target protein and the polypeptide 3-72-Protein A fusion protein (lane 5 from left). The high activity (HA) of a polypeptide for enhancing expression of a target protein in an unmodified arrangement is represented by the level of expression shown in lane 3 (from the left) of the dot blot. Improved activity compared to negative control (A) of a polypeptide for enhancing expression of a target protein is represented by the level of expression shown in lane 4 (from the left) of the dot blot. No activity (NA) of a polypeptide for enhancing expression of a target protein is shown in lane 5 (from the left) of the dot blot. Lane 1 (from the left) of the dot blot shows no target protein was expressed in the medium of a mock culture of cells that did not express the target protein or any polypeptide-Fc fusion protein.

Figure 19:
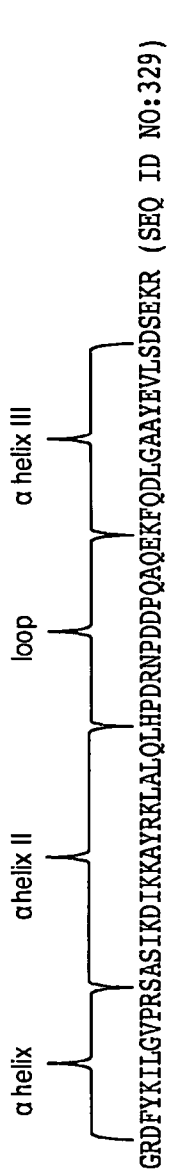

FIG. 19 shows an alignment of the amino acid sequence of the J domain of Erdj3 with the amino acid sequences of a series of polypeptides that were generated as N- and C-terminal deletion mutations of the full-length J domain as described in Example 11. The alpha helices and loop domains of the J domain are indicated by brackets. Also shown are a designation number, length (amino acid residues), protein expression enhancing activity (HA, NA), and sequence identification number for each of the polypeptides. (See, FIG. 18 and Example 10 for a description of high activity (HA), improved activity (A), and no activity (NA) for enhancing target protein expression.) As shown in the alignment, the J domain is designated polypeptide 3, is 61 amino acids in length, and has high activity (HA) for enhancing expression of a target protein in an unmodified arrangement.

Figure 20A:
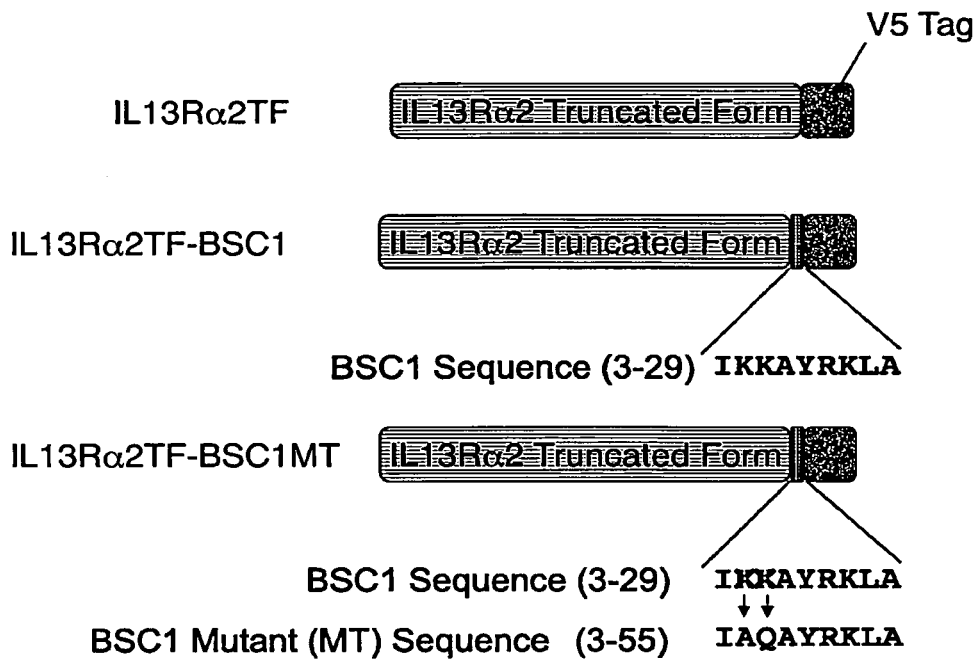
Figure 20B:
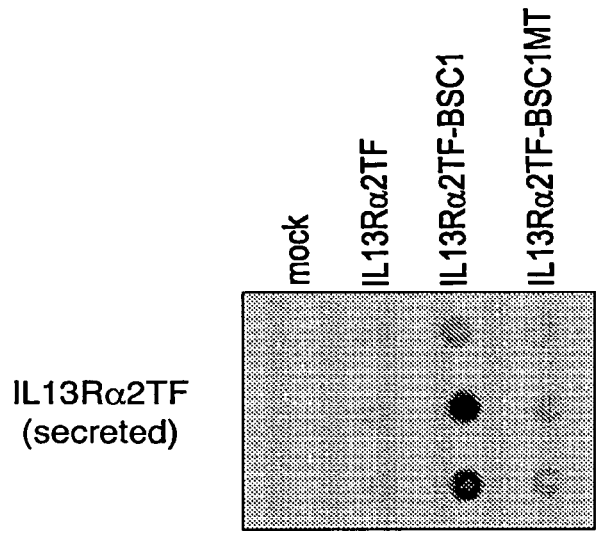

FIGS. 20A and 20B show results of a series of experiments described in Example 12 that compares the target protein expression enhancing activity of two polypeptides used in a modified arrangement. FIG. 20A shows diagrams of nucleic acid constructs for insertion into an expression vector used to transfect cells. The IL13Rα2TF construct encodes a fusion polypeptide comprising a truncated form of IL13Rα2 that contains the extracellular IL13 binding domain fused to a C-terminal V5 epitope tag. The IL13Rα2TF-BSC1 construct encodes a fusion polypeptide comprising the truncated form of IL13Rα2 fused to the BSC1 sequence (polypeptide 3-29, IKKAYRKLA, SEQ ID NO:48), which is fused to a C-terminal V5 epitope tag. The IL13Rα2TF-BSC1MT construct encodes the truncated from of IL13Rα2 fused to the BSC1MT sequence (polypeptide 3-55, IAQAYRKLA, SEQ ID NO:298), which is fused to a C-terminal V5 epitope tag. The amino acid sequence of polypeptide 3-55 differs from that of polypeptide 3-29 at two positions as shown at the bottom of FIG. 20A. Cells transfected with a vector containing the IL13Rα2TF construct were taken as the control (no fusion with a BSC1 or BSC1MT polypeptide).

FIG. 20B shows X-ray film images of chemiluminescent signals of a dot blot analysis of the media of cultures of transfected cells expressing the IL13Rα2TF, IL13Rα2TF-BSC1, and IL13Rα2TF-BSC1MT proteins using an anti-V5 antibody. Lane 2 (from the left) of FIG. 20B shows that only a very low level of IL13Rα2TF fusion protein was detected in medium of a culture of control cells. Lane 3 (from the left) in FIG. 20B shows that a significant level of the IL13Rα2TF-BSC1 fusion protein was expressed in the medium of a culture of cells transfected with a vector containing the IL13Rα2TF-BSC1 construct. Lane 4 (from the left) in FIG. 20B shows that only a very low level of the IL13Rα2TF-BSC1MT fusion protein was expressed in the medium of culture of cells transfected with a vector containing the IL13Rα2TF-BSC1MT construct. The results indicate that polypeptide 3-29 has "high activity" for enhancing expression of a target protein in a modified arrangement, whereas polypeptide 3-55 is considered to have "no activity" for enhancing expression of a target protein in a modified arrangement.

Figure 21:
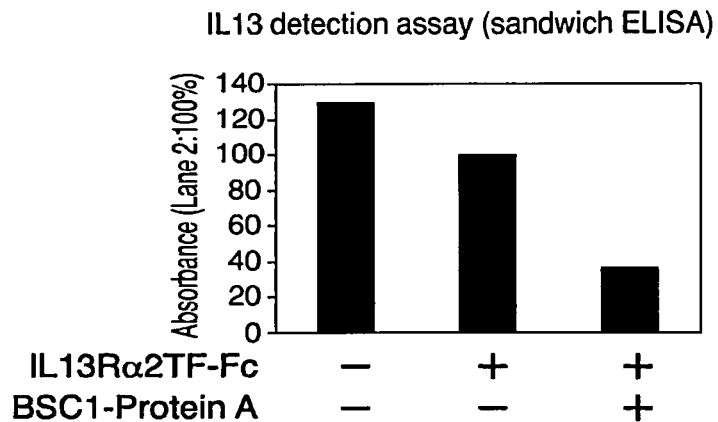

FIG. 21 is a bar graph showing IL13 binding activity of IL13Rα2TF-Fc target protein co-expressed in an unmodified arrangement with a BSC1-Protein A in HEK293 cells as described in Example 13. The BSC1-Protein A protein if a fusion protein comprising the polypeptide 3-29 (IKKAYRKLA, SEQ ID NO:48) linked to Protein A as shown in Example 13. The assay used for determining IL13 binding activity is a sandwich ELISA in which detection of human IL13 decreases when the IL13 is trapped by the IL13Rα2TF-Fc protein. The first bar graph (from the left) in FIG. 21 shows no IL13 binding activity was present in medium from a culture of control cells that did not express either IL13Rα2TF-Fc or the BSC1-Protein A fusion protein. Bar 2 (middle) in FIG. 21 shows that some low level of IL13 binding activity was detected in medium from a culture of cells expressing only the IL13Rα2TF-Fc protein. In contrast, as shown in Bar 3 (far right) in FIG. 21, a significant level of human IL13 binding activity was present in the medium of a culture of cells co-expressing IL13Rα2TF-Fc and the BSC1-Protein A fusion protein. The results shown that the IL13Rα2TF-Fc target protein expressed at enhanced levels in culture medium in an unmodified arrangement retains its IL13 binding activity.

Figure 22A:
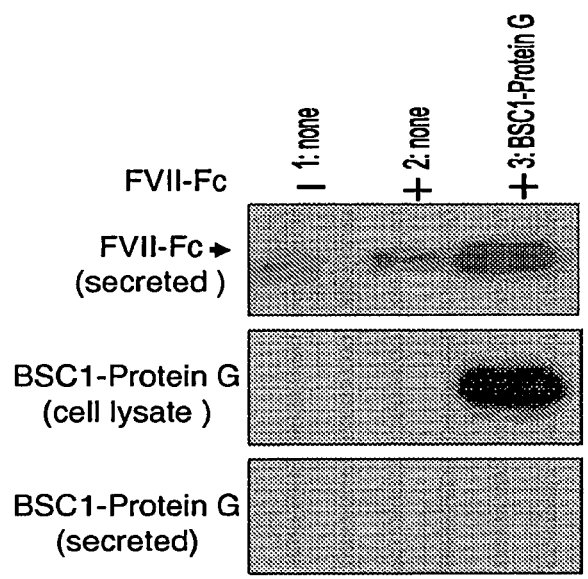
Figure 22B:
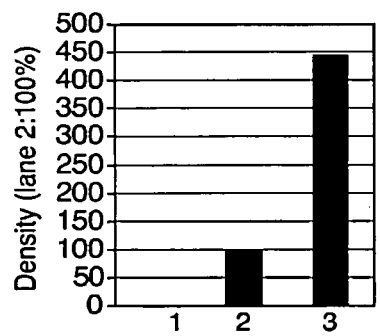

FIGS. 22A and 22B show results of an experiment that demonstrates significant enhancement in the level of expression of a Factor VII (FVII)-Fc fusion protein (target protein) secreted into culture medium when co-expressed in an unmodified arrangement with a BSC1-Protein G fusion protein comprising polypeptide 3-29 (IKKAYRKLA, SEQ ID NO:48) linked to Protein G as described in Example 14. FIG. 22A shows X-ray film images of chemiluminescent signals of a Western blot assay for expression of an FVII-Fc fusion protein (top panel) secreted into the media of cultures of transfected cells expressing the FVII-Fc fusion protein alone (lane 2) and of transfected cells co-expressing the FVII-Fc fusion protein and the BSC1-Protein G fusion protein (lane 3). Lane 1 shows non-expressing cell culture medium as a control. Anti-Flag antibody was used to detect BSC1-Protein G in cell lysate (middle panel) and secreted BSC1-Protein G (bottom panel), respectively. FIG. 22B provides the results of a densitometry analysis of the chemiluminescent signals in the top panel of FIG. 22A using the NIH ImageJ image processing program. Bar graphs 1, 2, and 3 in FIG. 22B correspond to the signals in lanes 1, 2, and 3 in the top panel of FIG. 22A. The results show that co-expression of the FVII-Fc target protein and the BSC1-Protein G fusion protein significantly elevated the level of expression of the FVII-Fc target protein secreted into the culture medium as compared to the level of expression of the target protein expressed in the absence of the BSC1-Protein G fusion protein. In addition, the BSC1-Protein G fusion protein was not secreted but remained in the cells. Compare expression of BSC1-Protein G fusion protein cell lysates (middle panel of FIG. 22A) with that in medium (bottom panel of FIG. 22A).

Figure 23A:
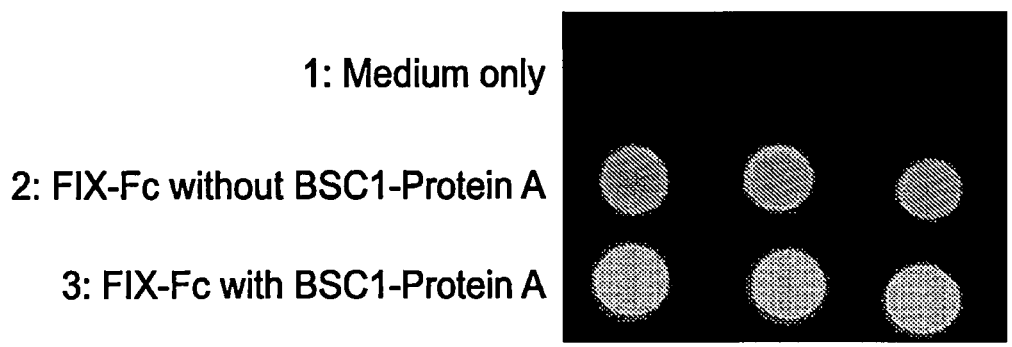
Figure 23B:
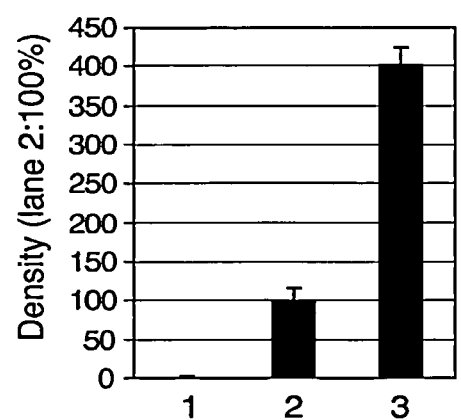

FIGS. 23A and 23B show results of an experiment to demonstrate improvement in the level of expression of a Factor IX (FIX)-Fc fusion protein (FIX-Fc) target protein in the presence of a BSC1-Protein A fusion protein comprising polypeptide 3-29 (IKKAYRKLA, SEQ ID NO:48) linked to Protein A as described in Example 15. FIG. 23A shows X-ray film images of chemiluminescent signals of a Western blot assay for expression of an FIX-Fc fusion protein secreted into the media of cultures of transfected cells expressing the FIX-Fc fusion protein alone (row 2) and of transfected cells co-expressing the FIX-Fc fusion protein and the BSC1-Protein A fusion protein (row 3). Row 1 shows non-expressing cell culture medium as a control. FIG. 23B provides the results of a densitometry analysis of the chemiluminescent signals in the top panel of FIG. 23A using the NIH ImageJ image processing program. Bar graphs 1, 2, and 3 in FIG. 23B correspond to the signals in rows 1, 2, and 3 in FIG. 23A. The results show that co-expression of the FIX-Fc target protein and the BSC1-Protein A fusion protein significantly elevated the level of expression of the FIX-Fc target protein secreted into the culture medium as compared to the level of expression of the target protein in the absence of the BSC1-Protein A fusion protein.

Figure 24:
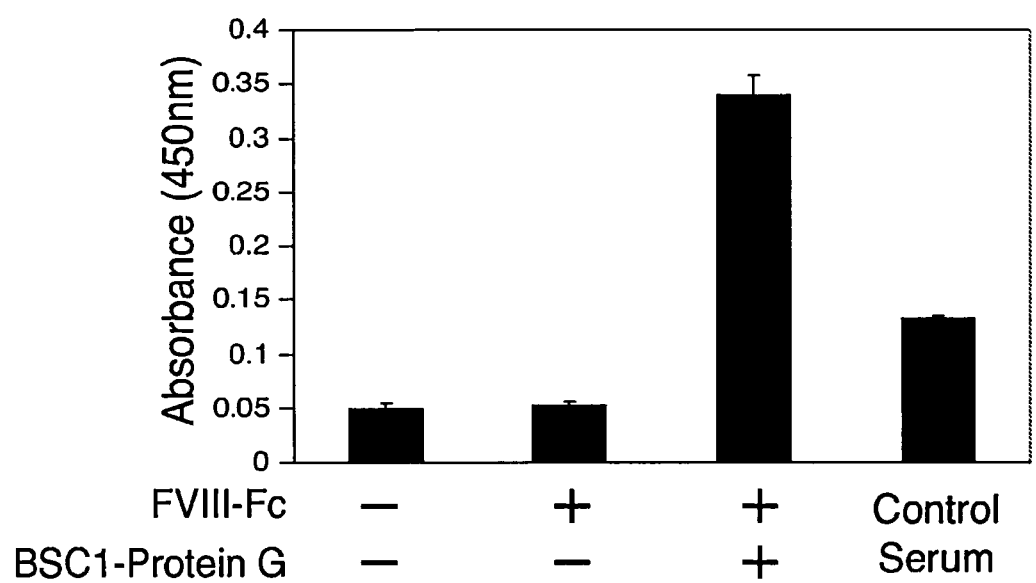

FIG. 24 provides results of a series of experiments that demonstrate significant enhancement of the level of expression of a Factor VIII (FVIII)-Fc fusion protein (FVIII-Fc) when co-expressed in an unmodified arrangement with a BSC1-Protein G fusion protein comprising polypeptide 3-29 (IKKAYRKLA, SEQ ID NO:48) linked to Protein G as described in Example 16. Media was harvested from cultures of transfected HEK293 cells co-expressing the FVIII-Fc fusion protein (target protein) with BSC1-Protein G fusion protein or cells expressing the FVIII-Fc fusion protein alone. The media was assayed for FVIII activity by ELISA (VisuLize™ FVIII Antigen Kit, Affinity Biologicals Inc.). Cell culture medium in which empty vector was transfected was used for a negative control (first bar from the left). Second bar from the left shows no FVIII was detected in medium from cells expressing the FVIII-Fc target protein alone. Third bar from the left shows that significant level of FVIII-Fc target protein was secreted into the medium of cells co-expressing the FVIII-Fc target protein and the BSC1-Protein G fusion protein. Human serum was used as a positive control (last bar from left). The results show that co-expression of the FVIII-Fc target protein and the BSC1-Protein G fusion protein significantly elevated the level of expression of the FVIII-Fc target protein secreted into the culture medium as compared to the level of expression of the target protein in the absence of the BSC1-Protein G fusion protein.

Figure 25A:
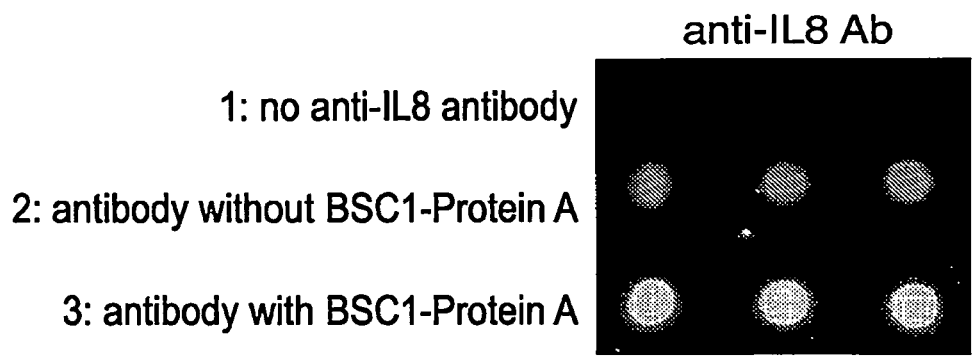
Figure 25B:
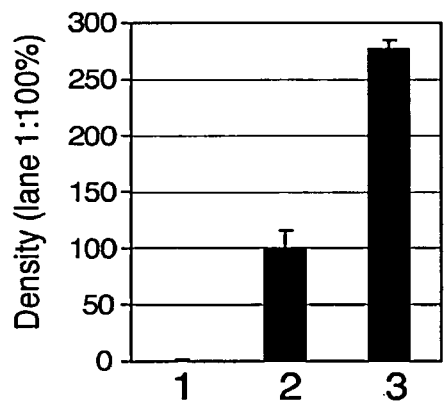
Figure 25C:
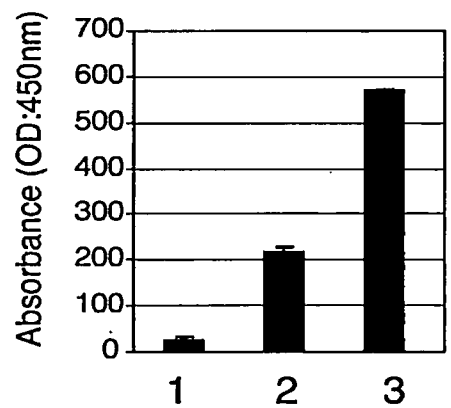

FIGS. 25A-25C show results of an experiment demonstrating improved levels of expression of an anti-IL8 antibody (target protein) secreted into the culture medium when co-expressed in an unmodified arrangement with a BSC1-Protein A comprising the 3-29 polypeptide (IKKAYRKLA, SEQ ID NO:48) linked to Protein A as described in Example 17. FIG. 25A shows X-ray film images of chemiluminescent signals of a dot blot assay for expression of the anti-IL8 antibody (target protein) secreted into the media of cultures of transfected cells expressing the anti-IL8 antibody alone (row 2) and of cells co-expressing the anti-IL8 antibody and a BSC1-Protein A fusion protein (row 3, BSC1-Protein A). Expression of the anti-IL8 antibody in culture media was analyzed in the dot blot assay using an anti-human IgG antibody. Mock cultures contained cells transfected with expression vector lacking a structural gene for expressing any protein (no anti-IL8 antibody, row 1). It can be seen that co-expression in transfected cells of the anti-IL8 antibody with a BSC1-Protein A fusion protein (row 3) significantly enhanced the level of expression of anti-IL8 antibody secreted into the culture medium as compared to the level of the antibody expressed in transfected cells expressing the anti-IL8 antibody alone (row 2).

FIG. 25B shows the results of a densitometry analysis of the chemiluminescent signals in each of the rows in FIG. 25A using the NIH ImageJ image processing program. The bars of FIG. 25B are numbered to correspond to the row numbers of FIG. 25A. The results of this series of experiments clearly show that co-expression of the targeted anti-IL8 antibody with a BSC1-Protein A fusion protein significantly enhanced the expression of secreted anti-IL8 antibody compared to the level of expression of the antibody in the absence of the BSC1-Protein A fusion protein.

FIG. 25C shows a bar graph of the results of an ELISA to detect IL8 binding activity by the expressed anti-IL8 antibody (target protein). A 96-well plate was coated with recombinant purified human IL8, and incubated with the anti-IL8 antibody (target protein) secreted into the media of cultures of transfected cells expressing the anti-IL8 antibody alone (bar graph 2) or co-expressing the anti-IL8 antibody with the BSC1-Protein A fusion protein (bar graph 3, BSC1-Protein A). Mock cultures contained cells transfected with expression vector lacking a structural gene for expressing any protein (no anti-IL8 antibody, bar graph 1). The results of this series of experiments clearly show that the anti-IL8 antibody expressed at enhanced levels and secreted into the culture medium retains its binding activity for human IL8, indicating proper conformation of the antibody.

FIGS. 26A-26C show results of a series of experiments demonstrating significant enhancement in the level of expression of the anti-VEGF antibody, bevacizumab, when co-expressed with a BSC1-Protein A fusion comprising the 3-29 polypeptide (IKKAYRKLA, SEQ ID NO:48) linked to Protein A as described in Example 18. FIG. 26A shows X-ray film images of chemiluminescent signals of a dot blot assay for expression of the anti-VEGF antibody secreted into the media of cultures of transfected cells expressing the anti-VEGF antibody alone (row 2) or co-expressing the anti-VEGF antibody and a BSC1-Protein A fusion protein (row 3). Mock cultures contained cells transfected with expression vector lacking a structural gene for expressing any protein (no anti-VEGF antibody, row 1). Expression of the anti-VEGF antibody in culture media was analyzed in the dot blot assay using an anti-human IgG antibody. It can be seen that co-expression in transfected cells of the anti-VEGF antibody with the BSC1-Protein A fusion protein (row 3) significantly enhanced the level of expression of anti-VEGF antibody secreted into the culture medium as compared to the level of the antibody expressed in transfected cells expressing the anti-VEGF antibody alone (row 2).

FIG. 26B shows the results of a densitometry analysis of the chemiluminescent signals in each of the rows in FIG. 26A using the NIH ImageJ image processing program. The bar graphs in FIG. 26B are numbered to correspond to the row numbers in FIG. 26A. The results clearly show that co-expression of the anti-VEGF antibody with a BSC1-Protein A fusion protein significantly enhanced the expression of secreted anti-VEGF antibody compared to the level of the antibody expressed alone.

FIG. 26C shows the results of an ELISA to detect VEGF binding by the anti-VEGF antibody expressed in the media of cultures of transfected cells. A 96-well plate was coated with recombinant purified human VEGF-A, and incubated with the anti-VEGF antibody (target protein) secreted into the media of cultures of transfected cells expressing the anti-VEGF antibody alone (bar graph 2) or co-expressing anti-VEGF antibody and the BSC1-Protein A fusion protein of the invention (bar graph 3). Mock cultures contained cells transfected with expression vector lacking a structural gene for expressing any protein (no anti-VEGF antibody, bar graph 1). The results of this series of experiments clearly show that the anti-VEGF antibody expressed at enhanced levels and secreted into the culture medium retains its binding activity for human VEGF-A, indicating proper conformation of the secreted antibody.

FIGS. 27A-27C show results from a series of experiments demonstrating significant enhancement in the level of expression the therapeutic anti-TNFα antibody, adalimumab (Humira®, AbbVie), when co-expressed with a BSC1-Protein A fusion comprising the 3-29 polypeptide (IKKAYRKLA, SEQ ID NO:48) linked to Protein A as described in Example 19. FIG. 27A shows X-ray film images of chemiluminescent signals of a dot blot assay for expression of the anti-TNFα antibody secreted into the media of cultures of transfected cells expressing the anti-TNFα antibody alone (row 2) or co-expressing the anti-TNFα antibody and the BSC1-Protein A fusion (row 3). Mock cultures contained cells transfected with expression vector lacking a structural gene for expressing any protein (row 1, no anti-TNFα antibody). Expression of the anti-TNFα antibody in culture media was analyzed in the dot blot assay using an anti-human IgG antibody. It can be seen that co-expression in transfected cells of the anti-TNFα antibody with a BSC1-Protein A fusion protein (bottom row) significantly enhanced the level of expression of anti-TNFα antibody secreted into the culture medium as compared to the level of the antibody expressed in transfected cells expressing the anti-TNFα antibody alone (middle).

FIG. 27B shows the results of a densitometry analysis of the chemiluminescent signals in each of the rows in FIG.

27A using the NIH ImageJ image processing program. The bar graphs of FIG. 27B are numbered to correspond to the row numbers of FIG. 27A. The results of this series of experiments clearly show that co-expression of the anti-TNFα antibody (target protein) with the BSC1-Protein A fusion protein significantly enhanced the expression of secreted anti-TNFα antibody.

FIG. 27C shows the results of an ELBA to detect TNFα binding activity by the anti-TNFα antibody expressed in the media of cultures of transfected cells. A 96-well plate was coated with recombinant purified human TNFα and incubated with the anti-TNFα antibody (target protein) secreted into the media of cultures of transfected cells expressing the anti-TNFα antibody alone (bar graph 2) or cells co-expressing the anti-TNFα antibody and the BSC1-Protein A fusion protein (bar graph 3). Mock cultures contained cells transfected with expression vector lacking a structural gene for expressing any protein (bar graph 1). The results of this series of experiments clearly show that the anti-TNFα antibody expressed at enhanced levels and secreted into the culture medium retains its binding activity for human TNFα, indicating proper conformation of the secreted antibody.

Figure 28A:
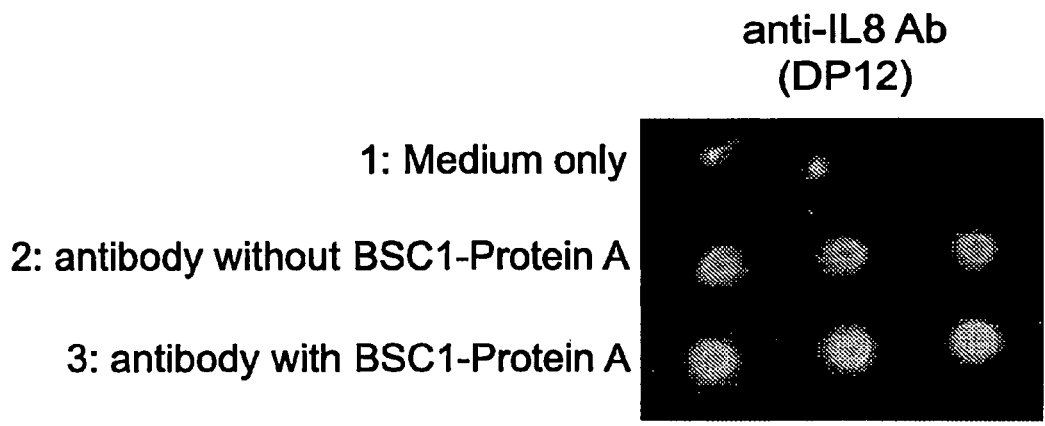
Figure 28B:
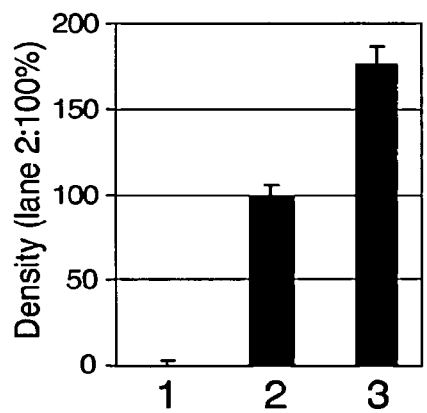
Figure 28C:
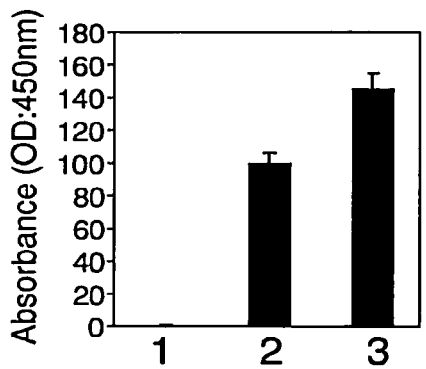

FIGS. 28A-28C provide results that demonstrate that the level of expression of a protein that is already stably produced in an established commercially relevant cell line can be enhanced when co-expressed with as BSC1-Protein A fusion comprising the 3-29 polypeptide (IKKAYRKLA, SEQ ID NO:48) linked to Protein A as described in Example 20. FIG. 28A shows X-ray film images of chemiluminescent signals of a dot blot assay for expression of the anti-IL8 antibody (target protein) secreted into the media of cultures of cells of a CHO-DP12 cell line (accession no. CRL-124444, American Type Culture Collection, Manassas, Va.) expressing the anti-IL8 antibody alone (row 2) and of transfected cells co-expressing the anti-IL8 antibody and the BSC1-Protein A fusion protein (row 3). It can be seen that co-expression of the antibody with the BSC1-Protein A fusion protein significantly enhanced the level of expression of the antibody secreted into the culture medium (row 3) as compared to the level of the antibody expressed in the absence of the BSC1-Protein A fusion protein (row 2). Row 1 is control (Medium Only). FIG. 28B shows the results of a densitometry analysis of the chemiluminescent signals in the dot blots in the rows in FIG. 28A using the NIH ImageJ image processing program are shown in the respective bar graphs in FIG. 28B. The results indicate that co-expression of the antibody with the BSC1-Protein A fusion molecule (bar graph 3) significantly enhanced expression of the secreted antibody, providing an approximately four to five-fold greater enhancement in the level of expression, as compared to that obtained when the antibody was expressed in the absence of the BSC1-Protein A fusion molecule (bar graph 2).

FIG. 28C shows the results of an ELISA to detect IL8 binding activity by the anti-IL8 antibody expressed in the media of cultures of transfected cells. A 96-well plate was coated with recombinant purified human IL8 and incubated with the anti-IL8 antibody (target protein) secreted into the media of cultures stably expressing the anti-IL8 antibody (bar graph 2) or co-expressing the antibody and the BSC1-Protein A fusion protein (bar graph 3). Culture medium was used as a negative control (bar graph 1, no IL8 binding activity). The results of this series of experiments clearly show that the anti-IL8 antibody secreted at enhanced levels into the culture medium retains its binding activity for human IL8, indicating proper conformation of the secreted antibody.

Figure 29:
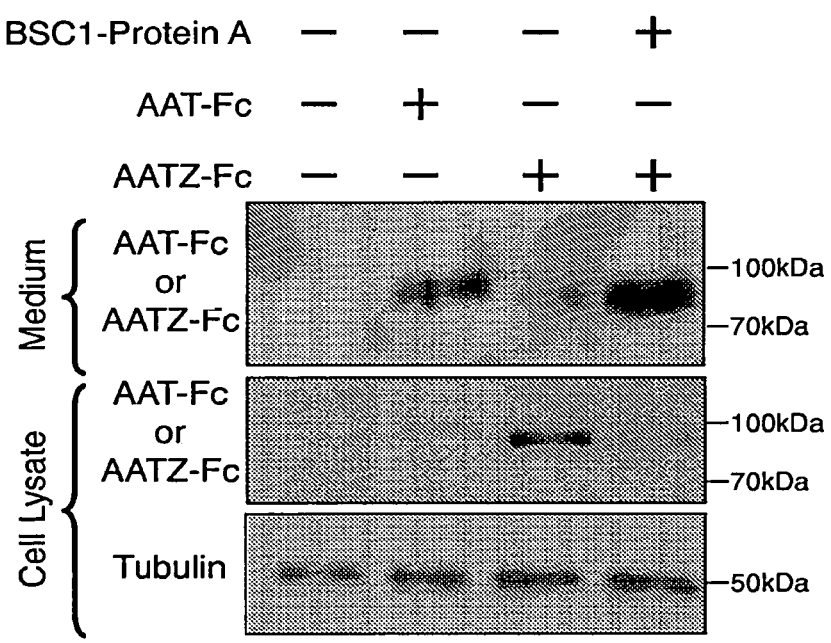

FIG. 29 provides results of an experiment described in Example 21 that indicate that protein expression enhancing polypeptides of the invention may be used to treat a disease caused by a mutant protein that does not fold into its proper conformation. FIG. 29 shows X-ray film images of chemiluminescent signals of a Western blot assay for expression of fusion proteins comprising wild type alpha1-antitrypsin (AAT) or the mutant alpha1-antitrypsin containing the Z mutation (AATZ, wherein Glu is replaced by Lys at codon 342) linked to the Fc domain from human IgG with or without co-expression of a BSC1-Protein A comprising the 3-29 polypeptide (IKKAYRKLA, SEQ ID NO:48) linked to Protein A. The top panel of FIG. 29 shows expression of Fc fusion proteins in the media of cultures of transfected cells expressing the AAT-Fc fusion protein alone (lane 2, from the left), of transfected cells expressing the AATZ-Fc fusion protein alone (lane 3, from the left), and of transfected cells co-expressing the AATZ-Fc fusion protein and the BSC1-Protein A fusion protein (lane 4, from the left). Lane 1 shows non-expressing cell culture medium as a control. Clearly, no AATZ-Fc fusion protein was secreted into media of cultures of cells expressing AATZ-Fc fusion protein alone (lane 3, from the left). As shown in the middle panel (Cell Lysate) of FIG. 29, for cells expressing the AATZ-Fc fusion protein alone, the AATZ-Fc fusion protein remained in the cells (lane 3, from the left), presumably lodged in the endoplasmic reticulum as is known for the unfused AATZ protein. In contrast, co-expression of the AATZ-Fc fusion protein and the BSC1-Protein A fusion protein significantly enhanced the level of AATZ-Fc fusion protein secreted into the culture medium as shown in lane 4 (from the left) in the top panel (medium) of FIG. 29. Moreover, as shown in lane 4 (from the left) in the middle panel (Cell Lysate) of FIG. 29, virtually no AATZ-Fc fusion protein was retained in the cells. The same membrane was blotted with anti-Tubulin antibody for a loading control (lower panel) in FIG. 29. The results show that co-expression of the BSC1-Protein A fusion protein significantly elevated the level the AATZ-Fc target protein secreted into the culture medium as compared to the level of expression of the target protein in the absence of the BSC1-Protein A fusion protein with virtually no AATZ-Fc retained in the cells.

DETAILED DESCRIPTION OF THE INVENTION

The invention provides a new family of polypeptides for enhancing the level of expression of a target protein of interest. The invention is based on the discovery that a target protein of interest can be expressed at a significantly higher level and in the proper cellular or extracellular location when co-expressed in either of two arrangements in a host cell with a protein expression enhancing polypeptide comprising:

an isolated J domain of a J protein,
a protein expression enhancing polypeptide fragment of a J domain, or
a protein expression enhancing J domain analog polypeptide comprising the formula:
X1-X2-X3-X4-X5-X6-X7-X8-X9 (SEQ ID NO:47),
wherein:
X1 is isoleucine (I), leucine (L), valine (V), alanine (A), or methionine (M);
X2 and X3 are each independently any amino acid with the proviso that at least one is lysine (K) or arginine (R);

X4 is any amino acid; or X4 may be absent when X1 through X3 are present and X5 through X9 are present;

X5 is tyrosine (Y), tryptophan (W), or phenylalanine (F);

X6 and X7 are each independently any amino acid with the proviso at least one is lysine (K) or arginine (R); or one of X6 and X7 may be absent when the other is K or R and when X1 through X5 are present and X8 and X9 are present; and X8 and X9 are any amino acid with the proviso that at least one is leucine (L) or alanine (A); or one of X8 and X9 may be absent when the other is L or A and when X1 through X7 are present.

A protein expression enhancing polypeptide of the invention may be employed in either of two arrangements for enhancing expression of a target protein of interest by a host cell. In a "modified" arrangement, a fusion protein comprises a protein expression enhancing polypeptide linked (fused) to a target protein of interest. The fusion protein is thus a "modified" target protein that acts as a functional surrogate for the target protein of interest and is expressed at an enhanced level by a host cell compared to the level of expression of the unmodified target protein alone. In an "unmodified" arrangement, a fusion protein comprises a protein expression enhancing polypeptide of the invention linked to a target protein binding domain that has an affinity for and binds the regular "unmodified" target protein of interest, wherein co-expression of the fusion protein and the target protein of interest in a host cell enhances the expression of the unmodified target protein as compared to the level of expression in the absence of the target protein-binding fusion protein according to the invention. In accordance with the invention, the enhanced level of protein expression in the modified and unmodified arrangements includes expression of the respective modified or unmodified target protein of interest in the proper location (cellular or extracellular) of the target protein of interest.

Accordingly, the invention provides a technical solution when there is a failure to express desired quantities of an endogenous or heterologous (recombinant) protein of interest in cells. The present invention also provides compositions and methods for treating individuals for a disease or disorder in which there is a failure to express sufficient levels of a functional protein in vivo, where inadequate expression of the protein or a functional version thereof leads to a pathological state. Examples of diseases in which an improperly folded protein species has been demonstrated or implicated include, but are not limited to, prion-associated disease (transmissible spongiform encephalopathy), Alzheimer's disease; Parkinson's disease; Huntington's disease; and cystic fibrosis (CF).

In order to more clearly describe the invention the following comments and definitions of terms apply.

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedent over any dictionary or extrinsic definition. Further, unless otherwise required by context, singular terms shall include pluralities and plural terms shall include the singular. In this application, the use of the term "or" means "and/or," unless stated otherwise. Furthermore, the use of the term "including", as well as other forms, such as "includes" and "included", is not limiting.

Generally, nomenclatures used in connection with and techniques of protein and nucleic acid chemistry (including methods of recombinant nucleic acid and polymerase chain reaction (PCR)), cell and tissue culture, molecular biology, genetics, microbiology, biochemistry, proteomics, pharmacology, and pharmaceutical science described herein are those well-known and commonly used in the art. The methods and techniques of the present invention are generally performed according to conventional methods in the art and as described in various general and more specific references available in the art. Assays and purification techniques are performed according to protocols available in the art, including in manuals of laboratory techniques and manufacturer's specifications, as commonly accomplished in the art or as described herein.

Unless indicated otherwise, when the terms "about" and "approximately" are used in combination with an amount, number, or value, then that combination describes the recited amount, number, or value alone as well as the amount, number, or value plus or minus 10% of that amount, number, or value. By way of example, the phrases "about 40%" and "approximately 40%" disclose both "40%" and "from 36% to 44%, inclusive".

The term "target protein of interest", "target protein", or "protein of interest" refers to any protein for which there is a need or desire to enhance the level of expression in its intended cellular (including intracellular and membrane-associated) or extracellular (secreted) location.

The term "isolated" as in an "isolated molecule" (e.g., "isolated protein" or "isolated nucleic acid") is a molecule that by virtue of its origin or source of derivation: is not associated with naturally associated components that accompany it in its native state; is substantially free of other kinds of molecules from the same species; is expressed by a cell from a different species; or does not occur in nature. Thus, a protein or nucleic acid molecule that is chemically synthesized or synthesized in a cellular system different from the cell from which it naturally originates will be "isolated" from its naturally associated components. A protein or nucleic acid molecule may also be rendered substantially free of naturally associated components by isolation, using respectively protein or nucleic acid purification techniques well known in the art.

The term "vector", as used herein, is intended to refer to a nucleic acid molecule capable of transporting another nucleic acid to which it has been linked One type of vector is a "plasmid", which refers to a circular double stranded nucleic acid (typically, DNA) loop into which additional nucleic acid segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include other forms of expression vectors, such as viral vectors (e.g., replication defective retroviruses, lentivirus-derived vectors, and adenovirus-derived viruses), which serve equivalent or comparable functions.

The term "operably linked" refers to a juxtaposition of described components wherein the components are in a relationship permitting them to function in their intended manner. A control sequence "operably linked" to a coding sequence is ligated in such a way that expression of the coding sequence is achieved under conditions compatible with the control sequences. "Operably linked" sequences may include both expression control sequences that are contiguous with the gene of interest and expression control sequences that act in trans or at a distance to control the gene of interest. The term "expression control sequence" refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (such as, a Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences. Unless stated otherwise, a description or statement herein of inserting a nucleic acid molecule encoding a fusion protein of the invention into an expression vector means that the inserted nucleic acid has also been operably linked within the vector to a functional promoter and other transcriptional and translational control elements required for expression of the encoded fusion protein when the expression vector containing the inserted nucleic acid molecule is introduced into compatible host cells or compatible cells of an organism.

As used herein, the term "recombinant" when used as an adjective describes non-naturally altered or manipulated nucleic acids, host cells transfected with exogenous nucleic acids, or polypeptides expressed non-naturally, through manipulation of isolated nucleic acid (typically DNA) and transfection of host cells or through manipulation of endogenous nucleic acid to alternative expression by introduction of non-endogenous nucleic acid. "Recombinant" is a term that specifically encompasses DNA molecules that have been constructed in vitro using genetic engineering techniques, and use of the term "recombinant" as an adjective to describe a molecule, construct, vector, cell, protein, polypeptide, peptide, or polynucleotide specifically excludes naturally occurring ("endogenous") such molecules, constructs, vectors, cells, proteins, polypeptides, peptides, and polynucleotides in their respective, unisolated, native locations (for example, intracellular, tissue, or organ locations).

The term "recombinant host cell" (or simply, in context, "host cell"), as used herein, is intended to refer to a cell into which exogenous nucleic acid has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Host cells useful in various aspects of the invention may be prokaryotic and eukaryotic cells. Preferred prokaryotic host cells include various bacterial cells, including *Escherichia coli*. While some manipulations, constructions, expressions, or replications of nucleic acids or encoded polypeptides related to the invention may be conducted using prokaryotic or eukaryotic host cells, the preferred host cells for enhanced expression of a target protein of interest, whether in the modified or unmodified arrangements described herein, are eukaryotic host cells. Preferred eukaryotic host cells include, without limitation, a mammalian host cell, an insect host cell, a plant host cell, a fungal host cell, a eukaryotic algal host cell, a nematode host cell, a protozoan host cell, and a fish host cell. Preferably, a mammalian host cell is a Chinese Hamster Ovary (CHO) cell, a COS cell, a Vero cell, an SP2/0 cell, an NS/0 myeloma cell, a human embryonic kidney (HEK293) cell, a baby hamster kidney (BHK) cell, a HeLa cell, a human B cell, a CV-1/EBNA cell, an L cell, a 3T3 cell, an HEPG2 cell, a PerC6 cell, or an MDCK cell. Preferred fungal host cells include *Aspergillus, Neurospora, Saccharomyces, Pichia, Hansenula, Schizosaccharomyces, Kluyveromyces, Yarrowia*, and *Candida*. A particularly preferred *Saccharomyces* host cell is a *Saccharomyces cerevisiae* cell. A particularly preferred insect host cell is an Sf9 cell.

The terms "heterologous" and "exogenous" are synonymous and are used broadly as adjectives to describe any molecule (e.g., protein, polypeptide, nucleic acid) that is not native to a host cell containing or expressing the molecule. Accordingly, "heterologous" and "exogenous" encompass the term "recombinant" as defined above.

"Transgenic organism", as known in the art and as used herein, refers to an organism having cells that contain a transgene, wherein the transgene introduced into the organism (or an ancestor of the organism) expresses a polypeptide not naturally expressed in the organism or not naturally expressed at the normal or proper level to provide the intended function of the polypeptide to the organism. A "transgene" is a nucleic acid construct, which is stably and operably integrated into the genome of a cell from which a transgenic organism develops, directing the expression of an encoded gene product in one or more cell types or tissues of the transgenic organism.

The terms "disease" and "disorder" are used interchangeably to indicate a pathological state identified according to acceptable medical standards and practices in the art.

As used herein, the term "effective amount" refers to the amount of a therapy that is sufficient to reduce or ameliorate the severity and/or duration of a disease or one or more symptoms thereof; to prevent the advancement of a detrimental or pathological state; to cause regression of a pathological state; to prevent recurrence, development, onset, or progression of one or more symptoms associated with a pathological state; to detect a disorder; or to enhance or improve the prophylactic or therapeutic effect(s) of a therapy (e.g., the administration of another prophylactic or therapeutic agent).

A "biological sample," as used herein, includes, but is not limited to, any quantity of a substance from a living organism or formerly living organism. Such organisms include, but are not limited to, humans, non-human primates, mice, rats, monkeys, dogs, rabbits, ruminants, and other animals. Such substances of a biological sample may include, but are not limited to, blood, serum, plasma, urine, saliva, sputum, mucus, synovial fluid, milk, semen, cells, organs (for example, heart, spleen, lung, kidney, breast, brain, eye, tongue, stomach, pancreas, intestines, gall bladder, reproductive organs, appendix), tissues (for example, bone, cartilage, muscle, skin), bone marrow, and lymph nodes.

A composition or method described herein as "comprising" (or which "comprises") one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited, composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and close-ended composition or method "consisting of" (or which "consists of") the named elements or steps to the exclusion of any other unnamed element or step.

The term "J domain analog" as used herein refers to a target protein expression enhancing polypeptide (or PEEP) that comprises the sequence of amino acids of formula I (SEQ ID NO:47). Such polypeptides, where incorporated into a target protein sequence to make a modified target protein or when used to construct a protein expression enhancing polypeptide-target protein binding domain fusion protein, are useful for effecting an increase in expression of a target protein of interest.

The terms "J domain active fragment" or "active fragment of a J domain" refer to a fragment of a J domain of a J protein which retains the ability to increase the level of expression of a target protein when used in the two types of fusion proteins (PEEP/target protein fusion or PEEP/target protein binding domain fusion) described herein. The Examples below indicate that J domain active fragments will commonly retain the region of a J domain at the C-terminal extremity of a helix II. Larger portions of a J domain may be active as well, but excision of all or part of the C-terminal nine amino acids of a helix II invariably leads to loss of protein expression enhancement activity.

In any composition or method disclosed herein, known or disclosed equivalents of any named essential element or step may be substituted for that element or step.

Unless specifically indicated, a composition or method is not limited by any particular order of the listed elements or steps, unless a particular method step requires the prior performance of another step.

It is also understood that an element or step "selected from the group consisting of" or "any of" (or equivalent phrase) refers to one or more of the elements or steps in the list that follows, including combinations of any two or more of the listed elements or steps.

J Domains Useful in the Invention

The J domains of a variety of J proteins have been determined. See, for example, Kampinga et al., *Nat. Rev.*, 11: 579-592 (2010); Hennessy et al., *Protein Science*, 14:1697-1709 (2005). A J domain useful in preparing a fusion protein of the invention (whether in the modified or unmodified arrangement) has the key defining features of a J domain of any member of the J protein family. Accordingly, an isolated J domain useful in the invention comprises a polypeptide domain from a J protein, which is characterized by four α-helices (I, II, III, IV) and usually having the highly conserved tripeptide sequence of histidine, proline, and aspartic acid (referred to as the "HPD motif") between helices II and III. Typically, the J domain of a J protein is between fifty and seventy amino acids in length, and the site of interaction (binding) of a J domain with an Hsp70-ATP chaperone protein is believed to be a region extending from within helix II and including the HPD motif. Representative J domains include, but are not limited, a J domain of an ERdj protein (for example, a J domain of ERdj3 or ERdj5), a J domain of a large T antigen of SV40, and a J domain of a mammalian cysteine string protein (CSP-α). The amino acid sequences for these and other J domains that may be used in fusion proteins of the invention are provided in Table 1.

TABLE 1

Amino acid sequences of representative isolated J domains.

| J Protein Source of J Domain | SEQ ID NO: | J Domain Amino Acid Sequence 12345678901234567890123456789 0 |
|---|---|---|
| human Hsp40 (NP_006136; Heat Shock Protein 40) | 1 | KDYYQTLGLARGASDEEIKRAYRRQALRYH PDKNKEPGAEEKFKEIAEAYDVLSDPRK |
| human ErdJ1 (NM_022365; DnaJC1, HTJ1, MTJ1, DnaJ homolog subfamily C member 1 protein, DNAJL1) | 2 | LNFYQFLGVQQDASSADIRKAYRKLSLTLH PDKNKDENAETQFRQLVAIYEVLKDDER |
| human ErdJ2 (NM_001017975; HFM1, SEC63 domain containing 1 protein, MER3, hHFM1) | 3 | YNPYEVLNLDPGATVAEIKKQYRLLSLKYH PDKGGDEVMFMRIAKAYAALTDEES |
| human ErdJ3 (NM_016306; DNAJB11, DnaJ (Hsp40) homolog, subfamily B, member 11, ERj3p, HEDJ, ERj3, ABBP2, ER-associated DNAJ protein 3) | 4 | RDFYKILGVPRSASIKDIKKAYRKLALQLH PDRNPDDPQAQEKFQDLGAAYEVLSDSEK |

TABLE 1-continued

Amino acid sequences of representative isolated J domains.

| J Protein Source of J Domain | SEQ ID NO: | J Domain Amino Acid Sequence<br>12345678901234567890123456789 0 |
|---|---|---|
| human ErdJ4<br>(NM_012328; DNAJB9,<br>microvascular differentiation gene<br>1 protein, MDG1, endothelial<br>Mdg1) | 5 | KSYYDILGVPKSASERQIKKAFHKLAMKYH<br>PDKNKSPDAEAKFREIAEAYETLSDANR |
| human ErdJ5<br>(NM_018981; DNAJC10, ER-<br>resident protein ERdj5, JPD1, J-<br>domain-containing protein<br>disulfide isomerase-like protein,<br>DnaJ (Hsp40)<br>homolog,<br>subfamily C,<br>member 10,<br>hMTHr protein) | 6 | QDFYSLLGVSKTASSREIRQAFKKLALKLH<br>PDKNPNNPNAHGDFLKINRAYEVLKDEDL |
| human ErdJ6<br>(NM_006260; DNAJC3,<br>DnaJ (Hsp40)<br>homolog,<br>subfamily C, member 3 protein,<br>protein-kinase, interferon-<br>inducible double stranded RNA<br>dependent inhibitor protein,<br>P58IPK protein, PRKRI, 58 kDa<br>cellular inhibitor protein, p58<br>inhibitor of protein kinase) | 7 | RDYYKILGVKRNAKKQEIIKAYRKLALQWH<br>PDNFQNEEEKKKAEKKFIDIAAAKEVLSDP<br>EM |
| human CSP<br>(NP_079495; cysteine string<br>protein alpha, CSPalpha protein,<br>DNAJC5 protein, cysteine string<br>protein, DnaJ (Hsp40) homolog,<br>subfamily C, member 5 protein,<br>CSP protein) | 8 | ESLYHVLGLDKNATSDDIKKSYRKLALKYH<br>PDKNPDNPEAADKFKEINNAHAILTDATK |
| SV40 large T antigen<br>(YP_003708382; large tumor<br>antigen T-ag [Simian virus 40]) | 9 | LQLMDLLGLERSAWGNIPLMRKAYLKKCKE<br>FHPDKGGDEEKMKKMNTLYKKMEDGVK |
| DnaJ | 10 | QDYYEILGVSKTAEEREIKKAYKRLAMKYH<br>PDRNQGDKEAEAKFKEIKEAYEVLTDSQK |
| human dnaJ homolog subfamily C,<br>member 8 | 11 | NPFEVLQIDPEVTDEEIKKRFRQLSILVHP<br>DKNQDDADRAQKAFEAVDKAYKLLLDQEQK<br>KRALDVIQ |
| human dnaJ homolog subfamily C,<br>member 5B | 12 | EALYEIGLHKGASNEEIKKTYRKLALKHH<br>PDKNPDDPAATEKFKEINNAHAILTDISK |
| human dnaJ homolog subfamily C,<br>member 14 | 13 | LNPFHVLGVEATASDVELKKAYRQLAVMVH<br>PDKNHHPRAEEAFKVLRAAWDIVSNAEK |
| human dnaJ homolog subfamily C,<br>member 25 precursor | 14 | RDCYEVLGVSRSAGKAEIARAYRQLARRYH<br>PDRYRPQPGDEGPGRTPQSAEEAFLLVATA<br>YETLKDEET |
| human dnaJ homolog subfamily B,<br>member 2, isoform a | 15 | ASYYEILDVPRSASADDIKKAYRRKALQWH<br>PDKNPDNKEFAEKKFKEVAEAYEVLSDKHK |
| human dnaJ homolog subfamily B,<br>member 2, isoform b | 16 | ASYYEILDVPRSASADDIKKAYRRKALQWH<br>PDKNPDNKEFAEKKFKEVAEAYEVLSDKHK |
| Chain A,<br>nmr structure of Bc008182 protein,<br>a human Dnaj-like domain | 17 | TTYYDVLGVKPNATQEELKKAYRKLALKYH<br>PDKNPNEGEKFKQISQAYEVLSDAKK |
| Chain A,<br>solution structure of J Domain of<br>Hsj1a | 18 | ASYYEILDVPRSASADDIKKAYRRKALQWH<br>PDKNPDNKEFAEKKFKEVAEAYEVLSDKHK |
| Chain A,<br>solution structure of a Dnaj-like | 19 | KDSWDMLGVKPGASRDEVNKAYRKLAVLLH<br>PDKCVAPGSEDAFKAVVNARTALLKNIK |

TABLE 1-continued

Amino acid sequences of representative isolated J domains.

| J Protein Source of J Domain | SEQ ID NO: | J Domain Amino Acid Sequence |
|---|---|---|
| domain from human ras-associated protein Rap1 | | |
| Chain A, solution structure of Dnaj domain of human protein Hcg3, a hypothetical protein Tmp_locus_21 | 20 | VDYYEVLDVPRQASSEAIKKAYRKLALKWH PDKNPENKEEAERRFKQVAEAYEVLSDAKK |
| Chain A, solution structure of J domain from Dnaj homolog, human Tid1 protein | 21 | GDYYQILGVPRNASQKEIKKAYYQLAKKYH PDTNKDDPKAKEKFSQLAEAYEVLSDEVK |
| Chain A, solution structure of J domain from human Dnaj subfamily B, member 9 | 22 | GSYYDILGVPKSASERQIKKAFHKLAMKYH PDKNKSPDAEAKFREIAEAYETLSDANR |
| Chain A, solution structure of J domain from human Dnaj subfamily B, member 12 | 23 | GDYYEILGVSRGASDEDLKKAYRRLALKFH PDKNHAPGATEAFKAIGTAYAVLSNPEK |
| Chain A, human Hsp40 (HDJ-1), nmr | 24 | KDYYQTLGLARGASDEEIKRAYRRQALRYH PDKNKEPGAEEKFKEIAEAYDVLSDFRK |
| Chain A, solution structure of Dnaj domain from human Williams-Beuren syndrome chromosome region 18 protein | 25 | TALYDLLGVPSTATQAQIKAAYYRQCFLYH PDRNSGSAEAAERFTRISQAYVVLGSATL |
| Chain A, solution structure of J domain of Dnaj homolog subfamily B, member 8 | 26 | ANYYEVLGVQASASPEDIKKAYRKLALRWH PDKNPDNKEEAEKKFKLVSEAYEVLSDSKK |
| Chain A, solution structure of J domain of Dnaj homolog subfamily C, member 12 | 27 | EDYYTLLGCDELSSVEQILAEFKVRALECH PDKHPENPKAVETFQKLQKAKEILTNEES |
| Chain A, Dnaj domain of human Kiaa0730 protein | 28 | SILKEVTSVVEQAWKLPESERKKIIRRLYL KWHPDKNPENHDIANEVFKHLQNEINR |
| human DnaJ homolog, subfamily B, member 6, isoform a | 29 | VDYYEVLGVQRHASPEDIKKAYRKLALKWH PDKNPENKEEAERKFKQVAEAYEVLSDAKK |
| human DnaJ homolog, subfamily B, member 6, isoform b | 30 | VDYYEVLGVQRHASPEDIKKAYRKLALKWH PDKNPENKEEAERKFKQVAEAYEVLSDAKK |
| human DnaJ homolog, subfamily B, member 9 precursor | 31 | KSYYDILGVPKSASERQIKKAFHKLAMKYH PDKNKSPDAEAKFREIAEAYETLSDANR |
| human DnaJ (Hsp40) homolog, subfamily C, member 8, isoform CRA_c | 32 | LNPFEVLQIDPEVTDEEIKKRFRQLSILVH PDKNQDDADRAQKAFEAVDKAYKLLLDQEQ |
| human DnaJ (Hsp40) homolog, subfamily C, member 13, isoform CRA_b | 33 | DDAYEVLNLPQGQGPHDESKIRKAYFRLAQ KYHPDKNPEGRDMFEKVNKAYEFLCTKSA |
| human DnaJ (Hsp40) homolog, subfamily C, member 19, isoform CRA_e | 34 | REAALILGVSPTANKGKIRDAHRRIMLLNH PDKGK |
| human DnaJ (Hsp40) homolog, subfamily C, member 5, isoform CRA_b | 35 | ESLYHVLGLDKNATSDDIKKSYRKLALKYH PDKNPDNPEAADKFKEINNAHAILTDATK |

TABLE 1-continued

Amino acid sequences of representative isolated J domains.

| J Protein Source of J Domain | SEQ ID NO: | J Domain Amino Acid Sequence<br>1234567890123456789012345678 90 |
|---|---|---|
| human DnaJ (Hsp40) homolog, subfamily C, member 4, isoform CRA_f | 36 | STYYELLGVHPGASTEEVKRAFFSKSKELH PDRDPGNPSLHSRFVELSEAYRVLSREQS |
| human zinc finger, CSL-type containing 3, isoform CRA_c | 37 | KDWYSILGADPSANISDLKQKYQKLILMYH PDKQSTDVPAGTVEECVQKFIEIDQAWKIL GNEET |
| human DnaJ (Hsp40) homolog, subfamily C, member 17, isoform CRA_a | 38 | MDLYALLGIEEKAADKEVKKAYRQKALSCH PDKNPDNPRAAELFKQLSQALEVLTDAAA |
| human DnaJ (Hsp40) homolog, subfamily B, member 9, isoformCRA_a | 39 | KSYYDILGVPKSASERQIKKAFHKLAMKYH PDKNKSPDAEAKFREIAEGASVPAASSF |
| human DnaJ (Hsp40) homolog, subfamily C, member 4, isoform CRA_g | 40 | STYYELLGVHPGASTEEVKRAFFSKSKELH PDRDPGNPSLHSRFVELSEAYRVLSREQS |
| human DnaJ (Hsp40) homolog, subfamily C, member 4, isoform CRA_a | 41 | STYYELLGVHPGASTEEVKRAFFSKSKELH PDRDPGNPSLHSRFVELSEAYRVLSREQS |
| human DnaJ (Hsp40) homolog, subfamily C, member 11, isoform CRA_c | 42 | EDYYSLLNVRREASSEELKAAYRRLCMLYH PDKHRDPELKSQAERLFNLVHQAYEVLSDP QT |
| human zinc finger, CSL-type containing 3, isoform CRA_b | 43 | KDWYSILGADPSANISDLKQKYQKLILMYH PDKQSTDVPAGTVEECVQKFIEIDQAWKIL GNEET |
| human J-type co-chaperone HSC20, isoform CRA_c | 44 | RDYFSLMDCNRSFRVDTAKLQHRYQQLQRL VHPDFFSQRSQTEKDFSEKHSTLVNDAYKT LLAPLS |
| human hCG1994888, isoform CRA_d | 45 | RDCYEVLGVSRSAGKAEIARAYRQLARRYH PDRYRPQPGDEGPGRTPQSAEEAFLLVATA YETLKDEET |
| human DnaJ (Hsp40) homolog, subfamily A, member 1, isoform CRA_a | 46 | TTYYDVLGVKPNATQEELKKAYRKLALKYH PDKNPNEGEKVKMLY1SSQ |

J Domain Fragments and Analogs with Protein Expression Enhancing Activity

Further study of J domains using sequence analysis, including amino and carboxy terminal deletion analysis, revealed that only a relatively small portion of a J domain is required to provide protein expression enhancement activity. Surprisingly, the analysis determined that protein expression enhancement activity according to the invention can be provided by a polypeptide fragment isolated from within a J domain and that consists of as little as 9 or 10 amino acids. See, Examples 10 and 11, infra. As with isolated J domains, such J domain polypeptide fragments may be used in the methods and compositions described herein to enhance expression of a target protein of interest in its intended cellular (intracellular, membrane-associated) or extracellular (secreted) location. The individual J domain polypeptide fragments are not all identical in amino acid sequence, but may share some sequence homology and structural features in addition to providing a protein expression enhancement activity in either a modified or an unmodified arrangement described herein.

Further deletion and substitution mutation analysis of the above-mentioned J domain polypeptide fragments provided the basis for defining a structural formula for a new family of J domain analog polypeptides that possess target protein expression enhancement activity. The members of this family of analog polypeptides comprise 8 to 9 amino acids and include some J domain polypeptide fragments as well as polypeptides that have not been previously identified in the current library of J domains. See, Example 11.

The smaller size of J domain polypeptide fragments and of J domain analog polypeptides compared to complete (full-length) J domains reduces the size of fusion proteins that can be constructed and expressed in the modified and unmodified arrangements of the invention for enhancing expression of a target protein of interest. Thus, the size of recombinant nucleic acid molecules encoding such fusion proteins can be correspondingly smaller than nucleic acid molecules that encode fusion proteins comprising a complete J domain. The relatively small size of J domain polypeptide fragments and J domain analog polypeptides of the invention may be particularly beneficial in reducing the immunogenicity of fusion proteins of the modified arrangement in which a protein expression enhancing polypeptide is linked (fused) to a target protein of interest to form a modified (fusion) target protein that is expressed in or administered to a subject in place of the (unlinked) target protein of interest. The less immunogenic the fusion protein is, the more likely the fusion protein can persist in the subject in order to provide the subject with the beneficial property or effect of the fusion protein without being rapidly eliminated or inhibited by an immune response directed to the fusion protein.

Fusion Proteins Comprising a Protein Expression Enhancing Polypeptide

According to the invention, a protein expression enhancing polypeptide described herein is used as a component of a fusion protein that enhances expression of a target protein of interest for which there is a need to improve expression in a host cell. The protein expression enhancing polypeptide is used to enhance expression of a target protein of interest in either of two arrangements that describe the primary structure (amino acid sequence) of the expressed target protein of interest.

In the "modified" arrangement for enhancing protein expression, a protein expression enhancing polypeptide is linked to a target protein of interest to form a fusion protein, i.e., a "modified" target protein of interest, which is expressed at an enhanced level compared to that of the unmodified target protein that is poorly expressed in the absence of a protein expression enhancing polypeptide. Thus, the fusion protein in the modified arrangement is a modified form of the target protein of interest that is expressed and employed as a surrogate in place of the poorly expressed, unmodified target protein.

In the "unmodified" arrangement for enhancing protein expression, the primary structure of the target protein of interest remains unaltered ("unmodified") in that it is not fused to a protein expression enhancing polypeptide. A protein expression enhancing polypeptide of the invention is linked to a target protein binding domain that has an affinity for and binds to a target protein of interest. Co-expression of the fusion protein and the unmodified target protein of interest in a host cell results in an enhanced level of expression of the target protein of interest as compared to the level of expression in the absence of the target protein-binding fusion protein.

As the primary structure (amino acid sequence) of a target protein of interest remains unaltered (not linked in a fusion protein) in the unmodified arrangement, it is likely that for many applications, the unmodified arrangement for enhancing protein expression will be preferred over the modified arrangement. However, as explained below, it is also possible to engineer the fusion protein of a modified arrangement so that the protein expression enhancing polypeptide component of the fusion protein is easily cleaved to liberate the target protein component comprising the original amino acid sequence of the target protein with no or only a few additional remnant amino acids from the fusion protein. Such a fusion protein may be more suitable than the unmodified target protein for certain applications.

While it is possible to synthesize a fusion protein in either arrangement using direct synthesis (for example, solid-phase peptide synthesis, solution-phase synthesis, etc.), it is likely that in most cases a fusion protein described herein will be more economically produced using standard recombinant nucleic acid techniques, including polymerase chain reaction (PCR) techniques, in concert with cell culture methods or transgenic methods.

Standard techniques may be used for recombinant DNA, oligonucleotide synthesis, transfection of cells (for example, without limitation, electroporation, liposome-mediated transfection, transformation methods), and cell and tissue culture methods to express a fusion protein of the invention. Enzymatic reactions and purification techniques may be performed as commonly accomplished in the art, as described in a manufacturer's specifications, or as described herein. The foregoing techniques and procedures may be generally performed according to conventional methods well known in the art and as described in various general and more specific references that are cited and discussed throughout the present specification. See e.g., Sambrook et al., eds., *Molecular Cloning: A Laboratory Manual, Second Edition* (Cold Spring Harbor Laboratory Press, Cold Spring Harbor, N.Y., 1989) and Ausubel et al. (eds.), *Current Protocols in Molecular Biology* (John Wiley & Sons, New York, 2012), which are incorporated herein by reference.

As noted above, the terms "modified" and "unmodified" refer to whether or not a target protein of interest is linked to a protein expression enhancing polypeptide. It is understood that in some embodiments of both the modified and unmodified arrangements, it may be beneficial to link one or more additional domains may to a fusion protein or target protein of interest. For example, any of the well-known epitope tag peptides (epitope tags) may be incorporated into a protein to facilitate detection and/or purification of the expressed protein. Such epitope tags include, but are not limited to, a V5 epitope tag (GKPIPNPLLGLDST (SEQ ID NO:110)), a Flag epitope tag (DYKDDDDK (SEQ ID NO:111)), a hexa-histidine epitope tag (HHHHHH (SEQ ID NO:112)), a hemagglutinin epitope tag (YPYDVPDYA (SEQ ID NO:113)), a c-myc epitope tag (EQKLISEEDL (SEQ ID NO:114)), a VSV-G epitope tag (YTDIEMNRLGK (SEQ ID NO:115)), and a HSV epitope tag (QPELAPEDPED (SEQ ID NO:116)). As explained below, it is also possible to link a protein with such an epitope tag using a linker that can be cleaved by a proteolytic enzyme and thereby removed (or substantially removed) from the protein.

Linkers

Any domain may be linked to another domain within a fusion protein of the invention by methods known in the art. For example, in the modified arrangement of the invention, a fusion protein comprises a protein expression enhancing polypeptide linked to a target protein of interest. The expressed fusion protein is therefore a modified target protein that can be used as a surrogate for the unfused and poorly expressed target protein of interest. The protein expression enhancing polypeptide may be linked directly to the target protein of interest or linked indirectly via a linker molecule. In the unmodified arrangement of the invention, a fusion protein comprises a protein expression enhancing polypeptide linked to a target protein binding domain that has an affinity for and binds to a target protein of interest. Co-expression of the fusion protein with the target protein of interest enhances the level of expression of the unmodified (unfused) target protein of interest compared to the level of expression in the absence of the fusion protein. The protein expression enhancing polypeptide may be linked directly to the target protein binding domain or linked indirectly via a linker molecule. Other domains may also be linked to a fusion protein or unfused protein in either the modified and unmodified arrangements to provide one or more additional features. For example, an epitope tag may be linked to a fusion protein or unfused protein to facilitate detection or purification of the tagged protein.

At the amino acid level, a linker may be one or more amino acids, including 1 to 10 amino acids, 1 to 20 amino acids, and even 1 to 50 amino acids. Typically, with respect to linking a protein expression enhancing polypeptide to a target protein of interest (in the modified arrangement) or to a target protein binding domain (in the unmodified arrangement), it is not necessary to use a linker that is more than 20 amino acids because linking a protein expression enhancing polypeptide directly to a target protein of interest or to a target protein binding domain does not appear to significantly diminish the necessary biochemical and functional properties of the protein of interest or the target protein binding domain (data not shown).

Selecting one or more linkers to produce a fusion protein according to the invention is within the knowledge and skill of the art. See, for example, Arai et al., Protein Eng., 14(8): 529-532 (2001); Crasto et al., Protein Eng., 13(5): 309-314 (2000); George et al., Protein Eng., 15(11): 871-879 (2003); Robinson et al., Proc. Natl. Acad. Sci. USA, 95: 5929-5934 (1998). General considerations for using a particular linker to link a protein expression enhancing polypeptide to a target protein of interest or to a target protein binding domain may include those in making other fusion proteins in which one functional domain is linked to another functional domain, for example, as may be considered in linking immunoglobulin variable and/or constant domains in a wide variety of formats for producing engineered functional binding proteins. Clearly, a linker should not interfere with the folding of a target protein of interest or a target protein binding domain that is linked to a protein expression enhancing polypeptide. A linker, if present in a fusion protein, is selected to optimize the contribution of the protein expression enhancing polypeptide to increase levels of expression or yield of the fusion protein in the modified arrangement or the (unfused) target protein of interest in the in the unmodified arrangement, and it may be omitted if direct attachment of a protein expression enhancement polypeptide to the target protein of interest or target protein binding domain achieves a desired enhanced level of expression. Linker molecules present in a fusion protein of the invention may comprise one or more amino acids encoded by a nucleotide sequence present on a segment of nucleic acid in or around a cloning site of an expression vector into which is inserted in frame a nucleic acid segment encoding a protein domain (e.g., protein expression enhancing polypeptide, protein of interest, target protein binding domain) or an entire fusion protein.

Linker molecules, especially those that are four amino acids and longer, preferably possess a flexibility that permits the protein of interest to fold into its proper conformation. A variety of relatively flexible linkers are known in the field for linking functional domains. A linker may also be used to link one or more additional domains, such as an epitope tag, to the protein expression enhancing polypeptide or protein of interest of a fusion protein of the invention. Linkers that may be used in preparing a fusion protein according to the invention, include, by are not limited to, DIAAA (SEQ ID NO:117); DIAAALE (SEQ ID NO:118); GTGSEF (SEQ ID NO:119); AS; TVA; ASTK (SEQ ID NO:120); GGGSGGSGGSGG (SEQ ID NO:121); DIGGGSGGSGGSGGAAA (SEQ ID NO:122); AKTTP-KLEEGEFSEAR (SEQ ID NO:123); AKTTPKLEEGEFSEARV (SEQ ID NO:124); AKTTPKLGG (SEQ ID NO:125); SAKTTPKLGG (SEQ ID NO:126); SAKTTP (SEQ ID NO:127); RADAAP (SEQ ID NO:128); RADAAPTVS (SEQ ID NO:129); RADAAAAGGPGS (SEQ ID NO:130); RADAAAA ($G_4S$)$_4$ (SEQ ID NO:131); SAKTTPKLEEGEFSEARV (SEQ ID NO:132); ADAAP (SEQ ID NO:133); ADAAPTVSIFPP (SEQ ID NO:134); TVAAP (SEQ ID NO:135); TVAAPSVFIFPP (SEQ ID NO:136); QPKAAP (SEQ ID NO:137); QPKAAPSVTLFPP (SEQ ID NO:138); AKTTPP (SEQ ID NO:139); AKTTPPSVTPLAP (SEQ ID NO:140); AKTTAP (SEQ ID NO:141); AKTTAPSVYPLAP (SEQ ID NO:142); ASTKGP (SEQ ID NO:143); ASTKGPSVFPLAP (SEQ ID NO:144), GGGGSGGGGSGGGGS (SEQ ID NO:145); GENKVEYAPALMALS (SEQ ID NO:146); GPAKELTPLKEAKVS (SEQ ID NO:147); GHEAAAVMQVQYPAS (SEQ ID NO:148); GGGGGGGP (SEQ ID NO:149); GGGGGGGGP (SEQ ID NO:150); PAPNLLGGP (SEQ ID NO:151); PNLLGGP (SEQ ID NO:152); GGGGGGP (SEQ ID NO:153); PAPELLGGP (SEQ ID NO:154); PTISPAPNLLGGP (SEQ ID NO:155); TVAADDDDKSVFIVPP (SEQ ID NO:156); TVDDDDKAAP (SEQ ID NO:157); LVPRGSAAP (SEQ ID NO:158); ASTKGPSV (SEQ ID NO:159); ASTKGPSVFP (SEQ ID NO:160); TVAAPSV (SEQ ID NO:161); TVAAPSVFI (SEQ ID NO:162); and the like.

In some embodiments, a fusion protein may contain one or more linkers that can be cleaved by one or more proteases. Such linkers possess an amino acid sequence that is recognized by a protease for cleavage of the protein at or near the recognition sequence. Incorporating one or more cleavable linker molecules into a fusion protein provides the option of removing one or more domains from the expressed fusion protein. By way of non-limiting examples, in some applications or preparations, it may be desirable to remove the polypeptide expression enhancing polypeptide linked to the protein of interest (for example, to reduce potential immunogenicity) and/or to remove an epitope tag that had been incorporated into a fusion protein to facilitate detection or purification of the expressed fusion protein. In another example, if the fusion protein is secreted, a polypeptide expression enhancing polypeptide (or other domain) linked by a cleavable linker to the protein of interest may be removed by adding the appropriate protease directly to the medium of cultures expressing the fusion protein. Alternatively, the protein expression enhancing polypeptide (or other domain) linked by the cleavable linker may be removed after performing one or more steps to purify the fusion protein from the culture medium.

It may be useful in some situations to remove a domain or epitope tag linked to a protein. This can be accomplished, for example, by expressing the protein comprising the additional domain or tag in cells in which the expression of a protease that can cleave a linker of the protein is regulated, such as incorporating into the cell a recombinant gene for the appropriate protease under the control of a promoter that can be regulated by a signal (e.g., temperature shift) or agent (ion change) that can be applied to a culture after the cells have expressed the fusion protein. A variety of promoters are available in the art for regulating gene expression in prokaryotic or eukaryotic cells. In addition, some cells express one or more proteases that can cleave a linker molecule containing a corresponding cleavage site. It is within the skill of a practitioner in the art to determine whether use of a protease that may be expressed by a host cell may be useful to cleave a linker in a fusion protein expressed by the same host cell. Alternatively, it is possible to add an appropriate protease to a sample, such as culture medium or cell lysate, containing a protein linked to an additional domain or tag via a protease-cleavable linker.

A variety of linker molecules containing proteolytic cleavage sites are known and available in the art for linking one protein or protein domain to another. Such linkers include, but are not limited to, one of more of the following examples, where the asterisk (*) indicates the proteolytic cleavage site: DYKDDDDK* (SEQ ID NO:163); ASDDDDK*GGP (SEQ ID NO:164); ALVPR*GSGP (SEQ ID NO:165); ASTDDDDK*SVFPLAP (SEQ ID NO:166); TVALVPR*GSVFIFPP (SEQ ID NO:167); ASTLVPR*GSVFPLAP (SEQ ID NO: 168); TVAADDDK*SVFIVPP (SEQ ID NO:169); ASTDDDK*SVFPLAP (SEQ ID NO:170); LEVLFQ*GP (SEQ ID NO:171); TVAALEVLFQ*GPAP (SEQ ID NO:172); ASTLEVLFQ*GPLAP (SEQ ID NO:173); PAPLEVLFQ*GP (SEQ ID NO:174); TAENLYFQ*GAP (SEQ ID NO:175); AENLYFQ*GA (SEQ ID NO:176); PGPFGR*SAGGP (SEQ ID NO:177); PGPFGR*SAGG (SEQ ID NO:178); PQRGR*SAG (SEQ ID NO:179); PHYGR*SGG (SEQ ID NO:180); GPFGR*SAGP (SEQ ID NO:181); GDDDDK*GGP (SEQ ID NO:182); AGDDDDK*GGP (SEQ ID NO:183); GGDDDDK*GGP (SEQ ID NO:184); ENLYFQ*G (SEQ ID NO:185); ENLYFQ*S (SEQ ID NO:186); and the like.

A variety of proteolytic enzymes are known in the art that may be used to cleave a cleavable linker employed in a protein of the invention. Clearly, a protease that is selected to cleave a cleavable linker in a fusion protein comprising a target protein of interest should not also cleave the target protein of interest or any other domain that is desired to be retained after cleavage of the linker Proteolytic enzymes that may be used to cleave a fusion protein at a site in a linker within the fusion protein include, but are not limited to, enterokinase, factor Xa, thrombin, PreScission, tobacco etch virus (TEV) protease, tissue plasminogen activator (tPA), a zinc-dependent endopeptidase, a matrix metalloproteinase (MMP), a serralysin, an astacin, an adamalysin, a disintegrin, an ADAM, a caspase, a cathespsin, a calpain, and the like.

Nucleic Acids Encoding Fusion Proteins

Using standard methods available in the art, a nucleic acid (typically DNA) molecule is constructed that encodes a fusion protein employed in a modified or unmodified arrangement for enhancing expression of a target protein of interest. One or more additional domains may also be incorporated into a protein, such as a standard epitope tag used to facilitate detection and/or purification of the protein. A nucleic acid molecule encoding a desired fusion protein can be inserted into any of a variety cloning vectors available in the art for the purpose of replicating the recombinant structural gene for the fusion protein. For expressing a fusion protein, a nucleic acid molecule encoding the fusion protein can be inserted into any of a variety of expression vectors available in the art. An expression vector with the inserted nucleic acid encoding the fusion protein is then introduced into compatible host cells that permit expression of the fusion protein from the expression vector. In the case of an unmodified arrangement, a vector may also contain a copy of functional structural gene encoding the unmodified target protein of interest if the host cell does not possess a functional gene for the target protein of interest.

Expression vectors of the invention include expression vector molecules comprising a nucleic acid segment encoding a protein expression enhancing polypeptide described herein and one or more cloning sites (for example, unique restriction enzyme sites) located 5' or 3' to the protein expression enhancing polypeptide coding sequence into which a nucleic acid molecule encoding another domain of the fusion protein may be inserted: in a modified arrangement, a nucleic acid encoding a target protein of interest may be inserted to form the desired fusion protein (modified target protein); whereas in an unmodified arrangement, a nucleic acid encoding a target protein binding domain may be inserted to form a fusion protein that is capable of binding to and enhancing expression of an unmodified target protein of interest. An expression vector may also possess multiple cloning sites that permit the insertion of one or more additional nucleic acid segments encoding one or more other desired domains (for example, an epitope tag, Fc region, etc.) to construct and express a desired fusion protein. The final nucleic acid fusion construct encoding a desired fusion is operably linked to a promoter on the expression vector. Engineering cloning sites into a vector molecule and operably linking an inserted nucleic acid segment encoding a desired protein to a promoter and other signals required for expression of the protein in a compatible host cell are within the skill in the art.

While a description herein for assembling a nucleic acid construct encoding a fusion protein of the invention may suggest a particular stepwise order to the linking of various nucleic acid molecules followed by insertion of the fully assembled nucleic acid construct into an expression vector, it is understood and appreciated that the exact order of linking segments of nucleic acid molecules to produce a nucleic acid construct encoding a desired fusion protein is within the discretion, skill, and experience of a practitioner in this art. Moreover, although it is possible to first link all segments together to form a nucleic acid molecule encoding a fusion protein prior to insertion into an expression vector, in some cases, a nucleic acid segment encoding one or more domains may already properly reside within an expression vector so that it is practical to insert one or more nucleic acid segments adjacent to the segment(s) already residing in the expression vector and thereby assemble within the expression vector an operably linked structural gene for a desired fusion protein of the invention.

Expression vectors encoding a fusion protein of the invention may be transfected into any of a variety of host cells that are compatible for expressing the fusion protein from the particular expression vector. Although some steps in the process of constructing a recombinant structural gene encoding a fusion protein of the invention may be conducted in either prokaryotic or eukaryotic cells, the preferred host cell for enhanced expression of fusion proteins according to the invention are eukaryotic cells. Eukaryotic host cells useful in the invention include, but are not limited to, a mammalian host cell, an insect host cell, a plant host cell, a fungal host cell, a eukaryotic algal host cell, a nematode host cell, a protozoan host cell, and a fish host cell. Mammalian host cells useful for expressing a fusion protein of the invention include, but are not limited to, a Chinese Hamster Ovary (CHO) cell, a COS cell, a Vero cell, an SP2/0 cell, an NS/0 myeloma cell, a human embryonic kidney (HEK293) cell, a baby hamster kidney (BHK) cell, a HeLa cell, a human B cell, a CV-1/EBNA cell, an L cell, a 3T3 cell, an HEPG2 cell, a PerC6 cell, and an MDCK cell. Fungal host cells useful for expressing a J domain fusion protein of the invention include, but are not limited to, *Aspergillus, Neurospora, Saccharomyces, Pichia, Hansenula, Schizosaccharomyces, Kluyveromyces, Yarrowia*, and *Candida*. A particularly useful *Saccharomyces* host cell is a *Saccharomyces cerevisiae* cell.

Using methods available in the art, nucleic acid molecules encoding a fusion protein of the invention may be introduced into cells of a plant or non-human animal for the purpose of expressing the fusion protein in levels that permit easy purification of the fusion protein or as a gene therapy to provide the plant, human, or non-human animal with the benefit of the function provided by the protein of interest within the expressed fusion protein. Such methods can be used to provide transgenic plants or animals that express the fusion protein encoded by the transferred nucleic acid (transgene) encoding the fusion protein. In the case of plants and non-human animals, techniques are available for incorporating expressible nucleic acid encoding a protein into the germline so that progeny of the transgenic organism also can express the fusion protein. A variety of vectors and methods are available for introducing nucleic acid into cells of a plant or non-human animal including, but not limited to, syringe injection of naked DNA into cells, ballistic transfer (for example, using a gene gun), liposomes, and virus-derived vector molecules.

A gene therapy for treating a human subject according to the invention may employ a recombinant gene encoding a fusion protein that comprises an expression enhancing polypeptide in either a modified or unmodified arrangement described herein. Such gene therapy is especially useful in diseases in which an improperly folded protein species results in loss or substantial loss of function as to cause a clinically recognized pathological condition. Examples of diseases in which an improperly folded protein species resulting in loss of function has been demonstrated or implicated include, but are not limited to, prion-associated disease (transmissible spongiform encephalopathy), Alzheimer's disease; Parkinson's disease; Huntington's disease; cystic fibrosis (CF), and al-antitrypsin (AAT) deficiency.

In a gene therapy employing a modified arrangement of the invention, a recombinant gene is constructed encoding a fusion protein comprising a protein expression enhancing polypeptide linked to a target protein of interest. The recombinant gene is inserted into a vector, which in turn is integrated into the genome of somatic cells of a human subject. In most cases, it is not necessary for the recombinant vector to be taken up and integrated into the genome of all somatic cells, but only a sub-population of cells that may be relevant to a particular disease. The fusion protein expressed from the integrated recombinant gene in the somatic cells of the human subject treats the disease by restoring a function of the endogenous target protein of interest that is otherwise missing, has been lost, or is so diminished as to cause a clinically recognized disease in a human subject.

In a gene therapy employing an unmodified arrangement of the invention, a recombinant gene is constructed encoding a fusion protein comprising a protein expression enhancing polypeptide linked to a target protein binding domain that has an affinity for and binds a target protein of interest. The recombinant gene is inserted into a vector, which in turn is integrated into the genome of somatic cells of a human subject. Again, in most cases, it is not necessary for the recombinant vector to be taken up and integrated into that genome of all somatic cells, but only a sub-population of cells that may be relevant to a particular disease. Expression of the fusion protein from the integrated recombinant gene in the cells of the human subject enhances expression of the endogenous target protein of interest so that the protein can provide the cells with the required function provided by the target protein to avoid a clinically recognized disease. If the endogenous gene for the endogenous target protein of interest is not functional or has been deleted, then a recombinant gene encoding the target protein of interest must also be constructed and inserted into a vector for integration into the genome of a human subject for expression along with the fusion protein.

Any of a variety of vectors, agents, and methods may be used to introduce nucleic acid molecules into the somatic cells of a human subject including, but not limited to, modified viruses (e.g., a modified adenovirus, a modified lentivirus), virus-associated virus (e.g., an adenovirus-associated virus), naked DNA (such as naked plasmid DNA), compacted DNA in nanoparticles, and liposomes (e.g., using various cationic lipids).

Fusion Proteins Comprising a Protein Expression Enhancing Polypeptide and a Target Protein of Interest in a Modified Arrangement A fusion protein in a modified arrangement of the invention comprises a protein expression enhancing polypeptide (or PEEP, comprising an isolated J domain, an active J domain polypeptide fragment, or J domain analog polypeptide as described herein) linked to a target protein of interest. Preferably, the protein expression enhancing polypeptide is linked to the amino (N) terminus or carboxy (C) terminus of the target protein of interest. The protein expression enhancing polypeptide may also be spaced from the protein of interest by one or more intervening polypeptide sequences such as linkers, enzyme cleavage sites, epitope tags, and the like. Insertion of a protein expression enhancing polypeptide within a target protein of interest is possible, however as a practical matter this requires more complicated recombinant DNA engineering and has a high likelihood of interfering with the proper folding, desired function, or other properties of the target protein of interest, and is therefore generally less preferred. A target protein of interest that may be used to make a fusion protein of a modified arrangement according to the invention may be any protein or polypeptide that has a desirable property, including soluble proteins that normally reside in an intracellular location; membrane-associated proteins (including transmembrane proteins); secreted proteins; and genetically engineered, non-naturally occurring, proteins. Such engineered, non-naturally occurring proteins may include, but are not limited to, recombinant soluble forms of natural membrane-associated proteins, for example, the extracellular domain of a transmembrane protein (for example, integrins, complement regulatory proteins). Another example of engineered, non-naturally occurring proteins that may be used as a target protein component of a fusion protein in a modified arrangement are recombinant fusion proteins comprising a recombinant soluble receptor molecule in which an extracellular binding domain of a cell surface receptor is fused to an immunoglobulin Fc domain or immunoglobulin scaffold. A non-limiting example of such a non-naturally occurring fusion protein is etanercept in which the extracellular domain of the p75 human TNFα receptor molecule is linked to the hinge and Fc domain of an IgG1 immunoglobulin. Other proteins that may be used as a target protein of interest in a fusion protein of a modified arrangement of the invention include, but are not limited to, antibodies and antigen-binding portions thereof, cytokines, peptide hormones, enzymes (e.g., thrombin, lactase, proteases, transferases, kinases, etc.), and morphogenetic proteins.

Fusion Proteins Comprising a Protein Enhancing Expression Polypeptide and a Target Protein Binding Domain in an Unmodified Arrangement A protein expression enhancing polypeptide (comprising an isolated J domain, active J domain polypeptide fragment, or J domain analog polypeptide as described herein) may also be used in an unmodified arrangement to enhance expression of a target protein of interest at its intended location. In an unmodified arrangement according to this invention, a fusion protein comprises a protein expression enhancing polypeptide linked to a target protein binding domain that has an affinity for and binds a target protein of interest. Thus, in an unmodified arrangement of the invention, the target protein of interest is not a component of a fusion protein and therefore retains its unaltered primary structure (amino acid sequence). While not intending to be bound by any particular mechanism, the binding of a target protein of interest to a target protein binding domain of the fusion protein appears to bring the target protein of interest into relatively close proximity to the protein expression enhancing polypeptide (also present in the fusion protein) to provide an enhanced level of expression of the target protein at its intended cellular or extracellular location as compared to the level of expression of the target protein in the absence of the fusion protein. This may involve increased recruitment of chaperone proteins or other post-translational cellular mechanisms involved in protein folding, compartmentalization, or secretion, or may involve increase avoidance of cellular degradation pathways. The effect is evidenced by a significant increase in the appearance of expressed protein in the desired intracellular or extracellular location.

Target Protein Binding Domains Useful in an Unmodified Arrangement

A fusion protein in an unmodified arrangement of the invention comprises a target protein binding domain that binds a target protein of interest for which an elevation of expression in its proper cellular or extracellular location is desired. A target protein binding domain of a target protein-binding fusion protein of the invention may be any protein or binding domain thereof that is known to bind to a target protein. The more specific the binding affinity of a protein or binding domain thereof is for a target protein, the less likely other proteins may potentially interfere with the enhancement in the level of expression desired for the target protein of interest.

Examples of target protein binding domains include antigen binding sites isolated from natural and genetically engineered antibodies and antigen binding fragments thereof, wherein the antigen binding site of an antibody or antigen binding fragment binds a target protein for which an elevation of expression is desired. In this context, antibodies and antigen binding fragments can easily be raised that bind a target protein of interest using standard methods available in the art. A variety of genetically engineered antibody formats are known in the art that may be used as a source of a target protein binding domain of a fusion protein in an unmodified arrangement of the invention. Such formats include, but not limited to, Fab fragments, F(ab')$_2$ fragments, single chain Fv (scFv) antibodies, and single domain antibodies (dAb). See, for example, a review of the variety of functional genetically engineered antibody binding formats available in the art in Marvin et al., *Acta Pharmacol. Sin.*, 26(6): 649-658 (2005); Kufer et al, *Trends Biotechnol.*, 22(5): 238-244 (2004); Kontermann, *Acta Pharmacol. Sin.*, 26(1): 1-9 (2005), and Chan et al., *Nat. Rev,* 10: 301-316 (2010).

Particularly useful in the invention are antibody molecules or fragments in which an antigen binding domain directed to a target protein is provided in a single polypeptide because such polypeptides can be easily linked to a protein expression enhancing polypeptide to form a fusion protein of the invention using standard in vitro DNA methods. For example, a single chain Fv antibody (scFv) comprises both VH and VL domains of an antigen binding site linked in a single polypeptide. Another source of a single chain antigen binding site is a single domain antibody (dAb) in which the entire antigen binding site is present in a single heavy chain variable domain. See, for example, Ward et al., *Nature,* 341: 544-546 (1989); Muyldermans et al., *Protein Eng.,* 7: 1129-1135 (1994); Vu et al., *Mol. Immunol.,* 34: 1121-1131 (1997); Muyldermans et al., *Trends Biochem. Sci.,* 26: 230-235 (2001); Nguyen et al., *Immunogenetics,* 54: 39-47 (2002).

For a target protein that possesses an immunoglobulin Fc domain, a target protein binding domain may be an antibody or antigen (Fc domain) binding fragment thereof as discussed above. An alternative to an antibody or antigen binding domain thereof is any of a variety of non-immunoglobulin proteins and polypeptides that are known to specifically bind Fc domains. Proteins that possess Fc binding domains include, but are not limited to, Protein A, Protein G, gE protein of herpes simplex virus type 1 (HSV-1), and the like. A number of synthetic peptides also have been identified that bind Fc domains. See, for example, DeLano et al., *Science,* 287:1279-1283 (2000); Yang et al., *J. Peptide Res.,* 66(Suppl. 1): 120-137 (2006). As shown in the Examples below, such Fc-binding proteins and peptides are readily employed as target binding domains for fusion proteins of the invention directed to target proteins of interest comprising an Fc domain.

In the case in which a target protein of interest is a receptor or functional portion thereof that binds a protein ligand, the protein ligand may be used as a target binding domain in a fusion protein of the invention. Functional portions of receptors include, but are not limited to, the extracellular domain of a membrane-associated receptor that includes a functional ligand binding domain. Typically, such extracellular portions comprising a functional ligand binding domain are referred to as "truncated receptors" because the transmembrane and cytoplasmic domains of the receptor have been removed. According to the invention, the expression of such truncated receptor molecules may be elevated by co-expression with a fusion protein of the invention comprising a protein ligand of the receptor. Accordingly, particularly suited for use as a target binding domain of a fusion protein in a modified arrangement of the invention are ligand proteins that are single polypeptides, such as certain cytokine polypeptides (for example, IL8, IL13, and the like) as shown in the Examples below. Other protein ligands that may be used in a fusion protein to bind a target receptor protein or ligand binding portion thereof, include polypeptide co-receptors, polypeptide co-repressors, and polypeptide co-factors.

In the case in which the target protein is a protein ligand (for example, a cytokine) that is bound by a known receptor molecule, a target protein binding domain of a fusion protein in an unmodified arrangement of the invention may comprise the cognate receptor or extracellular ligand binding portion of the receptor that binds the target protein.

BAG domains have been suggested in the art as fusion partners for enhancement of expression of target proteins. BAG domains of a variety of BAG proteins have been determined. See, for example, Takayama et al., *Nat. Cell Biol.,* 3: E237-E241 (2001). A BAG domain has the key defining features of a BAG domain of any member of the BAG protein family. Accordingly, a BAG domain comprises a polypeptide domain of a BAG protein that is typically 85-124 amino acids in length, binds the ATPase domain of Hsp70 chaperone proteins, and is characterized by three anti-parallel α-helices (I, II, III, IV), wherein helices III and IV interact with the ATPase domain of Hsp70 chaperone proteins. Recently, it has been reported that when desired recombinant proteins are linked to a BAG domain, the resulting fusion proteins are expressed at levels that are greater than those of the protein alone. See, International Publication No. WO 2012/087835 A2.

From the Examples, below, BAG domains employed in an unmodified arrangement did not provide significant enhancement of the level of expression of target proteins of interest. In contrast, the protein expression enhancing polypeptides described herein significantly enhance levels of expression of target proteins of interest in both modified and unmodified arrangements. As shown in the Examples below, fusion proteins comprising a protein expression enhancing polypeptide (such as an isolated J domain, an active J domain fragment, or a J domain analog polypeptide, e.g., of formula I or particular 10-12 amino acid cognates thereof disclosed herein) linked to a target protein of interest (in a modified arrangement of the invention) were expressed at significantly greater levels than that of control cells (no fusion protein). Other studies showed that fusion proteins comprising a protein expression enhancing polypeptide described herein linked to target protein binding domains (in an unmodified arrangement) were effective in providing significantly greater levels of expression of unmodified target proteins of interest as compared to the levels in the absence of such fusion proteins (control) or fusion proteins comprising a BAG domain linked to a target protein binding domain. Accordingly, protein expression enhancing polypeptides as described herein provide a new family of polypeptides for use in enhancing expression of target proteins of interest in both modified and unmodified arrangements.

Gene Therapy Approaches for Treating Cystic Fibrosis

Cystic fibrosis (CF) is an autosomal recessive disorder caused by mutations in the gene encoding the cystic fibrosis transmembrane conductance regulator (CFTR) protein, a cAMP-regulated chloride channel and channel regulator. The deletion of phenylalanine at position 508 (Δ508F) in CFTR is the most common mutation that changes the conformation of the CFTR protein, which is then rapidly degraded by the endoplasmic reticulum (ER) quality systems. A general consensus is that only partial recovery of the wild-type CFTR protein function is required to provide a beneficial treatment to CF patients. Therefore, a number of gene therapy trials with CFTR have been attempted, but have not yet been successful owing to inefficient delivery of a gene for CFTR and to immunogenicity of the vehicle (e.g., viral vector). In view of the fact that proper protein folding of wild-type CFTR is known to be difficult, it would be very useful if protein folding of the CFTR protein could be improved.

Over twenty clinical trials of a gene therapy to treat cystic fibrosis (CF) have been conducted since the identity and isolation of the CFTR gene over twenty years ago. See a review of gene therapy for cystic fibrosis in Davies et al., Proc. Am. Thor. Soc., 7: 408-414 (2010). Such clinical trials have already established proof of concept to provide replacement cystic fibrosis transmembrane conductance regulator (CFTR) protein, however the sustainability of effective levels of expression of the replacement CFTR protein in the cells of human subjects remains among the most persistent challenges in the development of an effective gene therapy to treat CF. The CFTR wild-type protein is a protein well-known for its instability. Over 90% of CF patients possess at least one copy of a mutated gene for CFTR (CFTRΔ508F) in which the absence of a phenylalanine at position 508 results in a highly unstable protein that is rapidly degraded in cells. This suggests a fusion gene therapy approach for treating CF that would lead to increased CFTR function or restored CFTR function to those afflicted with CF. Such a gene therapy provides a nucleic acid encoding a fusion protein in either a modified or unmodified arrangement of the invention.

As shown in the Examples below, fusion proteins in which either a wild-type CFTR protein or the CFTRΔ508F protein is fused to a protein expression enhancing polypeptide (such as J domain) in a modified arrangement were expressed in significantly higher levels than either unfused protein. This suggests that a J domain fusion gene therapy approach for treating CF that would lead to increased CFTR function or restored CFTR function to those afflicted with CF. Accordingly, the modified arrangement of the invention provides new forms of gene therapies that use fusion proteins that are expressed at significantly higher levels and therefore are more effective than past therapies to replace or restore missing or lost protein functions that are associated with various diseases.

For an unmodified arrangement, a fusion protein comprises a protein expression enhancing polypeptide linked to a binding domain that binds the wild-type CFTR protein or the CFTRΔ508F protein. A number of proteins are known to contain PDZ domains that bind to the highly conserved, carboxy terminal, PDZ binding region of CFTR. A protein that can be used as a source of a PDZ domain for use as a target protein binding domain in a fusion protein in an unmodified arrangement of the invention includes, but is not limited to, any of the members of the NHERF family of PDZ adapter proteins including, but not limited to, of NHERF1 (also known as NHERF, EBP50, or SLC9A3R1), NHERF2 (also known as E3KARP or SLC9A3R2), and PDZK1 (also known as CAP70 or NHERF3). See, for example, Haggie et al., J. Biol. Chem., 279(7): 5494-5500 (2004); Guggino, W. B., Proc. Am. Thorac. Soc., 1: 28-32 (2004); and Singh et al., J. Clin. Investig., 119(3): 540-550 (2009). Accordingly, a PDZ domain of a PDZ protein may be particularly useful as a target protein binding domain in a fusion protein designed to target either or both CFTRΔ508F and wild-type CFTR proteins in a gene therapy of the invention.

Accordingly, the invention provides new forms of gene therapies that provide fusion proteins that significantly elevate the levels of expression of an endogenous unstable protein (such as the unstable CFTRΔ508F) and/or the levels of expression of a desired heterologous protein (such as a wild-type CFTR) and therefore are more effective than past therapies to replace or restore missing or lost protein functions that are associated with various diseases.

Additional embodiments and features of the invention will be apparent from the following non-limiting examples.

EXAMPLES

Example 1. Compositions and Methods for Enhancing Expression of Target Proteins of Interest Using a Modified Arrangement Expression vector plasmids were constructed for expressing a target protein of interest linked to protein expression enhancing polypeptide described herein, which in turn may be linked to an standard epitope tag, which is usually attached at the carboxy (C) terminus or amino (N) terminus of the protein construct for easy identification or isolation using a corresponding anti-tag antibody and standard immunoblot assays.

A DNA linker molecule having a nucleotide sequence containing various restriction enzyme sites was produced by annealing two single-stranded DNA molecules having the sequences shown below (5' to 3'):

(SEQ ID NO: 187)
AGCTTGGTACCGGATCCGAATTCGATATCGCGGCCGCTCTCGAGTCTAGA
GGGCC and (SEQ ID NO: 188)
CTCTAGACTCGAGAGCGGCCGCGATATCGAATTCGGATCCGGTACCA.

The annealed linker molecule was then inserted into plasmid pcDNA3 (catalogue no. V790-20, Invitrogen) digested with HindIII and ApaI to yield plasmid pcDNA'.

DNA molecules encoding the V5 epitope tag (GKPIPN-PLLGLDST (SEQ ID NO:47)) or the Flag epitope tag (DYKDDDDK (SEQ ID NO:111)) were inserted into plasmid pcDNA'. A double-stranded DNA molecule having the coding sequence for the V5 epitope tag along with an N-terminal methionine, i.e., ATGGGTAAGCCTATC-CCTAACCCTCTCCTCGGTCTCGATTCTACG (SEQ ID NO:189), was inserted into pcDNA' digested with XhoI and XbaI to yield plasmid V5(C)-pcDNA' or with HindIII and KpnI to yield plasmid V5(N)-pcDNA'.

A DNA molecule having the coding sequence for the Flag epitope tag, i.e., GATTACAAGGATGACGATGACAAG (SEQ ID NO:190), was inserted into plasmid pcDNA' digested with XhoI and XbaI to yield plasmid Flag(N)-pcDNA'.

Preparation of DNA Molecules

DNA molecules encoding protein sequences were obtained by polymerase chain reaction (PCR), gene synthesis, or annealing of complementary DNA molecules using standard protocols. A DNA molecule encoding the amino acid sequence of an immunoglobulin Fc region was produced by standard oligonucleotide synthesis. A DNA molecule having a DNA sequence GGAGGCGGAAGTGGT GGGAGCGGTGGAAGCGGAGGC (SEQ ID NO:191) encoding the glycine-serine linker sequence GGGSGGSGGSGG (SEQ ID NO:121), was produced by annealing complementary single strands synthesized by standard methods.

Preparation of Expression Vector Plasmids for Expressing J Domain Fusion Proteins To express C-terminally V5-tagged IL13Rα2 receptor protein (see, FIG. 1A), a DNA molecule encoding an IL13Rα2 receptor protein was inserted into plasmid V5(C)-pcDNA' digested with HindIII and KpnI.

To express the fusion protein in which a J domain or BAG domain is attached to the N-terminus of IL13Rα2 receptor protein (see, FIG. 3A), a truncated IL13Rα2 receptor protein with its signal sequence deleted was inserted into plasmid V5(C)-pcDNA' digested with NotI and XhoI.

Figure 5A:
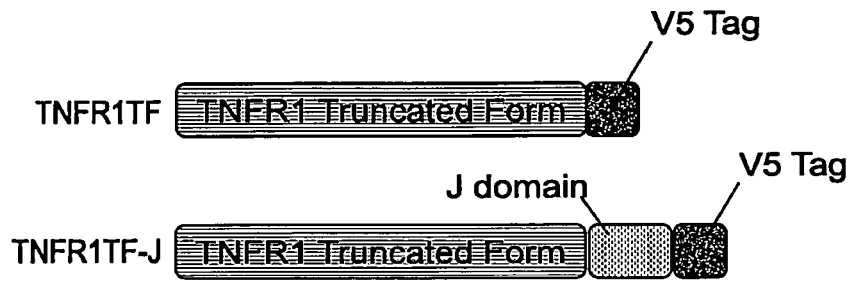

To express a V5-tagged, truncated TNR1 receptor protein (see, FIG. 5A), a DNA molecule encoding a truncated (extracellular domain only) TNR1 receptor protein was inserted into plasmid V5(C)-pcDNA' digested with HindIII and KpnI.

Figure 7A:
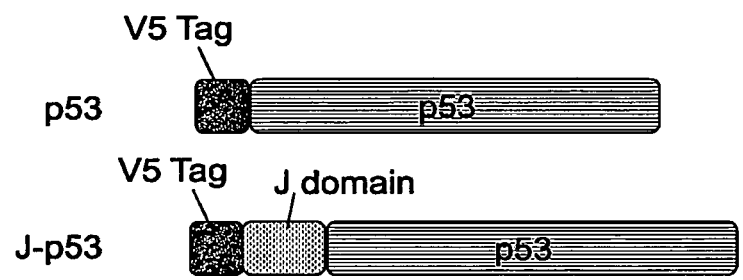
FIGS. 7A and 7B show results of an experiment described in Example 2 that demonstrates improvement in the level of expression of the cytoplasmic p53 protein in a modified arrangement in which p53 is linked to (fused with) a J domain fusion partner in comparison to the p53 protein alone.

To express a V5-tagged α1 anti-trypsin ("α1AT") (see, FIG. 4A), a DNA molecule encoding an α1 anti-trypsin was inserted into plasmid V5(C)-pcDNA' digested with HindIII and KpnI To express an N-terminally V5-tagged p53 protein (see, FIG. 7A), a DNA molecule encoding a p53 protein was inserted into plasmid V5(N)-pcDNA' digested with NotI and XhoI.

To express V-tagged CFTR and V5-tagged mutant CFTRΔ508F (see, FIG. 8A), a DNA molecule encoding a CFTR protein or a CFTRΔ508F protein was inserted into plasmid V5(N)-pcDNA' digested with NotI and XhoI.

For expressing fusion proteins comprising a protein of interest fused to a J domain, DNA molecules encoding J domains were subcloned into the EcoRI site of plasmid V5(C)-pcDNA' or the EcoRV plasmid V5(N)-pcDNA' to yield plasmid vectors J-V5(C)-pcDNA' or V5(N)-J-pcDNA', respectively. Fusion proteins were produced using Hsp40, SV40, and CSP J domains.

To express fusion proteins comprising a protein of interest fused to a BAG domain, DNA molecules encoding a BAG domain were subcloned into EcoRI and EcoRV sites of plasmid V5(C)-pcDNA' or plasmid V5(N)-pcDNA' to yield plasmid vectors BAG-V5(C)-pcDNA' or V5(N)-BAG-pcDNA', respectively. Fusion proteins were produced using BAG3, BAG4, BAG5, and BAG6 domains as indicated below.

DNA molecules encoding IL13Rα2, TNFR1, α1AT, p53, or CFTR (wild type or Δ508F mutant) were then inserted in frame with the J domain (or, in some instances, a BAG domain) sequence in one or more of the expression vectors to express the resulting fusion protein, which also possessed an N-terminal or C-terminal V5 epitope tag for convenient identification of the encoded protein.

Expression and Detection of Proteins in HEK293 Cells

Expression vector plasmids encoding various protein constructs were transfected into HEK293 cells with X-tremeGENE HP transfection reagent (catalogue no. 06365752001, Roche). As indicated in the examples below, a separate plasmid expressing the green fluorescent protein (GFP) was co-transfected with each expression vector plasmid encoding a fusion protein of the invention to monitor the transfection efficiency. Cultures of transfectant cells were incubated for two days, and culture medium and/or cell lysates were analyzed for expressed proteins using dot blot or Western immunoblot assays. Samples of culture media were centrifuged to remove debris prior to analysis. For cell lysates, cells were lysed in lysis buffer (10 mM Tris-HCl, pH8.0, 150 mM NaCl, 10 mM EDTA, 2% SDS) containing 2 mM PMSF. After brief sonication, the sample was analyzed for express proteins using dot blot or Western immunoblot assays. For Western blot analysis, samples were boiled in SDS-sample buffer and run on polyacrylamide electrophoresis, followed by transfer of separated protein bands to membrane (PVDF membrane).

The expression of GFP as an internal transfection control was detected using an anti-GFP antibody. Expressed proteins in dot blots and Western blots were detected using a chemiluminescent signal. Briefly, blots were reacted with a primary antibody that binds the particular epitope tag (e.g., V5 or Flag) carried by the proteins. After rinsing away unreacted primary antibody, a secondary, enzyme-linked antibody (e.g., horse radish peroxidase linked anti-IgG antibody) was allowed to react with primary antibody molecules bound to the blots. After rinsing, manufacturer's chemiluminescent reagent was added. Chemiluminescent signals in blots were captured on x-ray film. Where indicated, the images of the chemiluminescent signals were scanned with a densitometer and analyzed using the NIH ImageJ image processing program.

Assays for Protein Activities

Standard assays are available for detecting activities of the proteins of interest used in preparing J domain fusion proteins described herein.

A binding assay for IL13Rα2 binding function is described in "Identification of distinct roles for a dileucine and a tyrosine internalization motif in the interleukin (IL)-13 binding component IL13 receptor alpha 2 chain," *J. Biol. Chem.*, 276(27): 25114-25120 (2001).

A binding assay for TNFR binding function is described in "Recombinant 55-kDa tumor necrosis factor (TNF) receptor: Stoichiometry of binding to TNF alpha and TNF beta and inhibition of TNF activity," *J. Biol. Chem.*, 266(27): 18324-18329 (1991)

An assay for α1-antitrypsin (α1AT) activity is described in "Alpha 1-antitrypsin and protease complexation is induced by lipopolysaccharide, interleukin-1beta, and tumor necrosis factor-alpha in monocytes," *Am. J. Respir. Crit. Care Med.*, 157(1): 246-255 (1998).

An assay for p53 activity is described in "Influenza virus infection increases p53 activity: role of p53 activity in cell death and viral replication," *J. Virol.*, 79(14): 8802-8811 (2005).

An assay for CFTR activity is described in "Pharmacology of CFTR chloride channel activity," *Physiol. Rev.*, 79(1 Suppl.): S109-S144 (1999).

Figure 1A:
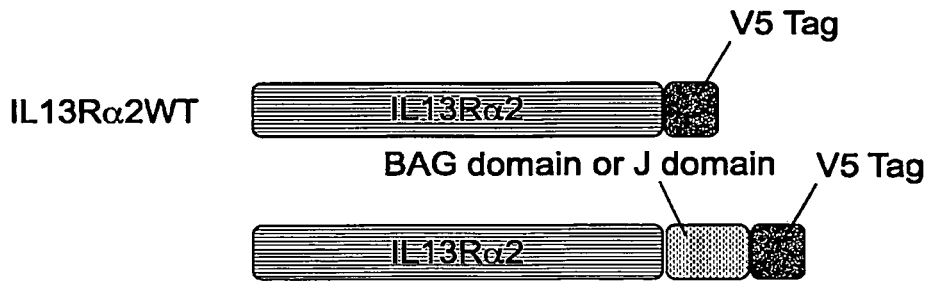
FIGS. 1A-1C illustrate a series of experiments described in Example 2 that demonstrate improvement in the level of expression of a target protein of interest (the IL13Rα2 receptor protein) in a modified arrangement in which the target protein is linked to a J domain (from Hsp40, SV40, or CSP J proteins) in comparison to the protein alone (IL13Rα2WT) or expressed as a fusion protein with a BAG domain (from BAG3, BAG4, BAG5, or BAG6 proteins).
Figure 1B:
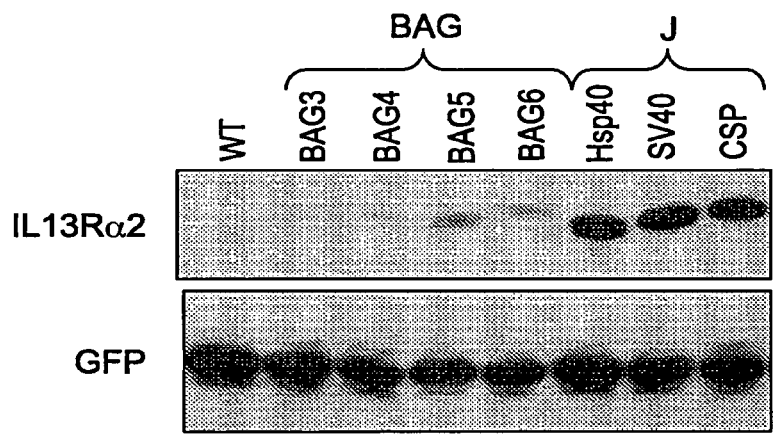
Figure 1C:
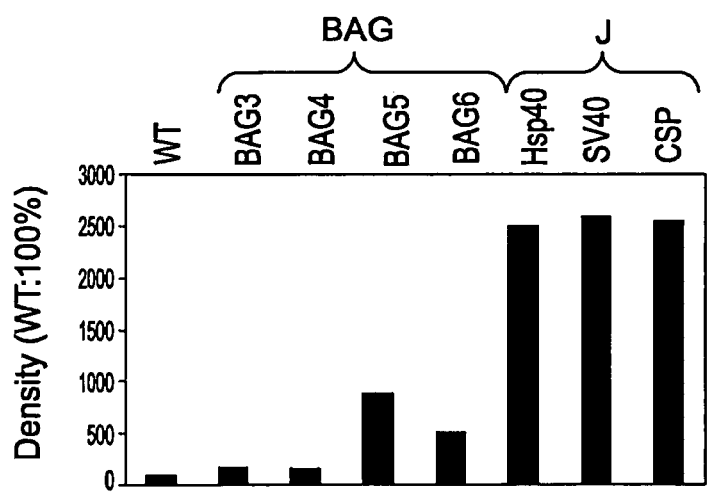

Example 2. Enhancement of Expression of Target Proteins in a Modified Arrangement FIG. 1A shows general diagrams of constructs for a C-terminally V5 epitope-tagged, full-length IL13Rα2 protein ("IL13Rα2WT") and for a C-terminally V5 epitope-tagged fusion protein comprising IL13Rα2 fused to a BAG or to a J domain.

The V5-tagged IL13Rα2WT protein comprises an amino acid sequence for a full-length IL13Rα2 protein linked at the C terminus to a V5 epitope tag, which in turn is linked to twelve C-terminal amino acid residues from the cloning site of the expression vector. The amino acid sequence for the V5-tagged IL13Rα2WT is shown in the table below.

TABLE 2

Amino Acid Sequence of a V5-Tagged IL13Rα2WT Protein.

| Protein Region (N- to C- terminal) | Sequence Identifier | Amino Acid Sequence 12345678901234567890123456 7890 |
|---|---|---|
| IL13Rα2WT domain (full-length) | SEQ ID NO: 192 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDTGTGSEFDIAA ALEGKPIPNPLLGLDSTSRGPYSIVSPKC |
| IL13Rα2FL | residues 1-380 of SEQ ID NO: 192 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDT |
| Linker | residues 381-393 of SEQ ID NO: 192 | GTGSEFDIAAALE |
| V5 epitope domain | residues 394-407 of SEQ ID NO: 192 | GKPIPNPLLGLDST |
| C-terminal vector residues | residues 408-419 of SEQ ID NO: 192 | SRGPYSIVSPKC |

The V5-tagged IL13Rα2WT-BAG3 domain fusion protein comprises an amino (N)-terminal amino acid sequence for a full-length IL13Rα2 protein linked to a BAG domain from the BAG3 protein, which in turn is linked to a V5 epitope tag, which in turn is linked to twelve C-terminal amino acid residues from the cloning site of the expression vector. The amino acid sequence for the IL13Rα2WT-BAG3 domain fusion protein is shown in the table below.

TABLE 3

Amino Acid Sequence of an IL13Rα2WT-BAG3 Domain Fusion Protein.

| Protein Region (N- to C-terminal) | Sequence Identifier | Amino Acid Sequence 12345678901234567890123456789 0 |
|---|---|---|
| IL13Rα2WT-BAG3 fusion protein | SEQ ID NO: 193 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDTGTGSEFHPGV LKVEAILEKVQGLEQAVDNFEGKKTDKKYL MIEEYLTKELLALDSVDPEGRADVRQARRD GVRKVQTILEKLEQKAIDDIAAALEGKPIP NPLLGLDSTSRGPYSIVSPKC |
| IL13Rα2WT domain (full-length) | residues 1-380 of SEQ ID NO: 193 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDT |
| Linker | residues 381-386 of SEQ ID NO: 193 | GTGSEF |
| BAG domain (from BAG3) | residues 387-468 of SEQ ID NO: 193 | HPGVLKVEAILEKVQGLEQAVDNFEGKKTD KKYLMIEEYLTKELLALDSVDPEGRADVRQ ARRDGVRKVQTILEKLEQKAID |
| Linker | residues 469-475 of SEQ ID NO: 193 | DIAAALE |
| V5 epitope domain | residues 476-489 of SEQ ID NO: 193 | GKPIPNPLLGLDST |
| C-terminal vector residues | residues 490-501 of SEQ ID NO: 193 | SRGPYSIVSPKC |

The V5-tagged IL13Rα2WT-BAG4 domain fusion protein comprises an amino (N)-terminal amino acid sequence for a full-length IL13Rα2 protein linked to a BAG domain from the BAG4 protein, which in turn is linked to a V5 epitope tag, which in turn is linked to twelve C-terminal amino acid residues from the cloning site of the expression vector. The amino acid sequence for the IL13Rα2WT-BAG4 domain fusion protein is shown in the table below.

TABLE 4

Amino Acid Sequence of an IL13Rα2WT-BAG4 Domain Fusion Protein.

| Protein Region (N- to C-terminal) | Sequence Identifier | Amino Acid Sequence 12345678901234567890123456789 0 |
|---|---|---|
| IL13Rα2WT-BAG4 Domain Fusion Protein | SEQ ID NO: 194 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDTGTGSEFESTP PSIKKIIHVLEKVQYLEQEVEEFVGKKTDK AYWLLEEMLTKELLELDSVETGGQDSVRQA RKEAVCKIQAILEKLEKKGLDIAAALEGKP IPNPLLGLDSTSRGPYSIVSPKC |
| IL13Rα2WT (full-length) | residues 1-380 of SEQ ID NO: 194 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDT |
| Linker | residues 381-386 of SEQ ID NO: 194 | GTGSEF |
| BAG domain (from BAG4) | residues 387-470 of SEQ ID NO: 194 | ESTPPSIKKIIHVLEKVQYLEQEVEEFVGK KTDKAYWLLEEMLTKELLELDSVETGGQDS VRQARKEAVCKIQAILEKLEKKGL |
| Linker | residues 471-477 of SEQ ID NO: 194 | DIAAALE |
| V5 epitope domain | residues 478-491 of SEQ ID NO: 194 | GKPIPNPLLGLDST |
| C-terminal vector residues | residues 492-503 of SEQ ID NO: 194 | SRGPYSIVSPKC |

The V5-tagged IL13Rα2WT-BAG5 domain fusion protein comprises an amino (N)-terminal amino acid sequence for a full-length IL13Rα2 protein linked to a BAG domain from the BAG5 protein, which in turn is linked to a V5 epitope tag, which in turn is linked to twelve C-terminal amino acid residues from the cloning site of the expression vector. The amino acid sequence for the IL13Rα2WT-BAG5 domain fusion protein is shown in the table below.

TABLE 5

Amino Acid Sequence of an IL13Rα2WT-BAG5 Domain Fusion Protein.

| Protein Region (N- to C-terminal) | Sequence Identifier | Amino Acid Sequence 12345678901234567890123456789 0 |
|---|---|---|
| IL13Rα2WT-BAG5 domain fusion protein | SEQ ID NO: 195 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDTGTGSEFEHPS HKAVWNVLGNLSEIQGEVLSFDGNRTDKNY IRLEELLTKQLLALDAVDPQGEEKCKAARK QAVRLAQNILSYLDLKSDEDIAAALEGKPI PNPLLGLDSTSRGPYSIVSPKC |
| IL13Rα2WT (full-length) | residues 1-380 of SEQ ID NO: 195 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDT |
| Linker | residues 381-386 of SEQ ID NO: 195 | GTGSEF |
| BAG domain (from BAG5) | residues 387-469 of SEQ ID NO: 195 | EHPSHKAVWNVLGNLSEIQGEVLSFDGNRT DKNYIRLEELLTKQLLALDAVDPQGEEKCK AARKQAVRLAQNILSYLDLKSDE |
| Linker | residues 470-476 of SEQ ID NO: 195 | DIAAALE |
| V5 epitope domain | residues 477-490 of SEQ ID NO: 195 | GKPIPNPLLGLDST |
| C-terminal residues | residues 491-502 of SEQ ID NO: 195 | SRGPYSIVSPKC |

The V5-tagged IL13Rα2WT-BAG6 domain fusion protein comprises an amino (N)-terminal amino acid sequence for a full-length IL13Rα2 protein linked to a BAG domain from the BAG6 protein, which in turn is linked to a V5 epitope tag, which in turn is linked to twelve C-terminal amino acid residues from the cloning site of the expression vector. The amino acid sequence for the IL13Rα2WT-BAG6 domain fusion protein is shown in the table below.

TABLE 6

Amino Acid Sequence of an IL13Rα2WT-BAG6 Domain Fusion Protein.

| Protein Region (N- to C-terminal) | Sequence Identifier | Amino Acid Sequence 12345678901234567890123456789 0 |
|---|---|---|
| IL13Rα2WT-BAG6 domain fusion protein | SEQ ID NO: 196 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDTGTGSEFMPAK RRKTMQGEGPQLLLSEAVSRAAKAAGARPL TSPESLSRDLEAPEVQESYRQQLRSDIQKR LQEDPNYSPQRFPNAQRAFADDPDIAAALE GKPIPNPLLGLDSTSRGPYSIVSPKC |
| IL13Rα2WT (full-length) | residues 1-380 of SEQ ID NO: 196 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDT |
| Linker | residues 381-386 of SEQ ID NO: 196 | GTGSEF |
| BAG domain (from BAG6) | residues 387-473 of SEQ ID NO: 196 | MPAKRRKTMQGEGPQLLLSEAVSRAAKAAG ARPLTSPESLSRDLEAPEVQESYRQQLRSD IQKRLQEDPNYSPQRFPNAQRAFADDP |
| Linker | residues 474-480 of SEQ ID NO: 196 | DIAAALE |
| V5 epitope domain | residues 481-494 of SEQ ID NO: 196 | GKPIPNPLLGLDST |
| C-terminal vector residues | residues 495-506 of SEQ ID NO: 196 | SRGPYSIVSPKC |

The V5-tagged IL13Rα2WT-Hsp40 J domain fusion protein comprises an amino (N)-terminal amino acid sequence for a full-length IL13Rα2 protein linked to a J domain from the Hsp40 protein, which in turn is linked to a V5 epitope tag, which in turn is linked to twelve C-terminal amino acid residues from the cloning site of the expression vector. The amino acid sequence for the IL13Rα2-Hsp40 J domain fusion protein is shown in the table below.

TABLE 7

Amino Acid Sequence of an IL13Rα2WT-Hsp40 J Domain Fusion Protein.

| Protein Region (N- to C-terminal) | Sequence Identifier | Amino Acid Sequence 12345678901234567890123456 7890 |
|---|---|---|
| IL13Rα2WT-Hsp40 J domain fusion protein | SEQ ID NO: 197 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDTGTGSEFMGKD YYQTLGLARGASDEEIKRAYRRQALRYHPD KNKEPGAEEKFKEIAEAYDVLSDPRKREIF DRYDIAAALEGKPIPNPLLGLDSTSRGPYS IVSPKC |
| IL13Rα2WT domain (full-length) | residues 1-380 of SEQ ID NO: 197 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDT |
| Linker | residues 381-386 of SEQ ID NO: 197 | GTGSEF |
| Hsp40 J domain | residues 387-453 of SEQ ID NO: 197 | MGKDYYQTLGLARGASDEEIKRAYRRQALR YHPDKNKEPGAEEKFKEIAEAYDVLSDPRK REIFDRY |
| Linker | residues 454-460 of SEQ ID NO: 197 | DIAAALE |
| V5 epitope | residues 461-474 of SEQ ID NO: 197 | GKPIPNPLLGLDST |
| C-terminal vector residues | residues 475-486 of SEQ ID NO: 197 | SRGPYSIVSPKC |

The V5-tagged IL13Rα2WT-SV40 J domain fusion protein comprises an amino (N)-terminal amino acid sequence for a full-length IL13Rα2 protein linked to a J domain from the SV40 J protein, which in turn is linked to a V5 epitope tag, which in turn is linked to twelve C-terminal amino acid residues from the cloning site of the expression vector. The amino acid sequence for the IL13Rα2-SV40 J domain fusion protein is shown in the table below.

TABLE 8

Amino Acid Sequence of an IL13Rα2WT-SV40 J Domain Fusion Protein.

| Protein Region (N- to C-terminal) | Sequence Identifier | Amino Acid Sequence 12345678901234567890123456 7890 |
|---|---|---|
| IL13Rα2WT-SV40 J domain fusion protein | SEQ ID NO: 198 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDTGTGSEFMDKV LNREESLQLMDLLGLERSAWGNIPLMRKAY LKKCKEFHPDKGGDEEKMKKMNTLYKKMED GVKYAHQPDFGGFWDADIAAALEGKPIPNP LLGLDSTSRGPYSIVSPKC |
| IL13Rα2WT domain (full-length) | residues 1-380 of SEQ ID NO: 198 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDT |
| Linker | residues 381-386 of SEQ ID NO: 198 | GTGSEF |
| SV40 J domain | residues 387-466 of SEQ ID NO: 198 | MDKVLNREESLQLMDLLGLERSAWGNIPLM RKAYLKKCKEFHPDKGGDEEKMKKMNTLYK KMEDGVKYAHQPDFGGFWDA |
| Linker | residues 467-473 of SEQ ID NO: 198 | DIAAALE |
| V5 epitope | residues 474-487 of SEQ ID NO: 198 | GKPIPNPLLGLDST |
| C-terminal vector residues | residues 488-499 of SEQ ID NO: 198 | SRGPYSIVSPKC |

The V5-tagged IL13Rα2WT-CSP J domain fusion protein comprises an amino (N)-terminal amino acid sequence for a full-length IL13Rα2 protein linked to a J domain from the CSP protein, which in turn is linked to a V5 epitope tag, which in turn is linked to twelve C-terminal amino acid residues from the cloning site of the expression vector. The amino acid sequence for the IL13Rα2WT-CSP J domain fusion protein is shown in the table below.

TABLE 9

Amino Acid Sequence of an IL13Rα2WT-CSP J Domain Fusion Protein.

| Protein Region (N- to C-terminal) | Sequence Identifier | Amino Acid Sequence 123456789012345678901234567890 |
|---|---|---|
| IL13Rα2WT-CSP J domain fusion protein | SEQ ID NO: 199 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDTGTGSEFMADQ RQRSLSTSGESLYHVLGLDKNATSDDIKKS YRKLALKYHPDKNPDNPEAADKFKEINNAH AILTDATKRNIYDKYGSLGLYVDIAAALEG KPIPNPLLGLDSTSRGPYSIVSPKC |
| IL13Rα2 domain | residues 1-380 of SEQ ID NO: 199 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKTLLRFWLPFGFILILVIFVTG LLLRKPNTYPKMIPEFFCDT |
| Linker | residues 381-386 of SEQ ID NO: 199 | GTGSEF |
| CSP J domain | residues 387-472 of SEQ ID NO: 199 | MADQRQRSLSTSGESLYHVLGLDKNATSDD IKKSYRKLALKYHPDKNPDNPEAADKFKEI NNAHAILTDATKRNIYDKYGSLGLYV |
| Linker | residues 473-479 of SEQ ID NO: 199 | DIAAALE |
| V5 epitope tag | residues 480-493 of SEQ ID NO: 199 | GKPIPNPLLGLDST |
| C-terminal vector residues | residues 494-505 of SEQ ID NO: 199 | SRGPYSIVSPKC |

Using the expression vectors described above, the level of expression IL13Rα2-V5 was compared with that of various IL13Rα2 fusion proteins comprising a BAG domain or J domain in transfected HEK293 cells. The expression level of various fusion proteins in cells are shown in the Western blot in FIG. 1B. The first row shows lanes of the gel loaded with equal amounts of cell lysate protein. The second row shows expression of GFP as an internal transfection control. As shown in the first row of FIG. 1B, only a faint band was detected for the V5-tagged IL13Rα2, which was used to represent expression of the wild-type (WT) IL13Rα2 protein, indicating poor expression. Fusion proteins comprising IL13Rα2 and a BAG domain (BAG3, BAG4, BAG5, BAG6) were expressed at slightly higher levels. In contrast, fusion proteins comprising IL13Rα2 and any of the J domains were all expressed at dramatically higher levels than either the V5 tagged IL13Rα2 or the fusion proteins comprising IL13Rα2 and a BAG domain. The results of a densitometry analysis of the signals in FIG. 1B are shown in FIG. 1C. The fusion proteins comprising IL13Rα2 and any of the J domains were expressed at a level as much as 25-fold higher than the V5 epitope tagged IL13Rα2 (taken as 100%). See, bar graphs in FIG. 1C.

Truncated Form of IL13Rα2 Expression and Secretion IL13Rα2 is a membrane receptor protein that binds to interleukin-13 (IL13) and mediates allergic inflammation. Binding of IL13 to the membrane-associated IL13Rα2 receptor transduces a signal to the cytoplasm that sets off an inflammatory response. Such a response is particularly detrimental in the case of asthma. A portion of the expressed, membrane-associated IL13Rα2 molecules is cleaved on the cell surface, releasing a soluble truncated form of IL13Rα2 (IL13Rα2TF) into the extracellular space. The truncated form of IL13Rα2 retains the ability to bind IL13 but cannot transmit a signal to the cell due to the absence of the transmembrane and cytoplasmic regions found in the full-length, membrane-associates protein. Accordingly, the truncated form of IL13Rα2 has been employed as a decoy receptor to treat asthma by binding to IL13 molecules without transducing a signal to the cell to set off an inflammatory response. For such therapeutic applications, a genetically engineered, truncated form of IL13Rα2 has been expressed in mammalian cells and purified as a secreted protein from culture medium. However, the production of the truncated form of IL13Rα2 is inefficient due to difficulties in expression and secretion of the protein.

Figure 2A:
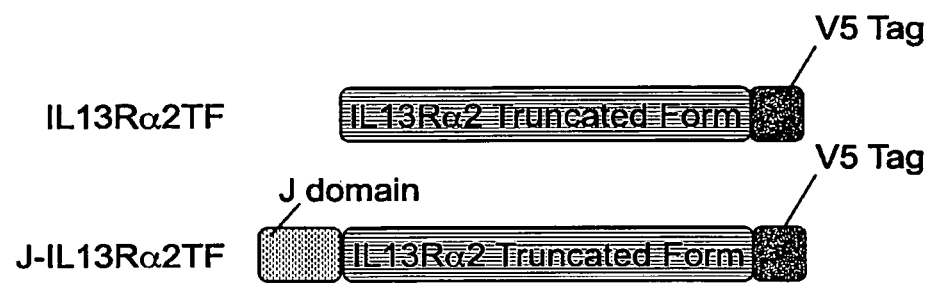
FIGS. 2A and 2B show the results of an experiment described in Example 2 that examined improvement in the level of expression of a secreted target protein of interest in a modified arrangement in which a truncated form ("TF") of the IL13Rα2 receptor protein (which is the extracellular portion of the IL13Rα2 receptor protein containing the ligand binding domain) is linked to a J domain (J-IL13Rα2TF) in comparison to the truncated receptor protein alone (IL13Rα2TF).

The ability of a J domain to enhance expression of a soluble, truncated form of IL13Rα2 (IL13Rα2TF) was studied. In order to confirm if conjugation of a J domain to a truncated form of IL13Rα2 enhances expression of the secreted protein, plasmids that expressed an IL13Rα2TF or a fusion protein comprising IL13Rα2TF and an N-terminal J domain from Erdj3 were constructed. The proteins also possessed the V5 epitope tag for easy identification. See, diagrams of constructs in FIG. 2A.

The amino acid sequence for a V5 tagged IL13Rα2TF used in this experiment is shown in the table below.

TABLE 10

Amino Acid Sequence of a V5-Tagged IL13Rα2TF Fusion Protein.

| Protein Region (N- to C-terminal) | Sequence Identifier | Amino Acid Sequence 1234567890123456789012345678 90 |
|---|---|---|
| IL13Rα2TF protein | SEQ ID NO: 200 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKGTGSEFDIAAALEGKPIPNPL LGLDSTSRGPYSIVSPKC |
| IL13Rα2TF | residues 1-339 of SEQ ID NO: 200 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKK |
| Linker | residues 340-352 of SEQ ID NO: 200 | GTGSEFDIAAALE |
| V5 epitope domain | residues 353-366 of SEQ ID NO: 200 | GKPIPNPLLGLDST |
| Linker | residues 367-378 of SEQ ID NO: 200 | SRGPYSIVSPKC |

The amino acid sequence for a J domain fusion protein comprising an N-terminal J domain of the Erdj3 J protein, a mature (i.e., no signal sequence) and truncated IL13Rα2 (IL13Rα2TF), and the V5 epitope tag is shown in the table below.

TABLE 11

Amino Acid Sequence of a V5-Tagged Erdj3 J domain-IL13Rα2TF Protein.

| Protein Region (N- to C-terminal) | Sequence Identifier | Amino Acid Sequence 123456789012345678901234567890 |
|---|---|---|
| Erdj3 J domain-IL13Rα2TF fusion protein | SEQ ID NO: 201 | MAPQNLSTFCLLLLYLIGAVIAGRDFYKIL GVPRSASIKDIKKAYRKLALQLHPDRNPDD PQAQEKFQDLGAAYEVLSDSEKRDIAAASD TEIKVNPPQDFEIVDPGYLGYLYLQWQPPL SLDHFKECTVEYELKYRNIGSETWKTIITK NLHYKDGFDLNKGIEAKIHTLLPWQCTNGS EVQSSWAETTYWISPQGIPETKVQDMDCVY YNWQYLLCSWKPGIGVLLDTNYNLFYWYEG LDHALQCVDYIKADGQNIGCRFPYLEASDY KDFYICVNGSSENKPIRSSYFTFQLQNIVK PLPPVYLTFTRESSCEIKLKWSIPLGPIPA RCFDYEIEIREDDTTLVTATVENETYTLKT TNETRQLCFVVRSKVNIYCSDDGIWSEWSD KQCWEGEDLSKKLEGKPIPNPLLGLDSTSR GPYSIVSPKC |
| Erdj3 J domain | residues 1-83 of SEQ ID NO: 201 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-88 of SEQ ID NO: 201 | DIAAA |
| IL13Rα2TF (with mature N-terminus) | residues 89-402 of SEQ ID NO: 201 | SDTEIKVNPPQDFEIVDPGYLGYLYLQWQP PLSLDHFKECTVEYELKYRNIGSETWKTII TKNLHYKDGFDLNKGIEAKIHTLLPWQCTN GSEVQSSWAETTYWISPQGIPETKVQDMDC VYYNWQYLLCSWKPGIGVLLDTNYNLFYWY EGLDHALQCVDYIKADGQNIGCRFPYLEAS DYKDFYICVNGSSENKPIRSSYFTFQLQNI VKPLPPVYLTFTRESSCEIKLKWSIPLGPI PARCFDYEIEIREDDTTLVTATVENETYTL KTTNETRQLCFVVRSKVNIYCSDDGIWSEW SDKQCWEGEDLSKK |
| Linker | residues 403-404 of SEQ ID NO: 201 | LE |
| V5 epitope domain | residues 405-418 of SEQ ID NO: 201 | GKPIPNPLLGLDST |
| C-terminal vector residues | residues 419-430 of SEQ ID NO: 201 | SRGPYSIVSPKC |

The amino acid sequence for a BAG domain fusion protein comprising a signal sequence, a BAG domain of BAG3, a mature (i.e., no signal sequence) and truncated IL13Rα2 (IL13Rα2TF), and the V5 epitope tag is shown in the table below.

TABLE 12

Amino Acid Sequence of a V5-Tagged BAG domain-IL13Rα2TF Fusion Protein.

| Protein Region (N- to C-terminal) | Sequence Identifier | Amino Acid Sequence 12345678901234567890123456789 0 |
|---|---|---|
| BAG domain-IL13Rα2TF fusion protein | SEQ ID NO: 202 | MGVKVLFALICIAVAEAGTGSEFHPGVLKV EAILEKVQGLEQAVDNFEGKKTDKKYLMIE EYLTKELLALDSVDPEGRADVRQARRDGVR KVQTILEKLEQKAIDDIAAASDTEIKVNPP QDFEIVDPGYLGYLYLQWQPPLSLDHFKEC TVEYELKYRNIGSETWKTIITKNLHYKDGF DLNKGIEAKIHTLLPWQCTNGSEVQSSWAE TTYWISPQGIPETKVQDMDCVYYNWQYLLC SWKPGIGVLLDTNYNLFYWYEGLDHALQCV DYIKADGQNIGCRFPYLEASDYKDFYICVN GSSENKPIRSSYFTFQLQNIVKPLPPVYLT FTRESSCEIKLKWSIPLGPIPARCFDYEIE IREDDTTLVTATVENETYTLKTTNETRQLC FVVRSKVNIYCSDDGIWSEWSDKQCWEGED LSKKLEGKPIPNPLLGLDSTSRGPYSIVSP KC |
| Signal Sequence | residues 1-17 of SEQ ID NO: 202 | MGVKVLFALICIAVAEA |
| Linker | residues 18-23 of SEQ ID NO: 202 | GTGSEF |
| BAG domain (from BAG3) | residues 24-105 of SEQ ID NO: 202 | HPGVLKVEAILEKVQGLEQAVDNFEGKKTD KKYLMIEEYLTKELLALDSVDPEGRADVRQ ARRDGVRKVQTILEKLEQKAID |
| Linker | residues 106-110 of SEQ ID NO: 202 | DIAAA |
| IL13Rα2TF (with mature N-terminus) | residues 111-424 of SEQ ID NO: 202 | SDTEIKVNPPQDFEIVDPGYLGYLYLQWQP PLSLDHFKECTVEYELKYRNIGSETWKTII TKNLHYKDGFDLNKGIEAKIHTLLPWQCTN GSEVQSSWAETTYWISPQGIPETKVQDMDC VYYNWQYLLCSWKPGIGVLLDTNYNLFYWY EGLDHALQCVDYIKADGQNIGCRFPYLEAS DYKDFYICVNGSSENKPIRSSYFTFQLQNI VKPLPPVYLTFTRESSCEIKLKWSIPLGPI PARCFDYEIEIREDDTTLVTATVENETYTL KTTNETRQLCFVVRSKVNIYCSDDGIWSEW SDKQCWEGEDLSKK |
| Linker | residues 425-426 of SEQ ID NO: 202 | LE |
| V5 epitope domain | residues 427-440 of SEQ ID NO: 202 | GKPIPNPLLGLDST |
| C-terminal vector residues | residues 441-452 of SEQ ID NO: 202 | SRGPYSIVSPKC |

Figure 2B:
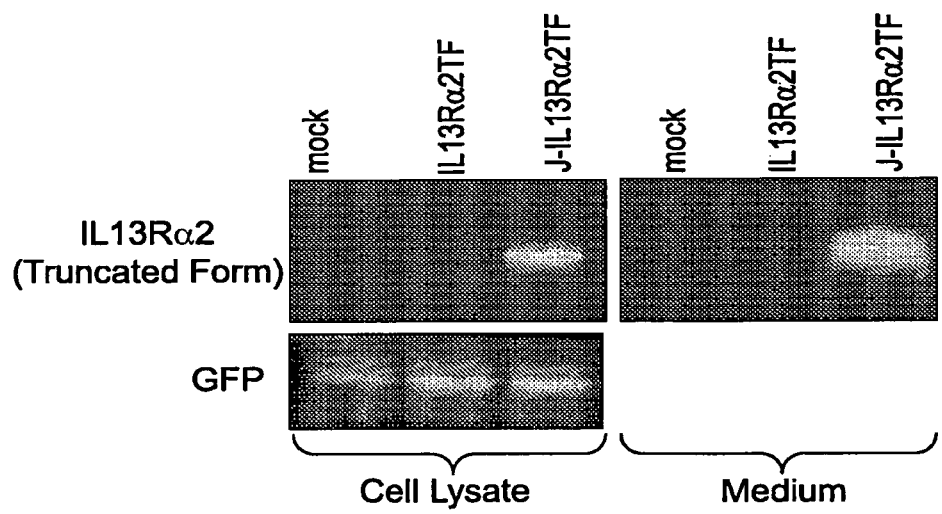

The expression plasmids were transfected into HEK293 cells. Samples of cell lysates and culture media from two-day cultures of the transfected cells were analyzed by immunoblotting with anti-V5 antibody for expression of IL13Rα2TF or IL13Rα2TF-J domain fusion protein. As shown in FIG. 2B, the expression of the IL13Rα2TF protein was barely detected in cell lysates (lane 2), and no detection was observed in the medium. In contrast, the level of expression of the IL13Rα2TF-J domain fusion protein was dramatically higher both inside the cell (cell lysate samples) and also as secreted into the medium. See, FIG. 2B. A similar effect was observed when the J domain was attached to the C-terminus of the truncated form of IL13Rα2 (data not shown).

Figure 3A:
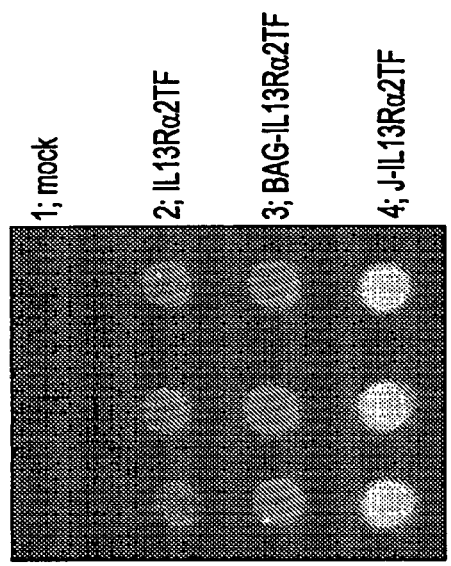
FIGS. 6A-6C-3 show results of a series of experiments described in Example 2 that demonstrate improvement in the level of expression of target Fc fusion proteins of interest in a modified arrangement in which each of three target proteins of interest is linked to a J domain fusion partner.
Figure 3B:
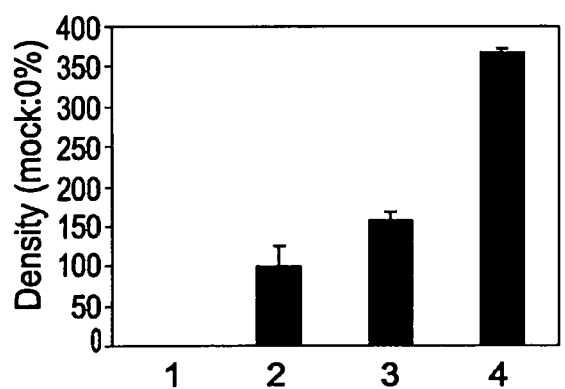

Another experiment was performed to better quantify the secreted proteins using a dot blot immunoassay. HEK293 cells were transfected with an expression vector plasmid for expressing IL13Rα2TF, a BAG domain fused to IL13Rα2TF (BAG-IL13RαTF), or a J domain fused to IL13Rα2TF (J-IL13RαTF). Transfected cells were cultured for two days, and samples of cell culture media were analyzed for secreted proteins using a dot blot immunoassay. The results are shown in FIGS. 3A and 3B. FIG. 3A shows x-ray film images of chemiluminescent signals for V5-tagged proteins secreted into culture media. As shown in FIG. 3A, although the fusion protein comprising a BAG domain linked to IL13Rα2TF (lane 3) may have provided some minor enhancement in the level of secreted protein compared to the unfused IL13Rα2TF (lane 2), a fusion protein comprising a J domain linked to IL13Rα2TF (lane 3) exhibited a significantly enhanced level of secreted protein relative to either the unfused IL13Rα2TF (lane 2) or the or the BAG domain-IL13Rα2TF fusion protein (lane 3). The results of a densitometry analysis of the signals of the dot blots in FIG. 3A using the NIH ImageJ image processing program are shown in FIG. 3B. The bar graphs in FIG. 3B clearly show the significantly higher level of expression of secreted J domain-IL13Rα2TF fusion protein (bar graph 4) compared to either the IL13Rα2TF (bar graph 2) or the BAG domain-IL13Rα2TF fusion protein (bar graph 3). Use of the J domain fusion resulted in an approximate 3.5-fold increase in the amount of IL13Rα2TF being secreted by the transformed cells, compared to the expression level of cells transformed to express the IL13Rα2TF protein alone.

J Domain-α1 Anti-Trypsin Fusion Protein in a Modified Arrangement in Human Cells The α1 anti-trypsin (α1AT) protein is secreted from the liver, and circulates in blood vessels. The function of α1AT is to protect tissues, particularly lung tissue, from excess proteases. The lung is damaged by proteases in a disease called α1 anti-trypsin deficiency. Subjects affected by α1 anti-trypsin deficiency may develop emphysema, asthma, and/or chronic obstructive pulmonary disease (COPD). Currently α1AT (purified from human serum) is used for the treatment of patients with al anti-trypsin deficiency. This treatment is expensive, and subjects that receive the human serum are at risk of contracting pathogens present in the human serum.

Figure 4A:
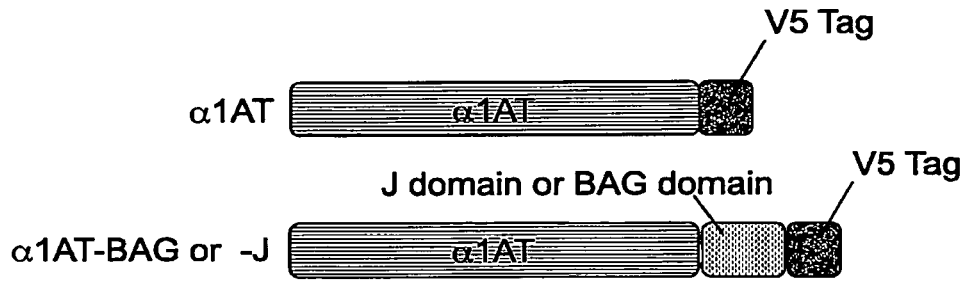

The effect of fusing a J domain to an α1 anti-trypsin (α1AT) was studied as a possible strategy for enhancing the levels of expression and secretion of a desired therapeutically useful protein in transfected cells. As shown in FIG. 4A, DNA constructs were prepared encoding a V5-tagged α1AT, a V5-tagged α1AT-BAG domain fusion protein, and a V5-tagged α1AT-J domain fusion protein.

The amino acid sequence of a V5-tagged α1AT protein is shown in the table below.

TABLE 13

Amino Acid Sequence of a V5-Tagged α1AT Protein.

| Protein Region (N- to C-terminal) | Sequence Identifier | Amino Acid Sequence 12345678901234567890123456 7890 |
|---|---|---|
| α1AT protein | SEQ ID NO: 203 | MPSSVSWGILLLAGLCCLVPVSLAEDPQGD AAQKTDTSHHDQDHPTFNKITPNLAEFAFS LYRQLAHQSNSTNIFFSPVSIATAFAMLSL GTKADTHDEILEGLNFNLTEIPEAQIHEGF QELLRTLNQPDSQLQLTTGNGLFLSEGLKL VDKFLEDVKKLYHSEAFTVNFGDTEEAKKQ INDYVEKGTQGKIVDLVKELDRDTVFALVN YIFFKGKWERPFEVKDTEEEDFHVDQVTTV KVPMMKRLGMFNIQHCKKLSSWVLLMKYLG NATAIFFLPDEGKLQHLENELTHDIITKFL ENEDRRSASLHLPKLSITGTYDLKSVLGQL GITKVFSNGADLSGVTEEAPLKLSKAVHKA VLTIDEKGTEAAGAMFLEAIPMSIPPEVKF NKPFVFLMIEQNTKSPLFMGKVVNPTQKGT GSEFDIAAALEGKPIPNPLLGLDSTSRGPY SIVSPKC |
| α1AT | residues 1-418 of SEQ ID NO: 203 | MPSSVSWGILLLAGLCCLVPVSLAEDPQGD AAQKTDTSHHDQDHPTFNKITPNLAEFAFS LYRQLAHQSNSTNIFFSPVSIATAFAMLSL GTKADTHDEILEGLNFNLTEIPEAQIHEGF QELLRTLNQPDSQLQLTTGNGLFLSEGLKL VDKFLEDVKKLYHSEAFTVNFGDTEEAKKQ INDYVEKGTQGKIVDLVKELDRDTVFALVN YIFFKGKWERPFEVKDTEEEDFHVDQVTTV KVPMMKRLGMFNIQHCKKLSSWVLLMKYLG NATAIFFLPDEGKLQHLENELTHDIITKFL ENEDRRSASLHLPKLSITGTYDLKSVLGQL GITKVFSNGADLSGVTEEAPLKLSKAVHKA VLTIDEKGTEAAGAMFLEAIPMSIPPEVKF NKPFVFLMIEQNTKSPLFMGKVVNPTQK |
| Linker | residues 419-431 of SEQ ID NO: 203 | GTGSEFDIAAALE |
| V5 epitope domain | residues 432-445 of SEQ ID NO: 203 | GKPIPNPLLGLDST |
| C-terminal vector residues | residues 446-457 of SEQ ID NO: 203 | SRGPYSIVSPKC |

The amino acid sequence of a BAG domain fusion protein comprising α1AT, the BAG domain of BAG3, and the V5 epitope tag is shown in the table below.

TABLE 14

Amino Acid Sequence of α1AT-BAG Fusion Protein.

| Protein Region (N- to C-terminal) | Sequence Identifier | Amino Acid Sequence |
|---|---|---|
| α1AT-BAG domain fusion protein | SEQ ID NO: 204 | MPSSVSWGILLLAGLCCLVPVSLAEDPQGD AAQKTDTSHHDQDHPTFNKITPNLAEFAFS LYRQLAHQSNSTNIFFSPVSIATAFAMLSL GTKADTHDEILEGLNFNLTEIPEAQIHEGF QELLRTLNQPDSQLQLTTGNGLFLSEGLKL VDKFLEDVKKLYHSEAFTVNFGDTEEAKKQ INDYVEKGTQGKIVDLVKELDRDTVFALVN YIFFKGKWERPFEVKDTEEEDFHVDQVTTV KVPMMKRLGMFNIQHCKKLSSWVLLMKYLG NATAIFFLPDEGKLQHLENELTHDIITKFL ENEDRRSASLHLPKLSITGTYDLKSVLGQL GITKVFSNGADLSGVTEEAPLKLSKAVHKA VLTIDEKGTEAAGAMFLEAIPMSIPPEVKF NKPFVFLMIEQNTKSPLFMGKVVNPTQKGT GSEFHPGVLKVEAILEKVQGLEQAVDNFEG KKTDKKYLMIEEYLTKELLALDSVDPEGRA DVRQARRDGVRKVQTILEKLEQKAIDDIAA ALEGKPIPNPLLGLDSTSRGPYSIVSPKC |
| α1AT | residues 1-418 of SEQ ID NO: 204 | MPSSVSWGILLLAGLCCLVPVSLAEDPQGD AAQKTDTSHHDQDHPTFNKITPNLAEFAFS LYRQLAHQSNSTNIFFSPVSIATAFAMLSL GTKADTHDEILEGLNFNLTEIPEAQIHEGF QELLRTLNQPDSQLQLTTGNGLFLSEGLKL VDKFLEDVKKLYHSEAFTVNFGDTEEAKKQ INDYVEKGTQGKIVDLVKELDRDTVFALVN YIFFKGKWERPFEVKDTEEEDFHVDQVTTV KVPMMKRLGMFNIQHCKKLSSWVLLMKYLG NATAIFFLPDEGKLQHLENELTHDIITKFL ENEDRRSASLHLPKLSITGTYDLKSVLGQL GITKVFSNGADLSGVTEEAPLKLSKAVHKA VLTIDEKGTEAAGAMFLEAIPMSIPPEVKF NKPFVFLMIEQNTKSPLFMGKVVNPTQK |
| Linker | residues 419-424 of SEQ ID NO: 204 | GTGSEF |
| BAG domain (from BAG3) | residues 425-506 of SEQ ID NO: 204 | HPGVLKVEAILEKVQGLEQAVDNFEGKKTD KKYLMIEEYLTKELLALDSVDPEGRADVRQ ARRDGVRKVQTILEKLEQKAID |
| Linker | residues 507-513 of SEQ ID NO: 204 | DIAAALE |
| V5 epitope domain | residues 514-527 of SEQ ID NO: 204 | GKPIPNPLLGLDST |
| C-terminal vector residues | residues 528-539 of SEQ ID NO: 204 | SRGPYSIVSPKC |

The amino acid sequence of a J domain fusion protein comprising α1AT, the Erdj3 J domain, and the V5 epitope tag is shown in the table below.

TABLE 15

Amino Acid Sequence of α1AT-J Domain Protein.

| Protein Region (N- to C-terminal) | Sequence Identifier | Amino Acid Sequence<br>123456789012345678901234567890 |
|---|---|---|
| α1AT-Erdj3 J domain fusion protein | SEQ ID NO: 205 | MPSSVSWGILLLAGLCCLVPVSLAEDPQGD<br>AAQKTDTSHHDQDHPTFNKITPNLAEFAFS<br>LYRQLAHQSNSTNIFFSPVSIATAFAMLSL<br>GTKADTHDEILEGLNFNLTEIPEAQIHEGF<br>QELLRTLNQPDSQLQLTTGNGLFLSEGLKL<br>VDKFLEDVKKLYHSEAFTVNFGDTEEAKKQ<br>INDYVEKGTQGKIVDLVKELDRDTVFALVN<br>YIFFKGKWERPFEVKDTEEEDFHVDQVTTV<br>KVPMMKRLGMFNIQHCKKLSSWVLLMKYLG<br>NATAIFFLPDEGKLQHLENELTHDIITKFL<br>ENEDRRSASLHLPKLSITGTYDLKSVLGQL<br>GITKVFSNGADLSGVTEEAPLKLSKAVHKA<br>VLTIDEKGTEAAGAMFLEAIPMSIPPEVKF<br>NKPFVFLMIEQNTKSPLFMGKVVNPTQKGT<br>GSEFGRDFYKILGVPRSASIKDIKKAYRKL<br>ALQLHPDRNPDDPQAQEKFQDLGAAYEVLS<br>DSEKRDIAAALEGKPIPNPLLGLDSTSRGP<br>YSIVSPKC |
| α1AT | residues 1-418 of SEQ ID NO: 205 | MPSSVSWGILLLAGLCCLVPVSLAEDPQGD<br>AAQKTDTSHHDQDHPTFNKITPNLAEFAFS<br>LYRQLAHQSNSTNIFFSPVSIATAFAMLSL<br>GTKADTHDEILEGLNFNLTEIPEAQIHEGF<br>QELLRTLNQPDSQLQLTTGNGLFLSEGLKL<br>VDKFLEDVKKLYHSEAFTVNFGDTEEAKKQ<br>INDYVEKGTQGKIVDLVKELDRDTVFALVN<br>YIFFKGKWERPFEVKDTEEEDFHVDQVTTV<br>KVPMMKRLGMFNIQHCKKLSSWVLLMKYLG<br>NATAIFFLPDEGKLQHLENELTHDIITKFL<br>ENEDRRSASLHLPKLSITGTYDLKSVLGQL<br>GITKVFSNGADLSGVTEEAPLKLSKAVHKA<br>VLTIDEKGTEAAGAMFLEAIPMSIPPEVKF<br>NKPFVFLMIEQNTKSPLFMGKVVNPTQK |
| Linker | residues 419-424 of SEQ ID NO: 205 | GTGSEF |
| Erdj3 J domain | residues 425-485 of SEQ ID NO: 205 | GRDFYKILGVPRSASIKDIKKAYRKLALQL<br>HPDRNPDDPQAQEKFQDLGAAYEVLSDSEK<br>R |
| Linker | residues 486-492 of SEQ ID NO: 205 | DIAAALE |
| V5 epitope domain | residues 493-506 of SEQ ID NO: 205 | GKPIPNPLLGLDST |
| C-terminal vector residues | residues 507-518 of SEQ ID NO: 205 | SRGPYSIVSPKC |

Figure 4B:
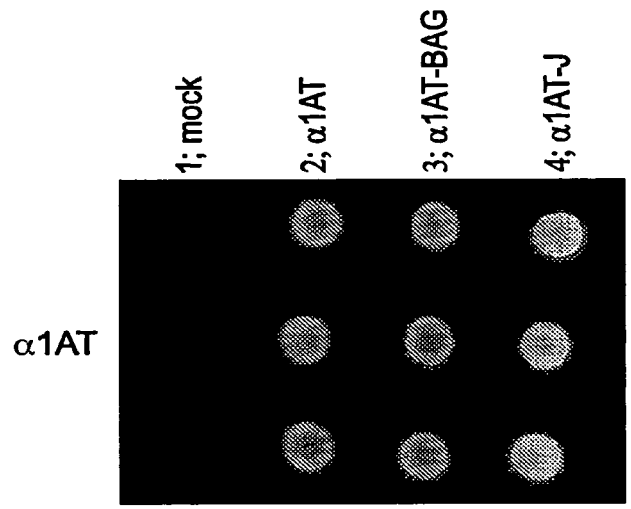
Figure 4C:
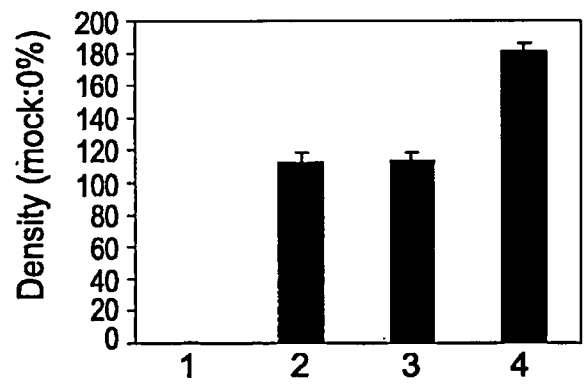

Expression vector plasmids encoding the above three recombinant α1AT protein constructs were transfected into HEK293 cells. Culture media from two-day cultures of transfected cells were harvested, and the level of the recombinant α1AT proteins secreted into the media determined by dot blot immunoassays. FIG. 4B shows x-ray film chemiluminescent signals of the dot blot assays. Although detectable amounts of both unfused α1AT (lane 2) and α1AT-BAG domain fusion protein (lane 3) were secreted into culture media, an even higher level of expression was obtained for secreted α1AT-J domain fusion protein (lane 3). The results of a densitometry analysis of the signals of the dot blots in FIG. 4B using the NIH ImageJ image processing program are shown in FIG. 4C. The bar graphs in FIG. 4C clearly show the significantly higher level of expression of secreted α1AT-J domain fusion protein (bar graph 4) compared to the level of expression of either α1AT (bar graph 2) or the α1AT-BAG domain fusion protein (bar graph 3). Use of the J domain fusion resulted in greater than a 1.5-fold increase in the amount of IL13Rα2TF being secreted by the transformed cells, compared to the expression level of cells transformed to express the α1AT protein alone or an α1AT-BAG fusion protein.

Truncated Form of TNFR1 Protein in a Modified Arrangement

One format for designing therapeutically active fusion proteins combines a binding domain, which specifically binds a desired target molecule, linked to an immunoglobulin Fc region, which endues the fusion protein with an enhanced in vivo half-life. An example of this class of drugs is etanercept, which binds and inhibits the effect of tumor necrosis factor (TNFα), which is a key protein of the immune system involved in a number of autoimmune diseases. For example, etanercept possesses a truncated form of a tumor necrosis factor α receptor (TNFR1TF) linked to an immunoglobulin Fc domain. The TNFR1 TF portion of etanercept provides specificity for the drug target (TNFα), and the Fc domain is believed to add stability and deliverability of the drug in vivo. Nevertheless, the Fc domain is also known to possess certain effector functions that may not be desired in treatment protocols for some diseases.

The effect of fusing a J domain to a truncated form of a receptor molecule was studied as a possible strategy for enhancing levels of expression and secretion of a desired receptor-based molecule. Such a J domain fusion protein may provide a possible alternative to prior drug designs involving truncated forms of receptor molecules linked to immunoglobulin Fc domains. The expression of a truncated form of a tumor necrosis factor receptor (TNFR1TF) with or without a J domain was studied using expression vector plasmids TNFR1TF-V5-pcDNA' and TNFR1TF-J domain-V5-pcDNA'. The expression vectors add a V5 epitope tag to both proteins for easy detection with an anti-V5 antibody. See, diagrams of constructs in FIG. 5A.

The amino acid sequence of a V5-tagged TNFR1TF is shown in the table below.

TABLE 16

Amino Acid Sequence of a V5-Tagged TNFR1TF Protein.

| Protein Region (N- to C-terminal) | Sequence Identifier | Amino Acid Sequence 12345678901234567890123456789 0 |
|---|---|---|
| TNFR1TF protein | SEQ ID NO: 206 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV SCSNCKKSLECTKLCLPQIENVKGTEDSGT TGTGSEFDIAAALEGKPIPNPLLGLDSTSR GPYSIVSPKC |
| TNFR1TF | residues 1-211 of SEQ ID NO: 206 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV SCSNCKKSLECTKLCLPQIENVKGTEDSGT T |
| Linker | residues 212-224 of SEQ ID NO: 206 | GTGSEFDIAAALE |
| V5 epitope domain | residues 225-238 of SEQ ID NO: 206 | GKPIPNPLLGLDST |
| C-terminal vector residues | residues 239-250 of SEQ ID NO: 206 | SRGPYSIVSPKC |

The amino acid sequence of a J domain fusion protein comprising TNFR1TF, the Erdj3 J domain, and the V5 epitope tag is shown in the table below.

TABLE 17

Amino Acid Sequence of a V5-Tagged TNFR1TF-Erdj3 J Domain Fusion Protein.

| Protein Region (N- to C-terminal) | Sequence Identifier | Amino Acid Sequence 12345678901234567890123456789 0 |
|---|---|---|
| TNFR1TF-J domain fusion protein | SEQ ID NO: 207 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV |

TABLE 17-continued

Amino Acid Sequence of a V5-Tagged TNFR1TF-Erdj3 J Domain Fusion Protein.

| Protein Region (N- to C-terminal) | Sequence Identifier | Amino Acid Sequence 12345678901234567890123456789 0 |
|---|---|---|
| | | SCSNCKKSLECTKLCLPQIENVKGTEDSGT TGTGSEFGRDFYKILGVPRSASIKDIKKAY RKLALQLHPDRNPDDPQAQEKFQDLGAAYE VLSDSEKRDIAAALEGKPIPNPLLGLDSTS RGPYSIVSPKC |
| TNFR1TF | residues 1-211 of SEQ ID NO: 207 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV SCSNCKKSLECTKLCLPQIENVKGTEDSGT T |
| Linker | residues 212-217 of SEQ ID NO: 207 | GTGSEF |
| Erdj3 J domain | residues 218-278 of SEQ ID NO: 207 | GRDFYKILGVPRSASIKDIKKAYRKLALQL HPDRNPDDPQAQEKFQDLGAAYEVLSDSEK R |
| Linker | residues 279-285 of SEQ ID NO: 207 | DIAAALE |
| V5 epitope domain | residues 286-299 of SEQ ID NO: 207 | GKPIPNPLLGLDST |
| C-terminal vector residues | residues 300-311 of SEQ ID NO: 207 | SRGPYSIVSPKC |

Figure 5B:
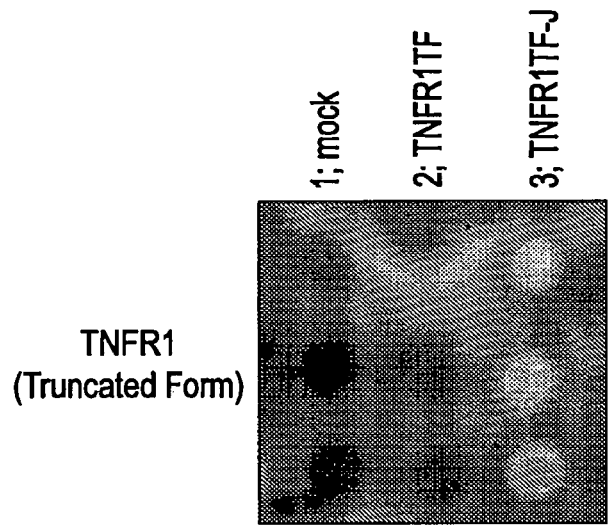
Figure 5C:
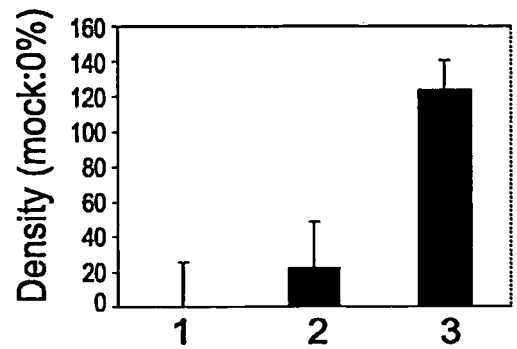

The expression plasmids were transfected into HEK293 cells. Samples of cell lysates and culture media from two-day cultures of transfected cells were analyzed by immunoblotting with anti-V5 antibody for expression of TNFR1TF or the TNFR1TF-J domain fusion protein. As shown in the dot blots in FIG. 5B, some TNFR1TF was detected in medium (lane 2), however, the level of the TNFR1TF-J domain fusion protein detected in the medium was significantly greater (lane 3). The results of a densitometry analysis of the signals of the dot blots in FIG. 5B using the NIH ImageJ image processing program are shown in FIG. 5C. Clearly, the level of expression of secreted TNFR1TF-J domain fusion protein (bar graph 3) was significantly higher than that of the (unfused) TNFR1TF protein (bar graph 2), i.e., about a 6-fold increase over the level of TNFR1TF alone.

Secretion of Fc-Fusion Proteins in a Modified Arrangement

In view of the above results showing that the level of expression of secreted truncated form of TNFR1 was enhanced by the conjugation of J domain (FIGS. 5B and 5C), it was of interest to examine whether a J domain would enhance expression of a protein of interest fused to an immunoglobulin Fc domain, such as a TNF1TF-Fc fusion protein. Such Fc-fusion molecules are a type of drug format illustrated by the drug etanercept (commercially available as ENBREL®), which is a TNF1TF-Fc fusion protein approved for treating a number of autoimmune diseases, such as severe rheumatoid arthritis, polyarticular juvenile idiopathic arthritis (JIA), psoriatic arthritis, ankylosing spondylitis, and plaque psoriasis.

For this study, a cDNA encoding each protein of interest (TNFR1TF, IL13Rα2TF, or α1AT) was augmented with a segment encoding a V5 epitope tag at the 3' end, which was linked in turn to a segment encoding the constant domains of an immunoglobulin Fc region. For J-domain fusions, a cDNA encoding a J domain was linked in frame between the cDNA encoding each protein of interest and the segment encoding a V5 epitope tag. See, illustration of constructs in FIG. 6A. The corresponding expression vector plasmids were transfected into HEK293 cells. Culture media were assayed for secreted proteins by dot blot assay.

The amino acid sequence of the TNFR1TF-Fc fusion protein is shown in the table below.

TABLE 18

Amino Acid Sequence of a V5-Tagged TNFR1TF-Fc Fusion Protein.

| Protein Region (N- to C-terminal) | Sequence Identifier | Amino Acid Sequence 12345678901234567890123456 7890 |
|---|---|---|
| TNFR1TF Fc fusion protein | SEQ ID NO: 208 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV SCSNCKKSLECTKLCLPQIENVKGTEDSGT TGTGSEFDIAAALEGKPIPNPLLGLDSTSR PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |
| TNFR1TF | residues 1-211 of SEQ ID NO: 208 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV SCSNCKKSLECTKLCLPQIENVKGTEDSGT T |
| Linker | residues 212-224 of SEQ ID NO: 208 | GTGSEFDIAAALE |
| V5 epitope domain | residues 225-238 of SEQ ID NO: 208 | GKPIPNPLLGLDST |
| Linker | residues 239-240 of SEQ ID NO: 208 | SR |
| Fc domain | residues 241-471 of SEQ ID NO: 208 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

The amino acid sequence of a TNFR1TF-J domain-Fc fusion protein is shown in the table below.

TABLE 19

Amino Acid Sequence of a V5-Tagged TNFR1TF-Erdj3 J Domain-Fc Protein.

| Protein Region (N- to C-terminal) | Sequence Identifier | Amino Acid Sequence 12345678901234567890123456 7890 |
|---|---|---|
| TNFR1TF-J domain Fc fusion protein | SEQ ID NO: 209 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV SCSNCKKSLECTKLCLPQIENVKGTEDSGT TGTGSEFGRDFYKILGVPRSASIKDIKKAY RKLALQLHPDRNPDDPQAQEKFQDLGAAYE VLSDSEKRDIAAALEGKPIPNPLLGLDSTS RPKSCDKTHTCPPCPAPELLGGPSVFLFPP |

TABLE 19-continued

Amino Acid Sequence of a V5-Tagged TNFR1TF-Erdj3 J Domain-Fc Protein.

| Protein Region (N- to C-terminal) | Sequence Identifier | Amino Acid Sequence 12345678901234567890123456 7890 |
|---|---|---|
| | | KPKDTLMISRTPEVTCVVVDVSHEDPEVKF NWYVDGVEVHNAKTKPREEQYNSTYRVVSV LTVLHQDWLNGKEYKCKVSNKALPAPIEKT ISKAKGQPREPQVYTLPPSRDELTKNQVSL TCLVKGFYPSDIAVEWESNGQPENNYKTTP PVLDSDGSFFLYSKLTVDKSRWQQGNVFSC SVMHEALHNHYTQKSLSLSPGK |
| TNFR1TF | residues 1-211 of SEQ ID NO: 209 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV SCSNCKKSLECTKLCLPQIENVKGTEDSGT T |
| Linker | residues 212-217 of SEQ ID NO: 209 | GTGSEF |
| Erdj3 J domain | residues 218-278 of SEQ ID NO: 209 | GRDFYKILGVPRSASIKDIKKAYRKLALQL HPDRNPDDPQAQEKFQDLGAAYEVLSDSEK R |
| Linker | residues 279-285 of SEQ ID NO: 209 | DIAAALE |
| V5 epitope domain | residues 286-299 of SEQ ID NO: 209 | GKPIPNPLLGLDST |
| Linker | residues 300-301 of SEQ ID NO: 209 | SR |
| Fc domain | residues 302-532 of SEQ ID NO: 209 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

The amino acid sequence of an IL13Rα2TF-Fc fusion protein is shown in the table below.

TABLE 20

Amino Acid Sequence of a V5-Tagged IL13Rα2TF-Fc Fusion Protein.

| Protein Region (N- to C-terminal) | Sequence Identifier | Amino Acid Sequence 12345678901234567890123456 7890 |
|---|---|---|
| IL13Rα2TF-Fc fusion protein | SEQ ID NO: 210 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKGTGSEFDIAAALEGKPIPNPL |

TABLE 20-continued

Amino Acid Sequence of a V5-Tagged IL13Rα2TF-Fc Fusion Protein.

| Protein Region (N- to C-terminal) | Sequence Identifier | Amino Acid Sequence 12345678901234567890123456 7890 |
|---|---|---|
| | | LGLDSTSRPKSCDKTHTCPPCPAPELLGGP SVFLFPPKPKDTLMISRTPEVTCVVVDVSH EDPEVKFNWYVDGVEVHNAKTKPREEQYNS TYRVVSVLTVLHQDWLNGKEYKCKVSNKAL PAPIEKTISKAKGQPREPQVYTLPPSRDEL TKNQVSLTCLVKGFYPSDIAVEWESNGQPE NNYKTTPPVLDSDGSFFLYSKLTVDKSRWQ QGNVFSCSVMHEALHNHYTQKSLSLSPGK |
| IL13Rα2TF | residues 1-339 of SEQ ID NO: 210 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKK |
| Linker | residues 340-352 of SEQ ID NO: 210 | GTGSEFDIAAALE |
| V5 epitope domain | residues 353-366 of SEQ ID NO: 210 | GKPIPNPLLGLDST |
| Linker | residues 367-368 of SEQ ID NO: 210 | SR |
| Fc domain | residues 369-599 of SEQ ID NO: 210 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

The amino acid sequence of an IL13Rα2TF-J domain-Fc fusion protein is shown in the table below.

TABLE 21

Amino Acid Sequence of a V5-Tagged IL13Rα2TF-Erdj3 J Domain-Fc Protein.

| Protein Region (N- to C-terminal) | Sequence Identifier | Amino Acid Sequence 12345678901234567890123456 7890 |
|---|---|---|
| IL13Rα2TF-J domain-Fc fusion protein | SEQ ID NO: 211 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKGTGSEFGRDFYKILGVPRSAS IKDIKKAYRKLALQLHPDRNPDDPQAQEKF QDLGAAYEVLSDSEKRDIAAALEGKPIPNP LLGLDSTSRPKSCDKTHTCPPCPAPELLGG |

TABLE 21-continued

Amino Acid Sequence of a V5-Tagged IL13Rα2TF-Erdj3 J Domain-Fc Protein.

| Protein Region (N- to C-terminal) | Sequence Identifier | Amino Acid Sequence 12345678901234567890123456789 0 |
|---|---|---|
| | | PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSRDE LTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| IL13Rα2TF | residues 1-339 of SEQ ID NO: 211 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKK |
| Linker | residues 340-345 of SEQ ID NO: 211 | GTGSEF |
| Erdj3 J domain | residues 346-406 of SEQ ID NO: 211 | GRDFYKILGVPRSASIKDIKKAYRKLALQL HPDRNPDDPQAQEKFQDLGAAYEVLSDSEK R |
| Linker | residues 407-413 of SEQ ID NO: 211 | DIAAALE |
| V5 epitope domain | residues 414-427 of SEQ ID NO: 211 | GKPIPNPLLGLDST |
| Linker | residues 428-429 of SEQ ID NO: 211 | SR |
| Fc domain | residues 430-660 of SEQ ID NO: 211 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

The amino acid sequence of an α1AT-Fc fusion protein is shown in the table below.

TABLE 22

Amino Acid Sequence of V5-Tagged α1AT-Fc Protein.

| Protein Region (N- to C-terminal) | Sequence Identifier | Amino Acid Sequence 12345678901234567890123456789 0 |
|---|---|---|
| α1AT protein-Fc fusion protein | SEQ ID NO: 212 | MPSSVSWGILLLAGLCCLVPVSLAEDPQGD AAQKTDTSHHDQDHPTFNKITPNLAEFAFS LYRQLAHQSNSTNIFFSPVSIATAFAMLSL GTKADTHDEILEGLNFNLTEIPEAQIHEGF QELLRTLNQPDSQLQLTTGNGLFLSEGLKL VDKFLEDVKKLYHSEAFTVNFGDTEEAKKQ INDYVEKGTQGKIVDLVKELDRDTVFALVN YIFFKGKWERPFEVKDTEEEDFHVDQVTTV KVPMMKRLGMFNIQHCKKLSSWVLLMKYLG |

TABLE 22-continued

Amino Acid Sequence of V5-Tagged α1AT-Fc Protein.

| Protein Region (N- to C-terminal) | Sequence Identifier | Amino Acid Sequence<br>12345678901234567890123456789 |
|---|---|---|
| | | NATAIFFLPDEGKLQHLENELTHDIITKFL<br>ENEDRRSASLHLPKLSITGTYDLKSVLGQL<br>GITKVFSNGADLSGVTEEAPLKLSKAVHKA<br>VLTIDEKGTEAAGAMFLEAIPMSIPPEVKF<br>NKPFVFLMIEQNTKSPLFMGKVVNPTQKGT<br>GSEFDIAAALEGKPIPNPLLGLDSTSRPKS<br>CDKTHTCPPCPAPELLGGPSVFLFPPKPKD<br>TLMISRTPEVTCVVVDVSHEDPEVKFNWYV<br>DGVEVHNAKTKPREEQYNSTYRVVSVLTVL<br>HQDWLNGKEYKCKVSNKALPAPIEKTISKA<br>KGQPREPQVYTLPPSRDELTKNQVSLTCLV<br>KGFYPSDIAVEWESNGQPENNYKTTPPVLD<br>SDGSFFLYSKLTVDKSRWQQGNVFSCSVMH<br>EALHNHYTQKSLSLSPGK |
| α1AT | residues 1-418 of SEQ ID NO: 212 | MPSSVSWGILLLAGLCCLVPVSLAEDPQGD<br>AAQKTDTSHHDQDHPTFNKITPNLAEFAFS<br>LYRQLAHQSNSTNIFFSPVSIATAFAMLSL<br>GTKADTHDEILEGLNFNLTEIPEAQIHEGF<br>QELLRTLNQPDSQLQLTTGNGLFLSEGLKL<br>VDKFLEDVKKLYHSEAFTVNFGDTEEAKKQ<br>INDYVEKGTQGKIVDLVKELDRDTVFALVN<br>YIFFKGKWERPFEVKDTEEEDFHVDQVTTV<br>KVPMMKRLGMFNIQHCKKLSSWVLLMKYLG<br>NATAIFFLPDEGKLQHLENELTHDIITKFL<br>ENEDRRSASLHLPKLSITGTYDLKSVLGQL<br>GITKVFSNGADLSGVTEEAPLKLSKAVHKA<br>VLTIDEKGTEAAGAMFLEAIPMSIPPEVKF<br>NKPFVFLMIEQNTKSPLFMGKVVNPTQK |
| Linker | residues 419-431 of SEQ ID NO: 212 | GTGSEFDIAAALE |
| V5 epitope domain | residues 432-445 of SEQ ID NO: 212 | GKPIPNPLLGLDST |
| Linker | residues 446-447 of SEQ ID NO: 212 | SR |
| Fc domain | residues 448-678 of SEQ ID NO: 212 | PKSCDKTHTCPPCPAPELLGGPSVFLFPPK<br>PKDTLMISRTPEVTCVVVDVSHEDPEVKFN<br>WYVDGVEVHNAKTKPREEQYNSTYRVVSVL<br>TVLHQDWLNGKEYKCKVSNKALPAPIEKTI<br>SKAKGQPREPQVYTLPPSRDELTKNQVSLT<br>CLVKGFYPSDIAVEWESNGQPENNYKTTPP<br>VLDSDGSFFLYSKLTVDKSRWQQGNVFSCS<br>VMHEALHNHYTQKSLSLSPGK |

The amino acid sequence of an α1AT-J domain-Fc fusion protein is shown in the table below.

TABLE 23

Amino Acid Sequence of a V5-Tagged α1 AT-Erdj3 J Domain-Fc Protein.

| Protein Region (N- to C-terminal) | Sequence Identifier | Amino Acid Sequence<br>12345678901234567890123456789 |
|---|---|---|
| α1AT-J domain-Fc fusion protein | SEQ ID NO: 213 | MPSSVSWGILLLAGLCCLVPVSLAEDPQGD<br>AAQKTDTSHHDQDHPTFNKITPNLAEFAFS<br>LYRQLAHQSNSTNIFFSPVSIATAFAMLSL<br>GTKADTHDEILEGLNFNLTEIPEAQIHEGF<br>QELLRTLNQPDSQLQLTTGNGLFLSEGLKL<br>VDKFLEDVKKLYHSEAFTVNFGDTEEAKKQ<br>INDYVEKGTQGKIVDLVKELDRDTVFALVN<br>YIFFKGKWERPFEVKDTEEEDFHVDQVTTV |

TABLE 23-continued

Amino Acid Sequence of a V5-Tagged α1 AT-Erdj3 J Domain-Fc Protein.

| Protein Region (N- to C-terminal) | Sequence Identifier | Amino Acid Sequence 12345678901234567890123456 7890 |
|---|---|---|
| | | KVPMMKRLGMFNIQHCKKLSSWVLLMKYLG NATAIFFLPDEGKLQHLENELTHDIITKFL ENEDRRSASLHLPKLSITGTYDLKSVLGQL GITKVFSNGADLSGVTEEAPLKLSKAVHKA VLTIDEKGTEAAGAMFLEAIPMSIPPEVKF NKPFVFLMIEQNTKSPLFMGKVVNPTQKGT GSEFGRDFYKILGVPRSASIKDIKKAYRKL ALQLHPDRNPDDPQAQEKFQDLGAAYEVLS DSEKRDIAAALEGKPIPNPLLGLDSTSRPK SCDKTHTCPPCPAPELLGGPSVFLFPPKPK DTLMISRTPEVTCVVVDVSHEDPEVKFNWY VDGVEVHNAKTKPREEQYNSTYRVVSVLTV LHQDWLNGKEYKCKVSNKALPAPIEKTISK AKGQPREPQVYTLPPSRDELTKNQVSLTCL VKGFYPSDIAVEWESNGQPENNYKTTPPVL DSDGSFFLYSKLTVDKSRWQQGNVFSCSVM HEALHNHYTQKSLSLSPGK |
| α1AT | residues 1-418 of SEQ ID NO: 213 | MPSSVSWGILLLAGLCCLVPVSLAEDPQGD AAQKTDTSHHDQDHPTFNKITPNLAEFAFS LYRQLAHQSNSTNIFFSPVSIATAFAMLSL GTKADTHDEILEGLNFNLTEIPEAQIHEGF QELLRTLNQPDSQLQLTTGNGLFLSEGLKL VDKFLEDVKKLYHSEAFTVNFGDTEEAKKQ INDYVEKGTQGKIVDLVKELDRDTVFALVN YIFFKGKWERPFEVKDTEEEDFHVDQVTTV KVPMMKRLGMFNIQHCKKLSSWVLLMKYLG NATAIFFLPDEGKLQHLENELTHDIITKFL ENEDRRSASLHLPKLSITGTYDLKSVLGQL GITKVFSNGADLSGVTEEAPLKLSKAVHKA VLTIDEKGTEAAGAMFLEAIPMSIPPEVKF NKPFVFLMIEQNTKSPLFMGKVVNPTQK |
| Linker | residues 419-424 of SEQ ID NO: 213 | GTGSEF |
| Erdj3 J domain | residues 425-485 of SEQ ID NO: 213 | GRDFYKILGVPRSASIKDIKKAYRKLALQL HPDRNPDDPQAQEKFQDLGAAYEVLSDSEK R |
| Linker | residues 486-492 of SEQ ID NO: 213 | DIAAALE |
| V5 epitope domain | residues 493-506 of SEQ ID NO: 213 | GKPIPNPLLGLDST |
| Linker | residues 507-508 of SEQ ID NO: 213 | SR |
| Fc domain | residues 509-739 of SEQ ID NO: 213 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

Figures 1, 6C:
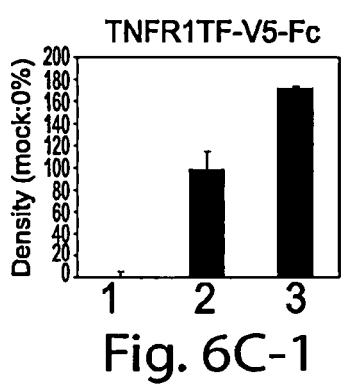
Figures 2, 6C:
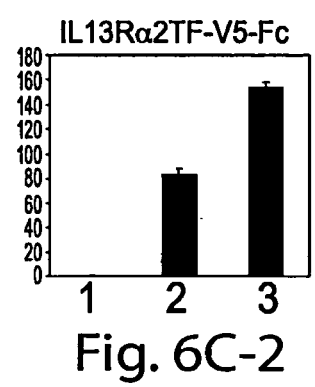
Figures 3, 6C:
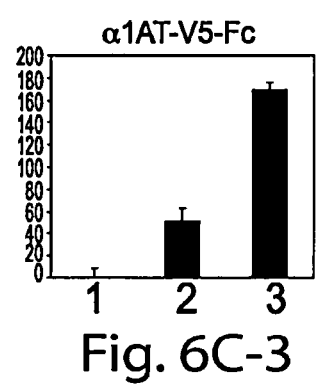

Each of the Fc fusion proteins (TNFRI-V5-Fc, IL13Rα2TF-Fc, α1AT-Fc) were expressed in culture media as shown in the dot blots in the middle lane of each panel in FIG. 6B. This level of expression of the Fc fusion proteins was greater than that for each of the proteins of interest alone (i.e., without fusion to an Fc domain; data not shown). However, significantly higher levels of expression were obtained in each case when a J domain was linked to the protein of interest segment within the Fc fusion proteins as shown in the dot blots in the right lane of each panel in FIG. 6B. The results of a densitometry analysis of the chemiluminescent signals of the dot blots in FIG. 6B are shown in the corresponding panels of FIG. 6C, where the significantly higher level of expression of the J domain fusion proteins is clearly evident.

Enhanced Expression of p53 Protein in a Modified Arrangement in Human Cells

Proteins such as IL13Rα2, TNFR, and α1AT are synthesized in the endoplasmic reticulum (ER) for delivery to the cell membrane or secretion from the cell. To determine the effect of the presence of a J domain on the expression of cytoplasmic proteins, the expression of a fusion of the p53 protein and J domain was studied. The p53 protein is a transcription factor that plays pivotal roles in genomic stability. More than half of cancer patients have some abnormalities in the pathway involving p53. Therefore, overexpression of p53 in a cancer patient has been attempted as a treatment for cancer.

A cDNA encoding p53 was inserted into expression plasmid V5(N)-pcDNA' to yield plasmid V5(N)-p53-pcDNA' to express a p53 protein containing an N-terminal V5 epitope tag. To express the p53-J domain fusion protein, a cDNA encoding a J domain of the SV40 large T antigen was then inserted into the V5(N)-p53-pcDNA' vector between the V5 and p53 coding regions. See, diagrams of constructs in FIG. 7A.

The amino acid sequence of a V5-tagged p53 protein is shown in the table below.

TABLE 24

Amino Acid Sequence of a V5-Tagged p53 Protein.

| Protein Region (N- to C-terminal) | Sequence Identifier | Amino Acid Sequence 12345678901234567890123456789 0 |
|---|---|---|
| p53 protein | SEQ ID NO: 214 | MGKPIPNPLLGLDSTGTGSEFDIAAAMEEP QSDPSVEPPLSQETFSDLWKLLPENNVLSP LPSQAMDDLMLSPDDIEQWFTEDPGPDEAP RMPEAAPPVAPAPAAPTPAAPAPAPSWPLS SSVPSQKTYQGSYGFRLGFLHSGTAKSVTC TYSPALNKMFCQLAKTCPVQLWVDSTPPPG TRVRAMAIYKQSQHMTEVVRRCPHHERCSD SDGLAPPQHLIRVEGNLRVEYLDDRNTFRH SVVVPYEPPEVGSDCTTIHYNYMCNSSCMG GMNRRPILTIITLEDSSGNLLGRNSFEVRV CACPGRDRRTEEENLRKKGEPHHELPPGST KRALPNNTSSSPQPKKKPLDGEYFTLQIRG RERFEMFRELNEALELKDAQAGKEPGGSRA HSSHLKSKKGQSTSRHKKLMFKTEGPDSDA AALESRGPYSIVSPKC |
| V5 epitope domain | residues 1-15 of SEQ ID NO: 214 | MGKPIPNPLLGLDST |
| Linker | residues 16-26 of SEQ ID NO: 214 | GTGSEFDIAAA |
| p53 | residues 27-422 of SEQ ID NO: 214 | MEEPQSDPSVEPPLSQETFSDLWKLLPENN VLSPLPSQAMDDLMLSPDDIEQWFTEDPGP DEAPRMPEAAPPVAPAPAAPTPAAPAPAPS WPLSSSVPSQKTYQGSYGFRLGFLHSGTAK SVTCTYSPALNKMFCQLAKTCPVQLWVDST PPPGTRVRAMAIYKQSQHMTEVVRRCPHHE RCSDSDGLAPPQHLIRVEGNLRVEYLDDRN TFRHSVVVPYEPPEVGSDCTTIHYNYMCNS SCMGGMNRRPILTIITLEDSSGNLLGRNSF EVRVCACPGRDRRTEEENLRKKGEPHHELP PGSTKRALPNNTSSSPQPKKKPLDGEYFTL QIRGRERFEMFRELNEALELKDAQAGKEPG GSRAHSSHLKSKKGQSTSRHKKLMFKTEGP DSDAAA |
| C-terminal vector residues | residues 423-436 of SEQ ID NO: 214 | LESRGPYSIVSPKC |

The amino acid sequence of a J domain fusion protein comprising the V5 epitope tag, the SV40 J domain, and the p53 protein is shown in the table below.

TABLE 25

Amino Acid Sequence of a V5-Tagged SV40 J Domain-p53 Fusion Protein.

| Protein Region (N- to C-terminal) | Sequence Identifier | Amino Acid Sequence 12345678901234567890123456789 0 |
|---|---|---|
| p53-SV40 J domain fusion protein | SEQ ID NO: 215 | MGKPIPNPLLGLDSTGTGSEFMDKVLNREE SLQLMDLLGLERSAWGNIPLMRKAYLKKCK EFHPDKGGDEEKMKKMNTLYKKMEDGVKYA HQPDFGGFWDADIAAAMEEPQSDPSVEPPL SQETFSDLWKLLPENNVLSPLPSQAMDDLM LSPDDIEQWFTEDPGPDEAPRMPEAAPPVA PAPAAPTPAAPAPAPSWPLSSSVPSQKTYQ GSYGFRLGFLHSGTAKSVTCTYSPALNKMF CQLAKTCPVQLWVDSTPPPGTRVRAMAIYK QSQHMTEVVRRCPHHERCSDSDGLAPPQHL IRVEGNLRVEYLDDRNTFRHSVVVPYEPPE VGSDCTTIHYNYMCNSSCMGGMNRRPILTI ITLEDSSGNLLGRNSFEVRVCACPGRDRRT EEENLRKKGEPHHELPPGSTKRALPNNTSS SPQPKKKPLDGEYFTLQIRGRERFEMFREL NEALELKDAQAGKEPGGSRAHSSHLKSKKG QSTSRHKKLMFKTEGPDSDAAALESRGPYS IVSPKC |
| V5 epitope domain | residues 1-15 of SEQ ID NO: 215 | MGKPIPNPLLGLDST |
| Linker | residues 16-21 of SEQ ID NO: 215 | GTGSEF |
| SV40 J domain | residues 22-101 of SEQ ID NO: 215 | MDKVLNREESLQLMDLLGLERSAWGNIPLM RKAYLKKCKEFHPDKGGDEEKMKKMNTLYK KMEDGVKYAHQPDFGGFWDA |
| Linker | residues 102-106 of SEQ ID NO: 215 | DIAAA |
| p53 | residues 107-502 of SEQ ID NO: 215 | MEEPQSDPSVEPPLSQETFSDLWKLLPENN VLSPLPSQAMDDLMLSPDDIEQWFTEDPGP DEAPRMPEAAPPVAPAPAAPTPAAPAPAPS WPLSSSVPSQKTYQGSYGFRLGFLHSGTAK SVTCTYSPALNKMFCQLAKTCPVQLWVDST PPPGTRVRAMAIYKQSQHMTEVVRRCPHHE RCSDSDGLAPPQHLIRVEGNLRVEYLDDRN TFRHSVVVPYEPPEVGSDCTTIHYNYMCNS SCMGGMNRRPILTIITLEDSSGNLLGRNSF EVRVCACPGRDRRTEEENLRKKGEPHHELP PGSTKRALPNNTSSSPQPKKKPLDGEYFTL QIRGRERFEMFRELNEALELKDAQAGKEPG GSRAHSSHLKSKKGQSTSRHKKLMFKTEGP DSDAAA |
| Linker | residues 503-516 of SEQ ID NO: 215 | LESRGPYSIVSPKC |

Figure 7B:
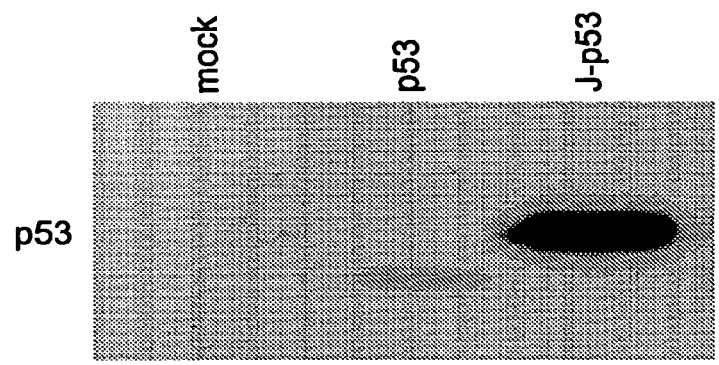

Plasmids V5(N)-p53-pcDNA' and V5(N)-J-p53-pcDNA' were transfected into MCF cells, and incubated for two days. Cells were lysed in lysis buffer, and protein was detected by Western immunoblot assay using anti-V5 antibody. As shown in FIG. 7B, the level of expression of the p53-J domain fusion protein (lane 3) was significantly greater than that of the p53 protein without a J domain. Accordingly, the results indicate that fusion with a J domain can enhance not only membrane-associated and secreted proteins, but cytoplasmic proteins as well.

CFTR Expression in a Modified Arrangement in Human Cells

Cystic fibrosis (CF) is an autosomal recessive disorder caused by mutations in the gene encoding the cystic fibrosis transmembrane conductance regulator (CFTR) protein, a cAMP-regulated chloride channel and channel regulator. The deletion of phenylalanine at position 508 (Δ508F) in CFTR is the most common mutation that changes the conformation of the CFTR protein, which is then rapidly degraded by the ER quality systems. A general consensus is that only partial recovery of the wild-type CFTR protein function is required to provide a beneficial treatment to CF patients. Therefore, a number of gene therapy trials with CFTR have been attempted, but have not yet been successful owing to inefficient delivery of a gene for CFTR and to immunogenicity of the vehicle (e.g., viral vector). In view of the fact that proper protein folding of wild-type CFTR is known to be difficult, it would be very useful if protein folding of the CFTR protein could be improved.

Figure 8A:
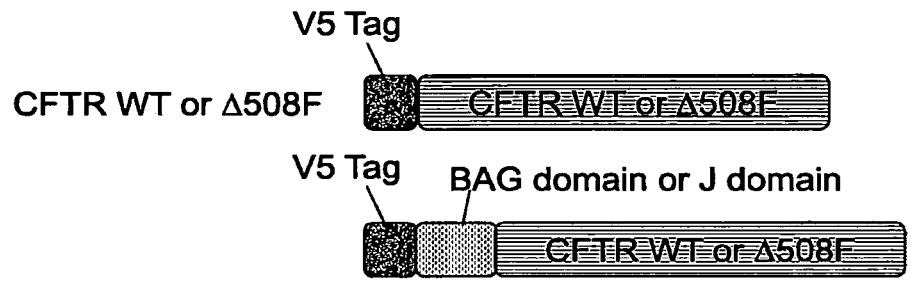
FIGS. 8A and 8B show results of a series of experiments described in Example 2 that demonstrate improvement in the levels of expression of two target proteins of interest, i.e., a wild-type CFTR protein and the corresponding CFTR Δ508F mutant protein (deletion at position 508 of a phenylalanine residue results in defective folding and rapid degradation of the CFTR Δ508F mutant protein), in a modified arrangement in which each of the proteins is linked to (fused with) a J domain fusion partner in comparison to each of the proteins alone or each of the proteins expressed as a fusion with a BAG domain.

The cftr gene or its Phe$_{508}$ deletion mutant (cftrΔ508F) was inserted into plasmid V5(N)-pcDNA'. A DNA coding for the BAG domain of the BAG3 protein or a DNA coding for the J domain from the Hsp40 J protein was inserted in the plasmids between V5 and the cftr coding sequences to yield plasmids to express a wild-type CFTR or mutant CFTR (Δ508F) protein linked to an N-terminal V5 epitope tag or to express a wild-type or mutant CFTR protein fused at its N-terminus to a BAG or J domain, which in turn was fused to an N-terminal V5 epitope tag. Diagrams of the various constructs used in this experiment are shown in FIG. 8A.

The amino acid sequence a V5-tagged wild-type CFTR (CFTR WT) is shown in the table below.

TABLE 26

Amino Acid Sequence of a V5-Tagged CFTR Protein.

| Protein Region (N- to C-terminal) | Sequence Identifier | Amino Acid Sequence 12345678901234567890123456 7890 |
|---|---|---|
| V5-tagged CFTR protein | SEQ ID NO: 216 | MGKPIPNPLLGLDSTGTGSEFDIAAAMQRS PLEKASVVSKLFFSWTRPILRKGYRQRLEL SDIYQIPSVDSADNLSEKLEREWDRELASK KNPKLINALRRCFFWRFMFYGIFLYLGEVT KAVQPLLLGRIIASYDPDNKEERSIAIYLG IGLCLLFIVRTLLLHPAIFGLHHIGMQMRI AMFSLIYKKTLKLSSRVLDKISIGQLVSLL SNNLNKFDEGLALAHFVWIAPLQVALLMGL IWELLQASAFCGLGFLIVLALFQAGLGRMM MKYRDQRAGKISERLVITSEMIENIQSVKA YCWEEAMEKMIENLRQTELKLTRKAAYVRY FNSSAFFFSGFFVVFLSVLPYALIKGIILR KIFTTISFCIVLRMAVTRQFPWAVQTWYDS LGAINKIQDFLQKQEYKTLEYNLTTTEVVM ENVTAFWEEGFGELFEKAKQNNNNRKTSNG DDSLFFSNFSLLGTPVLKDINFKIERGQLL AVAGSTGAGKTSLLMVIMGELEPSEGKIKH SGRISFCSQFSWIMPGTIKENIIFGVSYDE YRYRSVIKACQLEEDISKFAEKDNIVLGEG GITLSGGQRARISLARAVYKDADLYLLDSP FGYLDVLTEKEIFESCVCKLMANKTRILVT SKMEHLKKADKILILHEGSSYFYGTFSELQ NLQPDFSSKLMGCDSFDQFSAERRNSILTE TLHRFSLEGDAPVSWTETKKQSFKQTGEFG EKRKNSILNPINSIRKFSIVQKTPLQMNGI EEDSDEPLERRLSLVPDSEQGEAILPRISV ISTGPTLQARRRQSVLNLMTHSVNQGQNIH RKTTASTRKVSLAPQANLTELDIYSRRLSQ ETGLEISEEINEEDLKECFFDDMESIPAVT TWNTYLRYITVHKSLIFVLIWCLVIFLAEV AASLVVLWLLGNTPLQDKGNSTHSRNNSYA VIITSTSSYYVFYIYVGVADTLLAMGFFRG LPLVHTLITVSKILHHKMLHSVLQAPMSTL NTLKAGGILNRFSKDIAILDDLLPLTIFDF IQLLLIVIGAIAVVAVLQPYIFVATVPVIV AFIMLRAYFLQTSQQLKQLESEGRSPIFTH LVTSLKGLWTLRAFGRQPYFETLFHKALNL HTANWFLYLSTLRWFQMRIEMIFVIFFIAV TFISILTTGEGEGRVGIILTLAMNIMSTLQ WAVNSSIDVDSLMRSVSRVFKFIDMPTEGK PTKSTKPYKNGQLSKVMIIENSHVKKDDIW PSGGQMTVKDLTAKYTEGGNAILENISFSI SPGQRVGLLGRTGSGKSTLLSAFLRLLNTE GEIQIDGVSWDSITLQQWRKAFGVIPQKVF IFSGTFRKNLDPYEQWSDQEIWKVADEVGL RSVIEQFPGKLDFVLVDGGCVLSHGHKQLM CLARSVLSKAKILLLDEPSAHLDPVTYQII RRTLKQAFADCTVILCEHRIEAMLECQQFL VIEENKVRQYDSIQKLLNERSLFRQAISPS DRVKLFPHRNSSKCKSKPQIAALKEETEEE VQDTRL |
| V5 epitope domain | residues 1-15 of SEQ ID NO: 216 | MGKPIPNPLLGLDST |
| Linker | residues 16-26 of SEQ ID NO: 216 | GTGSEFDIAAA |

TABLE 26-continued

Amino Acid Sequence of a V5-Tagged CFTR Protein.

| Protein Region (N- to C-terminal) | Sequence Identifier | Amino Acid Sequence 12345678901234567890123456 7890 |
|---|---|---|
| CFTR | residues 27-1506 of SEQ ID NO: 216 | MQRSPLEKASVVSKLFFSWTRPILRKGYRQ RLELSDIYQIPSVDSADNLSEKLEREWDRE LASKKNPKLINALRRCFFWRFMFYGIFLYL GEVTKAVQPLLLGRIIASYDPDNKEERSIA IYLGIGLCLLFIVRTLLLHPAIFGLHHIGM QMRIAMFSLIYKKTLKLSSRVLDKISIGQL VSLLSNNLNKFDEGLALAHFVWIAPLQVAL LMGLIWELLQASAFCGLGFLIVLALFQAGL GRMMMKYRDQRAGKISERLVITSEMIENIQ SVKAYCWEEAMEKMIENLRQTELKLTRKAA YVRYFNSSAFFFSGFFVVFLSVLPYALIKG IILRKIFTTISFCIVLRMAVTRQFPWAVQT WYDSLGAINKIQDFLQKQEYKTLEYNLTTT EVVMENVTAFWEEGFGELFEKAKQNNNNRK TSNGDDSLFFSNFSLLGTPVLKDINFKIER GQLLAVAGSTGAGKTSLLMVIMGELEPSEG KIKHSGRISFCSQFSWIMPGTIKENIIFGV SYDEYRYRSVIKACQLEEDISKFAEKDNIV LGEGGITLSGGQRARISLARAVYKDADLYL LDSPFGYLDVLTEKEIFESCVCKLMANKTR ILVTSKMEHLKKADKILILHEGSSYFYGTF SELQNLQPDFSSKLMGCDSFDQFSAERRNS ILTETLHRFSLEGDAPVSWTETKKQSFKQT GEFGEKRKNSILNPINSIRKFSIVQKTPLQ MNGIEEDSDEPLERRLSLVPDSEQGEAILP RISVISTGPTLQARRRQSVLNLMTHSVNQG QNIHRKTTASTRKVSLAPQANLTELDIYSR RLSQETGLEISEEINEEDLKECFFDDMESI PAVTTWNTYLRYITVHKSLIFVLIWCLVIF LAEVAASLVVLWLLGNTPLQDKGNSTHSRN NSYAVIITSTSSYYVFYIYVGVADTLLAMG FFRGLPLVHTLITVSKILHHKMLHSVLQAP MSTLNTLKAGGILNRFSKDIAILDDLLPLT IFDFIQLLLIVIGAIAVVAVLQPYIFVATV PVIVAFIMLRAYFLQTSQQLKQLESEGRSP IFTHLVTSLKGLWTLRAFGRQPYFETLFHK ALNLHTANWFLYLSTLRWFQMRIEMIFVIF FIAVTFISILTTGEGEGRVGIILTLAMNIM STLQWAVNSSIDVDSLMRSVSRVFKIDMP TEGKPTKSTKPYKNGQLSKVMIIENSHVKK DDIWPSGGQMTVKDLTAKYTEGGNAILENI SFSISPGQRVGLLGRTGSGKSTLLSAFLRL LNTEGEIQIDGVSWDSITLQQWRKAFGVIP QKVFIFSGTFRKNLDPYEQWSDQEIWKVAD EVGLRSVIEQFPGKLDFVLVDGGCVLSHGH KQLMCLARSVLSKAKILLLDEPSAHLDPVT YQIIRRTLKQAFADCTVILCEHRIEAMLEC QQFLVIEENKVRQYDSIQKLLNERSLFRQA ISPSDRVKLFPHRNSSKCKSKPQIAALKEE TEEEVQDTRL |

The amino acid sequence of a V5-tagged BAG-CFTR (wild-type) protein is shown in the table below.

TABLE 27

Amino Acid Sequence of a V5-Tagged BAG Domain-CFTR Protein.

| Protein Region (N- to C-terminal) | Sequence Identifier | Amino Acid Sequence 12345678901234567890123456 7890 |
|---|---|---|
| V5-tagged BAG domain-CFTR fusion protein | SEQ ID NO: 217 | MGKPIPNPLLGLDSTGTGSEFHPGVLKVEA ILEKVQGLEQAVDNFEGKKTDKKYLMIEEY LTKELLALDSVDPEGRADVRQARRDGVRKV QTILEKLEQKAIDDIAAAMQRSPLEKASVV SKLFFSWTRPILRKGYRQRLELSDIYQIPS VDSADNLSEKLEREWDRELASKKNPKLINA LRRCFFWRFMFYGIFLYLGEVTKAVQPLLL GRIIASYDPDNKEERSIAIYLGIGLCLLFI |

TABLE 27-continued

Amino Acid Sequence of a V5-Tagged BAG Domain-CFTR Protein.

| Protein Region (N- to C-terminal) | Sequence Identifier | Amino Acid Sequence 12345678901234567890 |
|---|---|---|
| | | VRTLLLHPAIFGLHHIGMQMRIAMFSLIYK KTLKLSSRVLDKISIGQLVSLLSNNLNKFD EGLALAHFVWIAPLQVALLMGLIWELLQAS AFCGLGFLIVLALFQAGLGRMMMKYRDQRA GKISERLVITSEMIENIQSVKAYCWEEAME KMIENLRQTELKLTRKAAYVRYFNSSAFFF SGFFVVFLSVLPYALIKGIILRKIFTTISF CIVLRMAVTRQFPWAVQTWYDSLGAINKIQ DFLQKQEYKTLEYNLTTTEVVMENVTAFWE EGFGELFEKAKQNNNNRKTSNGDDSLFFSN FSLLGTPVLKDINFKIERGQLLAVAGSTGA GKTSLLMVIMGELEPSEGKIKHSGRISFCS QFSWIMPGTIKENIIFGVSYDEYRYRSVIK ACQLEEDISKFAEKDNIVLGEGGITLSGGQ RARISLARAVYKDADLYLLDSPFGYLDVLT EKEIFESCVCKLMANKTRILVTSKMEHLKK ADKILILHEGSSYFYGTFSELQNLQPDFSS KLMGCDSFDQFSAERRNSILTETLHRFSLE GDAPVSWTETKKQSFKQTGEFGEKRKNSIL NPINSIRKFSIVQKTPLQMNGIEEDSDEPL ERRLSLVPDSEQGEAILPRISVISTGPTLQ ARRRQSVLNLMTHSVNQGQNIHRKTTASTR KVSLAPQANLTELDIYSRRLSQETGLEISE EINEEDLKECFFDDMESIPAVTTWNTYLRY ITVHKSLIFVLIWCLVIFLAEVAASLVVLW LLGNTPLQDKGNSTHSRNNSYAVIITSTSS YYVFYIYVGVADTLLAMGFFRGLPLVHTLI TVSKILHHKMLHSVLQAPMSTLNTLKAGGI LNRFSKDIAILDDLLPLTIFDFIQLLLIVI GAIAVVAVLQPYIFVATVPVIVAFIMLRAY FLQTSQQLKQLESEGRSPIFTHLVTSLKGL WTLRAFGRQPYFETLFHKALNLHTANWFLY LSTLRWFQMRIEMIFVIFFIAVTFISILTT GEGEGRVGIILTLAMNIMSTLQWAVNSSID VDSLMRSVSRVFKFIDMPTEGKPTKSTKPY KNGQLSKVMIIENSHVKKDDIWPSGGQMTV KDLTAKYTEGGNAILENISFSISPGQRVGL LGRTGSGKSTLLSAFLRLLNTEGEIQIDGV SWDSITLQQWRKAFGVIPQKVFIFSGTFRK NLDPYEQWSDQEIWKVADEVGLRSVIEQFP GKLDFVLVDGGCVLSHGHKQLMCLARSVLS KAKILLLDEPSAHLDPVTYQIIRRTLKQAF ADCTVILCEHRIEAMLECQQFLVIEENKVR QYDSIQKLLNERSLFRQAISPSDRVKLFPH RNSSKCKSKPQIAALKEETEEEVQDTRL |
| V5 epitope domain | residues 1-15 of SEQ ID NO: 217 | MGKPIPNPLLGLDST |
| Linker | residues 16-21 of SEQ ID NO: 217 | GTGSEF |
| BAG domain (from BAG3) | residues 22-103 of SEQ ID NO: 217 | HPGVLKVEAILEKVQGLEQAVDNFEGKKTD KKYLMIEEYLTKELLALDSVDPEGRADVRQ ARRDGVRKVQTILEKLEQKAID |
| Linker | residues 104-108 of SEQ ID NO: 217 | DIAAA |
| CFTR | residues 109-1588 of SEQ ID NO: 217 | MQRSPLEKASVVSKLFFSWTRPILRKGYRQ RLELSDIYQIPSVDSADNLSEKLEREWDRE LASKKNPKLINALRRCFFWRFMFYGIFLYL GEVTKAVQPLLLGRIIASYDPDNKEERSIA IYLGIGLCLLFIVRTLLLHPAIFGLHHIGM QMRIAMFSLIYKKTLKLSSRVLDKISIGQL VSLLSNNLNKFDEGLALAHFVWIAPLQVAL LMGLIWELLQASAFCGLGFLIVLALFQAGL GRMMMKYRDQRAGKISERLVITSEMIENIQ SVKAYCWEEAMEKMIENLRQTELKLTRKAA YVRYFNSSAFFFSGFFVVFLSVLPYALIKG |

TABLE 27-continued

Amino Acid Sequence of a V5-Tagged BAG Domain-CFTR Protein.

| Protein Region (N- to C-terminal) | Sequence Identifier | Amino Acid Sequence 123456789012345678901234567890 |
|---|---|---|
| | | IILRKIFTTISFCIVLRMAVTRQFPWAVQT WYDSLGAINKIQDFLQKQEYKTLEYNLTTT EVVMENVTAFWEEGFGELFEKAKQNNNNRK TSNGDDSLFFSNFSLLGTPVLKDINFKIER GQLLAVAGSTGAGKTSLLMVIMGELEPSEG KIKHSGRISFCSQFSWIMPGTIKENIIFGV SYDEYRYRSVIKACQLEEDISKFAEKDNIV LGEGGITLSGGQRARISLARAVYKDADLYL LDSPFGYLDVLTEKEIFESCVCKLMANKTR ILVTSKMEHLKKADKILILHEGSSYFYGTF SELQNLQPDFSSKLMGCDSFDQFSAERRNS ILTETLHRFSLEGDAPVSWTETKKQSFKQT GEFGEKRKNSILNPINSIRKFSIVQKTPLQ MNGIEEDSDEPLERRLSLVPDSEQGEAILP RISVISTGPTLQARRRQSVLNLMTHSVNQG QNIHRKTTASTRKVSLAPQANLTELDIYSR RLSQETGLEISEEINEEDLKECFFDDMESI PAVTTWNTYLRYITVHKSLIFVLIWCLVIF LAEVAASLVVLWLLGNTPLQDKGNSTHSRN NSYAVIITSTSSYYVFYIYVGVADTLLAMG FFRGLPLVHTLITVSKILHHKMLHSVLQAP MSTLNTLKAGGILNRFSKDIAILDDLLPLT IFDFIQLLLIVIGAIAVVAVLQPYIFVATV PVIVAFIMLRAYFLQTSQQLKQLESEGRSP IFTHLVTSLKGLWTLRAFGRQPYFETLFHK ALNLHTANWFLYLSTLRWFQMRIEMIFVIF FIAVTFISILTTGEGEGRVGIILTLAMNIM STLQWAVNSSIDVDSLMRSVSRVFKFIDMP TEGKPTKSTKPYKNGQLSKVMIIENSHVKK DDIWPSGGQMTVKDLTAKYTEGGNAILENI SFSISPGQRVGLLGRTGSGKSTLLSAFLRL LNTEGEIQIDGVSWDSITLQQWRKAFGVIP QKVFIFSGTFRKNLDPYEQWSDQEIWKVAD EVGLRSVIEQFPGKLDFVLVDGGCVLSHGH KQLMCLARSVLSKAKILLLDEPSAHLDPVT YQIIRRTLKQAFADCTVILCEHRIEAMLEC QQFLVIEENKVRQYDSIQKLLNERSLFRQA ISPSDRVKLFPHRNSSKCKSKPQIAALKEE TEEEVQDTRL |

The amino acid sequences a J domain fusion comprising the V5 epitope tag, the SV40 J domain, and the CFTR wild-type protein is shown in the table below.

TABLE 28

Amino Acid Sequence of a V5-Tagged SV40 J Domain-CFTR Protein.

| Protein Region (N- to C-terminal) | Sequence Identifier | Amino Acid Sequence 123456789012345678901234567890 |
|---|---|---|
| V5-tagged SV40 J domain-CFTR fusion protein | SEQ ID NO: 218 | MGKPIPNPLLGLDSTGTGSEFMDKVLNREE SLQLMDLLGLERSAWGNIPLMRKAYLKKCK EFHPDKGGDEEKMKKMNTLYKKMEDGVKYA HQPDFGGFWDADIAAAMQRSPLEKASVVSK LFFSWTRPILRKGYRQRLELSDIYQIPSVD SADNLSEKLEREWDRELASKKNPKLINALR RCFFWRFMFYGIFLYLGEVTKAVQPLLLGR IIASYDPDNKEERSIAIYLGIGLCLLFIVR TLLLHPAIFGLHHIGMQMRIAMFSLIYKKT LKLSSRVLDKISIGQLVSLLSNNLNKFDEG LALAHFVWIAPLQVALLMGLIWELLQASAF CGLGFLIVLALFQAGLGRMMMKYRDQRAGK ISERLVITSEMIENIQSVKAYCWEEAMEKM IENLRQTELKLTRKAAYVRYFNSSAFFFSG FFVVFLSVLPYALIKGIILRKIFTTISFCI VLRMAVTRQFPWAVQTWYDSLGAINKIQDF LQKQEYKTLEYNLTTTEVVMENVTAFWEEG |

TABLE 28-continued

Amino Acid Sequence of a V5-Tagged SV40 J Domain-CFTR Protein.

| Protein Region (N- to C-terminal) | Sequence Identifier | Amino Acid Sequence 12345678901234567890123 4567890 |
|---|---|---|
| | | FGELFEKAKQNNNNRKTSNGDDSLFFSNFS LLGTPVLKDINFKIERGQLLAVAGSTGAGK TSLLMVIMGELEPSEGKIKHSGRISFCSQF SWIMPGTIKENIIFGVSYDEYRYRSVIKAC QLEEDISKFAEKDNIVLGEGGITLSGGQRA RISLARAVYKDADLYLLDSPFGYLDVLTEK EIFESCVCKLMANKTRILVTSKMEHLKKAD KILILHEGSSYFYGTFSELQNLQPDFSSKL MGCDSFDQFSAERRNSILTETLHRFSLEGD APVSWTETKKQSFKQTGEFGEKRKNSILNP INSIRKFSIVQKTPLQMNGIEEDSDEPLER RLSLVPDSEQGEAILPRISVISTGPTLQAR RRQSVLNLMTHSVNQGQNIHRKTTASTRKV SLAPQANLTELDIYSRRLSQETGLEISEEI NEEDLKECFFDDMESIPAVTTWNTYLRYIT VHKSLIFVLIWCLVIFLAEVAASLVVLWLL GNTPLQDKGNSTHSRNNSYAVIITSTSSYY VFYIYVGVADTLLAMGFFRGLPLVHTLITV SKILHHKMLHSVLQAPMSTLNTLKAGGILN RFSKDIAILDDLLPLTIFDFIQLLLIVIGA IAVVAVLQPYIFVATVPVIVAFIMLRAYFL QTSQQLKQLESEGRSPIFTHLVTSLKGLWT LRAFGRQPYFETLFHKALNLHTANWFLYLS TLRWFQMRIEMIFVIFFIAVTFISILTTGE GEGRVGIILTLAMNIMSTLQWAVNSSIDVD SLMRSVSRVFKFIDMPTEGKPTKSTKPYKN GQLSKVMIIENSHVKKDDIWPSGGQMTVKD LTAKYTEGGNAILENISFSISPGQRVGLLG RTGSGKSTLLSAFLRLLNTEGEIQIDGVSW DSITLQQWRKAFGVIPQKVFIFSGTFRKNL DPYEQWSDQEIWKVADEVGLRSVIEQFPGK LDFVLVDGGCVLSHGHKQLMCLARSVLSKA KILLLDEPSAHLDPVTYQIIRRTLKQAFAD CTVILCEHRIEAMLECQQFLVIEENKVRQY DSIQKLLNERSLFRQAISPSDRVKLFPHRN SSKCKSKPQIAALKEETEEEVQDTRL |
| V5 epitope domain | residues 1-15 of SEQ ID NO: 218 | MGKPIPNPLLGLDST |
| Linker | residues 16-21 of SEQ ID NO: 218 | GTGSEF |
| SV40 J domain | residues 22-101 of SEQ ID NO: 218 | MDKVLNREESLQLMDLLGLERSAWGNIPLM RKAYLKKCKEFHPDKGGDEEKMKKMNTLYK KMEDGVKYAHQPDFGGFWDA |
| Linker | residues 102-106 of SEQ ID NO: 218 | DIAAA |
| CFTR | residues 107-1586 of SEQ ID NO: 218 | MQRSPLEKASVVSKLFFSWTRPILRKGYRQ RLELSDIYQIPSVDSADNLSEKLEREWDRE LASKKNPKLINALRRCFFWRFMFYGIFLYL GEVTKAVQPLLLGRIIASYDPDNKEERSIA IYLGIGLCLLFIVRTLLLHPAIFGLHHIGM QMRIAMFSLIYKKTLKLSSRVLDKISIGQL VSLLSNNLNKFDEGLALAHFVWIAPLQVAL LMGLIWELLQASAFCGLGFLIVLALFQAGL GRMMMKYRDQRAGKISERLVITSEMIENIQ SVKAYCWEEAMEKMIENLRQTELKLTRKAA YVRYFNSSAFFFSGFFVVFLSVLPYALIKG IILRKIFTTISFCIVLRMAVTRQFPWAVQT WYDSLGAINKIQDFLQKQEYKTLEYNLTTT EVVMENVTAFWEEGFGELFEKAKQNNNNRK TSNGDDSLFFSNFSLLGTPVLKDINFKIER GQLLAVAGSTGAGKTSLLMVIMGELEPSEG KIKHSGRISFCSQFSWIMPGTIKENIIFGV SYDEYRYRSVIKACQLEEDISKFAEKDNIV LGEGGITLSGGQRARISLARAVYKDADLYL LDSPFGYLDVLTEKEIFESCVCKLMANKTR |

TABLE 28-continued

Amino Acid Sequence of a V5-Tagged SV40 J Domain-CFTR Protein.

| Protein Region (N- to C- terminal) | Sequence Identifier | Amino Acid Sequence 12345678901234567890 |
|---|---|---|
| | | ILVTSKMEHLKKADKILILHEGSSYFYGTF SELQNLQPDFSSKLMGCDSFDQFSAERRNS ILTETLHRFSLEGDAPVSWTETKKQSFKQT GEFGEKRKNSILNPINSIRKFSIVQKTPLQ MNGIEEDSDEPLERRLSLVPDSEQGEAILP RISVISTGPTLQARRRQSVLNLMTHSVNQG QNIHRKTTASTRKVSLAPQANLTELDIYSR RLSQETGLEISEEINEEDLKECFFDDMESI PAVTTWNTYLRYITVHKSLIFVLIWCLVIF LAEVAASLVVLWLLGNTPLQDKGNSTHSRN NSYAVIITSTSSYYVFYIYVGVADTLLAMG FFRGLPLVHTLITVSKILHHKMLHSVLQAP MSTLNTLKAGGILNRFSKDIAILDDLLPLT IFDFIQLLLIVIGAIAVVAVLQPYIFVATV PVIVAFIMLRAYFLQTSQQLKQLESEGRSP IFTHLVTSLKGLWTLRAFGRQPYFETLFHK ALNLHTANWFLYLSTLRWFQMRIEMIFVIF FIAVTFISILTTGEGEGRVGIILTLAMNIM STLQWAVNSSIDVDSLMRSVSRVFKFIDMP TEGKPTKSTKPYKNGQLSKVMIIENSHVKK DDIWPSGGQMTVKDLTAKYTEGGNAILENI SFSISPGQRVGLLGRTGSGKSTLLSAFLRL LNTEGEIQIDGVSWDSITLQQWRKAFGVIP QKVFIFSGTFRKNLDPYEQWSDQEIWKVAD EVGLRSVIEQFPGKLDFVLVDGGCVLSHGH KQLMCLARSVLSKAKILLLDEPSAHLDPVT YQIIRRTLKQAFADCTVILCEHRIEAMLEC QQFLVIEENKVRQYDSIQKLLNERSLFRQA ISPSDRVKLFPHRNSSKCKSKPQIAALKEE TEEEVQDTRL |

The amino acid sequence of a V5-tagged CFTR (Δ508F) protein is shown in the table below.

TABLE 29

Amino Acid Sequence of a V5-Tagged CFTR(Δ508F) Protein.

| Protein Region (N- to C- terminal) | Sequence Identifier | Amino Acid Sequence 12345678901234567890 |
|---|---|---|
| V5-tagged CFTR(Δ508F) protein | SEQ ID NO: 219 | MGKPIPNPLLGLDSTGTGSEFDIAAAMQRS PLEKASVVSKLFFSWTRPILRKGYRQRLEL SDIYQIPSVDSADNLSEKLEREWDRELASK KNPKLINALRRCFFWRFMFYGIFLYLGEVT KAVQPLLLGRIIASYDPDNKEERSIAIYLG IGLCLLFIVRTLLLHPAIFGLHHIGMQMRI AMFSLIYKKTLKLSSRVLDKISIGQLVSLL SNNLNKFDEGLALAHFVWIAPLQVALLMGL IWELLQASAFCGLGFLIVLALFQAGLGRMM MKYRDQRAGKISERLVITSEMIENIQSVKA YCWEEAMEKMIENLRQTELKLTRKAAYVRY FNSSAFFFSGFFVVFLSVLPYALIKGIILR KIFTTISFCIVLRMAVTRQFPWAVQTWYDS LGAINKIQDFLQKQEYKTLEYNLTTTEVVM ENVTAFWEEGFGELFEKAKQNNNNRKTSNG DDSLFFSNFSLLGTPVLKDINFKIERGQLL AVAGSTGAGKTSLLMVIMGELEPSEGKIKH SGRISFCSQFSWIMPGTIKENIIGVSYDEY RYRSVIKACQLEEDISKFAEKDNIVLGEGG ITLSGGQRARISLARAVYKDADLYLLDSPF GYLDVLTEKEIFESCVCKLMANKTRILVTS KMEHLKKADKILILHEGSSYFYGTFSELQN LQPDFSSKLMGCDSFDQFSAERRNSILTET LHRFSLEGDAPVSWTETKKQSFKQTGEFGE KRKNSILNPINSIRKFSIVQKTPLQMNGIE EDSDEPLERRLSLVPDSEQGEAILPRISVI STGPTLQARRRQSVLNLMTHSVNQGQNIHR KTTASTRKVSLAPQANLTELDIYSRRLSQE |

TABLE 29-continued

Amino Acid Sequence of a V5-Tagged CFTR(Δ508F) Protein.

| Protein Region (N- to C-terminal) | Sequence Identifier | Amino Acid Sequence<br>12345678901234567890123456789 0 |
|---|---|---|
| | | TGLEISEEINEEDLKECFFDDMESIPAVTT<br>WNTYLRYITVHKSLIFVLIWCLVIFLAEVA<br>ASLVVLWLLGNTPLQDKGNSTHSRNNSYAV<br>IITSTSSYYVFYIYVGVADTLLAMGFFRGL<br>PLVHTLITVSKILHHKMLHSVLQAPMSTLN<br>TLKAGGILNRFSKDIAILDDLLPLTIFDFI<br>QLLLIVIGAIAVVAVLQPYIFVATVPVIVA<br>FIMLRAYFLQTSQQLKQLESEGRSPIFTHL<br>VTSLKGLWTLRAFGRQPYFETLFHKALNLH<br>TANWFLYLSTLRWFQMRIEMIFVIFFIAVT<br>FISILTTGEGEGRVGIILTLAMNIMSTLQW<br>AVNSSIDVDSLMRSVSRVFKFIDMPTEGKP<br>TKSTKPYKNGQLSKVMIIENSHVKKDDIWP<br>SGGQMTVKDLTAKYTEGGNAILENISFSIS<br>PGQRVGLLGRTGSGKSTLLSAFLRLLNTEG<br>EIQIDGVSWDSITLQQWRKAFGVIPQKVFI<br>FSGTFRKNLDPYEQWSDQEIWKVADEVGLR<br>SVIEQFPGKLDFVLVDGGCVLSHGHKQLMC<br>LARSVLSKAKILLLDEPSAHLDPVTYQIIR<br>RTLKQAFADCTVILCEHRIEAMLECQQFLV<br>IEENKVRQYDSIQKLLNERSLFRQAISPSD<br>RVKLFPHRNSSKCKSKPQIAALKEETEEEV<br>QDTRL |
| V5 epitope domain | residues 1-15 of SEQ ID NO: 219 | MGKPIPNPLLGLDST |
| Linker | residues 16-26 of SEQ ID NO: 219 | GTGSEFDIAAA |
| CFTR(Δ508F) | residues 27-1505 of SEQ ID NO: 219 | MQRSPLEKASVVSKLFFSWTRPILRKGYRQ<br>RLELSDIYQIPSVDSADNLSEKLEREWDRE<br>LASKKNPKLINALRRCFFWRFMFYGIFLYL<br>GEVTKAVQPLLLGRIIASYDPDNKEERSIA<br>IYLGIGLCLLFIVRTLLLHPAIFGLHHIGM<br>QMRIAMFSLIYKKTLKLSSRVLDKISIGQL<br>VSLLSNNLNKFDEGLALAHFVWIAPLQVAL<br>LMGLIWELLQASAFCGLGFLIVLALFQAGL<br>GRMMMKYRDQRAGKISERLVITSEMIENIQ<br>SVKAYCWEEAMEKMIENLRQTELKLTRKAA<br>YVRYFNSSAFFFSGFFVVFLSVLPYALIKG<br>IILRKIFTTISFCIVLRMAVTRQFPWAVQT<br>WYDSLGAINKIQDFLQKQEYKTLEYNLTTT<br>EVVMENVTAFWEEGFGELFEKAKQNNNNRK<br>TSNGDDSLFFSNFSLLGTPVLKDINFKIER<br>GQLLAVAGSTGAGKTSLLMVIMGELEPSEG<br>KIKHSGRISFCSQFSWIMPGTIKENIIGVS<br>YDEYRYRSVIKACQLEEDISKFAEKDNIVL<br>GEGGITLSGGQRARISLARAVYKDADLYLL<br>DSPFGYLDVLTEKEIFESCVCKLMANKTRI<br>LVTSKMEHLKKADKILILHEGSSYFYGTFS<br>ELQNLQPDFSSKLMGCDSFDQFSAERRNSI<br>LTETLHRFSLEGDAPVSWTETKKQSFKQTG<br>EFGEKRKNSILNPINSIRKFSIVQKTPLQM<br>NGIEEDSDEPLERRLSLVPDSEQGEAILPR<br>ISVISTGPTLQARRRQSVLNLMTHSVNQGQ<br>NIHRKTTASTRKVSLAPQANLTELDIYSRR<br>LSQETGLEISEEINEEDLKECFFDDMESIP<br>AVTTWNTYLRYITVHKSLIFVLIWCLVIFL<br>AEVAASLVVLWLLGNTPLQDKGNSTHSRNN<br>SYAVIITSTSSYYVFYIYVGVADTLLAMGF<br>FRGLPLVHTLITVSKILHHKMLHSVLQAPM<br>STLNTLKAGGILNRFSKDIAILDDLLPLTI<br>FDFIQLLLIVIGAIAVVAVLQPYIFVATVP<br>VIVAFIMLRAYFLQTSQQLKQLESEGRSPI<br>FTHLVTSLKGLWTLRAFGRQPYFETLFHKA<br>LNLHTANWFLYLSTLRWFQMRIEMIFVIFF<br>IAVTFISILTTGEGEGRVGIILTLAMNIMS<br>TLQWAVNSSIDVDSLMRSVSRVFKFIDMPT<br>EGKPTKSTKPYKNGQLSKVMIIENSHVKKD<br>DIWPSGGQMTVKDLTAKYTEGGNAILENIS<br>FSISPGQRVGLLGRTGSGKSTLLSAFLRLL |

TABLE 29-continued

Amino Acid Sequence of a V5-Tagged CFTR(Δ508F) Protein.

| Protein Region (N- to C-terminal) | Sequence Identifier | Amino Acid Sequence 12345678901234567890123456789 0 |
|---|---|---|
| | | NTEGEIQIDGVSWDSITLQQWRKAFGVIPQ KVFIFSGTFRKNLDPYEQWSDQEIWKVADE VGLRSVIEQFPGKLDFVLVDGGCVLSHGHK QLMCLARSVLSKAKILLLDEPSAHLDPVTY QIIRRTLKQAFADCTVILCEHRIEAMLECQ QFLVIEENKVRQYDSIQKLLNERSLFRQAI SPSDRVKLFPHRNSSKCKSKPQIAALKEET EEEVQDTRL |

The amino acid sequence of a V5-tagged BAG domain-CFTR (Δ508F) fusion protein is shown in the table below.

TABLE 30

Amino Acid Sequence of a V5-Tagged BAG Domain-CFTR(Δ508F) Fusion Protein.

| Protein Region (N- to C-terminal) | Sequence Identifier | Amino Acid Sequence 12345678901234567890123456789 0 |
|---|---|---|
| V5-tagged BAG domain-CFTR(Δ508F) fusion protein | SEQ ID NO: 220 | MGKPIPNPLLGLDSTGTGSEFHPGVLKVEA ILEKVQGLEQAVDNFEGKKTDKKYLMIEEY LTKELLALDSVDPEGRADVRQARRDGVRKV QTILEKLEQKAIDDIAAAMQRSPLEKASVV SKLFFSWTRPILRKGYRQRLELSDIYQIPS VDSADNLSEKLEREWDRELASKKNPKLINA LRRCFFWRFMFYGIFLYLGEVTKAVQPLLL GRIIASYDPDNKEERSIAIYLGIGLCLLFI VRTLLLHPAIFGLHHIGMQMRIAMFSLIYK KTLKLSSRVLDKISIGQLVSLLSNNLNKFD EGLALAHFVWIAPLQVALLMGLIWELLQAS AFCGLGFLIVLALFQAGLGRMMMKYRDQRA GKISERLVITSEMIENIQSVKAYCWEEAME KMIENLRQTELKLTRKAAYVRYFNSSAFFF SGFFVVFLSVLPYALIKGIILRKIFTTISF CIVLRMAVTRQFPWAVQTWYDSLGAINKIQ DFLQKQEYKTLEYNLTTTEVVMENVTAFWE EGFGELFEKAKQNNNNRKTSNGDDSLFFSN FSLLGTPVLKDINFKIERGQLLAVAGSTGA GKTSLLMVIMGELEPSEGKIKHSGRISFCS QFSWIMPGTIKENIIGVSYDEYRYRSVIKA CQLEEDISKFAEKDNIVLGEGGITLSGGQR ARISLARAVYKDADLYLLDSPFGYLDVLTE KEIFESCVCKLMANKTRILVTSKMEHLKKA DKILILHEGSSYFYGTFSELQNLQPDFSSK LMGCDSFDQFSAERRNSILTETLHRFSLEG DAPVSWTETKKQSFKQTGEFGEKRKNSILN PINSIRKFSIVQKTPLQMNGIEEDSDEPLE RRLSLVPDSEQGEAILPRISVISTGPTLQA RRRQSVLNLMTHSVNQGQNIHRKTTASTRK VSLAPQANLTELDIYSRRLSQETGLEISEE INEEDLKECFFDDMESIPAVTTWNTYLRYI TVHKSLIFVLIWCLVIFLAEVAASLVVLWL LGNTPLQDKGNSTHSRNNSYAVIITSTSSY YVFYIYVGVADTLLAMGFFRGLPLVHTLIT VSKILHHKMLHSVLQAPMSTLNTLKAGGIL NRFSKDIAILDDLLPLTIFDFIQLLLIVIG AIAVVAVLQPYIFVATVPVIVAFIMLRAYF LQTSQQLKQLESEGRSPIFTHLVTSLKGLW TLRAFGRQPYFETLFHKALNLHTANWFLYL STLRWFQMRIEMIFVIFFIAVTFISILTTG EGEGRVGIILTLAMNIMSTLQWAVNSSIDV DSLMRSVSRVFKFIDMPTEGKPTKSTKPYK NGQLSKVMIIENSHVKKDDIWPSGGQMTVK DLTAKYTEGGNAILENISFSISPGQRVGLL GRTGSGKSTLLSAFLRLLNTEGEIQIDGVS WDSITLQQWRKAFGVIPQKVFIFSGTFRKN LDPYEQWSDQEIWKVADEVGLRSVIEQFPG KLDFVLVDGGCVLSHGHKQLMCLARSVLSK AKILLLDEPSAHLDPVTYQIIRRTLKQAFA |

TABLE 30-continued

Amino Acid Sequence of a V5-Tagged BAG Domain-CFTR(Δ508F) Fusion Protein.

| Protein Region (N- to C-terminal) | Sequence Identifier | Amino Acid Sequence 12345678901234567890123456789 0 |
|---|---|---|
| | | DCTVILCEHRIEAMLECQQFLVIEENKVRQ YDSIQKLLNERSLFRQAISPSDRVKLFPHR NSSKCKSKPQIAALKEETEEEVQDTRL |
| V5 epitope domain | residues 1-15 of SEQ ID NO: 220 | MGKPIPNPLLGLDST |
| Linker | residues 16-21 of SEQ ID NO: 220 | GTGSEF |
| BAG domain (from BAG3) | residues 22-103 of SEQ ID NO: 220 | HPGVLKVEAILEKVQGLEQAVDNFEGKKTD KKYLMIEEYLTKELLALDSVDPEGRADVRQ ARRDGVRKVQTILEKLEQKAID |
| Linker | residues 104-108 of SEQ ID NO: 220 | DIAAA |
| CFTR(Δ508F) | residues 109-1587 of SEQ ID NO: 220 | MQRSPLEKASVVSKLFFSWTRPILRKGYRQ RLELSDIYQIPSVDSADNLSEKLEREWDRE LASKKNPKLINALRRCFFWRFMFYGIFLYL GEVTKAVQPLLLGRIIASYDPDNKEERSIA IYLGIGLCLLFIVRTLLLHPAIFGLHHIGM QMRIAMFSLIYKKTLKLSSRVLDKISIGQL VSLLSNNLNKFDEGLALAHFVWIAPLQVAL LMGLIWELLQASAFCGLGFLIVLALFQAGL GRMMMKYRDQRAGKISERLVITSEMIENIQ SVKAYCWEEAMEKMIENLRQTELKLTRKAA YVRYFNSSAFFFSGFFVVFLSVLPYALIKG IILRKIFTTISFCIVLRMAVTRQFPWAVQT WYDSLGAINKIQDFLQKQEYKTLEYNLTTT EVVMENVTAFWEEGFGELFEKAKQNNNNRK TSNGDDSLFFSNFSLLGTPVLKDINFKIER GQLLAVAGSTGAGKTSLLMVIMGELEPSEG KIKHSGRISFCSQFSWIMPGTIKENIIGVS YDEYRYRSVIKACQLEEDISKFAEKDNIVL GEGGITLSGGQRARISLARAVYKDADLYLL DSPFGYLDVLTEKEIFESCVCKLMANKTRI LVTSKMEHLKKADKILILHEGSSYFYGTFS ELQNLQPDFSSKLMGCDSFDQFSAERRNSI LTETLHRFSLEGDAPVSWTETKKQSFKQTG EFGEKRKNSILNPINSIRKFSIVQKTPLQM NGIEEDSDEPLERRLSLVPDSEQGEAILPR ISVISTGPTLQARRRQSVLNLMTHSVNQGQ NIHRKTTASTRKVSLAPQANLTELDIYSRR LSQETGLEISEEINEEDLKECFFDDMESIP AVTTWNTYLRYITVHKSLIFVLIWCLVIFL AEVAASLVVLWLLGNTPLQDKGNSTHSRNN SYAVIITSTSSYYVFYIYVGVADTLLAMGF FRGLPLVHTLITVSKILHHKMLHSVLQAPM STLNTLKAGGILNRFSKDIAILDDLLPLTI FDFIQLLLIVIGAIAVVAVLQPYIFVATVP VIVAFIMLRAYFLQTSQQLKQLESEGRSPI FTHLVTSLKGLWTLRAFGRQPYFETLFHKA LNLHTANWFLYLSTLRWFQMRIEMIFVIFF IAVTFISILTTGEGEGRVGIILTLAMNIMS TLQWAVNSSIDVDSLMRSVSRVFKFIDMPT EGKPTKSTKPYKNGQLSKVMIIENSHVKKD DIWPSGGQMTVKDLTAKYTEGGNAILENIS FSISPGQRVGLLGRTGSGKSTLLSAFLRLL NTEGEIQIDGVSWDSITLQQWRKAFGVIPQ KVFIFSGTFRKNLDPYEQWSDQEIWKVADE VGLRSVIEQFPGKLDFVLVDGGCVLSHGHK QLMCLARSVLSKAKILLLDEPSAHLDPVTY QIIRRTLKQAFADCTVILCEHRIEAMLECQ QFLVIEENKVRQYDSIQKLLNERSLFRQAI SPSDRVKLFPHRNSSKCKSKPQIAALKEET EEEVQDTRL |

The amino acid of a V5-tagged J domain-CFTR (Δ508F) fusion protein is shown in the table below.

TABLE 31

Amino Acid Sequence of a V5-Tagged SV40 J Domain-CFTR(Δ508F) Fusion Protein.

| Protein Region (N- to C-terminal) | Sequence Identifier | Amino Acid Sequence 12345678901234567890123456 7890 |
|---|---|---|
| V5-tagged, SV40 J domain-CFTR(Δ508F) fusion protein | SEQ ID NO: 221 | MGKPIPNPLLGLDSTGTGSEFMDKVLNREE SLQLMDLLGLERSAWGNIPLMRKAYLKKCK EFHPDKGGDEEKMKKMNTLYKKMEDGVKYA HQPDFGGFWDADIAAAMQRSPLEKASVVSK LFFSWTRPILRKGYRQRLELSDIYQIPSVD SADNLSEKLEREWDRELASKKNPKLINALR RCFFWRFMFYGIFLYLGEVTKAVQPLLLGR IIASYDPDNKEERSIAIYLGIGLCLLFIVR TLLLHPAIFGLHHIGMQMRIAMFSLIYKKT LKLSSRVLDKISIGQLVSLLSNNLNKFDEG LALAHFVWIAPLQVALLMGLIWELLQASAF CGLGFLIVLALFQAGLGRMMMKYRDQRAGK ISERLVITSEMIENIQSVKAYCWEEAMEKM IENLRQTELKLTRKAAYVRYFNSSAFFFSG FFVVFLSVLPYALIKGIILRKIFTTISFCI VLRMAVTRQFPWAVQTWYDSLGAINKIQDF LQKQEYKTLEYNLTTTEVVMENVTAFWEEG FGELFEKAKQNNNNRKTSNGDDSLFFSNFS LLGTPVLKDINFKIERGQLLAVAGSTGAGK TSLLMVIMGELEPSEGKIKHSGRISFCSQF SWIMPGTIKENIIGVSYDEYRYRSVIKACQ LEEDISKFAEKDNIVLGEGGITLSGGQRAR ISLARAVYKDADLYLLDSPFGYLDVLTEKE IFESCVCKLMANKTRILVTSKMEHLKKADK ILILHEGSSYFYGTFSELQNLQPDFSSKLM GCDSFDQFSAERRNSILTETLHRFSLEGDA PVSWTETKKQSFKQTGEFGEKRKNSILNPI NSIRKFSIVQKTPLQMNGIEEDSDEPLERR LSLVPDSEQGEAILPRISVISTGPTLQARR RQSVLNLMTHSVNQGQNIHRKTTASTRKVS LAPQANLTELDIYSRRLSQETGLEISEEIN EEDLKECFFDDMESIPAVTTWNTYLRYITV HKSLIFVLIWCLVIFLAEVAASLVVLWLLG NTPLQDKGNSTHSRNNSYAVIITSTSSYYV FYIYVGVADTLLAMGFFRGLPLVHTLITVS KILHHKMLHSVLQAPMSTLNTLKAGGILNR FSKDIAILDDLLPLTIFDFIQLLLIVIGAI AVVAVLQPYIFVATVPVIVAFIMLRAYFLQ TSQQLKQLESEGRSPIFTHLVTSLKGLWTL RAFGRQPYFETLFHKALNLHTANWFLYLST LRWFQMRIEMIFVIFFIAVTFISILTTGEG EGRVGIILTLAMNIMSTLQWAVNSSIDVDS LMRSVSRVFKFIDMPTEGKPTKSTKPYKNG QLSKVMIIENSHVKKDDIWPSGGQMTVKDL TAKYTEGGNAILENISFSISPGQRVGLLGR TGSGKSTLLSAFLRLLNTEGEIQIDGVSWD SITLQQWRKAFGVIPQKVFIFSGTFRKNLD PYEQWSDQEIWKVADEVGLRSVIEQFPGKL DFVLVDGGCVLSHGHKQLMCLARSVLSKAK ILLLDEPSAHLDPVTYQIIRRTLKQAFADC TVILCEHRIEAMLECQQFLVIEENKVRQYD SIQKLLNERSLFRQAISPSDRVKLFPHRNS SKCKSKPQIAALKEETEEEVQDTRL |
| V5 epitope domain | residues 1-15 of SEQ ID NO: 221 | MGKPIPNPLLGLDST |
| Linker | residues 16-21 of SEQ ID NO: 221 | GTGSEF |
| SV40 J domain | residues 22-101 of SEQ ID NO: 221 | MDKVLNREESLQLMDLLGLERSAWGNIPLM RKAYLKKCKEFHPDKGGDEEKMKKMNTLYK KMEDGVKYAHQPDFGGFWDA |
| Linker | residues 102-106 of SEQ ID NO: 221 | DIAAA |

TABLE 31-continued

Amino Acid Sequence of a V5-Tagged SV40 J Domain-CFTR(Δ508F) Fusion Protein.

| Protein Region (N- to C-terminal) | Sequence Identifier | Amino Acid Sequence<br>12345678901234567890123456789 0 |
|---|---|---|
| CFTR(Δ508F) | residues 107-1585 of SEQ ID NO: 221 | MQRSPLEKASVVSKLFFSWTRPILRKGYRQ<br>RLELSDIYQIPSVDSADNLSEKLEREWDRE<br>LASKKNPKLINALRRCFFWRFMFYGIFLYL<br>GEVTKAVQPLLLGRIIASYDPDNKEERSIA<br>IYLGIGLCLLFIVRTLLLHPAIFGLHHIGM<br>QMRIAMFSLIYKKTLKLSSRVLDKISIGQL<br>VSLLSNNLNKFDEGLALAHFVWIAPLQVAL<br>LMGLIWELLQASAFCGLGFLIVLALFQAGL<br>GRMMMKYRDQRAGKISERLVITSEMIENIQ<br>SVKAYCWEEAMEKMIENLRQTELKLTRKAA<br>YVRYFNSSAFFFSGFFVVFLSVLPYALIKG<br>IILRKIFTTISFCIVLRMAVTRQFPWAVQT<br>WYDSLGAINKIQDFLQKQEYKTLEYNLTTT<br>EVVMENVTAFWEEGFGELFEKAKQNNNNRK<br>TSNGDDSLFFSNFSLLGTPVLKDINFKIER<br>GQLLAVAGSTGAGKTSLLMVIMGELEPSEG<br>KIKHSGRISFCSQFSWIMPGTIKENIIGVS<br>YDEYRYRSVIKACQLEEDISKFAEKDNIVL<br>GEGGITLSGGQRARISLARAVYKDADLYLL<br>DSPFGYLDVLTEKEIFESCVCKLMANKTRI<br>LVTSKMEHLKKADKILILHEGSSYFYGTFS<br>ELQNLQPDFSSKLMGCDSFDQFSAERRNSI<br>LTETLHRFSLEGDAPVSWTETKKQSFKQTG<br>EFGEKRKNSILNPINSIRKFSIVQKTPLQM<br>NGIEEDSDEPLERRLSLVPDSEQGEAILPR<br>ISVISTGPTLQARRRQSVLNLMTHSVNQGQ<br>NIHRKTTASTRKVSLAPQANLTELDIYSRR<br>LSQETGLEISEEINEEDLKECFFDDMESIP<br>AVTTWNTYLRYITVHKSLIFVLIWCLVIFL<br>AEVAASLVVLWLLGNTPLQDKGNSTHSRNN<br>SYAVIITSTSSYYVFYIYVGVADTLLAMGF<br>FRGLPLVHTLITVSKILHHKMLHSVLQAPM<br>STLNTLKAGGILNRFSKDIAILDDLLPLTI<br>FDFIQLLLIVIGAIAVVAVLQPYIFVATVP<br>VIVAFIMLRAYFLQTSQQLKQLESEGRSPI<br>FTHLVTSLKGLWTLRAFGRQPYFETLFHKA<br>LNLHTANWFLYLSTLRWFQMRIEMIFVIFF<br>IAVTFISILTTGEGEGRVGIILTLAMNIMS<br>TLQWAVNSSIDVDSLMRSVSRVFKFIDMPT<br>EGKPTKSTKPYKNGQLSKVMIIENSHVKKD<br>DIWPSGGQMTVKDLTAKYTEGGNAILENIS<br>FSISPGQRVGLLGRTGSGKSTLLSAFLRLL<br>NTEGEIQIDGVSWDSITLQQWRKAFGVIPQ<br>KVFIFSGTFRKNLDPYEQWSDQEIWKVADE<br>VGLRSVIEQFPGKLDFVLVDGGCVLSHGHK<br>QLMCLARSVLSKAKILLLDEPSAHLDPVTY<br>QIIRRTLKQAFADCTVILCEHRIEAMLECQ<br>QFLVIEENKVRQYDSIQKLLNERSLFRQAI<br>SPSDRVKLFPHRNSSKCKSKPQIAALKEET<br>EEEVQDTRL |

Figure 8B:
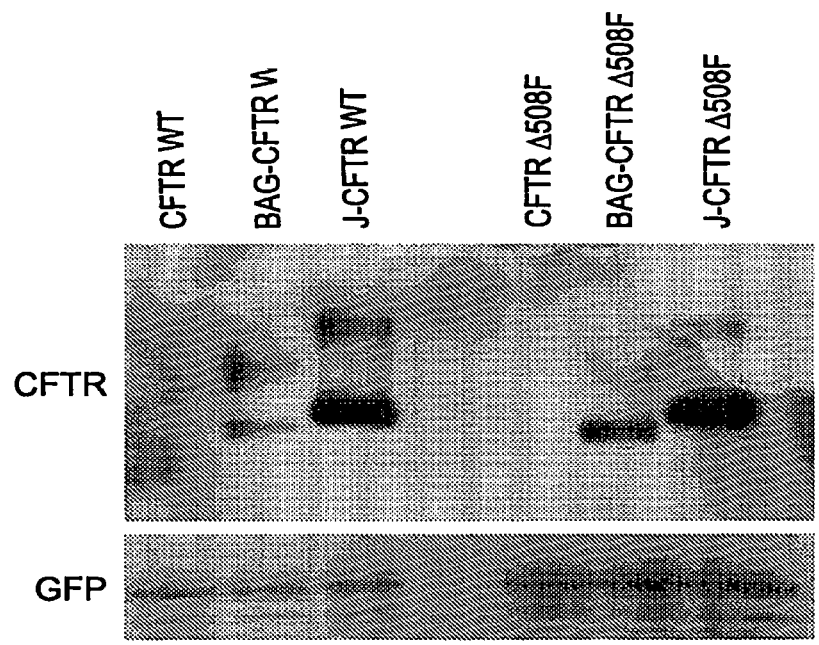

To study the expression of the various CFTR protein constructs, the plasmids were transfected to HEK293 cells. Samples of cell lysates from two-day cultures of transfected cells were analyzed by immunoblotting with anti-V5 antibody. As shown in FIG. 8B, neither the wild-type CFTR protein nor the mutant CFTR (Δ508F) protein expressed well in transfected cells. Fusion of either protein with a BAG3 domain (BAG-CFTR WT, BAG-CFTR Δ508F) provided some enhancement of expression. In contrast, fusion with a J domain significantly enhanced the level of expression of both wild-type and mutant proteins (J-CFTR WT, J-CFTR Δ508F). See, FIG. 8B Conclusion of Results The results of the above experiments clearly show that fusion with a J domain significantly enhances the level of expression of a protein of interest, including therapeutically useful proteins.

Example 3. Compositions and Methods for Enhancing Expression of Target Proteins of Interest Using an Unmodified Arrangement Expression vector plasmids were constructed for expressing fusion proteins for enhancing expression of specific proteins (target proteins). As described below, fusion proteins were usually linked to a standard epitope tag for easy identification or isolation using a corresponding anti-tag antibody and standard immunoblot (such as dot blot, Western blot) assays.

A DNA linker molecule having a nucleotide sequence containing various restriction enzyme sites for cloning heterologous DNA molecules was produced by annealing two single-stranded DNA molecules having the sequences shown below (5' to 3'):

```
                                                       (SEQ ID NO: 187)
AGCTTGGTACCGGATCCGAATTCGATATCGCGGCCGCTCTCGAGTCTA

GAGGGCC
and (SEQ ID NO: 188)
CTCTAGACTCGAGAGCGGCCGCGATATCGAATTCGGATCCGGTACCA.
```

The annealed linker molecule was then inserted into plasmid pcDNA3 (catalogue no. V790-20, Invitrogen) digested with HindIII and ApaI downstream of a CMV promoter to yield the expression vector plasmid pcDNA' for use in mammalian host cells.

DNA molecules encoding the V5 epitope tag (GKPIPN-PLLGLDST; SEQ ID NO:110) or the Flag epitope tag (DYKDDDDK; SEQ ID NO:111) were synthesized and inserted into plasmid pcDNA' digested with HindIII and KpnI. A double-stranded DNA molecule having the coding sequence for the V5 epitope tag with an N-terminal methionine, i.e., ATGGGTAAGCCTATCCCTAACCCTCTC-CTCGGTCTCGATTCTACG (SEQ ID NO:189), was inserted into pcDNA' digested with XhoI and XbaI to yield plasmid V5-pcDNA'.

A DNA molecule having the coding sequence for the Flag epitope tag, i.e., GATTACAAGGATGACGATGACAAG (SEQ ID NO:190), was inserted into plasmid pcDNA' digested with XhoI and XbaI to yield plasmid Flag-pcDNA'.

To express IL13Rα2 receptor protein, a DNA molecule encoding an IL13Rα2 receptor protein was inserted into plasmid V5-pcDNA' digested with HindIII and KpnI.

To express TNR1 receptor protein, a DNA molecule encoding a TNRI receptor protein was inserted into plasmid V5-pcDNA' digested with HindIII and KpnI.

To express α1 anti-trypsin ("α1AT"), a DNA molecule encoding an α1 anti-trypsin was inserted into plasmid V5-pcDNA' digested with HindIII and KpnI.

A DNA molecule encoding an Fc region polypeptide of a human IgG1 molecule was synthesized and inserted into V5-pcDNA' digested with XbaI and ApaI.

Unless indicated otherwise, a DNA molecule encoding a particular protein expression enhancing polypeptide was cloned into plasmid Flag-pcDNA' digested with EcoRI and EcoRV to insert a DNA segment encoding the J domain of an Erdj3 J protein, or digested with KpnI and BamHI to insert a DNA segment encoding the J domain of an Erdj5 J protein, to yield plasmid (J domain)-Flag-pcDNA', wherein "(J domain)" refers to the particular protein expression enhancing polypeptide specified in the examples below.

Unless indicated otherwise, each DNA molecule encoding a target binding domain for a corresponding target protein in the examples below was inserted into plasmid Flag-pcDNA' digested with NotI and XhoI.

Expression and Detection of Target Proteins in HEK293 Cells

Expression vector plasmids encoding various protein constructs were transfected into HEK293 cells with X-tremeGENE HP transfection reagent (catalogue no. 06365752001, Roche). As indicated in the examples below, a separate plasmid expressing the green fluorescent protein (GFP) was co-transfected with each expression vector plasmid encoding a fusion protein of the invention to monitor the transfection efficiency. Cultures of transfected cells were incubated for two days, and cells were lysed in lysis buffer (10 mM Tris-HCl, pH8.0, 150 mM NaCl, 10 mM EDTA, 2% SDS) containing 2 mM PMSF. After brief sonication, the sample was analyzed for express proteins using dot blot or Western immunoblot assays. For Western blot analysis, samples were boiled in SDS-sample buffer and run on polyacrylamide electrophoresis, followed by transfer of separated protein bands to membrane (PVDF membrane). The expression of GFP as an internal transfection control was detected using an anti-GFP antibody.

Expressed proteins in dot and Western blots were detected using a chemiluminescent signal. Briefly, blots were reacted with a primary antibody that binds the particular epitope tag (e.g., V5 or Flag) carried by the proteins. After rinsing away unreacted primary antibody, a secondary, enzyme-linked antibody (e.g., horse radish peroxidase linked anti-IgG antibody) was allowed to react with primary antibody molecules bound to the blots. After rinsing, manufacturer's chemiluminescent reagent was added. Chemiluminescent signals in blots were captured on x-ray film. Where indicated, the images of the chemiluminescent signals were scanned with a densitometer and analyzed using the NIH ImageJ image processing program.

Cells expressing humanized anti-IL-8 antibody (CHO DP-12 clone, clone No. 1933; catalog No. CRL-12444) and plasmid p6G425V11N35A.choSD (catalog No. 209552) were purchased from the American Type Culture Collection (Manassas, Va.).

Example 4. Enhanced Expression of Secreted IL13Rα2TF Protein in an Unmodified Arrangement The IL13 receptor, IL13Rα2 is a membrane protein that binds to interleukin-13 (IL13) and mediates allergic inflammation. The IL13Rα2 receptor protein is known to be an unstable protein in a mammalian cell due to the difficulties of protein folding (*Genetic Engineering & Biotechnology News,* 28(5) (2008)). Part of the expressed IL13Rα2 proteins is digested on the cell surface and shed into the extracellular space. This truncated form of IL13Rα2 (also referred to as "IL13Rα2TF") still possesses the ability to bind IL13, but cannot transmit a signal to the cell owing to the absence of transmembrane and cytoplasmic regions of the full-length IL13Rα2 protein. Therefore, the truncated form of IL13Rα2 has been used as a type of decoy receptor to treat asthma by binding IL13 molecules without transducing a signal to the cell to set off an inflammatory response (Zhang, et al., *J. Biol. Chem.,* 272(14): 9474-80 (1997)). A genetically engineered truncated form of IL13Rα2 has been expressed in bacteria, however the protein aggregated into inclusion bodies, from which the protein was purified (Tang et al., *Molec. Immunol.* 39: 719-727 (2003)). However, it is known that one limitation to the expression of the IL13Rα2TF protein by transfected cells has been ascribed to inefficient folding of into their proper functional conformations. When proteins cannot fold into their proper conformation they are ushered to the proteasome for degradation and scavenging of amino acids. Accordingly, production of IL13Rα2TF molecules in transfected cells has recognized attendant limitations of expression and secretion of the protein (Lee et al., *Cell Technol. for Cell Products,* 29-39 (2007)).

Figure 9A:
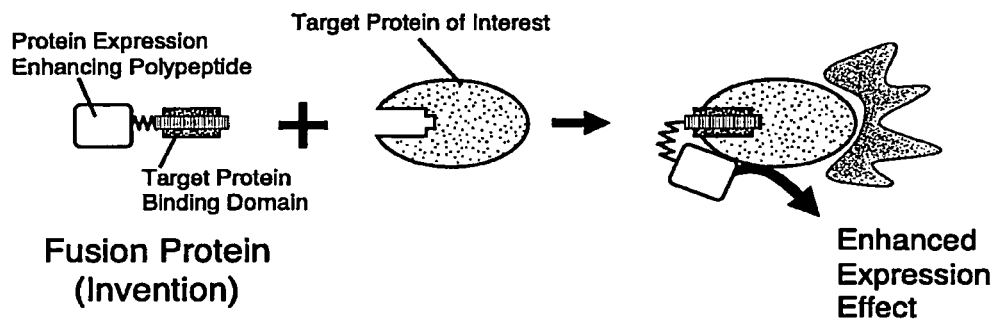
FIG. 9A depicts a diagram of a general scheme of an unmodified arrangement for enhancing expression of a target protein on interest in which co-expression of a fusion protein of the invention enhances expression of a target protein of interest as described in Example 4. In the scheme, a fusion protein of the invention comprises a protein expression enhancing polypeptide (PEEP) domain linked to a target protein binding domain, wherein the target protein binding domain binds a target protein of interest thereby bringing the target protein into close proximity with the PEEP domain, which in turn results in an elevation of the level of expression of the target protein in its proper cellular or extracellular location.

This experiment studied the enhancement in the level of and secretion of the IL13Rα2TF protein using an alternative arrangement to the "modified" arrangement described in Examples 1-3 in which a target protein of interest is modified by fusion to a protein expression enhancing polypeptide of the invention. In an "unmodified" arrangement, a target protein of interest is "unmodified" in that it is not fused to a protein expression enhancing polypeptide of the invention, but instead is co-expressed with a fusion protein comprising a protein expression enhancing polypeptide linked to a target protein binding domain. FIG. 9A shows a schematic diagram of this unmodified arrangement for enhancing expression of a target protein of interest. According to this scheme, a target protein of interest is bound by a target protein binding domain of the fusion protein, which also comprises a protein expression enhancing polypeptide domain. Presumably, binding of the target protein to the fusion protein brings the target protein into close proximity to the protein expression enhancing polypeptide domain, which in turn leads to enhanced expression of the target protein of interest.

Figure 9B:
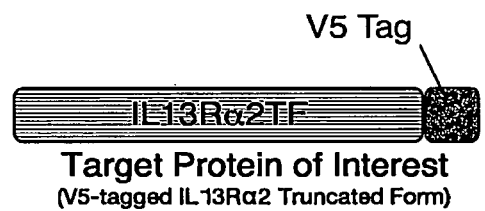
FIG. 9B is a diagram of a structural gene encoding an IL13Rα2TF fusion protein (target protein) for insertion into an expression vector plasmid, which was used to transfect host cells as described in Example 4, below. A cDNA encoding a truncated form of the IL13Rα2 receptor protein (IL13Rα2TF), which comprises the extracellular IL13 ligand binding domain of IL13Rα2, was augmented with a segment encoding a V5 epitope tag at the 3' end.
Figure 9C:
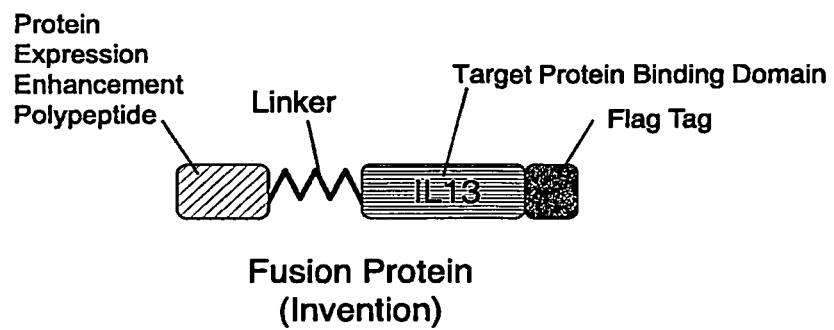
FIG. 9C depicts a construct for expressing a fusion protein of the invention to enhance expression of the V5-tagged IL13Rα2TF target protein depicted in FIG. 9B and as described in Example 4. A cDNA encoding a J domain of an Erdj3 J protein (protein expression enhancing polypeptide domain) was linked to a segment encoding the IL13 protein (target protein binding domain). A segment encoding a Flag epitope tag was linked to the 3' end of the segment encoding the IL13 target protein binding domain.

FIG. 9B shows a diagram of a nucleic acid construct in which a cDNA encoding an IL13Rα2TF protein is augmented at its 3' end with a nucleic acid encoding a V5 epitope tag. FIG. 9C shows a diagram of a nucleic acid construct for a fusion protein of the invention. For this experiment, the fusion protein according to the invention comprised a J domain of the Erdj3 J protein as a protein expression enhancing polypeptide linked to an IL13 protein as a target binding domain.

The amino acid sequence of the V5-tagged IL13Rα2TF protein is shown in the table below.

TABLE 32

Amino Acid Sequence of a V5-Tagged IL13Rα2TF Protein.

| Protein Region (N- to C-terminal) | Sequence Identifier | Amino Acid Sequence 12345678901234567890123456789 0 |
|---|---|---|
| V5-tagged IL13Rα2TF protein | SEQ ID NO: 222 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKGTGSEFDIAAALEGKPIPNPL LGLDSTSRGPYSIVSPKC |
| IL13Rα2TF | residues 1-339 of SEQ ID NO: 222 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKK |
| Linker | residues 340-352 of SEQ ID NO: 222 | GTGSEFDIAAALE |
| V5 epitope domain | residues 353-366 of SEQ ID NO: 222 | GKPIPNPLLGLDST |
| C-terminal vector residues | residues 367-378 of SEQ ID NO: 222 | SRGPYSIVSPKC |

The amino acid sequence of the IL13 protein as used in this experiment included a Flag epitope tag, a signal sequence, and 13 additional C-terminal amino acid residues from the expression vector used to express the protein as shown in the table below.

TABLE 33

Amino Acid Sequence of a Flag-Tagged IL13 Protein.

| Protein Region (N- to C-terminal) | Sequence Identifier | Amino Acid Sequence 12345678901234567890123456789 0 |
|---|---|---|
| Flag-tagged IL13 protein | SEQ ID NO: 223 | MGVKVLFALICIAVAEAGTGSEFDIAAALT CLGGFASPGPVPPSTALRELIEELVNITQN QKAPLCNGSMVWSINLTAGMYCAALESLIN |

TABLE 33-continued

Amino Acid Sequence of a Flag-Tagged IL13 Protein.

| Protein Region (N- to C-terminal) | Sequence Identifier | Amino Acid Sequence 12345678901234567890123 4567890 |
|---|---|---|
| | | VSGCSAIEKTQRMLSGFCPHKVSAGQFSSL HVRDTKIEVAQFVKDLLLHLKKLFREGQFN LEGDYKDDDDKGSRGPYSIVSPKC |
| Signal Sequence | residues 1-17 of SEQ ID NO: 223 | MGVKVLFALICIAVAEA |
| Linker | residues 18-28 of SEQ ID NO: 223 | GTGSEFDIAAA |
| IL13 | residues 29-150 of SEQ ID NO: 223 | LTCLGGFASPGPVPPSTALRELIEELVNIT QNQKAPLCNGSMVWSINLTAGMYCAALESL INVSGCSAIEKTQRMLSGFCPHKVSAGQFS SLHVRDTKIEVAQFVKDLLLHLKKLFREGQ FN |
| Linker | residues 151-153 of SEQ ID NO: 223 | LEG |
| Flag epitope domain | residues 154-161 of SEQ ID NO: 223 | DYKDDDDK |
| C-terminal vector residues | residues 162-174 of SEQ ID NO: 223 | GSRGPYSIVSPKC |

The amino acid sequence of a J domain-IL13 fusion protein included a Flag epitope tag as shown in the table below.

TABLE 34

Amino Acid Sequence of a Flag-Tagged Erdj3 J Domain-IL13 Fusion Protein.

| Protein Region (N- to C-terminal) | Sequence Identifier | Amino Acid Sequence 12345678901234567890123 4567890 |
|---|---|---|
| Flag-tagged J domain-IL13 fusion protein | SEQ ID NO: 224 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAALTCLGGFASPGPVPPSTALR ELIEELVNITQNQKAPLCNGSMVWSINLTA GMYCAALESLINVSGCSAIEKTQRMLSGFC PHKVSAGQFSSLHVRDTKIEVAQFVKDLLL HLKKLFREGQFNLEGDYKDDDDKGSRGPYS IVSPKC |
| Erdj3 J domain | residues 1-83 of SEQ ID NO: 224 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 224 | DIGGGSGGSGGSGGAAA |
| IL13 | residues 101-222 of SEQ ID NO: 224 | LTCLGGFASPGPVPPSTALRELIEELVNIT QNQKAPLCNGSMVWSINLTAGMYCAALESL INVSGCSAIEKTQRMLSGFCPHKVSAGQFS SLHVRDTKIEVAQFVKDLLLHLKKLFREGQ FN |
| Linker | residues 223-225 of SEQ ID NO: 224 | LEG |

TABLE 34-continued

Amino Acid Sequence of a Flag-Tagged Erdj3 J Domain-IL13 Fusion Protein.

| Protein Region (N- to C-terminal) | Sequence Identifier | Amino Acid Sequence 1234567890123456789012345678 90 |
|---|---|---|
| Flag epitope domain | residues 226-233 of SEQ ID NO: 224 | DYKDDDDK |
| C-terminal vector residues | residues 234-246 of SEQ ID NO: 224 | GSRGPYSIVSPKC |

Figure 10:
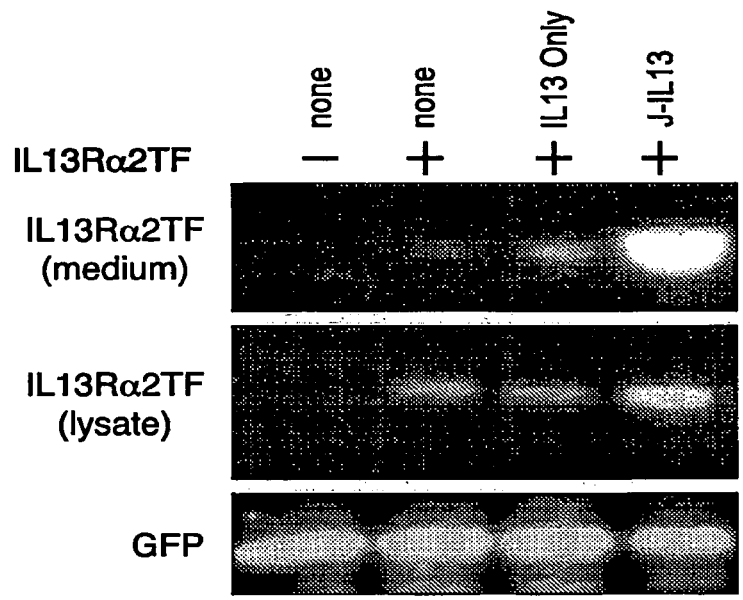
FIG. 10 shows x-ray film images of chemiluminescent signals of a Western blot analysis of culture medium (upper panel) and cell lysates (middle panel) of transfected cells expressing a truncated form of the IL13Rα2 receptor protein (IL13Rα2TF) when expressed alone (lane 2 from the left), when co-expressed with its IL13 ligand (IL13 Only, lane 3 from the left), and when co-expressed in an unmodified arrangement with a J domain-IL13 fusion protein of the invention (J-IL13, lane 4 from the left), as described in Example 4. A properly folded IL13Rα2TF protein (target protein) is expected to be secreted from the transfected host cells. It can be seen that co-expression of the IL13Rα2TF protein with the J domain-IL13 fusion protein significantly enhanced the level of expression of secreted IL13Rα2TF protein (top panel, lane 4 from the left) as compared to expression of IL13Rα2TF protein alone (top panel, lane 2 from the left) or co-expression of IL13Rα2TF protein with its IL13 ligand (top panel, lane 3 from the left). Moreover, co-expression of the IL13Rα2TF protein with the J domain-IL13 fusion protein significantly enhanced the level of expression of intracellular IL13Rα2TF protein (middle panel, lane 4 from the left) as compared to the level expression of IL13Rα2TF protein alone (middle panel, lane 2 from the left) or co-expression of IL13Rα2TF protein with its IL13 ligand (middle panel, lane 3 from the left). All transfectants were co-transfected with a reporter plasmid expressing green fluorescent protein (GFP) to show successful transfection and operability of the transfectants. See, lower panel of FIG. 10. Mock cultures contained cells transfected with "empty vector", i.e., an expression vector lacking a structural gene for expressing any protein (no IL13Rα2TF protein, no co-expression; "none" in lane 1 from the left of the blot). The empty vector transfectants were, however, co-transfected with the GFP vector, and successful co-transfection is shown by GPF expression detected in the lower panel of FIG. 10.

HEK293 cells were co-transfected with expression vectors for expressing the V5-tagged IL13Rα2TF and for expressing the J domain-IL13 fusion protein. Transfected cells were cultured for two days, and cell lysates and samples of cell media were harvested and analyzed by Western blot (immunoblot) assay using an anti-V5 antibody to detect secreted V5-tagged IL13Rα2TF. As shown in FIG. 10, cells transfected with an expression vector for expressing the IL13Rα2TF protein alone expressed some protein in the cells (middle panel, lane 2, from the left) but only a very little, if any, IL13Rα2TF protein was detected in culture medium (top panel, lane 2, from the left). Co-expression of the IL13Rα2TF protein and its IL13 protein ligand resulted in some detectable expression of IL13Rα2TF protein in the transfected cells (middle panel, lane 3, from the left) and in culture medium (top panel, lane 3, from the left). This result is consistent with earlier reports that co-expression of IL13Rα2TF with its IL13 ligand improves secretion of the IL13Rα2TF (Lee et al., *Cell Technol. for Cell Products*, 29-39 (2007)). However, co-expression IL13Rα2TF with a J domain-IL13 fusion protein according to the invention further enhanced the level of expression of IL13Rα2TF within the cells (middle panel, lane 4, from the left) and dramatically enhanced the level of expression of secreted IL13Rα2TF protein (top panel, lane 4, from the left) as compared to expression of IL13Rα2TF alone (top panel, lane 2, from the left) or co-expression of IL13Rα2TF and IL13 ligand (top panel, lane 3, from the left). The results indicate that both stability and secretion of the IL13Rα2TF protein were improved by co-expression with a J domain-IL13 fusion protein of the invention.

Example 5. Enhanced Expression of Secreted IL13Rα2TF-Fc Fusion Protein in an Unmodified Arrangement As noted above, a truncated form of IL13Rα2 (IL13Rα2TF) comprises the extracellular domain of the IL13Rα2 receptor protein, including a functional IL13 ligand binding domain. However, the production of IL13Rα2TF is also inefficient owing to difficulties in expression and secretion of the protein. One strategy that has been employed to generate more stable forms of therapeutically relevant proteins, and especially receptor proteins, is to prepare a fusion protein in which all or a functional portion of a protein of interest is linked to the constant domains of an immunoglobulin Fc domain. Such an Fc fusion protein format has been used to design a family of potentially useful drugs that provide a desired therapeutically relevant activity and, owing to the Fc domain, also exhibit an increased in vivo serum half-life, which in turn should reduce dosing frequencies. Within such Fc fusion proteins, a "protein of interest" domain (for example, the extracellular, ligand-binding domain of a receptor protein) retains its desired functional property (for example, ligand binding).

Figure 11A:
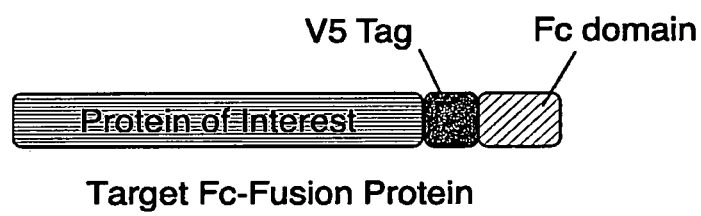
FIGS. 11A and 11B show schematic diagrams of nucleic acid constructs encoding proteins for insertion into expression vector plasmids used to transfect host cells for the experiments described in Example 5 below.
Figure 11B:
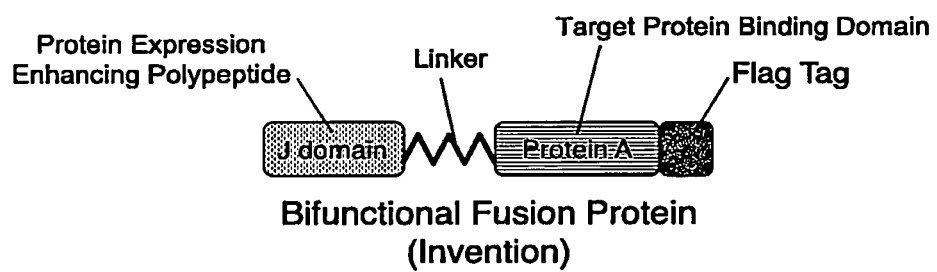

This experiment examined the effect on the level of expression of an Fc fusion protein (target protein) when the Fc fusion protein was co-expressed with a fusion protein of the invention in an unmodified arrangement. An IL13Rα2TF-Fc fusion protein was used as a representative example of an Fc fusion protein drug. The IL13Rα2TF-Fc fusion protein also possessed a V5 epitope tag between the IL13Rα2TF ("protein of interest") domain and the Fc domain for easy identification with an anti-V5 epitope antibody. See, an illustration of a DNA construct for the IL13Rα2TF-Fc fusion protein in FIG. 11A. For this experiment, examples of fusion proteins according to the invention comprised a J domain of a J protein as a protein expression enhancing polypeptide domain linked to Protein A, which binds immunoglobulin Fc domains, as a target binding domain. See, FIG. 11B.

The amino acid sequence for the V5-tagged IL13Rα2TF-Fc fusion protein used in this experiment is shown in the table below.

TABLE 35

Amino Acid Sequence of a V5-Tagged IL13Rα2TF-Fc Fusion Protein.

| Protein Region (N- to C-terminal) | Sequence Identifier | Amino Acid Sequence 1234567890123456789012345678 90 |
|---|---|---|
| V5-tagged IL13Rα2TF-Fc fusion protein | SEQ ID NO: 225 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF |

TABLE 35-continued

Amino Acid Sequence of a V5-Tagged IL13Rα2TF-Fc Fusion Protein.

| Protein Region (N- to C-terminal) | Sequence Identifier | Amino Acid Sequence 12345678901234567890 |
|---|---|---|
| | | YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKGTGSEFDIAAALEGKPIPNPL LGLDSTSRPKSCDKTHTCPPCPAPELLGGP SVFLFPPKPKDTLMISRTPEVTCVVVDVSH EDPEVKFNWYVDGVEVHNAKTKPREEQYNS TYRVVSVLTVLHQDWLNGKEYKCKVSNKAL PAPIEKTISKAKGQPREPQVYTLPPSRDEL TKNQVSLTCLVKGFYPSDIAVEWESNGQPE NNYKTTPPVLDSDGSFFLYSKLTVDKSRWQ QGNVFSCSVMHEALHNHYTQKSLSLSPGK |
| IL13Rα2TF | residues 1-339 of SEQ ID NO: 225 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKK |
| Linker | residues 340-352 of SEQ ID NO: 225 | GTGSEFDIAAALE |
| V5 epitope domain | residues 353-366 of SEQ ID NO: 225 | GKPIPNPLLGLDST |
| Linker | residues 367-368 of SEQ ID NO: 225 | SR |
| Fc domain | residues 369-599 of SEQ ID NO: 225 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

In one aspect of this experiment, the level of expression of an IL13Rα2TF-Fc fusion protein was examined when co-expressed with a Protein A molecule. The Protein A molecule was tagged with a Flag epitope tag for easy identification with a standard anti-Flag antibody. The amino acid sequence for a Flag-tagged Protein A is shown in the table below.

TABLE 36

Amino Acid Sequence of a Flag-Tagged Protein A.

| Protein Region (N- to C-terminal) | Sequence Identifier | Amino Acid Sequence 12345678901234567890 |
|---|---|---|
| Flag-tagged Protein A protein | SEQ ID NO: 226 | MGVKVLFALICIAVAEAGTGSEFDIAAAAD NKFNKEQQNAFYEILNMPNLNEEQRNGFIQ SLKDDPSQSANVLGEAKKLNDSQAPKLEGD YKDDDDKGSRGPYSIVSPKC |

TABLE 36-continued

Amino Acid Sequence of a Flag-Tagged Protein A.

| Protein Region (N- to C-terminal) | Sequence Identifier | Amino Acid Sequence 12345678901234567890123456 7890 |
|---|---|---|
| Signal Sequence | residues 1-17 of SEQ ID NO: 226 | MGVKVLFALICIAVAEA |
| Linker | residues 18-28 of SEQ ID NO: 226 | GTGSEFDIAAA |
| Protein A | residues 29-86 of SEQ ID NO: 226 | ADNKFNKEQQNAFYEILNMPNLNEEQRNGF IQSLKDDPSQSANVLGEAKKLNDSQAPK |
| Linker | residues 87-89 of SEQ ID NO: 226 | LEG |
| Flag epitope domain | residues 90-97 of SEQ ID NO: 226 | DYKDDDDK |
| C-terminal vector residues | residues 98-110 of SEQ ID NO: 226 | GSRGPYSIVSPKC |

An example of a fusion protein for enhancing expression of the IL13Rα2TF-Fc fusion protein possessed the J domain from the Erdj3 protein linked to Protein A. A Flag epitope tag was linked to the C-terminus of the Protein A domain. See illustration of DNA construct in FIG. 11B. The amino acid sequence for the J domain-Protein A fusion protein is shown in the table below.

TABLE 37

Amino Acid Sequence of a Flag-Tagged Erdj3 J domain-Protein A Fusion Protein.

| Protein Region (N- to C-terminal) | Sequence Identifier | Amino Acid Sequence 12345678901234567890123456 7890 |
|---|---|---|
| Flag-tagged Erdj3 J domain-Protein A fusion protein | SEQ ID NO: 227 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAAADNKFNKEQQNAFYEILNMP NLNEEQRNGFIQSLKDDPSQSANVLGEAKK LNDSQAPKLEGDYKDDDDKGSRGPYSIVSP KC |
| J domain (from Erdj3) | residues 1-83 of SEQ ID NO: 227 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 227 | DIGGGSGGSGGSGGAAA |
| Protein A | residues 101-158 of SEQ ID NO: 227 | ADNKFNKEQQNAFYEILNMPNLNEEQRNGF IQSLKDDPSQSANVLGEAKKLNDSQAPK |
| Linker | residues 159-161 of SEQ ID NO: 227 | LEG |
| Flag epitope domain | residues 162-169 of SEQ ID NO: 227 | DYKDDDDK |
| C-terminal vector residues | residues 170-182 of SEQ ID NO: 227 | GSRGPYSIVSPKC |

Another example of a fusion protein for enhancing expression of the IL13Rα2TF-Fc fusion protein possessed the J domain from the Erdj5 protein linked to Protein A. A Flag epitope tag was linked to the C-terminus of the Protein A domain. See illustration of DNA construct in FIG. 11B. The amino acid sequence for the Flag-tagged Erdj5 J domain-Protein A fusion protein is shown in the table below.

TABLE 38

Amino Acid Sequence of a Flag-Tagged Erdj5 J domain-Protein A Fusion Protein.

| Protein Region (N- to C-terminal) | Sequence Identifier | Amino Acid Sequence 123456789012345678901234567890 |
|---|---|---|
| Flag-tagged Erdj5 J domain-Protein A fusion protein | SEQ ID NO: 228 | MGVWLNKDDYIRDLKRIILCFLIVYMAILV GTDQDFYSLLGVSKTASSREIRQAFKKLAL KLHPDKNPNNPNAHGDFLKINRAYEVLKDE DGSEFDIGGGSGGSGGSGGAAAADNKFNKE QQNAFYEILNMPNLNEEQRNGFIQSLKDDP SQSANVLGEAKKLNDSQAPKLEGDYKDDDD KGSRGPYSIVSPKC |
| J domain (from Erdj5) | residues 1-91 of SEQ ID NO: 228 | MGVWLNKDDYIRDLKRIILCFLIVYMAILV GTDQDFYSLLGVSKTASSREIRQAFKKLAL KLHPDKNPNNPNAHGDFLKINRAYEVLKDE D |
| Linker | residues 92-112 of SEQ ID NO: 228 | GSEFDIGGGSGGSGGSGGAAA |
| Protein A | residues 113-170 of SEQ ID NO: 228 | ADNKFNKEQQNAFYEILNMPNLNEEQRNGF IQSLKDDPSQSANVLGEAKKLNDSQAPK |
| Linker | residues 171-173 of SEQ ID NO: 228 | LEG |
| Flag epitope domain | residues 174-181 of SEQ ID NO: 228 | DYKDDDDK |
| C-terminal vector residues | residues 182-194 of SEQ ID NO: 228 | GSRGPYSIVSPKC |

HEK293 cells were transfected with expression vector plasmids to compare levels of expression in culture medium of IL13Rα2TF-Fc fusion protein expressed alone, IL13Rα2TF-Fc fusion protein co-expressed with Protein A ("Protein A Only"), IL13Rα2TF-Fc fusion protein co-expressed with the Erdj3 J domain-Protein A fusion protein ("J-Protein A"), and IL13Rα2TF-Fc fusion protein co-expressed with the Erdj5 J domain-Protein A fusion protein ("J2-Protein A"). Transfected cells were cultured for two days, and samples of cell media were harvested and analyzed by Western blot (immunoblot) assay using an anti-V5 antibody to detect secreted V5-tagged IL13Rα2TF-Fc fusion protein. FIG. 12A shows x-ray film images of chemiluminescent signals of the Western blot analysis of culture media. Lane 1 of FIG. 12A is culture medium of a "mock" culture of cells transfected with expression vector lacking a structural gene for expressing any protein (empty vector). When expressed alone (lane 2), some IL13Rα2TF-Fc fusion protein was detected in the medium. As shown in lane 3 of the FIG. 12A, co-expression with Protein A (Protein A Only) provided no significant enhancement in the level of IL13Rα2TF-Fc fusion protein secreted to the medium. However, co-expression with the either J domain-Protein A fusion protein significantly enhanced the level of expression of IL13Rα2TF-Fc fusion protein secreted into the medium (lanes 4 and 5 of FIG. 12A). Importantly, the fact that co-expression of IL13Rα2TF-Fc with Protein A alone did not affect the secretion of IL13Rα2TF-Fc (lane 3) indicates that: (1) the J domain of a J domain-Protein A fusion protein is essential for enhancing the level of expression of secreted IL13Rα2TF-Fc and (2) the Protein A domain of the J domain-Protein A fusion protein is essential for providing the target specificity for enhancing the level of expression of the secreted IL13Rα2TF-Fc target protein.

The results of a densitometry analysis of the chemiluminescent signals in the lanes of FIG. 12A using the NIH ImageJ image processing program are shown in the respective bar graphs in FIG. 12B. The bar graphs in FIG. 12B clearly show that co-expression of IL13Rα2TF-Fc with either J domain-Protein A fusion protein (bar graphs 4 and 5) significantly enhanced the level of expression of secreted IL13Rα2TF-Fc as compared to expression of IL13Rα2TF-Fc alone (bar graph 2) or co-expression of IL13Rα2TF-Fc with Protein A alone (bar graph 3).

That the enhanced level of expression of secreted IL13Rα2TF-Fc protein in FIGS. 12A and 12B was dependent on the specificity of the target binding domain of the J domain-Protein A fusion protein for the Fc domain is supported by the results shown in FIG. 12C. As shown in the Western blot analysis of culture media in FIG. 12C, no significant expression of secreted IL13Rα2TF (no Fc domain) was detected in culture media when transfected cells expressed the IL13Rα2TF protein alone (lane 1), co-expressed the IL13Rα2TF protein with the J-Protein A fusion protein (lane 2), or co-expressed the IL13Rα2TF protein with Protein A alone (Protein A Only, lane 3). The results of a densitometry analysis of the chemiluminescent signals in the lanes of FIG. 12C using the NIH ImageJ image processing program are shown in the respective bar graphs in FIG. 12D.

Example 6. Enhanced Expression of an Additional Secreted Fc Fusion Proteins in an Unmodified Arrangement A series of experiments were performed to test and compare the effectiveness of a J domain-Protein A fusion protein of the invention to enhance several different Fc fusion proteins. The results are of a Western blot analysis of culture media from cultures of transfected cells are shown in FIG. 13.

Example 6.1. Enhanced Expression of a Secreted IL13Rα2TF-Fc Fusion Protein

Consistent with above results in Example 5, co-expression of the IL13Rα2TF-Fc protein with the Erdj3 J domain-Protein A fusion protein in transfected cells significantly enhanced the level of expression of IL13Rα2TF-Fc protein secreted into the culture medium (see, lane 2 of FIG. 13A-1) as compared to that observed for transfected cells expressing the IL13Rα2TF-Fc protein alone (lane 1 of FIG. 13A-1). The significant enhancement in the level of expression of secreted IL13Rα2TF-Fc protein is also clear from the results of a densitometry analysis of the chemiluminescent signals in FIG. 13A-1 using the NIH ImageJ image processing program are shown in the respective bar graphs in FIG. 13A-2.

Example 6.2. Enhanced Expression of a Secreted TNFR1TF-Fc Fusion Protein

Tumor necrosis factor-α (TNF-α) is a major cytokine that binds the TNF-α receptor (TNFR1) and induces an inflammatory response that is involved in a number of autoimmune diseases, such as rheumatoid arthritis, Crohn's disease, and psoriasis. The truncated protein of the TNF-α receptor (TNFR1TF) is used as a decoy receptor to bind to TNF-α and thereby inhibit TNF-α activity. Etanercept (commercially available as ENBREL®, Amgen) is a TNF-α blocker in which a truncated form of TNFR is fused to an Fc domain (TNFR1TF-Fc). The TNFR1TF domain of the molecule provides the desired TNF-α binding specificity, and the immunoglobulin Fc domain is believed to add in vivo stability to the drug circulating in a patient.

The TNFR1TF-Fc fusion target protein used in this experiment also possessed a V5 epitope tag between the TNFR1 and Fc domains. The amino acid sequence for the TNFR1TF-Fc fusion protein used in this experiment is shown in the table below.

TABLE 39

| Amino Acid Sequence of TNFR1TF-Fc Protein. | | |
|---|---|---|
| Protein Region (N- to C- terminal) | Sequence Identifier | Amino Acid Sequence 12345678901234567890123456 7890 |
| V5-tagged TNFR1TF protein | SEQ ID NO: 229 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV SCSNCKKSLECTKLCLPQIENVKGTEDSGT TGTGSEFDIAAALEGKPIPNPLLGLDSTSR PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |
| TNFR1TF | residues 1-211 of SEQ ID NO: 229 | MGLSTVPDLLLPLVLLELLVGIYPSGVIGL VPHLGDREKRDSVCPQGKYIHPQNNSICCT KCHKGTYLYNDCPGPGQDTDCRECESGSFT ASENHLRHCLSCSKCRKEMGQVEISSCTVD RDTVCGCRKNQYRHYWSENLFQCFNCSLCL NGTVHLSCQEKQNTVCTCHAGFFLRENECV SCSNCKKSLECTKLCLPQIENVKGTEDSGT T |
| Linker | residues 212-224 of SEQ ID NO: 229 | GTGSEFDIAAALE |
| V5 epitope domain | residues 225-238 of SEQ ID NO: 229 | GKPIPNPLLGLDST |
| Linker | residues 239-240 of SEQ ID NO: 229 | SR |

TABLE 39-continued

Amino Acid Sequence of TNFR1TF-Fc Protein.

| Protein Region (N- to C-terminal) | Sequence Identifier | Amino Acid Sequence 12345678901234567890123456 7890 |
|---|---|---|
| Fc domain | residues 241-471 of SEQ ID NO: 229 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

FIG. 13B-1 shows x-ray film images of chemiluminescent signals of a Western blot analysis of culture media from transfected cells expressing TNFR1TF-Fc fusion protein alone (lane 1) or co-expressing TNFR1TF-Fc fusion protein and the Erdj3 J domain-Protein A fusion protein described above (lane 2). The results show a significant enhancement in the level of expression of secreted TNFR1TF-Fc fusion protein in transfected cells co-expressing TNFR1TF-Fc fusion protein and the Erdj3 J domain-Protein A fusion protein as compared to the level of TNFR1TF-Fc fusion protein expressed in the absence of the J domain-Protein A fusion protein. The significant enhancement in the level of expression of secreted TNFR1TF-Fc fusion protein is also clear from the results of a densitometry analysis of the signals in the lanes in FIG. 13B-1 using the NIH ImageJ image processing program as shown in the respective bar graphs in FIG. 13B-2.

Example 6.3. Enhanced Expression of a Secreted α1AT-Fc Fusion Protein

The α1 anti-trypsin protein (α1AT) is secreted from the liver into the circulatory system. The function of α1AT is to protect tissues, particularly lung tissue, from excessive protease activities. The lung tissue of patients with α1 anti-trypsin deficiency can become severely damaged by proteases. Such patients may develop emphysema, asthma, and/or chronic obstructive pulmonary disease (COPD). Currently α1AT (purified from human serum) is used for the treatment of patients with α1 anti-trypsin deficiency. This treatment is expensive, and patients that receive the purified α1AT may be at risk of contracting pathogens present in the human serum.

The target α1AT-Fc fusion protein used in this experiment also possessed a V5 epitope tag between the α1AT and Fc domains. The amino acid sequence for the α1AT-Fc fusion protein (α1AT-Fc) used in this experiment is shown in the table below.

TABLE 40

| Protein Region (N- to C-terminal) | Sequence Identifier | Amino Acid Sequence 12345678901234567890123456 7890 |
|---|---|---|
| V5-tagged α1AT-Fc fusion protein | SEQ ID NO: 230 | MPSSVSWGILLLAGLCCLVPVSLAEDPQGD AAQKTDTSHHDQDHPTFNKITPNLAEFAFS LYRQLAHQSNSTNIFFSPVSIATAFAMLSL GTKADTHDEILEGLNFNLTEIPEAQIHEGF QELLRTLNQPDSQLQLTTGNGLFLSEGLKL VDKFLEDVKKLYHSEAFTVNFGDTEEAKKQ INDYVEKGTQGKIVDLVKELDRDTVFALVN YIFFKGKWERPFEVKDTEEEDFHVDQVTTV KVPMMKRLGMFNIQHCKKLSSWVLLMKYLG NATAIFFLPDEGKLQHLENELTHDIITKFL ENEDRRSASLHLPKLSITGTYDLKSVLGQL GITKVFSNGADLSGVTEEAPLKLSKAVHKA VLTIDEKGTEAAGAMFLEAIPMSIPPEVKF NKPFVFLMIEQNTKSPLFMGKVVNPTQKGT GSEFDIAAALEGKPIPNPLLGLDSTSRPKS CDKTHTCPPCPAPELLGGPSVFLFPPKPKD TLMISRTPEVTCVVVDVSHEDPEVKFNWYV DGVEVHNAKTKPREEQYNSTYRVVSVLTVL HQDWLNGKEYKCKVSNKALPAPIEKTISKA KGQPREPQVYTLPPSRDELTKNQVSLTCLV KGFYPSDIAVEWESNGQPENNYKTTPPVLD SDGSFFLYSKLTVDKSRWQQGNVFSCSVMH EALHNHYTQKSLSLSPGK |

TABLE 40-continued

Amino Acid Sequence of a V5-Tagged α1AT-Fc Fusion Protein.

| Protein Region (N- to C-terminal) | Sequence Identifier | Amino Acid Sequence 12345678901234567890123456789 0 |
|---|---|---|
| α1AT | residues 1-418 of SEQ ID NO: 230 | MPSSVSWGILLLAGLCCLVPVSLAEDPQGD AAQKTDTSHHDQDHPTFNKITPNLAEFAFS LYRQLAHQSNSTNIFFSPVSIATAFAMLSL GTKADTHDEILEGLNFNLTEIPEAQIHEGF QELLRTLNQPDSQLQLTTGNGLFLSEGLKL VDKFLEDVKKLYHSEAFTVNFGDTEEAKKQ INDYVEKGTQGKIVDLVKELDRDTVFALVN YIFFKGKWERPFEVKDTEEEDFHVDQVTTV KVPMMKRLGMFNIQHCKKLSSWVLLMKYLG NATAIFFLPDEGKLQHLENELTHDIITKFL ENEDRRSASLHLPKLSITGTYDLKSVLGQL GITKVFSNGADLSGVTEEAPLKLSKAVHKA VLTIDEKGTEAAGAMFLEAIPMSIPPEVKF NKPFVFLMIEQNTKSPLFMGKVVNPTQK |
| Linker | residues 419-431 of SEQ ID NO: 230 | GTGSEFDIAAALE |
| V5 epitope domain | residues 432-445 of SEQ ID NO: 230 | GKPIPNPLLGLDST |
| Linker | residues 446-447 of SEQ ID NO: 230 | SR |
| Fc domain | residues 448-678 of SEQ ID NO: 230 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

FIG. 13C-1 shows X-ray film images of chemiluminescent signals of a Western blot analysis of culture media from transfected cells expressing α1AT-Fc fusion protein alone (lane 1) or co-expressing α1AT-Fc fusion protein and the Erdj3 J domain-Protein A fusion protein described above (lane 2). The results show a significant enhancement in the level of secreted α1AT-Fc fusion protein (lane 2) as compared to the level of α1AT-Fc fusion protein expressed in the absence of the J domain-Protein A fusion protein (lane 1). The significant enhancement in the level of expression of secreted α1AT-Fc fusion protein is also clear from the results of a densitometry analysis of the signals in the lanes in FIG. 13C-1 using the NIH ImageJ image processing program as shown in the respective bar graphs in FIG. 13C-2.

Example 7. Enhancement of Expression of Secreted IgG1 Antibody Molecules in an Unmodified Arrangement The above studies showed that expression and secretion of Fc-fusion proteins were significantly enhanced by co-expression of a J domain-Protein A fusion protein. Protein A is a well-known example of a protein that binds to immunoglobulin Fc regions. This study examined whether fusion of other proteins that are known to bind immunoglobulin domains with a J domain of a J protein can enhance the expression level of a secreted target antibody.

In this study, a humanized IgG1 anti-IL8 antibody was used as a target antibody protein. The expression levels of the secreted anti-IL8 antibody were examined in the presence and absence of various J domain fusion proteins as explained below.

In one aspect of this experiment, the level of expression of the anti-IL8 antibody was examined when co-expressed with a Protein A molecule, which is known to bind the immunoglobulin Fc domain. The Protein A molecule was the same Flag-tagged Protein A described in Example 5, above.

In another aspect of this experiment, the level of expression of the anti-IL8 antibody was examined when co-expressed with a Protein L molecule, which is known to bind antibody light chains. As with the Protein A molecule described above, the Protein L molecule used in this experiment was tagged with a Flag epitope tag for easy identification with a standard anti-Flag antibody. The amino acid sequence for a Flag-tagged Protein L is shown in the table below.

TABLE 41

Amino Acid Sequence of a Flag-Tagged Protein L.

| Protein Region (N- to C-terminal) | Sequence Identifier | Amino Acid Sequence 12345678901234567890123456789 |
|---|---|---|
| Flag-tagged Protein L protein | SEQ ID NO: 231 | MGVKVLFALICIAVAEAGTGSEFDIAAAVT IKANLIFADGKTQTAEFKGTFEEATAEAYR YADLLAKENGEYTADLEDGGYTINIKFAKE TPETPEEPKEELEGDYKDDDDKGSRGPYSI VSPKC |
| Signal Sequence | residues 1-17 of SEQ ID NO: 231 | MGVKVLFALICIAVAEA |
| Linker | residues 18-28 of SEQ ID NO: 231 | GTGSEFDIAAA |
| Protein L | residues 29-101 of SEQ ID NO: 231 | VTIKANLIFADGKTQTAEFKGTFEEATAEA YRYADLLAKENGEYTADLEDGGYTINIKFA KETPETPEEPKEE |
| Linker | residues 102-104 of SEQ ID NO: 231 | LEG |
| Flag epitope domain | residues 105-112 of SEQ ID NO: 231 | DYKDDDDK |
| C-terminal vector residues | residues 113-125 of SEQ ID NO: 231 | GSRGPYSIVSPKC |

The amino acid sequence of an Erjd3 J domain-Protein L fusion protein included a Flag epitope tag as shown in the table below.

TABLE 42

Amino Acid Sequence of a Flag-Tagged Erdj3 J domain-Protein L Fusion Protein.

| Protein Region (N- to C-terminal) | Sequence Identifier | Amino Acid Sequence 12345678901234567890123456789 |
|---|---|---|
| Flag-tagged Erdj3 J domain-Protein L fusion protein | SEQ ID NO: 232 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAAVTIKANLIFADGKTQTAEFK GTFEEATAEAYRYADLLAKENGEYTADLED GGYTINIKFAKETPETPEEPKEELEGDYKD DDDKGSRGPYSIVSPKC |
| J domain (from Erdj3) | residues 1-83 of SEQ ID NO: 232 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 232 | DIGGGSGGSGGSGGAAA |
| Protein L | residues 101-173 of SEQ ID NO: 232 | VTIKANLIFADGKTQTAEFKGTFEEATAEA YRYADLLAKENGEYTADLEDGGYTINIKFA KETPETPEEPKEE |
| Linker | residues 174-176 of SEQ ID NO: 232 | LEG |
| Flag epitope domain | residues 177-184 of SEQ ID NO: 232 | DYKDDDDK |

TABLE 42-continued

Amino Acid Sequence of a Flag-Tagged Erdj3 J domain-Protein L Fusion Protein.

| Protein Region (N- to C-terminal) | Sequence Identifier | Amino Acid Sequence 12345678901234567890123456 7890 |
|---|---|---|
| C-terminal vector residues | residues 185-197 of SEQ ID NO: 232 | GSRGPYSIVSPKC |

The amino acid sequence of the IL8 protein used in this experiment included a Flag epitope tag, a signal sequence, and 13 additional C-terminal amino acid residues from the expression vector used to express the protein as shown in the table below.

TABLE 43

Amino Acid Sequence of a Flag-Tagged IL8 Protein.

| Protein Region (N- to C-terminal) | Sequence Identifier | Amino Acid Sequence 12345678901234567890123456 7890 |
|---|---|---|
| Flag-tagged IL8 protein | SEQ ID NO: 233 | MGVKVLFALICIAVAEAGTGSEFDIAAASA KELRCQCIKTYSKPFHPKFIKELRVIESGP HCANTEIIVKLSDGRELCLDPKENWVQRVV EKFLKRAENSLEGDYKDDDDKGSRGPYSIV SPKC |
| Signal Sequence | residues 1-17 of SEQ ID NO: 233 | MGVKVLFALICIAVAEA |
| Linker | residues 18-28 of SEQ ID NO: 233 | GTGSEFDIAAA |
| IL8 | residues 29-100 of SEQ ID NO: 233 | SAKELRCQCIKTYSKPFHPKFIKELRVIES GPHCANTEIIVKLSDGRELCLDPKENWVQR VVEKFLKRAENS |
| Linker | residues 101-103 of SEQ ID NO: 233 | LEG |
| Flag epitope domain | residues 104-111 of SEQ ID NO: 233 | DYKDDDDK |
| C-terminal vector residues | residues 112-124 of SEQ ID NO: 233 | GSRGPYSIVSPKC |

The amino acid sequence of an Erdj3 J domain-IL8 fusion protein included a Flag epitope tag as shown in the table below.

TABLE 44

Amino Acid Sequence of a Flag-Tagged Erdj3 J domain-IL8 Fusion Protein.

| Protein Region (N- to C-terminal) | Sequence Identifier | Amino Acid Sequence 12345678901234567890123456 7890 |
|---|---|---|
| Flag-tagged Erdj3 J domain-IL8 fusion protein | SEQ ID NO: 234 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAASAKELRCQCIKTYSKPFHPK |

TABLE 44-continued

Amino Acid Sequence of a Flag-Tagged Erdj3 J domain-IL8 Fusion Protein.

| Protein Region (N- to C-terminal) | Sequence Identifier | Amino Acid Sequence 12345678901234567890123456789 0 |
|---|---|---|
| | | FIKELRVIESGPHCANTEIIVKLSDGRELC LDPKENWVQRVVEKFLKRAENSLEGDYKDD DDKGSRGPYSIVSPKC |
| J domain (from Erdj3) | residues 1-83 of SEQ ID NO: 234 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 234 | DI GGGSGGSGGSGG AAA |
| IL8 | residues 101-172 of SEQ ID NO: 234 | SAKELRCQCIKTYSKPFHPKFIKELRVIES GPHCANTEIIVKLSDGRELCLDPKENWVQR VVEKFLKRAENS |
| Linker | residues 173-175 of SEQ ID NO: 234 | LEG |
| Flag epitope domain | residues 176-183 of SEQ ID NO: 234 | DYKDDDDK |
| C-terminal vector residues | residues 184-196 of SEQ ID NO: 234 | GSRGPYSIVSPKC |

HEK293 cells were transfected with an expression plasmid for expressing anti-IL8 antibody alone, co-expressing anti-IL8 antibody and Protein A (Protein A Only), co-expressing anti-IL8 antibody and an Erdj3 J domain-Protein A fusion protein of the invention (J-Protein A), co-expressing anti-IL8 antibody and Protein L (Protein L Only), co-expressing anti-IL8 antibody and an Erdj3 J domain-Protein L fusion protein of the invention (J-Protein L), co-expressing anti-IL8 antibody and its IL8 ligand (IL8), co-expressing an Erdj3 J domain-IL8 ligand fusion protein of the invention (J-IL8), expressing the Erdj3 J-Protein A fusion protein of the invention alone (J-Protein A), expressing the Erdj3 J domain-Protein L fusion protein of the invention alone (J-Protein L), and expressing the Erdj3 J domain-IL8 ligand fusion protein of the invention alone (J-IL8). Expression of the anti-IL8 antibody in culture media was analyzed by dot blot assay using an anti-human IgG antibody (anti-hIgG antibody, catalog no. AP112P, Millipore).

As shown in the dot blots of culture media in FIG. 14A, co-expression in transfected cells of the anti-IL8 antibody with a J domain-Protein A fusion protein (lane 4), with a J domain-Protein L fusion protein (lane 6), or with a J domain-IL8 fusion protein (lane 8) significantly enhanced the level of expression of anti-IL8 antibody secreted into the culture medium as compared to the level of the antibody expressed in transfected cells expressing the anti-IL8 antibody alone (lane 2), co-expressing with Protein A alone (lane 3, Protein A Only), co-expressing Protein L alone (lane 5, Protein L Only), or co-expressing IL8 ligand alone (lane 7). No signal was detected in culture media of transfected cells expressing the J domain-Protein A fusion protein alone (lane 9, J-Protein A), the J domain-Protein L fusion protein alone (lane 10, J-Protein L), or expressing the J domain-IL8 fusion protein alone (lane 10, J-IL8), indicating that all three fusion proteins specifically targeted and enhanced the co-expressed anti-IL8 antibody.

The results of a densitometry analysis of the signals in the lanes in FIG. 14A using the NIH ImageJ image processing program are shown in the respective bar graphs in FIG. 14B. The results of this series of experiments clearly show that co-expression of the targeted anti-IL8 antibody with a fusion protein of the invention comprising a protein expression enhancing polypeptide (here: Erdj3 J domain) linked to a target binding domain (here: Protein A, Protein L, or IL8) significantly enhanced the expression of secreted anti-IL8 antibody as compared to co-expression of the antibody with the unfused target binding domain protein alone (Protein G only, Protein L only, or IL8 only).

Example 8. Enhancement of Established Expression in CHO-DP12 Producing Cell Line Using an Unmodified Arrangement This example examined whether a fusion protein of the invention could be used to improve the level of expression of a target protein already being produced in an established commercially relevant production cell line. For this experiment a CHO-DP12 cell line was used that stably expresses a humanized anti-IL8 IgG1 antibody as obtained from the American Type Culture Collection (accession no. CRL-124444, American Type Culture Collection, Manassas, Va.) along with an expression vector plasmid for expressing the anti-IL8 antibody (accession no. 209552, ATCC, Manassas, Va.). The fusion protein of the invention was that Erdj3 J domain-Protein A fusion protein described above. Cells of the CHO-DP12 production cell line were transfected with an expression vector carrying an operably linked structural gene encoding the Erdj3 J domain-Protein A fusion protein. The transfection efficiency was not as high with the CHO-DP12 cells as compared with HEK293 cells. Nevertheless, as shown in the dot blot assays in FIG. 15A, co-expression of the humanized antibody with the J domain-Protein A fusion protein significantly enhanced the level of expression of the antibody secreted into the culture medium (lane 3) as compared to the level of the antibody expressed in the absence of the J domain-Protein A fusion protein (lane 2, none).

The results of a densitometry analysis of the chemiluminescent signals in the dot blots in the lanes in FIG. 15A using the NIH ImageJ image processing program are shown in the respective bar graphs in FIG. 15B. The results indicate that co-expression of the antibody with the J domain-Protein A fusion protein (bar graph 3) significantly enhanced expression of the secreted antibody, providing an approximately four to five-fold greater enhancement in the level of expression, as compared to that obtained when the antibody was expressed in the absence of the J domain-Protein A fusion protein (bar graph 2).

The results indicate that a fusion protein of the invention can be employed to significantly enhance the level of production of a protein that is already being stably expressed in an established production cell line.

Example 9. Other Fusion Proteins for Enhancing Expression of Secreted Fc-Containing Molecules in an Unmodified Arrangement

Example 9.1. Fusion Proteins Comprising Fc Binding Domains from Additional Protein Species This example provides a series of experiments to test various fusion proteins comprising a J domain (as a protein expression enhancing polypeptide domain) linked to any of a variety of polypeptides (as the target binding domain) that have been reported to bind the Fc region of antibody molecules. The various J domain fusion proteins were then tested and compared for their ability to enhance levels of expression of the IL13Rα2TF-Fc fusion protein as described in Example 5 above that was secreted into medium of transfected HEK293 cells.

The J-Protein A fusion protein of the invention used in this example is the Erdj3-Protein A fusion protein described in Example 5 above.

In another fusion protein used in the experiments described herein, the J domain from the Erdj3 J protein was linked to Protein G, which is known to bind certain immunoglobulin Fc domains. A Flag epitope tag was linked to the C-terminus of the Protein G domain as shown for the J-Protein A fusion protein in Example 5 and FIG. 11B. The amino acid sequence for a Flag-tagged J domain-Protein G fusion protein of the invention is shown in the table below.

TABLE 45

Amino Acid Sequence of a Flag-Tagged Erdj3 J domain-Protein G Fusion Protein.

| Protein Region (N- to C-terminal) | Sequence Identifier | Amino Acid Sequence 12345678901234567890123456 7890 |
|---|---|---|
| Flag-tagged Erdj3 J domain-Protein G fusion protein | SEQ ID NO: 235 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAATYKLVINGKTLKGETTTEAV DAATAEKVFKQYANDNGVDGEWTYDDATKT FTVTEKPEVIDASELTPAVTLEGDYKDDDD KGSRGPYSIVSPKC |
| J domain (from Erdj3) | residues 1-83 of SEQ ID NO: 235 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 235 | DIGGGSGGSGGSGGAAA |
| Protein G | residues 101-170 of SEQ ID NO: 235 | TYKLVINGKTLKGETTTEAVDAATAEKVFK QYANDNGVDGEWTYDDATKTFTVTEKPEVI DASELTPAVT |
| Linker | residues 171-173 of SEQ ID NO: 235 | LEG |
| Flag epitope domain | residues 174-181 of SEQ ID NO: 235 | DYKDDDDK |
| C-terminal vector residues | residues 182-194 of SEQ ID NO: 235 | GSRGPYSIVSPKC |

In another fusion protein used in the experiments described herein, the J domain from the Erdj3 J protein was linked to a human FcR (hFcR) receptor protein, which is a receptor that binds certain immunoglobulin Fc domains. A Flag epitope tag was linked to the C-terminus of the hFcR domain as shown for the J-Protein A fusion protein in Example 5 and FIG. 11B. The amino acid sequence for a Flag-tagged J domain-hFcR fusion protein is shown in the table below.

TABLE 46

Amino Acid Sequence of a Flag-Tagged Erdj3 J Domain-hFcR Fusion Protein.

| Protein Region (N- to C-terminal) | Sequence Identifier | Amino Acid Sequence 12345678901234567890123456789 |
|---|---|---|
| Flag-tagged Erdj3 J domain-hFcR fusion protein | SEQ ID NO: 236 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAAAVITLQPPWVSVFQEETVTL HCEVLHLPGSSSTQWFLNGTATQTSTPSYR ITSASVNDSGEYRCQRGLSGRSDPIQLEIH RGWLLLQVSSRVFTEGEPLALRCHAWKDKL VYNVLYYRNGKAFKFFHWNSNLTILKTNIS HNGTYHCSGMGKLEGDYKDDDDKGSRGPYS IVSPKC |
| J domain (from Erdj3) | residues 1-83 of SEQ ID NO: 236 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 236 | DIGGGSGGSGGSGGAAA |
| hFcR | residues 101-252 of SEQ ID NO: 236 | AVITLQPPWVSVFQEETVTLHCEVLHLPGS SSTQWFLNGTATQTSTPSYRITSASVNDSG EYRCQRGLSGRSDPIQLEIHRGWLLLQVSS RVFTEGEPLALRCHAWKDKLVYNVLYYRNG KAFKFFHWNSNLTILKTNISHNGTYHCSGM GK |
| Linker | residues 253-255 of SEQ ID NO: 236 | LEG |
| Flag epitope domain | residues 256-263 of SEQ ID NO: 236 | DYKDDDDK |
| C-terminal vector residues | residues 264-276 of SEQ ID NO: 236 | GSRGPYSIVSPKC |

In another fusion protein used in the experiments described herein, the J domain from the Erdj3 J protein was linked to the *Macaca mulatta* rhadinovirus FcR receptor protein (vFcR), which is a receptor that binds certain immunoglobulin Fc domains. A Flag epitope tag was linked to the C-terminus of the vFcR domain as shown for the J-Protein A fusion protein in Example 5 and FIG. 11B. The amino acid sequence for a Flag-tagged J domain-vFcR fusion protein is shown in the table below.

TABLE 47

Amino Acid Sequence of a Flag-Tagged Erdj3 J domain-vFcR Fusion Protein.

| Protein Region (N- to C-terminal) | Sequence Identifier | Amino Acid Sequence 12345678901234567890123456789 |
|---|---|---|
| Flag-tagged Erdj3 J domain-vFcR protein | SEQ ID NO: 237 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAAAKLTSVPTWCPPHPGDTYLL TCRGTSTARDQRSTQWFRNNTLMRGSNFYG |

TABLE 47-continued

Amino Acid Sequence of a Flag-Tagged Erdj3 J domain-vFcR Fusion Protein.

| Protein Region (N- to C-terminal) | Sequence Identifier | Amino Acid Sequence 123456789012345678901234567890 |
|---|---|---|
| | | RLVSVTPNATISDRYACQTKTTTRSNNIDF RVSSSRLTLQERCSSYGYTYANNTRVLRCY SGGNVTLRNVVFHLNGTAVINGTTTNIHTF VLTEKTGGTYFCSAFLEGDYKDDDDKGSRG PYSIVSPKC |
| Erdj3 J domain | residues 1-83 of SEQ ID NO: 237 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 237 | DI GGGSGGSGGSGG AAA |
| vFcR | residues 101-255 of SEQ ID NO: 237 | AKLTSVPTWCPPHPGDTYLLTCRGTSTARD QRSTQWFRNNTLMRGSNFYGRLVSVTPNAT ISDRYACQTKTTTRSNNIDFRVSSSRLTLQ ERCSSYGYTYANNTRVLRCYSGGNVTLRNV VFHLNGTAVINGTTTNIHTFVLTEKTGGTY FCSAF |
| Linker | residues 256-258 of SEQ ID NO: 237 | LEG |
| Flag epitope domain | residues 259-266 of SEQ ID NO: 237 | DYKDDDDK |
| C-terminal vector residues | residues 267-279 of SEQ ID NO: 237 | GSRGPYSIVSPKC |

In another fusion protein used in the experiments described herein, the J domain from the Erdj3 J protein was linked to a herpes simplex virus type 1 gI protein, which has no significant Fc binding activity. A Flag epitope tag was linked to the C-terminus of the gI domain as shown for the J-Protein A fusion protein in Example 5 and FIG. 11B. The amino acid sequence for a Flag-tagged J domain-gI fusion protein is shown in the table below.

TABLE 48

Amino Acid Sequence of a Flag-Tagged Erdj3 J Domain-gI Fusion Protein.

| Protein Region (N- to C-terminal) | Sequence Identifier | Amino Acid Sequence 123456789012345678901234567890 |
|---|---|---|
| Flag-tagged Erdj3 J domain-gI protein | SEQ ID NO: 238 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAALVVRGPTVSLVSNSFVDAGA LGPDGVVEEDLLILGELRFVGDQVPHTTYY DGVVELWHYPMGHKCPRVVHVVTVTACPRR PAVAFALCRATDSTHSPAYPTLELNLAQQP LLRVRRATRDYAGVYVLRVWVGDAPNASLF VLGMAIAAEGTLAYNGSAHGSCDPKLLPYS APRLAPASVYQPAPNPASTPSTTIPAPQAS TTPFPTGDPKPQLEGDYKDDDDKGSRGPYS IVSPKC |
| J domain (from Erdj3) | residues 1-83 of SEQ ID NO: 238 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 238 | DIGGGSGGSGGSGGAAA |

TABLE 48-continued

Amino Acid Sequence of a Flag-Tagged Erdj3 J Domain-gI Fusion Protein.

| Protein Region (N- to C-terminal) | Sequence Identifier | Amino Acid Sequence 12345678901234567890123456789 0 |
|---|---|---|
| gI | residues 101-312 of SEQ ID NO: 238 | LVVRGPTVSLVSNSFVDAGALGPDGVVEED LLILGELRFVGDQVPHTTYYDGVVELWHYP MGHKCPRVVHVVTVTACPRRPAVAFALCRA TDSTHSPAYPTLELNLAQQPLLRVRRATRD YAGVYVLRVWVGDAPNASLFVLGMAIAAEG TLAYNGSAHGSCDPKLLPYSAPRLAPASVY QPAPNPASTPSTTIPAPQASTTPFPTGDPK PQ |
| Linker | residues 313-315 of SEQ ID NO: 238 | LEG |
| Flag epitope domain | residues 316-323 of SEQ ID NO: 238 | DYKDDDDK |
| C-terminal vector residues | residues 324-336 of SEQ ID NO: 238 | GSRGPYSIVSPKC |

In another fusion protein used in the experiments described herein, the J domain from the Erdj3 J protein was linked to a herpes simplex virus type 1 gE protein, which has a relatively weak affinity for the immunoglobulin Fc domain. A Flag epitope tag was linked to the C-terminus of the gE domain as shown for the J-Protein A fusion protein in Example 5 and FIG. 11B. The amino acid sequence for a Flag-tagged J domain-gE fusion protein is shown in the table below.

TABLE 49

Amino Acid Sequence of a Flag-Tagged Erdj3 J domain-gE Fusion Protein.

| Protein Region (N- to C-terminal) | Sequence Identifier | Amino Acid Sequence 12345678901234567890123456789 0 |
|---|---|---|
| Flag-tagged Erdj3 J domain-gE fusion protein | SEQ ID NO: 239 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAAGTPKTSWRRVSVGEDVSLLP APGPTGRGPTQKLLWAVEPLDGCGPLHPSW VSLMPPKQVPETVVDAACMRAPVPLAMAYA PPAPSATGGLRTDFVWQERAAVVNRSLVIH GVRETDSGLYTLSVGDIKDPARQVASVVLV VQPAPVPTPPPTPADYDEDDNDEGEDESLA GTPASGTPRLPPPPAPPRSWPSAPEVSHVR GVTVRMETPEAILFSPGETFSTNVSIHAIA HDDQTYSMDVVWLRFDVPTSCAEMRIYESC LYHPQLPECLSPADAPCAASTWTSRLAVRS YAGCSRTNPPPRCSAEAHMEPVPGLAWQAA SVNLEFRDASPQHSGLYLCVVYVNDHIHAW GHITISTAAQYRNAVVEQPLPQRGADLAEL EGDYKDDDDKGSRGPYSIVSPKC |
| Erdj3 J domain | residues 1-83 of SEQ ID NO: 239 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 239 | DIGGGSGGSGGSGGAAA |
| gE | residues 101-479 of SEQ ID NO: 239 | GTPKTSWRRVSVGEDVSLLPAPGPTGRGPT QKLLWAVEPLDGCGPLHPSWVSLMPPKQVP ETVVDAACMRAPVPLAMAYAPPAPSATGGL RTDFVWQERAAVVNRSLVIHGVRETDSGLY TLSVGDIKDPARQVASVVLVVQPAPVPTPP PTPADYDEDDNDEGEDESLAGTPASGTPRL PPPPAPPRSWPSAPEVSHVRGVTVRMETPE |

TABLE 49-continued

Amino Acid Sequence of a Flag-Tagged Erdj3 J domain-gE Fusion Protein.

| Protein Region (N- to C-terminal) | Sequence Identifier | Amino Acid Sequence<br>12345678901234567890123456789 0 |
|---|---|---|
| | | AILFSPGETFSTNVSIHAIAHDDQTYSMDV<br>VWLRFDVPTSCAEMRIYESCLYHPQLPECL<br>SPADAPCAASTWTSRLAVRSYAGCSRTNPP<br>PRCSAEAHMEPVPGLAWQAASVNLEFRDAS<br>PQHSGLYLCVVYVNDHIHAWGHITISTAAQ<br>YRNAVVEQPLPQRGADLAE |
| Linker | residues 480-482 of SEQ ID NO: 239 | LEG |
| Flag epitope domain | residues 483-490 of SEQ ID NO: 239 | DYKDDDDK |
| C-terminal vector residues | residues 491-503 of SEQ ID NO: 239 | GSRGPYSIVSPKC |

HEK293 cells were transfected with expression vector plasmids to compare levels of expression in culture medium of the IL13Rα2TF-Fc fusion protein expressed alone, co-expressed with a J domain-Protein A fusion protein (as described above in Example 5), co-expressed with Protein A ("Protein A Only", as described in Example 5), co-expressed with a J domain-Protein G fusion protein (J-Protein G), co-expressed with a J domain fusion protein in which a J domain is linked to a human FcR receptor protein ("J-hFcR"), co-expressed with a J domain fusion protein in which a J domain is linked to a viral FcR receptor protein ("J-vFcR"), co-expressed with a J domain fusion protein in which a J domain is linked to a herpes simplex virus type 1 gI protein ("J-gI"), co-expressed with a J domain fusion protein in which a J domain is linked to a herpes simplex virus type 1 gE protein ("J-gE"), and co-expressed with both J-gI and J-gE fusion proteins ("J-gI+J-gE"). Transfected cells were cultured for two days, and samples of cell media were harvested and analyzed by Western blot (immunoblot) assay using an anti-V5 antibody to detect secreted V5-tagged IL13Rα2TF.

FIG. 16A shows X-ray film images of chemiluminescent signals of a Western blot analysis of culture media from cultures of transfected cells. Lane 1 of FIG. 16A is medium from a culture of cells transfected with an expression vector to express the IL13Rα2TF-Fc fusion protein alone. When expressed alone, some IL13Rα2TF-Fc fusion protein was detected in the medium (lane 1 of FIG. 16A). Some IL13Rα2TF-Fc protein was also detected when expressed with Protein A only (lane 3 of FIG. 16A), as previously noted above with respect to the results described in Example 5 and FIG. 12A. Also as previously described in Example 5 and FIG. 12A above, co-expression of IL13Rα2TF-Fc fusion protein with a J domain-Protein A fusion protein significantly enhanced the level of expression of IL13Rα2TF-Fc fusion protein secreted into culture medium (lane 2 of FIG. 16A) as compared to the level of expression of IL13Rα2TF alone (lane 1 of FIG. 16A) or co-expression of IL13Rα2TF-Fc with Protein A alone (lane 3 of FIG. 16A). Co-expression of the IL13Rα2TF-Fc protein with a J domain-Protein G fusion protein also significantly enhanced the level of expression of secreted IL13Rα2TF-Fc protein (lane 4 of FIG. 16A) as compared to the level of expression of IL13Rα2TF alone (lane 1 of FIG. 16A) or co-expression of IL13Rα2TF-Fc with Protein A alone (lane 3 of FIG. 16A).

Viral proteins gI and gE from herpes simplex virus type 1 are known to form a heterodimer, wherein the gE protein weakly binds antibody molecules. In addition, whereas the gE protein alone weakly binds to antibody molecules, gI alone does not bind antibody molecules. Consistent with these prior findings, co-expression of the IL13Rα2TF-Fc fusion protein with a J domain-gI fusion protein (lane 7 of FIG. 16A) resulted in a relatively low level of expression of secreted IL13Rα2TF-Fc that was similar to that observed in cells expressing the IL13Rα2TF-Fc alone (lane 1 of FIG. 16A). In contrast, co-expression of the IL13Rα2TF-Fc fusion protein with a J domain-gE fusion protein significantly enhanced the level of expression of secreted IL13Rα2TF-Fc (lane 8 of FIG. 16A). A similar enhancement in the level of secreted IL13Rα2TF-Fc was observed when IL13Rα2TF-Fc was co-expressed with both J-gI and J-gE fusion proteins (lane 9 of FIG. 16A), indicating that the J-gI fusion protein does not significantly enhance the level of expression of secreted IL13Rα2TF-Fc, consistent with the previous finding that the gI protein does not bind Fc domains.

The human Fc binding receptor (hFcR) and the *Macaca mulatta* rhadinovirus Fc binding receptor (vFcR) are well characterized receptors for binding Fc regions of antibody molecules. J domain fusions comprising these FcR molecules were prepared and tested for the ability to enhance expression of the IL13Rα2TF-Fc fusion protein. As shown in FIG. 16A, co-expression of the IL13Rα2TF-Fc protein with either a J domain-hFcR fusion protein or a J domain-vFcR fusion protein not only failed to enhance expression of secreted IL13Rα2TF-Fc (lanes 5 and 6 of FIG. 16A), but actually appeared to suppress even a low level of expression of secreted protein observed in cells expressing the IL13Rα2TF-Fc protein alone (lane 1 of FIG. 16A). One possible explanation for such apparent suppression of even baseline secretion may be that the J domain-FcR fusion proteins employed in these experiments becomes caught in the endoplasmic reticulum (ER). Further work is required to find functional constructs containing FcR regions to target and enhance expression of proteins that possess an Fc region.

The results of a densitometry analysis of the chemiluminescent signals in the Western blot in FIG. 16A using the NIH ImageJ image processing program are shown in the respective bar graphs in FIG. 16B.

Example 9.2. Fusion Proteins Comprising Fc Targeting Peptides for Use in Enhancing Expression of Target Proteins in an Unmodified Arrangement A variety of peptides are known that bind the Fc domain of immunoglobulin molecules. This experiment tested various fusion proteins comprising a J domain (as a protein expression enhancing polypeptide) linked to each of several representative Fc-binding peptides (as a target binding domain) for use in enhancing the level of expression of proteins that possess an Fc domain. The six peptides used to construct fusion proteins are shown in the table below.

Expression vector plasmids were prepared for expressing J domain fusion proteins comprising a J domain (from the Erdj3 protein) linked to each of the six peptides. The IL13Rα2TF-Fc fusion protein was used as a representative target protein comprising an Fc domain.

The amino acid sequence for a J domain fusion protein comprising a J domain of the Erdj3 J protein linked to the FcBP1 peptide used in this experiment included a Flag epitope tag and 13 additional C-terminal amino acid residues from the expression vector used to express the protein as shown in the table below.

TABLE 50

Amino Acid Sequences of Representative Peptides that Bind Fc Domains.

| Peptide Designation | Amino Acid Sequence | Reference |
|---|---|---|
| FcBP1 | DCAWHLGELVWCT (SEQ ID NO: 240) | DeLano et al., *Science*, 287: 1279-1283 (2000) |
| FcBP2 | HWRGWV (SEQ ID NO: 241) | Yang et al., *J. Peptide Res.*, 66 (Suppl. 1): 120-137 (2006) |
| FcBP3 | HVHYYW (SEQ ID NO: 242) | Yang et al., *J. Peptide Res.*, 66 (Suppl. 1): 120-137 (2006) |
| FcBP4 | YYWLHH (SEQ ID NO: 243) | Yang et al., *J. Peptide Res.*, 66 (Suppl. 1): 120-137 (2006) |
| FcBP5 | HVHYY (SEQ ID NO: 244) | Yang et al., *J. Peptide Res.*, 66 (Suppl. 1): 120-137 (2006) |
| FcBP6 | YYWL (SEQ ID NO: 245) | Yang et al., *J. Peptide Res.*, 66 (Suppl. 1): 120-137 (2006) |

TABLE 51

Amino Acid Sequence of a Flag-Tagged Erdj3 J Domain-FcBP1 Fusion Protein.

| Protein Region (N- to C-terminal) | Sequence Identifier | Amino Acid Sequence 12345678901234567890123456789 0 |
|---|---|---|
| Flag-tagged Erdj3 J domain-FcBP1 fusion protein | SEQ ID NO: 246 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAADCAWHLGELVWCTLEGDYKD DDDKGSRGPYSIVSPKC |
| J domain (from Erdj3) | residues 1-83 of SEQ ID NO: 246 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 246 | DIGGGSGGSGGSGGAAA |
| FcBP1 | residues 101-113 of SEQ ID NO: 246 | DCAWHLGELVWCT |
| Linker | residues 114-116 of SEQ ID NO: 246 | LEG |
| Flag epitope domain | residues 117-124 of SEQ ID NO: 246 | DYKDDDDK |

TABLE 51-continued

Amino Acid Sequence of a Flag-Tagged Erdj3 J Domain-FcBP1 Fusion Protein.

| Protein Region (N- to C-terminal) | Sequence Identifier | Amino Acid Sequence 12345678901234567890123456789 0 |
|---|---|---|
| C-terminal vector residues | residues 125-137 of SEQ ID NO: 246 | GSRGPYSIVSPKC |

The amino acid sequence for a J domain fusion protein comprising a J domain of the Erdj3 J protein linked to the FcBP2 peptide used in this experiment included a Flag epitope tag and 13 additional C-terminal amino acid residues from the expression vector used to express the protein as shown in the table below.

The amino acid sequence for a J domain fusion protein comprising a J domain of the Erdj3 J protein linked to the FcBP3 peptide used in this experiment included a Flag epitope tag and 13 additional C-terminal amino acid residues from the expression vector used to express the protein as shown in the table below.

TABLE 52

Amino Acid Sequence of a Flag-Tagged Erdj3 J Domain-FcBP2 Fusion Protein.

| Protein Region (N- to C-terminal) | Sequence Identifier | Amino Acid Sequence 12345678901234567890123456789 0 |
|---|---|---|
| Flag-tagged Erdj3 J domain-FcBP2 fusion protein | SEQ ID NO: 247 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAAHWRGWVLEGDYKDDDDKGSR GPYSIVSPKC |
| J domain (from Erdj3) | residues 1-83 of SEQ ID NO: 247 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 247 | DIGGGSGGSGGSGGAAA |
| FcBP2 | residues 101-106 of SEQ ID NO: 247 | HWRGWV |
| Linker | residues 107-109 of SEQ ID NO: 247 | LEG |
| Flag epitope domain | residues 110-117 of SEQ ID NO: 247 | DYKDDDDK |
| C-terminal vector residues | residues 118-130 of SEQ ID NO: 247 | GSRGPYSIVSPKC |

TABLE 53

Amino Acid Sequence of a Flag-Tagged Erdj3 J Domain-FcBP3 Fusion Protein.

| Protein Region (N- to C-terminal) | Sequence Identifier | Amino Acid Sequence 123456789012345678901234567890 |
|---|---|---|
| Flag-tagged Erdj3 J domain-FcBP3 fusion protein | SEQ ID NO: 248 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAAHVHYYWLEGDYKDDDDKGSR GPYSIVSPKC |
| J domain (from Erdj3) | residues 1-83 of SEQ ID NO: 248 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 248 | DI GGGSGGSGGSGG AAA |
| FcBP3 | residues 101-106 of SEQ ID NO: 248 | HVHYYW |
| Linker | residues 107-109 of SEQ ID NO: 248 | LEG |
| Flag epitope domain | residues 110-117 of SEQ ID NO: 248 | DYKDDDDK |
| C-terminal vector residues | residues 118-130 of SEQ ID NO: 248 | GSRGPYSIVSPKC |

The amino acid sequence for a J domain fusion protein comprising a J domain of the Erdj3 J protein linked to the FcBP4 peptide used in this experiment included a Flag epitope tag and 13 additional C-terminal amino acid residues from the expression vector used to express the protein as shown in the table below.

TABLE 54

Amino Acid Sequence of a Flag-Tagged Erdj3 J domain-FcBP4 Fusion Protein.

| Protein Region (N- to C-terminal) | Sequence Identifier | Amino Acid Sequence 123456789012345678901234567890 |
|---|---|---|
| Flag-tagged Erdj3 J domain-FcBP4 fusion protein | SEQ ID NO: 249 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAAYYWLHHLEGDYKDDDDKGSR GPYSIVSPKC |
| J domain (from Erdj3) | residues 1-83 of SEQ ID NO: 249 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 249 | DIGGGSGGSGGSGGAAA |
| FcBP4 | residues 101-106 of SEQ ID NO: 249 | YYWLHH |
| Linker | residues 107-109 of SEQ ID NO: 249 | LEG |
| Flag epitope domain | residues 110-117 of SEQ ID NO: 249 | DYKDDDDK |

TABLE 54-continued

Amino Acid Sequence of a Flag-Tagged Erdj3 J domain-FcBP4 Fusion Protein.

| Protein Region (N- to C-terminal) | Sequence Identifier | Amino Acid Sequence 12345678901234567890123456789 0 |
|---|---|---|
| C-terminal vector residues | residues 118-130 of SEQ ID NO: 249 | GSRGPYSIVSPKC |

The amino acid sequence for a J domain fusion protein comprising a J domain of the Erdj3 J protein linked to the FcBP5 peptide used in this experiment included a Flag epitope tag and 13 additional C-terminal amino acid residues from the expression vector used to express the protein as shown in the table below.

TABLE 55

Amino Acid Sequence of a Flag-Tagged Erdj3 J domain-FcBP5 Fusion Protein.

| Protein Region (N- to C-terminal) | Sequence Identifier | Amino Acid Sequence 12345678901234567890123456789 0 |
|---|---|---|
| Flag-tagged Erdj3 J domain-FcBP5 fusion protein | SEQ ID NO: 250 | MAPQNLSTFCLLLLYLIGAVIAGRDFYKIL GVPRSASIKDIKKAYRKLALQLHPDRNPDD PQAQEKFQDLGAAYEVLSDSEKRDIGGGSG GSGGSGGAAAHVHYYLEGDYKDDDDKGSRG PYSIVSPKC |
| J domain (from Erdj3) | residues 1-83 of SEQ ID NO: 250 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 250 | DI GGGSGGSGGSGG AAA |
| FcBP5 | residues 101-105 of SEQ ID NO: 250 | HVHYY |
| Linker | residues 106-108 of SEQ ID NO: 250 | LEG |
| Flag epitope domain | residues 109-116 of SEQ ID NO: 250 | DYKDDDDK |
| C-terminal vector residues | residues 117-129 of SEQ ID NO: 250 | GSRGPYSIVSPKC |

The amino acid sequence for a J domain fusion protein comprising a J domain of the Erdj3 J protein linked to the FcBP6 peptide used in this experiment included a Flag epitope tag and 13 additional C-terminal amino acid residues from the expression vector used to express the protein as shown in the table below.

TABLE 56

Amino Acid Sequence of a Flag-Tagged Erdj3 J domain-FcBP6 Fusion Protein.

| Protein Region (N- to C-terminal) | Sequence Identifier | Amino Acid Sequence 12345678901234567890123456789 0 |
|---|---|---|
| Flag-tagged Erdj3 J domain- | SEQ ID NO: 251 | MAPQNLSTFCLLLLYLIGAVIAGRDFYKIL GVPRSASIKDIKKAYRKLALQLHPDRNPDD |

TABLE 56-continued

Amino Acid Sequence of a Flag-Tagged Erdj3 J domain-FcBP6 Fusion Protein.

| Protein Region (N- to C-terminal) | Sequence Identifier | Amino Acid Sequence 12345678901234567890123456789 0 |
|---|---|---|
| FcBP6 fusion protein | | PQAQEKFQDLGAAYEVLSDSEKRDIGGGSG GSGGSGGAAAYYWLLEGDYKDDDDKGSRGP YSIVSPKC |
| J domain (from Erdj3) | residues 1-83 of SEQ ID NO: 251 | MAPQNLSTFCLLLLYLIGAVIAGRDFYKIL GVPRSASIKDIKKAYRKLALQLHPDRNPDD PQAQEKFQDLGAAYEVLSDSEKR |
| Linker | residues 84-100 of SEQ ID NO: 251 | DIGGGSGGSGGSGGAAA |
| FcBP6 | residues 101-104 of SEQ ID NO: 251 | YYWL |
| Linker | residues 105-107 of SEQ ID NO: 251 | LEG |
| Flag epitope domain | residues 108-115 of SEQ ID NO: 251 | DYKDDDDK |
| C-terminal vector residues | residues 116-128 of SEQ ID NO: 251 | GSRGPYSIVSPKC |

Transfected cells were cultured for two days, and samples of cell media were harvested and analyzed by Western blot assay using an anti-V5 antibody to detect secreted V5-tagged IL13Rα2TF-Fc fusion protein. FIG. 17A shows X-ray film images of chemiluminescent signals of the Western blot analysis of culture media. As shown in FIG. 17A, co-expression of the IL13Rα2TF-Fc fusion protein with each of the six J domain-peptide fusion proteins in HEK293 transfectants significantly enhanced the level of expression of secreted IL13Rα2TF-Fc fusion protein (lanes 4-9) as compared to the level of expression of IL13Rα2TF-Fc fusion protein alone (lanes 1 and 3). The experiment also included for comparison the effect of co-expression of IL13Rα2TF-Fc fusion protein with a J domain-Protein A fusion protein (lane 2) or with a J domain-Protein G fusion protein (lane 10) on the expression of secreted IL13Rα2TF-Fc fusion protein. As shown in FIG. 17A, co-expression of IL13Rα2TF-Fc fusion protein with either J domain-Protein A fusion protein (lane 2) or the J domain-Protein G fusion protein (lane 10) significantly enhanced the level of expression of secreted the IL13Rα2TF-Fc fusion protein.

The results of a densitometry analysis of the chemiluminescent signals in the Western blot in FIG. 17A using the NIH ImageJ image processing program are shown in the respective bar graphs in FIG. 17B.

Conclusion of Results of Experiments

The results of the experiments described above indicate that co-expression of a target protein of interest and a fusion protein comprising a protein expression enhancing polypeptide domain linked to a target protein binding domain that binds the target protein significantly enhances the level of expression of the target protein in its proper cellular or extracellular location as compared to the level of expression of the target protein in the absence of the fusion protein.

Example 10. Minimal Sequence Requirements for Protein Expression Enhancing Polypeptides Further analysis was undertaken to determine the minimal amino acid sequence that is effective for enhancing the level of expression of a target protein of interest when employed in an unmodified or a modified arrangement.

Sequence homology analysis using BLAST was conducted on the existing library of J domain sequences to determine whether J domains shared a similar minimal "core" sequence that could enhance the level of protein expression. The analysis indicated that the J domain of the Erdj3 protein was typical of J domains of other J proteins. Since the J domain of Erdj3 was already known to be effective at enhancing protein expression in both the modified and unmodified arrangements (see, examples above), it was chosen for further deletion and substitution mutation analysis to determine whether a minimal polypeptide sequence could be identified that retained protein expression enhancing activity.

In this study, various deletion and substitution mutations of the J domain of Erdj3 were assessed for enhancing expression of an engineered IL13Rα2TF-V5-Fc protein as the target protein of interest. This engineered protein possesses a V5 epitope tag between the IL13Rα2TF polypeptide and the Fc domain, permitting easy detection with an anti-V5 antibody. Fusion proteins were constructed comprising either the full length J domain of Erdj3 or the various mutated polypeptides linked to Protein A, which binds the Fc domain of the engineered IL13Rα2-Fc target protein (thus acting as a target protein binding domain) Thus, for each of the mutated polypeptides, the general formula of the corresponding fusion proteins used in the study was:

signal sequence-linker 1-(J domain, fragment or J domain analog polypeptide sequence-linker 2-Protein A-linker 3-Flag epitope tag.

The amino acid sequences of the domains of these fusion proteins, excluding the inserted J domain, J domain fragment, or J domain analog sequences, is shown in the table below.

TABLE 57

Amino Acid Structure of Test Flag-Tagged Protein A Fusions.

| Protein Region | Sequence Identifier | Amino Acid Sequence 12345678901234567890123456789 0 |
|---|---|---|
| signal sequence | SEQ ID NO: 251 | MGVKVLFALICIAVAEA |
| linker 1 | SEQ ID NO: 252 | GTGSGEF |
| J domain, fragment or analog sequence | | (various polypeptide sequences) |
| linker 2 | SEQ ID NO: 122 | DIGGGSGGSGGSGGAAA |
| Protein A | SEQ ID NO: 254 | ADNKFNKEQQNAFYEILNMPNLNEEQRNGF IQSLKDDPSQSANVLGEAKKLNDSQAPK |
| linker 3 | SEQ ID NO: 255 | LEG |
| Flag epitope tag | SEQ ID NO: 111 | DYKDDDDK |

The protein expression enhancing activity of each fusion protein was determined by dot blot assay using detectable anti-V5 antibody. The IL13Rα2-V5-Fc target protein was expressed with or without the fusion proteins containing each mutated polypeptide sequence, and the cell culture medium was harvested and briefly spun to remove debris. The sample was blotted onto nitrocellulose membrane, and the dried membrane was processed for immunoblot assay. The deletion and substitution polypeptides tested for protein expression enhancement activity are shown in the table below along with the protein expression enhancing activity determined by immunoblotting.

TABLE 58

Amino Acid Sequences of Polypeptides Tested for Protein Expression Enhancing Activity.

| Polypeptide No. | Sequence Identifier | Polypeptide Amino Acid Sequence 12345678901234567890123456789 0 | Activity* |
|---|---|---|---|
| 3 | SEQ ID NO: 256 | GRDFYKILGVPRSASIKDIKKAYRKLALQL HPDRNPDDPQAQEKFQDLGAAYEVLSDSEK R | HA |
| 3-1 | SEQ ID NO: 257 | ILGVPRSASIKDIKKAYRKLALQLHPDRNP DDPQAQEKFQDLGAAYEVLSDSEKR | HA |
| 3-2 | SEQ ID NO: 258 | SASIKDIKKAYRKLALQLHPDRNPDDPQAQ EKFQDLGAAYEVLSDSEKR | HA |
| 3-3 | SEQ ID NO: 259 | GRDFYKILGVPRSASIKDIKKAYRKLALQL HPDRNPDDPQAQEKFQDLG | HA |
| 3-4 | SEQ ID NO: 260 | ILGVPRSASIKDIKKAYRKLALQLHPDRNP DDPQAQEKFQDLG | HA |
| 3-5 | SEQ ID NO: 261 | SASIKDIKKAYRKLALQLHPDRNPDDPQAQ EKFQDLG | HA |
| 3-6 | SEQ ID NO: 262 | KAYRKLALQLHPDRNPDDPQAQEKFQDLG | NA |
| 3-7 | SEQ ID NO: 263 | KAYRKLALQLHPDRNPDDPQAQEKFQDLGA AYEVLSDSEKR | NA |
| 3-8 | SEQ ID NO: 264 | LQLHPDRNPDDPQAQEKFQDLG | NA |
| 3-9 | SEQ ID NO: 265 | LQLHPDRNPDDPQAQEKFQDLGAAYEVLSD SEKR | NA |

TABLE 58-continued

Amino Acid Sequences of Polypeptides Tested for Protein Expression Enhancing Activity.

| Polypeptide No. | Sequence Identifier | Polypeptide Amino Acid Sequence 12345678901234567890123456789 0 | Activity* |
|---|---|---|---|
| 3-10 | SEQ ID NO: 266 | IKDIKKAYRKLALQLKPDRNPDDPQAQEKFQDLG | HA |
| 3-11 | SEQ ID NO: 267 | SASIKDIKKAYRKLALQLHPDRNPDDPQAQE | HA |
| 3-12 | SEQ ID NO: 268 | SASIKDIKKAYRKLALQLHP | HA |
| 3-13 | SEQ ID NO: 269 | IKDIKKAYRKLALQLHPDRNPDDPQAQE | HA |
| 3-14 | SEQ ID NO: 270 | IKDIKKAYRKLALQLHPDRN | HA |
| 3-15 | SEQ ID NO: 271 | DIKKAYRKLALQLHPDRNPDDPQAQE | HA |
| 3-16 | SEQ ID NO: 272 | IKDIKKAYRKLALQLHPD | HA |
| 3-17 | SEQ ID NO: 273 | IKDIKKAYRKLALQL | HA |
| 3-18 | SEQ ID NO: 274 | DIKKAYRKLALQL | HA |
| 3-19 | SEQ ID NO: 275 | DIKKAYRKLALQ | HA |
| 3-20 | SEQ ID NO: 276 | DIKKAYRKLAL | HA |
| 3-21 | SEQ ID NO: 277 | DIKKAYRKLA | HA |
| 3-22 | SEQ ID NO: 278 | DIKKAYRKL | NA |
| 3-23 | SEQ ID NO: 279 | DIKKAYRK | NA |
| 3-24 | SEQ ID NO: 280 | DIKKAYR | NA |
| 3-25 | SEQ ID NO: 281 | IKKAYRKLALQL | HA |
| 3-26 | SEQ ID NO: 282 | KKAYRKLALQL | NA |
| 3-27 | SEQ ID NO: 283 | IKKAYRKLALQ | HA |
| 3-28 | SEQ ID NO: 284 | IKKAYRKLAL | HA |
| 3-29 | SEQ ID NO: 48 | IKKAYRKLA | HA |
| 3-30 | SEQ ID NO: 285 | IKKAYRKL | A |
| 3-31 | SEQ ID NO: 286 | KKAYRKLALQ | NA |
| 3-32 | SEQ ID NO: 287 | KKAYRKLAL | NA |
| 3-33 | SEQ ID NO: 288 | KKAYRKLA | NA |
| 3-34 | SEQ ID NO: 289 | KAYRKLALQ | NA |
| 3-35 | SEQ ID NO: 290 | IKKAYRK | NA |
| 3-36 | SEQ ID NO: 291 | IKKAYR | NA |
| 3-37 | SEQ ID NO: 292 | IKAYRKLALQ | NA |
| 3-38 | SEQ ID NO: 293 | IKKYRKLALQ | A |
| 3-39 | SEQ ID NO: 294 | IKKARKLALQ | NA |
| 3-40 | SEQ ID NO: 49 | IKKAYKLALQ | HA |
| 3-41 | SEQ ID NO: 50 | IKKAYRLALQ | HA |
| 3-42 | SEQ ID NO: 51 | IKKAYRKALQ | HA |
| 3-43 | SEQ ID NO: 52 | IKKAYRKLLQ | HA |
| 3-44 | SEQ ID NO: 295 | IKAYRKLA | NA |
| 3-45 | SEQ ID NO: 53 | IKKYRKLA | A |

TABLE 58-continued

Amino Acid Sequences of Polypeptides Tested for Protein Expression Enhancing Activity.

| Polypeptide No. | Sequence Identifier | Polypeptide Amino Acid Sequence 12345678901234567890123456789 0 | Activity* |
|---|---|---|---|
| 3-46 | SEQ ID NO: 54 | IKKAYKLA | A |
| 3-47 | SEQ ID NO: 55 | IKKAYRLA | A |
| 3-48 | SEQ ID NO: 56 | IKKAYRKA | A |
| 3-49 | SEQ ID NO: 57 | LKKAYRKLA | HA |
| 3-50 | SEQ ID NO: 58 | VKKAYRKLA | HA |
| 3-51 | SEQ ID NO: 59 | MKKAYRKLA | HA |
| 3-52 | SEQ ID NO: 60 | AKKAYRKLA | HA |
| 3-53 | SEQ ID NO: 296 | SKKAYRKLA | NA |
| 3-54 | SEQ ID NO: 297 | FKKAYRKLA | NA |
| 3-55 | SEQ ID NO: 298 | IAQAYRKLA | NA |
| 3-56 | SEQ ID NO: 299 | ILAAYRKLA | NA |
| 3-57 | SEQ ID NO: 61 | IAKAYRKLA | A |
| 3-58 | SEQ ID NO: 62 | IKAAYRKLA | A |
| 3-59 | SEQ ID NO: 63 | IKKRYRKLA | HA |
| 3-60 | SEQ ID NO: 64 | IKKSYRKLA | A |
| 3-61 | SEQ ID NO: 65 | IKKQYRKLA | A |
| 3-62 | SEQ ID NO: 66 | IKKEYRKLA | A |
| 3-63 | SEQ ID NO: 67 | IKKFYRKLA | A |
| 3-64 | SEQ ID NO: 68 | IKKCYRKLA | A |
| 3-65 | SEQ ID NO: 69 | IKKAFRKLA | HA |
| 3-66 | SEQ ID NO: 300 | IKKAHRKLA | NA |
| 3-67 | SEQ ID NO: 301 | IKKAIRKLA | NA |
| 3-68 | SEQ ID NO: 70 | IKKAWRKLA | HA |
| 3-69 | SEQ ID NO: 302 | IKKAARKLA | NA |
| 3-70 | SEQ ID NO: 303 | IKKASRKLA | NA |
| 3-71 | SEQ ID NO: 304 | IKKAYHQLA | NA |
| 3-72 | SEQ ID NO: 305 | IKKAYYQLA | NA |
| 3-73 | SEQ ID NO: 306 | IKKAYFSLA | NA |
| 3-74 | SEQ ID NO: 307 | IKKAYRKQS | NA |
| 3-75 | SEQ ID NO: 308 | IKKAYRKQC | NA |
| 3-76 | SEQ ID NO: 309 | IKKAYRKDI | NA |
| 3-77 | SEQ ID NO: 71 | IKKAYRKQA | HA |
| 3-78 | SEQ ID NO: 72 | IKKAYRKMA | HA |
| 3-79 | SEQ ID NO: 73 | IKKAYRKIA | A |
| 3-80 | SEQ ID NO: 74 | IKKAYRKAA | A |
| 3-81 | SEQ ID NO: 75 | IKKAYRKVA | A |
| 3-82 | SEQ ID NO: 76 | IKKAYRKRA | A |

TABLE 58-continued

Amino Acid Sequences of Polypeptides Tested for Protein Expression Enhancing Activity.

| Polypeptide No. | Sequence Identifier | Polypeptide Amino Acid Sequence 123456789012345678901234567890 | Activity* |
|---|---|---|---|
| 3-83 | SEQ ID NO: 77 | IKKAYRKLM | HA |
| 3-84 | SEQ ID NO: 78 | IKKAYRKLI | HA |
| 3-85 | SEQ ID NO: 79 | IKKAYRKLV | HA |
| 3-86 | SEQ ID NO: 80 | IKKAYRKLC | A |
| 3-87 | SEQ ID NO: 81 | IKKAYRKLS | HA |
| 3-88 | SEQ ID NO: 82 | IKKAYRKLY | A |
| 3-89 | SEQ ID NO: 83 | IRKAYRKLSLTL | A |
| 3-90 | SEQ ID NO: 84 | IKKQYRLLSLKY | A |
| 3-91 | SEQ ID NO: 85 | IKKAFHKLAMKY | HA |
| 3-92 | SEQ ID NO: 86 | IRQAFKKLALKL | A |
| 3-93 | SEQ ID NO: 87 | IIKAYRKLALQW | A |
| 3-94 | SEQ ID NO: 88 | IARAYRQLARRY | HA |
| 3-95 | SEQ ID NO: 89 | IKRAYRRQALRY | HA |
| 3-96 | SEQ ID NO: 90 | IKKSYRKLALKY | HA |
| 3-97 | SEQ ID NO: 91 | IKKAYKRLAMKY | HA |
| 3-98 | SEQ ID NO: 310 | MRKAYLKKC | NA |
| 3-99 | SEQ ID NO: 311 | ILAEFKVRAL | NA |

*"HA" = high activity, i.e., protein expression enhancement activity is significantly enhanced, e.g. similar to that provided by the full-length J domain of the Erdj3 protein, as compared to negative control (no fusion protein used);
"A" = improved protein expression enhancement activity in comparison to negative control (no fusion protein used); level of protein production typically less than provided by the full-length J domain of Erdj3;
"NA" = no activity compared to negative control.

As indicated in the above table, each mutated polypeptide was assessed for expression enhancing activity when co-expressed with the IL13Rα2-V5-Fc target protein. The levels of expression were classified as high activity ("HA"), activity ("A"), or no activity ("NA"). Examples of these levels of expression are shown in the immunoblot in FIG. 18. The level of expression of the IL13Rα2-V5-Fc target protein in the absence of a fusion protein was taken as "no activity". See, lane 2 (from the left) in FIG. 18). Co-expression of a fusion protein comprising the complete J domain of Erdj3, designated polypeptide 3 in Table 58 above, linked to Protein A dramatically enhanced the level of expression of the secreted IL13Rα2-V5-Fc target protein. See, lane 3, from the left, in FIG. 18. This level of expression enhancement is designated "High Activity". As shown in lane 4 of FIG. 18, co-expression of a fusion protein comprising an internal deletion mutated polypeptide, designated 3-45, linked to Protein A clearly provided a significantly enhanced level of expression of the secreted IL13Rα2-V5-Fc target protein as compared to the control (no fusion protein, lane 2 of FIG. 18), but the expression level was somewhat less than the high activity shown in lane 3 of FIG. 18. This level of expression enhancement is designated "Activity." In contrast, as shown in lane 5 of FIG. 18, co-expression of a fusion protein comprising a substitution mutation within the minimal polypeptide sequence, designated 3-72, linked to Protein A provided no more than the level of expression detected for the control in lane 2 of FIG. 18. This was designated "No Activity".

The results of this analysis indicated that an internal polypeptide fragment of the J domain of Erdj3, designated 3-29, has the minimal polypeptide sequence (IKKAY-RKLA; SEQ ID NO:48) that provides a high activity for enhancing protein expression. The polypeptide 3-29 sequence is located within a helix II of the J domain, but does not include any residues of the adjacent (C-proximal) loop domain.

Various mutations of the J domain fragment 3-29 sequence were made and assessed for protein expression enhancing activity. The mutated sequences are shown in the table above, see polypeptide nos. 3-44 to 3-88.

The J domains of other J proteins were also assessed for internal polypeptide sequences located in positions similar to that of the 3-29 polypeptide within the J domain of Erdj3. Such sequences are designated 3-89 to 3-99 in the table above. Most of these polypeptides provided complete or partial activity in the assay for enhanced expression of the secreted IL13Rα2-V5-Fc target protein. However, two of the polypeptides, designated 3-98 and 3-99, possessed amino acid sequences that diverged considerably from that of polypeptide 3-29, and these polypeptides also lacked protein expression enhancing activity.

Example 11. Structural Formula Defining a New Family of Protein Expression Enhancing Polypeptides Below is an overview of the analysis of the polypeptide sequence mutation data that led not only to the discovery of the minimal sequence of a polypeptide fragment of the J domain of Erdj3 that provides protein expression enhancing activity (polypeptide 3-29, SEQ ID NO:48), but also to a structural formula that defines a new family of protein expression enhancing polypeptides as shown below.

FIG. 19 shows an alignment of the amino acid sequence for the J domain of Erdj3 with a series of deletion mutated polypeptides along with their protein expression enhancing activity determined using the unmodified arrangement in which each polypeptide was used to construct a Flag-tagged Protein A fusion protein as described above. The level of expression of secreted IL13Rα2-V5-Fc target protein in the media of cultures of cells co-expressing each Flag-tagged Protein A fusion and the IL13Rα2-V5-Fc target protein was determined by immunoblot using an anti-V5 antibody as described above.

Deletion mutated polypeptides designated 3-6, 3-7, 3-8, and 3-9 in FIG. 19 all lacked protein expression enhancing activity (no activity), indicating that αhelix II amino acid sequences are essential for activity. Deletion mutated polypeptides designated 3-15 and 3-17 in FIG. 19 retained high activity, indicating that the sequence DIKKAYRKLALQL (SEQ ID NO:274) was sufficient for providing high protein expression enhancing activity. This polypeptide was then subjected to further mutation analysis as shown in the table below.

protein expression enhancing activity. Similarly, the difference in activity between that of polypeptide 3-25 and that of polypeptide 3-26 indicated that the N-terminal isoleucine (I) is essential for activity. As noted previously, polypeptide 3-29 defines the minimal polypeptide sequence of the J domain of Erdj3 for providing complete protein expression enhancing activity.

In addition to the results described above, additional analyses as outlined below led to the identification of an essential amino acid consensus sequence for a protein expression enhancing polypeptide of the invention.

To identify the essential amino acid sequence for providing protein expression enhancing activity, each amino acid of the 3-29 sequence was deleted and the polypeptide tested for protein expression enhancing activity using the IL13Rα2-V5-Fc target protein in the unmodified arrangement described above.

Starting with the minimum sequence of the polypeptide fragment of the J domain of Erdj3, the polypeptide 3-29 sequence (IKKAYRKLA; SEQ ID NO:48) was subjected to the following mutation analysis at each of the nine amino acid positions:

(a) 3-29: IKKAYRKLA (SEQ ID NO:48), regarding position 1, see summary analysis (1) below,
(b) 3-44: IK_AYRKLA (SEQ ID NO:295), no activity, regarding position 3, see summary analysis (2) below,
(c) 3-45: IKK YRKLA (SEQ ID NO:53), some activity, regarding position 4, see summary analysis (3) below,
(d) 3-39: IKKA_RKLA (SEQ ID NO:294), no activity, regarding position 5, see summary analysis (4) below,
(e) 3-46: IKKAY_KLA (SEQ ID NO:54), some activity, regarding position 6, see summary analysis (5) below,
(f) 3-47: IKKAYR_LA (SEQ ID NO:55), some activity, regarding position 7, see summary analysis (5) below,

TABLE 59

Amino Acid Sequence and Protein Expression Enhancing Activity of Mutated Polypeptides.

| PP No. | aa | sequence | SEQ ID NO: | Act | |
|---|---|---|---|---|---|
| 3-18 | 13 | DIKKAYRKLALQL | 274 | HA | |
| 3-19 | 12 | DIKKAYRKLALQ | 275 | HA | |
| 3-20 | 11 | DIKKAYRKLAL | 276 | HA | |
| 3-21 | 10 | DIKKAYRKLA | 277 | HA | |
| 3-22 | 9 | DIKKAYRKL | 278 | NA | The last amino acid is essential |
| 3-23 | 8 | DIKKAYRK | 279 | NA | |
| 3-24 | 7 | DIKKAYR | 280 | NA | |
| 3-25 | 12 | IKKAYRKLALQL | 281 | HA | The first amino acid is essential |
| 3-26 | 11 | KKAYRKLALQL | 282 | NA | |
| 3-27 | 11 | IKKAYRKLALQ | 283 | HA | |
| 3-28 | 10 | IKKAYRKLAL | 284 | HA | |
| 3-29 | 9 | IKKAYRKLA | 48 | HA | ← Identified Minimum Sequence |
| 3-30 | 8 | IKKAYRKL | 285 | A | |
| 3-31 | 10 | KKAYRKLALQ | 286 | NA | |
| 3-32 | 9 | KKAYRKLAL | 287 | NA | |
| 3-33 | 8 | KKAYRKLA | 288 | NA | |
| 3-34 | 9 | KAYRKLALQ | 289 | NA | |
| 3-35 | 7 | IKKAYRK | 290 | NA | |
| 3-36 | 6 | IKKAYR | 291 | NA | |

As noted above, the difference in activity between that of the polypeptide designated 3-21 (high activity, HA) and that of the polypeptide designated 3-22 (no activity, NA) indicated that the C-terminal leucine (L) residue is essential for (g) 3-48: IKKAYRK_A (SEQ ID NO:56), some activity, regarding position 8, see summary analysis (6) below,
(h) IKKAYRLA (SEQ ID NO:48), high activity, regarding position 9, see summary analysis (6) below.

Summary Analyses (1) IKKAYRKLA    (SEQ ID NO: 48)

First amino acid is essential for the activity.

The result for the comparison of the first amino acid among J members (47 J proteins) indicated the following incidences of amino acids at position 1:

I (34), L (6), V (4), M (1), A (1), R (1)

All of these amino acids have a nonpolar side chain group, except Arg (R).

The following constructions derived from other J members were made and tested:

3-49:    (SEQ ID NO: 57)
LKKAYRKLA, high activity 3-50:    (SEQ ID NO: 58)
VKKAYRKLA, high activity 3-51:    (SEQ ID NO: 59)
MKKAYRKLA, high activity 3-52:    (SEQ ID NO: 60)
AKKAYRKLA, high activity 3-53:    (SEQ ID NO: 296)
SKKAYRKLA, no activity 3-54:    (SEQ ID NO: 297)
FKKAYRKLA, no activity.

Therefore, it the first position is preferably an amino acid with a nonpolar amino acid side group that is I, L, V, A, and M.

(2) IK_AYRKLA;    (SEQ ID NO: 295)

no activity

This implies two possibilities:

a) two amino acids are required at this position 3-55:    (SEQ ID NO: 298)
IAQAYRKLA, no activity 3-56:    (SEQ ID NO: 299)
ILAAYRKLA, no activity indicating some specific amino acid is required, b) two lysines are required or only one is enough.

Through the comparison of these two positions among J members (47 J proteins), these two positions are well conserved as indicated by the following incidences:

KK (26), KR (5), RK (3), AR (3), KA (2), KQ (2), KL (1), IK (1), NK (1), RQ (1), RD (1), LA (1)

All of these harbor at least one amino acid with a basic amino acid side chain with one exception.

Therefore, the following substitution mutations were made and tested:

3-57:    (SEQ ID NO: 61)
IAKAYRKLA, some activity 3-58:    (SEQ ID NO: 62)
IKAAYRKLA, some activity.

Therefore, it is concluded that at least one amino acid at positions 2 and 3 is a basic amino acid K or R.

(3) IKK_YRKLA,    (SEQ ID NO: 53)

some activity

This result indicates that it is better to have some amino acid in this position but not absolutely necessary.

Through a comparison of this position among J members (47 J proteins), this position is also well conserved as indicated by the following incidences:

A (36), K (2), R (2), S (2), Q (2), T (1), I (1), E (1)

The following polypeptides were constructed and tested:

Basic amino acid
3-59    (SEQ ID NO: 63)
IKKRYRKLA;

high activity

Polar uncharged amino acid
3-60    (SEQ ID NO: 64)
IKKSYRKLA;

some activity

Polar uncharged amino acid
3-61    (SEQ ID NO: 65)
IKKQYRKLA;

some activity

Acidic amino acid
3-62
IKK<u>E</u>YRKLA;                (SEQ ID NO: 66)

some activity

Aromatic amino acid
3-63
IKK<u>F</u>YRKLA;                (SEQ ID NO: 67)

some activity

Polar uncharged amino acid
3-64
IKK<u>C</u>YRKLA;                (SEQ ID NO: 68)

some activity.

From the above substitution mutations, it is concluded that any of the 20 naturally occurring amino acids may occupy position 4 since deletion at this position still retains activity.

(4) IKKA_RKLA;         (SEQ ID NO: 312)

This result implies that some amino acid in position 5 is essential.

Through the comparison of this position among J members (47 J proteins), the amino acid distribution is given below.

Y (34), F (10), H (2), I (1)

Therefore the following polypeptides were made and tested:

Aromatic amino acid
3-65
IKKA<u>F</u>RKLA,               (SEQ ID NO: 69)

high activity

Positive charged amino acid
3-66
IKKA<u>H</u>RKLA,               (SEQ ID NO: 300)

no activity

Nonpolar amino acid
3-67
IKKA<u>I</u>RKLA,               (SEQ ID NO: 301)

no activity

Aromatic amino acid
3-68
IKKA<u>W</u>RKLA,               (SEQ ID NO: 70)

high activity

Nonpolar amino acid
3-69
IKKA<u>A</u>RKLA,               (SEQ ID NO: 302)

no activity

Nonpolar amino acid
3-70
IKKA<u>S</u>RKLA,               (SEQ ID NO: 303)

no activity.

Therefore, the amino acid at position 5 is an aromatic amino acid that is Y, F, or W.

(5) IKKAY_KLA,         (SEQ ID NO: 313)

some activity

IKKAYR_LA              (SEQ ID NO: 314)

some activity

Through the comparison of this position among J members (47 J proteins), the case that at least one amino acid is a basic amino acid is 43 out of 47 (both 23, and either one 20).

The following mutated polypeptides have two amino acids replaced at positions 6 and 7:

3-71
IKKAY<u>HQ</u>LA,               (SEQ ID NO: 304)

no activity 3-72 IKKAY<u>YQ</u>LA,          (SEQ ID NO: 305)

no activity 3-73 IKKAY<u>FS</u>LA,          (SEQ ID NO: 306)

no activity.

Therefore, at least one of the amino acids at positions 6 and 7 is a basic amino acid K or R.

(6) IKKAYRK_A,         (SEQ ID NO: 56)

some activity

IKKAYRKL,              (SEQ ID NO: 315)

some activity

Through the comparison of these positions among J members (47 J proteins), the case that two positions are occupied with L and A is 25 out of 47, in which all of them are L-A. The case that at least one amino acid at these positions is L or A is 14, and 8 cases indicates neither L nor A.

The following mutated polypeptides were made with two amino acids replaced and tested for activity:

```
                                        (SEQ ID NO: 307)
                    3-74 IKKAYRKQS,
```
no activity

```
                                        (SEQ ID NO: 308)
                    3-75 IKKAYRKQC,
```
no activity

```
                                        (SEQ ID NO: 309)
                    3-76 IKKAYRKDI,
```
no activity.

The following mutated polypeptides have position 8 replaced as indicated:

```
                                         (SEQ ID NO: 71)
        Polar amino acid 3-77 IKKAYRKQA,
```
high activity

```
                                         (SEQ ID NO: 72)
     Nonpolar amino acid 3-78 IKKAYRKMA,
```
high activity

```
                                         (SEQ ID NO: 73)
     Nonpolar amino acid 3-79 IKKAYRKIA,
```
some activity

```
                                         (SEQ ID NO: 74)
     Nonpolar amino acid 3-80 IKKAYRKAA,
```
some activity

```
                                         (SEQ ID NO: 75)
     Nonpolar amino acid 3-81 IKKAYRKVA,
```
some activity

```
                                         (SEQ ID NO: 76)
        Basic amino acid 3-82 IKKAYRKRA,
```
some activity.

The following mutated polypeptides have position 9 replaced as indicated:

```
                                         (SEQ ID NO: 77)
     Nonpolar amino acid 3-83 IKKAYRKLM,
```
high activity

```
                                         (SEQ ID NO: 78)
     Nonpolar amino acid 3-84 IKKAYRKLI,
```
high activity

```
                                         (SEQ ID NO: 79)
     Nonpolar amino acid 3-85 IKKAYRKLV,
```
high activity

```
                                         (SEQ ID NO: 80)
 Polar uncharged amino acid 3-86 IKKAYRKLC,
```
some activity

```
                                         (SEQ ID NO: 81)
 Polar uncharged amino acid 3-87 IKKAYRKLS,
```
high activity

```
                                         (SEQ ID NO: 82)
     Aromatic amino acid 3-88 IKKAYRKLY,
```
some activity.

Results of other mutated polypeptides:

```
                                         (SEQ ID NO: 51)
         Replacement L and A 3-42 IKKAYRKALQ,
```
high activity

```
                                         (SEQ ID NO: 52)
              Double L 3-43 IKKAYRKLLQ,
```
high activity.

Therefore, at least one of the amino acids at X8 and X9 is L or A.

Through these studies, it is concluded that an isolated protein expression enhancing J domain analog polypeptide comprises the formula:

```
                                         (SEQ ID NO: 47)
              X1-X2-X3-X4-X5-X6-X7-X8-X9,
``` wherein:
- X1 is isoleucine (I), leucine (L), valine (V), alanine (A), or methionine (M);
- X2 and X3 are each independently any amino acid with the proviso that one or both are lysine (K) or arginine (R);
- X4 is any amino acid or X4 may be absent when X1 through X3 are present and X5 through X9 are present;
- X5 is tyrosine (Y), tryptophan (W), or phenylalanine (F);
- X6 and X7 are each independently any amino acid with the proviso that one or both are lysine (K) or arginine (R); or either one of X6 and X7 may be absent when the other is K or R and when X1 through X5 are present and X8 and X9 are present; and X8 and X9 are any amino acid with the proviso that one or both are leucine (L) or alanine (A); or one of X8 and X9 may be absent when the other is L or A and when X1 through X7 are present.

The above formula is applicable to the sequence of the following polypeptide fragments from other J proteins, and all of these polypeptides have activity:

Erdj1
3-89
(SEQ ID NO: 83)
IRKAYRKLSLTL, some activity

Erdj2
3-90
(SEQ ID NO: 84)
IKKQYRLLSLKY, some activity

Erdj4
3-91
(SEQ ID NO: 85)
IKKAFHKLAMKY, high activity

Erdj5
3-92
(SEQ ID NO: 86)
IRQAFKKLALKL, some activity

Erdj6
3-93
(SEQ ID NO: 87)
IIKAYRKLALQW, high activity

Erdj7
3-94
(SEQ ID NO: 88)
IARAYRQLARRY, high activity

Hsp40
3-95
(SEQ ID NO: 89)
IKRAYRRQALRY, high activity

CSP
3-96
(SEQ ID NO: 90)
IKKSYRKLALKY, high activity

DnaJ
3-97
(SEQ ID NO: 91)
IKKAYKRLAMKY,

The sequences below from other J proteins do not match the above formula and these polypeptides do not have protein expression enhancing activity:

From SV40 J protein
3-98
(SEQ ID NO: 310)
MRKAYLKKC, no activity

From Dnaj homolog subfamily C member 12
3-99
(SEQ ID NO: 311)
ILAEFKVRAL, no activity.

The analyses and results summarized above indicate that the above formula defines a new family of polypeptides that provide protein expression enhancing activity.

Example 12. Minimal Polypeptide of J Domain Enhances Target Protein Expression in a Modified Arrangement As explained above, the results of the mutation analysis of the J domain of Erdj3 indicated that an internal polypeptide sequence, designated 3-29, is the minimal sequence with the J domain for a polypeptide (IKKAYRKLA; SEQ ID NO:48) to provides high activity for enhancing protein expression using the above assay in an unmodified arrangement. The protein expression enhancing activity of the 3-29 polypeptide was also examined in a modified arrangement.

In this experiment, a first fusion protein comprised IL13Rα2TF as the target protein of interest linked to the BSC1 polypeptide (SEQ ID NO:48), which in turn was linked to an V5 epitope tag. This fusion protein was designated IL13Rα2TF-BSC1 shown in the table below.

TABLE 60

Amino Acid Sequence of a V5-Tagged IL13Rα2TF-BSC1 Fusion Protein.

| Protein Region (N- to C-terminal) | Sequence Identifier | Amino Acid Sequence 12345678901234567890123456789 0 |
|---|---|---|
| IL13Rα2TF-BSC1 protein | SEQ ID NO: 316 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW |

TABLE 60-continued

Amino Acid Sequence of a V5-Tagged IL13Rα2TF-BSC1 Fusion Protein.

| Protein Region (N- to C-terminal) | Sequence Identifier | Amino Acid Sequence 123456789012345678901234567890 |
|---|---|---|
| | | QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKGTGSEFIKKAYRKLADIGGGS GGSGGSGGAAALEGKPIPNPLLGLDST |
| IL13Rα2TF | residues 1-339 of SEQ ID NO: 316 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKK |
| Linker | residues 340-345 of SEQ ID NO: 316 | GTGSEF |
| BSC1 | residues 346-354 of SEQ ID NO: 316 | IKKAYRKLA |
| Linker | residues 355-373 of SEQ ID NO: 316 | DIGGGSGGSGGSGGAAALE |
| V5 epitope domain | residues 374-387 of SEQ ID NO: 316 | GKPIPNPLLGLDST |

A second fusion protein comprised IL13Rα2TF as the target protein of interest linked to a mutated version of the BSC1 polypeptide, designated "IL13Rα2TF-BSC1MT" in which the second and third positions of the BSC1 polypeptide were mutated from K-K to A-Q as shown in the table below. The BSC1MT polypeptide is designated 3-55.

TABLE 61

| Amino Acid Sequence of a V5-Tagged IL13Rα2TF-BSC1MT Fusion Protein. | | |
|---|---|---|
| Protein Region (N- to C-terminal) | Sequence Identifier | Amino Acid Sequence 123456789012345678901234567890 |
| IL13Rα2TF-BSC1MT protein | SEQ ID NO: 317 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKKGTGSEFIAQAYRKLADIGGGS GGSGGSGGAAALEGKPIPNPLLGLDST |
| IL13Rα2TF | residues 1-339 of SEQ ID NO: 317 | MAFVCLAIGCLYTFLISTTFGCTSSSDTEI KVNPPQDFEIVDPGYLGYLYLQWQPPLSLD HFKECTVEYELKYRNIGSETWKTIITKNLH YKDGFDLNKGIEAKIHTLLPWQCTNGSEVQ SSWAETTYWISPQGIPETKVQDMDCVYYNW |

TABLE 61-continued Amino Acid Sequence of a V5-Tagged IL13Rα2TF-BSC1MT Fusion Protein.

| Protein Region (N- to C-terminal) | Sequence Identifier | Amino Acid Sequence 12345678901234567890123456789 0 |
|---|---|---|
| | | QYLLCSWKPGIGVLLDTNYNLFYWYEGLDH ALQCVDYIKADGQNIGCRFPYLEASDYKDF YICVNGSSENKPIRSSYFTFQLQNIVKPLP PVYLTFTRESSCEIKLKWSIPLGPIPARCF DYEIEIREDDTTLVTATVENETYTLKTTNE TRQLCFVVRSKVNIYCSDDGIWSEWSDKQC WEGEDLSKK |
| Linker | residues 340-345 of SEQ ID NO: 317 | GTGSEF |
| BSC1MT | residues 346-354 of SEQ ID NO: 317 | IAQAYRKLA |
| Linker | residues 355-373 of SEQ ID NO: 317 | DIGGGSGGSGGSGGAAALE |
| V5 epitope domain | residues 374-387 of SEQ ID NO: 317 | GKPIPNPLLGLDST |

Schematic diagrams of IL13Rα2TF (target protein alone), IL13Rα2TF-BSC1, and IL13Rα2TF-BSC1MT proteins are shown in FIG. 20A. Cells were transfected with vector comprising a recombinant gene encoding IL13Rα2TF (control), IL13Rα2TF-BSC1, or IL13Rα2TF-BSC1MT and grown in separate cultures as described above. Culture media from each culture was assayed for the presence of the proteins by immunoblot using an anti-V5 antibody as described above.

As shown in FIG. 20B, relatively little IL13Rα2TF protein was detected in culture medium of the control cell culture. See, lane 2 of FIG. 20B. In contrast, a significantly higher level of the IL13Rα2TF-BSC1 fusion protein was detected in culture medium of cells transfected with a vector comprising a gene encoding the IL13Rα2TF-BSC1 fusion protein. See, lane 3 of FIG. 20B. The amount of IL13Rα2TF-BSC1 fusion protein detected in the culture medium was also significantly higher than the level of protein detected in culture medium of cells transfected with a vector encoding the IL13Rα2TF-BSC1MT fusion protein. This latter protein was expressed at approximately the same low level as detected for the IL13Rα2TF protein in control cells. See, lane 4 of FIG. 20B. The results show the BSC1 polypeptide (IKKAYRKLA; SEQ ID NO:48) is effective as a protein expression enhancing polypeptide in a modified arrangement of the invention and that alteration of the internal K-K dipeptide can destroy such activity.

Example 13. BSC1-Protein A Fusion Protein Enhances Expression of IL13Rα2TF-V5-Fc Target Protein in an Unmodified Arrangement The BSC1 polypeptide (IKKAYRKLA, SEQ ID NO:48), the minimal polypeptide fragment of the J domain of Erdj3 described above, was used to construct a BSC1-Protein A fusion protein shown in the table below to determine whether the BSC1-Protein A fusion protein could be used in an unmodified arrangement for enhancing expression of an IL13Rα2TF-V5-Fc target protein described above.

TABLE 62

Amino acid Sequence of a Flag-Tagged BSC1-Protein A Fusion Protein

| Protein Domain | Sequence Identifier | Amino Acid Sequence 12345678901234567890123456789 0 |
|---|---|---|
| Flag-tagged BSC1-Protein A Fusion | SEQ ID NO: 318 | MGVKVLFALICIAVAEAGTGSGEFIKKAYR KLADIGGGSGGSGGSGGAAAADNKFNKEQQ NAFYEILNMPNLNEEQRNGFIQSLKDDPSQ SANVLGEAKKLNDSQAPKLEGDYKDDDDK |
| signal sequence | residues 1-17 of SEQ ID NO: 318 | MGVKVLFALICIAVAEA |
| linker 1 | residues 18-24 of SEQ ID NO: 318 | GTGSGEF |

TABLE 62-continued

Amino acid Sequence of a Flag-Tagged BSC1-Protein A Fusion Protein

| Protein Domain | Sequence Identifier | Amino Acid Sequence<br>12345678901234567890123456789 |
|---|---|---|
| BSC1 polypeptide | residues 25-33 of SEQ ID NO: 318 | IKKAYRKLA |
| linker 2 | residues 34-50 of SEQ ID NO: 318 | DIGGGSGGSGGSGGAAA |
| Protein A | residues 51-108 of SEQ ID NO: 318 | ADNKFNKEQQNAFYEILNMPNLNEEQRNGF<br>IQSLKDDPSQSANVLGEAKKLNDSQAPK |
| linker 3 | residues 109-111 of SEQ ID NO: 318 | LEG |
| Flag epitope tag | residues 112-119 of SEQ ID NO: 318 | DYKDDDDK |

The IL13Rα2TF-V5-Fc target protein was expressed with or without BSC1-Protein A fusion protein in HEK293 cells. Cultures were grown for two days, and the media were harvested and centrifuged to remove the debris. Expression of the IL13Rα2TF-V5-Fc target protein was significantly enhanced in the medium of cells co-expressing the target protein and the BSC1-Protein A fusion compared to level of expression of the target protein in the absence of the BSC1-Protein A fusion protein (data not shown).

To determine whether the IL13Rα2TF-V5-Fc target protein expressed in culture medium retained IL13 binding activity, the following binding assay was performed. Recombinant human IL13 was added to samples of the media from cultures of cells that did not express either of the proteins (control), that expressed only the IL13Rα2TF-V5-Fc target protein, and that co-expressed the IL13Rα2TF-V5-Fc target protein and the BSC1-Protein A fusion protein. The samples were incubated with the IL13 for 2 hours. The samples were used in an IL13 detection assay (RayBio® Human IL13 ELISA Kit; ELH-IL13-001). In this assay, the detection of human IL13 decreases when human IL13 is trapped by IL13Rα2TF-V5-Fc target protein. As shown in FIG. 21B, the medium from a culture of cells expressing neither protein clearly did not bind IL13 as indicated by the high level absorbance (lane 1 of FIG. 21). Medium from a culture of cells expressing only the IL13Rα2TF-V5-Fc target protein bound some IL13 (lane 2), but a significantly greater amount of IL13 was bound the medium from a culture of cells co-expressing the IL13Rα2TF-V5-Fc target protein and the BSC1-Protein A fusion protein (lane 3). The results clearly show that more human IL13 was bound in medium containing the enhanced level of expression of the IL13Rα2TF-V5-Fc target protein. Accordingly, the IL13Rα2TF-V5-Fc target protein expressed in culture medium at an enhanced level retained its IL13 binding activity.

Example 14. BSC1-Protein G Fusion Protein Enhances Expression of a Factor VII-V5-Fc Target Protein in an Unmodified Arrangement Factor VII (FVII) is the serine esterase of the extrinsic coagulation pathway and widely used to treat a variety of bleeding complications. See, Hedner, *Semin. Hematol.*, 43(suppl 1): S105-S107 (2006). A complex of FVII and tissue factor (TF) in the presence of phospholipids and calcium activates Factor X to Factor Xa.

A BSC1 polypeptide was used to construct a BSC1-Protein G fusion protein to determine whether the fusion protein was effective in enhancing an FVII-V5-Fc target protein in an unmodified arrangement.

The amino acid sequence of the V5-tagged FVII-Fc target protein is shown in the table below.

TABLE 63

Amino Acid Sequence of a V5-Tagged FVII-Fc Target Protein.

| Protein Region (N- to C- terminal) | Sequence Identifier | Amino Acid Sequence<br>12345678901234567890123456789 |
|---|---|---|
| V5-tagged FVII-Fc target protein | SEQ ID NO: 319 | MVSQALRLLCLLLGLQGCLAAGGVAKASGG<br>ETRDMPWKPGPHRVFVTQEEAHGVLHRRRR<br>ANAFLEELRPGSLERECKEEQCSFEEAREI<br>FKDAERTKLFWISYSDGDQCASSPCQNGGS<br>CKDQLQSYICFCLPAFEGRNCETHKDDQLI<br>CVNENGGCEQYCSDHTGTKRSCRCHEGYSL<br>LADGVSCTPTVEYPCGKIPILEKRNASKPQ<br>GRIVGGKVCPKGECPWQVLLLVNGAQLCGG<br>TLINTIWVVSAAHCFDKIKNWRNLIAVLGE<br>HDLSEHDGDEQSRRVAQVIIPSTYVPGTTN |

TABLE 63-continued

Amino Acid Sequence of a V5-Tagged FVII-Fc Target Protein.

| Protein Region (N- to C-terminal) | Sequence Identifier | Amino Acid Sequence 123456789012345678901234567890 |
|---|---|---|
| | | HDIALLRLHQPVVLTDHVVPLCLPERTFSE RTLAFVRFSLVSGWGQLLDRGATALELMVL NVPRLMTQDCLQQSRKVGDSPNITEYMFCA GYSDGSKDSCKGDSGGPHATHYRGTWYLTG IVSWGQGCATVGHFGVYTRVSQYIEWLQKL MRSEPRPGVLLRAPFPLEGKPIPNPLLGLD STSRPKSCDKTHTCPPCPAPELLGGPSVFL FPPKPKDTLMISRTPEVTCVVVDVSHEDPE VKFNWYVDGVEVHNAKTKPREEQYNSTYRV VSVLTVLHQDWLNGKEYKCKVSNKALPAPI EKTISKAKGQPREPQVYTLPPSRDELTKNQ VSLTCLVKGFYPSDIAVEWESNGQPENNYK TTPPVLDSDGSFFLYSKLTVDKSRWQQGNV FSCSVMHEALHNHYTQKSLSLSPGK |
| FVII | residues 1-466 of SEQ ID NO: 319 | MVSQALRLLCLLLGLQGCLAAGGVAKASGG ETRDMPWKPGPHRVFVTQEEAHGVLHRRRR ANAFLEELRPGSLERECKEEQCSFEEAREI FKDAERTKLFWISYSDGDQCASSPCQNGGS CKDQLQSYICFCLPAFEGRNCETHKDDQLI CVNENGGCEQYCSDHTGTKRSCRCHEGYSL LADGVSCTPTVEYPCGKIPILEKRNASKPQ GRIVGGKVCPKGECPWQVLLLVNGAQLCGG TLINTIWVVSAAHCFDKIKNWRNLIAVLGE HDLSEHDGDEQSRRVAQVIIPSTYVPGTTN HDIALLRLHQPVVLTDHVVPLCLPERTFSE RTLAFVRFSLVSGWGQLLDRGATALELMVL NVPRLMTQDCLQQSRKVGDSPNITEYMFCA GYSDGSKDSCKGDSGGPHATHYRGTWYLTG IVSWGQGCATVGHFGVYTRVSQYIEWLQKL MRSEPRPGVLLRAPFP |
| Linker 1 | residues 467-468 of SEQ ID NO: 319 | LE |
| V5 epitope domain | residues 469-482 of SEQ ID NO: 319 | GKPIPNPLLGLDST |
| Linker 2 | residues 483-484 of SEQ ID NO: 319 | SR |
| Fc domain | residues 485-715 of SEQ ID NO: 319 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

The amino acid sequence of the Flag-tagged BSC1-Protein G fusion protein is shown in the table below.

TABLE 64

Amino Acid Sequence of a Flag-Tagged BSC1-Protein G Fusion Protein

| Protein Domain | Sequence Identifier | Amino Acid Sequence 123456789012345678901234567890 |
|---|---|---|
| Flag-tagged BSC1-Protein G Fusion | SEQ ID NO: 320 | MGVKVLFALICIAVAEAGTGSGEFIKKAYR KLADIGGGSGGSGGSGGAAAATYKLVINGK TLKGETTTEAVDAATAEKVFKQYANDNGVD GEWTYDDATKTFTVTEKPEVIDASELTPAV TLEGDYKDDDDK |

TABLE 64-continued

Amino Acid Sequence of a Flag-Tagged BSC1-Protein G Fusion Protein

| Protein Domain | Sequence Identifier | Amino Acid Sequence 12345678901234567890123456 7890 |
|---|---|---|
| signal sequence | residues 1-17 of SEQ ID NO: 320 | MGVKVLFALICIAVAEA |
| linker 1 | residues 18-24 of SEQ ID NO: 320 | GTGSGEF |
| BSC1 polypeptide | residues 25-33 of SEQ ID NO: 320 | IKKAYRKLA |
| linker 2 | residues 34-50 of SEQ ID NO: 320 | DIGGGSGGSGGSGGAAA |
| Protein G | residues 51-121 of SEQ ID NO: 320 | TYKLVINGKTLKGETTTEAVDAATAEKVFK QYANDNGVDGEWTYDDATKTFTVTEKPEVI DASELTPAVT |
| linker 3 | residues 122-124 of SEQ ID NO: 320 | LEG |
| Flag epitope tag | residues 126-132 of SEQ ID NO: 320 | DYKDDDDK |

The level of expression of the FVII-Fc target protein was determined by immunoblot assay using anti-Flag antibody in both culture media and lysates of cells expressing neither protein, of cells expressing only the FVII-Fc target protein, and of cells co-expressing the FVII-Fc target protein and the BSC1-Protein G fusion proteins. The results are shown in FIG. 22A. As shown in the top panel of FIG. 22A, the level of expression of the FVII-Fc target protein secreted into the culture medium was significantly greater in a culture of cells co-expressing the FVII-Fc target protein and the BSC1-Protein G fusion protein (lane 2) than in a culture of cells expressing the FVII-Fc target protein alone (lane 3). The middle panel of FIG. 22A is an immunoblot of cell lysates using an anti-Flag antibody. The immunoblot shows that the BSC1-Protein G fusion protein was expressed in cells expressing both the FVII-Fc target protein and the BSC1-Protein G fusion protein. As shown in the bottom panel of FIG. 22A, no significant amount of the BSC1-Protein G fusion protein was secreted into the medium with the FVII-Fc target protein (see, lane 3).

FIG. 22B shows bar graphs of a densitometry analysis of the signal of the for FVII-Fc target protein expression in culture media shown in the top immunoblot in FIG. 22A. Bar graphs 1, 2, and 3 of FIG. 22B correspond to the signals of lanes 1, 2, and 3 in the top immunoblot in FIG. 22A.

The results show that the co-expression of the BSC1-Protein G fusion protein and the FVII-Fc target protein significantly enhanced the level of expression of the target protein secreted into culture medium as compared to the level in that absence of the BSC1-Protein G fusion protein.

Example 15. BSC1-Protein a Fusion Protein Enhances Expression of a Factor IX-V5-Fc Target Protein in an Unmodified Arrangement Factor IX has been widely used for the treatment of hemophilia B, and its Fc fusion protein (FIX-Fc) is currently in a clinical trial (phase III) with positive result (prolonged effect).

In this experiment, the effect of the BSC1-Protein A fusion protein described above on the level of expression of an FIX-Fc target protein in an unmodified arrangement was determined The amino acid sequence of the V5-tagged FIX-Fc target protein is shown in the table below.

TABLE 65

Amino Acid Sequence of a V5-Tagged FIX-Fc Target Protein.

| Protein Region (N- to C-terminal) | Sequence Identifier | Amino Acid Sequence 12345678901234567890123456 7890 |
|---|---|---|
| V5-tagged FIX-Fc fusion molecule | SEQ ID NO: 321 | MQRVNMIMAESPGLITICLLGYLLSAECTV FLDHENANKILNRPKRYNSGKLEEFVQGNL ERECMEEKCSFEEAREVFENTERTTEFWKQ YVDGDQCESNPCLNGGSCKDDINSYECWCP FGFEGKNCELDVTCNIKNGRCEQFCKNSAD NKVVCSCTEGYRLAENQKSCEPAVPFPCGR |

TABLE 65-continued

Amino Acid Sequence of a V5-Tagged FIX-Fc Target Protein.

| Protein Region (N- to C-terminal) | Sequence Identifier | Amino Acid Sequence 12345678901234567890123456789 0 |
|---|---|---|
| | | VSVSQTSKLTRAETVFPDVDYVNSTEAETI LDNITQSTQSFNDFTRVVGGEDAKPGQFPW QVVLNGKVDAFCGGSIVNEKWIVTAAHCVE TGVKITVVAGEHNIEETEHTEQKRNVIRII PHHNYNAAINKYNHDIALLELDEPLVLNSY VTPICIADKEYTNIFLKFGSGYVSGWGRVF HKGRSALVLQYLRVPLVDRATCLRSTKFTI YNNMFCAGFHEGGRDSCQGDSGGPHVTEVE GTSFLTGIISWGEECAMKGKYGIYTKVSRY VNWIKEKTKLTLEGKPIPNPLLGLDSTSRP KSCDKTHTCPPCPAPELLGGPSVFLFPPKP KDTLMISRTPEVTCVVVDVSHEDPEVKFNW YVDGVEVHNAKTKPREEQYNSTYRVVSVLT VLHQDWLNGKEYKCKVSNKALPAPIEKTIS KAKGQPREPQVYTLPPSRDELTKNQVSLTC LVKGFYPSDIAVEWESNGQPENNYKTTPPV LDSDGSFFLYSKLTVDKSRWQQGNVFSCSV MHEALHNHYTQKSLSLSPGK |
| FIX | residues 1-461 of SEQ ID NO: 321 | MQRVNMIMAESPGLITICLLGYLLSAECTV FLDHENANKILNRPKRYNSGKLEEFVQGNL ERECMEEKCSFEEAREVFENTERTTEFWKQ YVDGDQCESNPCLNGGSCKDDINSYECWCP FGFEGKNCELDVTCNIKNGRCEQFCKNSAD NKVVCSCTEGYRLAENQKSCEPAVPFPCGR VSVSQTSKLTRAETVFPDVDYVNSTEAETI LDNITQSTQSFNDFTRVVGGEDAKPGQFPW QVVLNGKVDAFCGGSIVNEKWIVTAAHCVE TGVKITVVAGEHNIEETEHTEQKRNVIRII PHHNYNAAINKYNHDIALLELDEPLVLNSY VTPICIADKEYTNIFLKFGSGYVSGWGRVF HKGRSALVLQYLRVPLVDRATCLRSTKFTI YNNMFCAGFHEGGRDSCQGDSGGPHVTEVE GTSFLTGIISWGEECAMKGKYGIYTKVSRY VNWIKEKTKLT |
| Linker 1 | residues 462-463 of SEQ ID NO: 321 | LE |
| V5 epitope domain | residues 464-477 of SEQ ID NO: 321 | GKPIPNPLLGLDST |
| Linker 2 | residues 478-479 of SEQ ID NO: 321 | SR |
| Fc domain | residues 480-710 of SEQ ID NO: 321 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

FIG. 23A shows the expression of the FIX-Fc target protein secreted into the media of cultures of transfected cells expressing the FIX-Fc target protein alone (lane 2) and of transfected cells co-expressing the FIX-Fc fusion protein and the BSC1-Protein A fusion protein (lane 3). Lane 1 of FIG. 23A shows medium from a culture of non-expressing cells as a control. As shown in lane 2 of FIG. 23A, some FIX-Fc target protein is secreted by cells expressing the FIX-Fc target protein alone. However, as clearly shown in lane 3 of FIG. 23A, the level of expression of the target protein secreted into medium is significantly enhanced in cells expressing the FIX-Fc target protein and the BSC1-Protein A fusion protein. FIG. 23B shows bar graphs of a densitometry analysis of the signals in the immunoblot of FIG. 23A. Bar graphs 1, 2, and 3 of FIG. 23B correspond to the signals of lanes 1, 2, and 3 in FIG. 23A.

The results clearly show that the co-expression of the BSC1-Protein A fusion protein and the FIX-Fc target protein significantly enhanced the level of expression of the target protein secreted into culture medium as compared to the level in that absence of the BSC1-Protein A fusion protein.

Example 16. BSC1-Protein G Fusion Protein Enhances Expression of a Factor VIII-V5-Fc Target Protein in an Unmodified Arrangement The biological importance of Factor FVIII is demonstrated in hemophilia A, a congenital bleeding disorder occurring primarily in males that results from an X-chromosome-linked deficiency of FVIII. Standard treatment involves replacing the missing FVIII to stop the bleeding. A FVIII-Fc fusion protein was developed to provide a prolonged half-life of FVIII activity in hemophilia A patients (Powell et al., *Blood*, 119(13): 3031-3037 (2012)). The fusion protein was approved by the United States Food and Drug Administration in 2013 (ELOCTATE™; Biogen Idec).

This experiment examined the effect of the BSC1-Protein G fusion protein described above on the level of expression of a V5-tagged FVIII-Fc target protein in an unmodified arrangement. The amino acid sequence of the V5-tagged FVIII-Fc target protein is shown in the table below.

TABLE 66

Amino Acid Sequence of a V5-Tagged FVIII-Fc Target Protein.

| Protein Region (N- to C-terminal) | Sequence Identifier | Amino Acid Sequence 12345678901234567890123456789 0 |
|---|---|---|
| V5-tagged FVIII-Fc fusion molecule | SEQ ID NO: 322 | MQIELSTCFFLCLLRFCFSATRRYYLGAVE LSWDYMQSDLGELPVDARFPPRVPKSFPFN TSVVYKKTLFVEFTDHLFNIAKPRPPWMGL LGPTIQAEVYDTVVITLKNMASHPVSLHAV GVSYWKASEGAEYDDQTSQREKEDDKVFPG GSHTYVWQVLKENGPMASDPLCLTYSYLSH VDLVKDLNSGLIGALLVCREGSLAKEKTQT LHKFILLFAVFDEGKSWHSETKNSLMQDRD AASARAWPKMHTVNGYVNRSLPGLIGCHRK SVYWHVIGMGTTPEVHSIFLEGHTFLVRNH RQASLEISPITFLTAQTLLMDLGQFLLFCH ISSHQHDGMEAYVKVDSCPEEPQLRMKNNE EAEDYDDDLTDSEMDVVRFDDDNSPSFIQI RSVAKKHPKTWVHYIAAEEEDWDYAPLVLA PDDRSYKSQYLNNGPQRIGRKYKKVRFMAY TDETFKTREAIQHESGILGPLLYGEVGDTL LIIFKNQASRPYNIYPHGITDVRPLYSRRL PKGVKHLKDFPILPGEIFKYKWTVTVEDGP TKSDPRCLTRYYSSFVNMERDLASGLIGPL LICYKESVDQRGNQIMSDKRNVILFSVFDE NRSWYLTENIQRFLPNPAGVQLEDPEFQAS NIMHSINGYVFDSLQLSVCLHEVAYWYILS IGAQTDFLSVFFSGYTFKHKMVYEDTLTLF PFSGETVFMSMENPGLWILGCHNSDFRNRG MTALLKVSSCDKNTGDYYEDSYEDISAYLL SKNNAIEPRSFSQNSRHPSTRQKQFNATTI PENDIEKTDPWFAHRTPMPKIQNVSSSDLL MLLRQSPTPHGLSLSDLQEAKYETFSDDPS PGAIDSNNSLSEMTHFRPQLHHSGDMVFTP ESGLQLRLNEKLGTTAATELKKLDFKVSST SNNLISTIPSDNLAAGTDNTSSLGPPSMPV HYDSQLDTTLFGKKSSPLTESGGPLSLSEE NNDSKLLESGLMNSQESSWGKNVSSTESGR LFKGKRAHGPALLTKDNALFKVSISLLKTN KTSNNSATNRKTHIDGPSLLIENSPSVWQN ILESDTEFKKVTPLIHDRMLMDKNATALRL NHMSNKTTSSKNMEMVQQKKEGPIPPDAQN PDMSFFKMLFLPESARWIQRTHGKNSLNSG QGPSPKQLVSLGPEKSVEGQNFLSEKNKVV VGKGEFTKDVGLKEMVFPSSRNLFLTNLDN LHENNTHNQEKKIQEEIEKKETLIQENVVL PQIHTVTGTKNFMKNLFLLSTRQNVEGSYD GAYAPVLQDFRSLNDSTNRTKKHTAHFSKK GEEENLEGLGNQTKQIVEKYACTTRISPNT SQQNFVTQRSKRALKQFRLPLEETELEKRI IVDDTSTQWSKNMKHLTPSTLTQIDYNEKE KGAITQSPLSDCLTRSHSIPQANRSPLPIA KVSSFPSIRPIYLTRVLFQDNSSHLPAASY RKKDSGVQESSHFLQGAKKNNLSLAILTLE MTGDQREVGSLGTSATNSVTYKKVENTVLP KPDLPKTSGKVELLPKVHIYQKDLFPTETS NGSPGHLDLVEGSLLQGTEGAIKWNEANRP GKVPFLRVATESSAKTPSKLLDPLAWDNHY GTQIPKEEWKSQEKSPEKTAFKKKDTILSL NACESNHAIAAINEGQNKPEIEVTWAKQGR TERLCSQNPPVLKRHQREITRTTLQSDQEE IDYDDTISVEMKKEDFDIYDEDENQSPRSF QKKTRHYFIAAVERLWDYGMSSSPHVLRNR AQSGSVPQFKKVVFQEFTDGSFTQPLYRGE LNEHLGLLGPYIRAEVEDNIMVTFRNQASR PYSFYSSLISYEEDQRQGAEPRKNFVKPNE |

TABLE 66-continued

Amino Acid Sequence of a V5-Tagged FVIII-Fc Target Protein.

| Protein Region (N- to C-terminal) | Sequence Identifier | Amino Acid Sequence<br>12345678901234567890123456 7890 |
|---|---|---|
| | | TKTYFWKVQHHMAPTKDEFDCKAWAYFSDV<br>DLEKDVHSGLIGPLLVCHTNTLNPAHGRQV<br>TVQEFALFFTIFDETKSWYFTENMERNCRA<br>PCNIQMEDPTFKENYRFHAINGYIMDTLPG<br>LVMAQDQRIRWYLLSMGSNENIHSIHFSGH<br>VFTVRKKEEYKMALYNLYPGVFETVEMLPS<br>KAGIWRVECLIGEHLHAGMSTLFLVYSNKC<br>QTPLGMASGHIRDFQITASGQYGQWAPKLA<br>RLHYSGSINAWSTKEPFSWIKVDLLAPMII<br>HGIKTQGARQKFSSLYISQFIIMYSLDGKK<br>WQTYRGNSTGTLMVFFGNVDSSGIKHNIFN<br>PPIIARYIRLHPTHYSIRSTLRMELMGCDL<br>NSCSMPLGMESKAISDAQITASSYFTNMFA<br>TWSPSKARLHLQGRSNAWRPQVNNPKEWLQ<br>VDFQKTMKVTGVTTQGVKSLLTSMYVKEFL<br>ISSSQDGHQWTLFFQNGKVKVFQGNQDSFT<br>PVVNSLDPPLLTRYLRIHPQSWVHQIALRM<br>EVLGCEAQDLYLEGKPIPNPLLGLDSTSRP<br>KSCDKTHTCPPCPAPELLGGPSVFLFPPKP<br>KDTLMISRTPEVTCVVVDVSHEDPEVKFNW<br>YVDGVEVHNAKTKPREEQYNSTYRVVSVLT<br>VLHQDWLNGKEYKCKVSNKALPAPIEKTIS<br>KAKGQPREPQVYTLPPSRDELTKNQVSLTC<br>LVKGFYPSDIAVEWESNGQPENNYKTTPPV<br>LDSDGSFFLYSKLTVDKSRWQQGNVFSCSV<br>MHEALHNHYTQKSLSLSPGK |
| FVIII | residues 1-2351 of SEQ ID NO: 322 | MQIELSTCFFLCLLRFCFSATRRYYLGAVE<br>LSWDYMQSDLGELPVDARFPPRVPKSFPFN<br>TSVVYKKTLFVEFTDHLFNIAKPRPPWMGL<br>LGPTIQAEVYDTVVITLKNMASHPVSLHAV<br>GVSYWKASEGAEYDDQTSQREKEDDKVFPG<br>GSHTYVWQVLKENGPMASDPLCLTYSYLSH<br>VDLVKDLNSGLIGALLVCREGSLAKEKTQT<br>LHKFILLFAVFDEGKSWHSETKNSLMQDRD<br>AASARAWPKMHTVNGYVNRSLPGLIGCHRK<br>SVYWHVIGMGTTPEVHSIFLEGHTFLVRNH<br>RQASLEISPITFLTAQTLLMDLGQFLLFCH<br>ISSHQHDGMEAYVKVDSCPEEPQLRMKNNE<br>EAEDYDDDLTDSEMDVVRFDDDNSPSFIQI<br>RSVAKKHPKTWVHYIAAEEEDWDYAPLVLA<br>PDDRSYKSQYLNNGPQRIGRKYKKVRFMAY<br>TDETFKTREAIQHESGILGPLLYGEVGDTL<br>LIIFKNQASRPYNIYPHGITDVRPLYSRRL<br>PKGVKHLKDFPILPGEIFKYKWTVTVEDGP<br>TKSDPRCLTRYYSSFVNMERDLASGLIGPL<br>LICYKESVDQRGNQIMSDKRNVILFSVFDE<br>NRSWYLTENIQRFLPNPAGVQLEDPEFQAS<br>NIMHSINGYVFDSLQLSVCLHEVAYWYILS<br>IGAQTDFLSVFFSGYTFKHKMVYEDTLTLF<br>PFSGETVFMSMENPGLWILGCHNSDFRNRG<br>MTALLKVSSCDKNTGDYYEDSYEDISAYLL<br>SKNNAIEPRSFSQNSRHPSTRQKQFNATTI<br>PENDIEKTDPWFAHRTPMPKIQNVSSSDLL<br>MLLRQSPTPHGLSLSDLQEAKYETFSDDPS<br>PGAIDSNNSLSEMTHFRPQLHHSGDMVFTP<br>ESGLQLRLNEKLGTTAATELKKLDFKVSST<br>SNNLISTIPSDNLAAGTDNTSSLGPPSMPV<br>HYDSQLDTTLFGKKSSPLTESGGPLSLSEE<br>NNDSKLLESGLMNSQESSWGKNVSSTESGR<br>LFKGKRAHGPALLTKDNALFKVSISLLKTN<br>KTSNNSATNRKTHIDGPSLLIENSPSVWQN<br>ILESDTEFKKVTPLIHDRMLMDKNATALRL<br>NHMSNKTTSSKNMEMVQQKKEGPIPPDAQN<br>PDMSFFKMLFLPESARWIQRTHGKNSLNSG<br>QGPSPKQLVSLGPEKSVEGQNFLSEKNKVV<br>VGKGEFTKDVGLKEMVFPSSRNLFLTNLDN<br>LHENNTHNQEKKIQEEIEKKETLIQENVVL<br>PQIHTVTGTKNFMKNLFLLSTRQNVEGSYD<br>GAYAPVLQDFRSLNDSTNRTKKHTAHFSKK<br>GEEENLEGLGNQTKQIVEKYACTTRISPNT<br>SQQNFVTQRSKRALKQFRLPLEETELEKRI<br>IVDDTSTQWSKNMKHLTPSTLTQIDYNEKE<br>KGAITQSPLSDCLTRSHSIPQANRSPLPIA |

TABLE 66-continued

Amino Acid Sequence of a V5-Tagged FVIII-Fc Target Protein.

| Protein Region (N- to C-terminal) | Sequence Identifier | Amino Acid Sequence 12345678901234567890123456 7890 |
|---|---|---|
| | | KVSSFPSIRPIYLTRVLFQDNSSHLPAASY RKKDSGVQESSHFLQGAKKNNLSLAILTLE MTGDQREVGSLGTSATNSVTYKKVENTVLP KPDLPKTSGKVELLPKVHIYQKDLFPTETS NGSPGHLDLVEGSLLQGTEGAIKWNEANRP GKVPFLRVATESSAKTPSKLLDPLAWDNHY GTQIPKEEWKSQEKSPEKTAFKKKDTILSL NACESNHAIAAINEGQNKPEIEVTWAKQGR TERLCSQNPPVLKRHQREITRTTLQSDQEE IDYDDTISVEMKKEDFDIYDEDENQSPRSF QKKTRHYFIAAVERLWDYGMSSSPHVLRNR AQSGSVPQFKKVVFQEFTDGSFTQPLYRGE LNEHLGLLGPYIRAEVEDNIMVTFRNQASR PYSFYSSLISYEEDQRQGAEPRKNFVKPNE TKTYFWKVQHHMAPTKDEFDCKAWAYFSDV DLEKDVHSGLIGPLLVCHTNTLNPAHGRQV TVQEFALFFTIFDETKSWYFTENMERNCRA PCNIQMEDPTFKENYRFHAINGYIMDTLPG LVMAQDQRIRWYLLSMGSNENIHSIHFSGH VFTVRKKEEYKMALYNLYPGVFETVEMLPS KAGIWRVECLIGEHLHAGMSTLFLVYSNKC QTPLGMASGHIRDFQITASGQYGQWAPKLA RLHYSGSINAWSTKEPFSWIKVDLLAPMII HGIKTQGARQKFSSLYISQFIIMYSLDGKK WQTYRGNSTGTLMVFFGNVDSSGIKHNIFN PPIIARYIRLHPTHYSIRSTLRMELMGCDL NSCSMPLGMESKAISDAQITASSYFTNMFA TWSPSKARLHLQGRSNAWRPQVNNPKEWLQ VDFQKTMKVTGVTTQGVKSLLTSMYVKEFL ISSSQDGHQWTLFFQNGKVKVFQGNQDSFT PVVNSLDPPLLTRYLRIHPQSWVHQIALRM EVLGCEAQDLY |
| Linker | residues 2352-2353 of SEQ ID NO: 322 | LE |
| V5 epitope domain | residues 2354-2367 of SEQ ID NO: 322 | GKPIPNPLLGLDST |
| Linker | residues 2368-2369 of SEQ ID NO: 322 | SR |
| Fc domain | residues 2370-2600 of SEQ ID NO: 322 | PKSCDKTHTCPPCPAPELLGGPSVFLFPPK PKDTLMISRTPEVTCVVVDVSHEDPEVKFN WYVDGVEVHNAKTKPREEQYNSTYRVVSVL TVLHQDWLNGKEYKCKVSNKALPAPIEKTI SKAKGQPREPQVYTLPPSRDELTKNQVSLT CLVKGFYPSDIAVEWESNGQPENNYKTTPP VLDSDGSFFLYSKLTVDKSRWQQGNVFSCS VMHEALHNHYTQKSLSLSPGK |

In this experiment, the level of expression of the FVIII-Fc target protein in the presence and absence of the BSC1-Protein G fusion protein. Media from cultures of cells (HEK293) expressing neither protein, of cells expressing only the FVIII-Fc target protein, and of cells co-expressing the BSC1-Protein G fusion protein and the FVIII-Fc target protein was assayed for FVIII using a commercially available, enzyme-linked immunosorbent assay (ELISA) (Visulize™ FVIII Antigen Kit, Affinity Biologics Inc.). The results are shown as bar graphs of Absorbance at 450 nm in FIG. 24. Culture medium from cells transfected with an empty vector and expressing neither protein was used for a negative control (first bar graph from left in FIG. 24), and human serum was used as a positive control (last bar graph on right of FIG. 24). The results show that co-expression of the BSC1-Protein G fusion protein with the FVIII-Fc target protein significantly enhanced the level of expression of the FVIII-Fc target protein secreted into the culture medium (third bar graph from left in FIG. 24) as compared to the level of expression of the target protein in the absence of the BSC1-Protein G fusion protein (second bar graph from left in FIG. 24).

Example 17. BSC1-Protein a Fusion Protein Enhances Expression of an Anti-IL-8 Antibody Target Protein in an Unmodified Arrangement This experiment examined whether a BSC1-Protein A fusion protein as described above could be used in an unmodified arrangement to improve the level of expression of an anti-IL-8 antibody target protein expressed in transfected HEK293 cells.

Expression of anti-IL-8 antibody in culture media was determined by immunodot blot using an anti-IgG antibody. As shown in the immunodot blots in FIG. 25A, co-expression of the anti-IL8 antibody target protein with the BSC1-Protein A fusion protein significantly enhanced the level of expression of the antibody secreted into the culture medium (bottom row 3 of FIG. 25A) as compared to the level of the antibody expressed in cells expressing the antibody alone (middle row 2 of FIG. 25A). The top row of FIG. 25A shows no antibody was secreted into medium from a mock culture of control cells that expressed neither protein.

The results of a densitometry analysis of the chemiluminescent signals in the dot blots in the rows in FIG. 25A using the NIH ImageJ image processing program are shown in the respective bar graphs in FIG. 25B. The bars of FIG. 25B are numbered to correspond to the row numbers of FIG. 25A. The results of this series of experiments clearly show that co-expression of the anti-IL8 antibody target protein with a fusion protein of the invention comprising the BSC1 polypeptide linked to a Protein A (target protein binding domain) significantly enhanced the expression of secreted anti-IL8 antibody.

FIG. 25C shows the results of an ELISA assay. A 96-well plate was coated with recombinant purified human IL8, and incubated with the anti-IL-8 antibody (target protein) secreted into the media of cultures of transfected cells expressing the anti-IL8 antibody alone (lane 2) and of cells co-expressing anti-IL8 antibody target protein and the BSC1-Protein A fusion protein (lane 3, BSC1-Protein A). Mock cultures contained cells transfected with expression vector lacking a structural gene for expressing any protein (no anti-IL8 antibody, first lane). The results clearly show that the secreted anti-IL8 antibody that was expressed at enhanced levels when co-expressed with BSC1-Protein A fusion protein retained its binding activity for human IL8.

Example 18. BSC1-Protein A Fusion Protein Enhances Expression of a Therapeutic Anti-VEGF Antibody (Bevacizumab) Target Protein in an Unmodified Arrangement This experiment examined whether a BSC1-Protein A fusion protein as described above could be used in an unmodified arrangement to improve the level of expression of a therapeutic antibody.

Bevacizumab (Avastin®, Genentech/Roche) is a humanized monoclonal antibody that inhibits angiogenesis by inhibiting vascular endothelial growth factor A (VEGF-A). Sales of bevacizumab in 2010 were close to $7 billion and exceeded all other antibody drugs. The addition of bevacizumab to standard treatment can prolong the lives of breast and lung cancer patients by several months at a current cost of approximately $100,000 a year in the United States.

The amino acid sequences for the light and heavy chains of bevacizumab are shown in the table below.

TABLE 67

Amino Acid Sequences Light and Heavy Chains of Bevacizumab.

| Protein Region (N- to C-terminal) | Sequence Identifier | Amino Acid Sequence 12345678901234567890123456789 0 |
|---|---|---|
| Light chain | SEQ ID NO: 323 | MGWSCIILFLVATATGVHSDIQMTQSPSSL SASVGDRVTITCSASQDISNYLNWYQQKPG KAPKVLIYFTSSLHSGVPSRFSGSGSGTDF TLTISSLQPEDFATYYCQQYSTVPWTFGQG TKVEIKRTVAAPSVFIFPPSDEQLKSGTAS VVCLLNNFYPREAKVQWKVDNALQSGNSQE SVTEQDSKDSTYSLSSTLTLSKADYEKHKV YACEVTHQGLSSPVTKSFNRGEC |
| Heavy chain | SEQ ID NO: 327 | MGWSLIILFLVATATGVHSEVQLVESGGGL VQPGGSLRLSCAASGYTFTNYGMNWVRQAP GKGLEWVGWINTYTGEPTYAADFKRRFTFS LDTSKSTAYLQMNSLRAEDTAVYYCAKYPH YYGSSHWYFDVWGQGTLVTVSSASTKGPSV FPLAPSSKSTSGGTAALGCLVKDYFPEPVT VSWNSGALTSGVHTFPAVLQSSGLYSLSSV VTVPSSSLGTQTYICNVNHKPSNTKVDKKV EPKSCDKTHTCPPCPAPELLGGPSVFLFPP KPKDTLMISRTPEVTCVVVDVSHEDPEVKF NWYVDGVEVHNAKTKPREEQYNSTYRVVSV LTVLHQDWLNGKEYKCKVSNKALPAPIEKT ISKAKGQPREPQVYTLPPSRDELTKNQVSL TCLVKGFYPSDIAVEWESNGQPENNYKTTP PVLDSDGSFFLYSKLTVDKSRWQQGNVFSC SVMHEALHNHYTQKSLSLSPGK |

The anti-VEGF antibody bevacizumab (target protein) was expressed in human cells in the presence and absence of the BSC1-Protein A fusion protein. A mock culture contained cells that expressed neither protein. Samples of the media from cell cultures were assayed for antibody by immunodot blot assay using an anti-human IgG antibody.

FIG. 26A shows a dot blot assay for expression of the bevacizumab (anti-VEGF antibody) secreted into the media of cultures of transfected cells expressing bevacizumab alone (middle row) and co-expressing bevacizumab and the BSC1-Protein A fusion protein (bottom row). The top row of FIG. 26A shows that no antibody was secreted into medium from a mock culture of control cells that lacked a structural gene for either protein. The results show that co-expression in transfected cells of the bevacizumab target protein and the BSC1-Protein A fusion protein significantly enhanced the level of expression of bevacizumab secreted into the culture medium as compared to the level of the antibody secreted into medium of a culture of cells expressing bevacizumab alone.

FIG. 26B shows the results of a densitometry analysis of the chemiluminescent signals in each of the rows of the dot blot in FIG. 26A using the NIH ImageJ image processing program. The bar graphs of FIG. 26B are numbered to correspond to the row numbers of FIG. 26A. The results of this series of experiments clearly show that co-expression of the anti-VEGF antibody target protein with a BSC1-Protein A fusion protein significantly enhanced the level of expression of the anti-VEGF antibody secreted into the culture medium.

FIG. 26C shows the results of an ELISA to detect VEGF binding activity in culture media. A 96-well plate was coated with recombinant purified human VEGF-A and incubated with the bevacizumab (anti-VEGF antibody target protein) secreted into the media of cultures of transfected cells that expressed the anti-VEGF antibody alone (bar graph 2) or of transfected cells that co-expressed the anti-VEGF antibody and the BSC1-Protein A fusion protein (bar graph 3). Bar graph 1 of FIG. 26C shows that no significant VEGF binding activity was present in medium from a mock culture of cells transfected with expression vector lacking a structural gene for expressing either protein. The results clearly show that the secreted anti-VEGF antibody that was expressed at enhanced levels when co-expressed with the BSC1-Protein A fusion protein retained its binding activity for human VEGF-A.

Example 19. BSC1-Protein A Fusion Protein Enhances Expression of a Therapeutic Anti-TNFα Antibody (Adalimumab) Target Protein in an Unmodified Arrangement This experiment examined whether a BSC1-Protein A fusion protein as described above could be used in an unmodified arrangement to improve the level of expression of a therapeutic anti-TNFα antibody (adalimumab; Humira®, AbbVie).

TABLE 68

Amino Acid Sequences of Light and Heavy Chains of Adalimumab.

| Protein Region (N- to C-terminal) | Sequence Identifier | Amino Acid Sequence 12345678901234567890123456 7890 |
|---|---|---|
| Light chain | SEQ ID NO: 324 | MGWSCIILFLVATATGVHSDIQMTQSPSSL SASVGDRVTITCRSSQGIRNYLHWYQQKPG KAPKLLIYAASTLQSGVPSRFSGSGSGTDF TLTISSLQPEDVATYYCQRYNRAPYTFGQG TKVEIKRTVAAPSVFIFPPSDEQLKSGTAS VVCLLNNFYPREAKVQWKVDNALQSGNSQE SVTEQDSKDSTYSLSSTLTLSKADYEKHKV YACEVTHQGLSSPVTKSFNRGEC |
| Heavy chain | SEQ ID NO: 328 | MGWSLIILFLVATATGVHSEVQLVESGGGL VQPGRSLRLSCAASGFTFDDYAMHWVRQAP GKGLEWVSAITWNSGHIDYADSVEGRFTIS RDNAKNSLYLQMNSLRAEDTAVYYCAKVSY LSTASSLDVWGQGTLVTVSSASTKGPSVFP LAPSSKSTSGGTAALGCLVKDYFPEPVTVS WNSGALTSGVHTFPAVLQSSGLYSLSSVVT VPSSSLGTQTYICNVNHKPSNTKVDKKVEP KSCDKTHTCPPCPAPELLGGPSVFLFPPKP KDTLMISRTPEVTCVVVDVSHEDPEVKFNW YVDGVEVHNAKTKPREEQYNSTYRVVSVLT VLHQDWLNGKEYKCKVSNKALPAPIEKTIS KAKGQPREPQVYTLPPSRDELTKNQVSLTC LVKGFYPSDIAVEWESNGQPENNYKTTPPV LDSDGSFFLYSKLTVDKSRWQQGNVFSCSV MHEALHNHYTQKSLSLSPGK |

FIG. 27A shows a dot blot assay for expression of the anti-TNFα antibody (target protein) secreted into the media of cultures of transfected cells expressing the anti-TNFα antibody alone (middle row) and of transfected cells co-expressing the anti-TNFα antibody and the BSC1-Protein A fusion protein (bottom row of FIG. 27A). No anti-TNFα antibody was detected in medium of mock cultures containing cells transfected with expression vector lacking a structural gene for expressing either protein (top row of FIG. 27A). Expression of the anti-TNFα antibody in culture media was analyzed in the dot blot assay using an anti-human IgG antibody. It can be seen that co-expression in transfected cells of the anti-TNFα antibody and the BSC1-Protein A fusion protein (bottom row) significantly enhanced the level of expression of anti-TNFα antibody secreted into the culture medium as compared to the level of the antibody expressed in transfected cells expressing the anti-TNFα antibody alone (middle row).

FIG. 27B shows the results of a densitometry analysis of the chemiluminescent signals in dot blots in each of the rows in FIG. 27A using the NIH ImageJ image processing program. The bar graphs of FIG. 27B are numbered to correspond to the row numbers of FIG. 27A. The results of this series of experiments clearly show that co-expression of the anti-TNFα antibody target protein with a fusion protein comprising a BSC1 polypeptide linked to a target binding domain (Protein A) significantly enhanced the level of expression of secreted anti-TNFα antibody.

FIG. 27C shows the results of an ELISA for TNFα binding activity by the expressed anti-TNFα antibody. A 96-well plate was coated with recombinant purified human TNFα and incubated with the anti-TNFα antibody (target protein) secreted into the media of cultures of transfected cells expressing the anti-TNFα antibody alone (bar graph 2) or co-expressing anti-TNFα antibody and the BSC1-Protein A fusion protein (bar graph 3). No TNFα binding activity was detected in medium from mock cultures containing cells transfected with an expression vector lacking a structural gene for expressing either protein (bar graph 1). The results of this series of experiments clearly show that the secreted anti-TNFα antibody that was expressed at enhanced levels when co-expressed with the BSC1-Protein A fusion protein retained its binding activity for human TNFα.

Example 20. BSC1-Protein A Fusion Protein Enhances Established Expression of an Anti-IL8 Antibody in CHO-D12 Cell Line in an Unmodified Arrangement Similar in design to Example 8, above, this experiment examined whether a BSC1-Protein A fusion protein could enhance the level of expression of an anti-IL8 antibody already being produced in an established commercially relevant production CHO-DP12 cell line (American Type Culture Collection Accession No. CRL-124444, American Type Culture Collection, Manassas, Va.).

FIG. 28A shows results of an immune dot blot assay for expression of the anti-IL8 antibody (target protein) secreted into the media of cultures of cells of a CHO-DP12 cell line expressing the anti-IL8 antibody alone (middle row 2) and of cells co-expressing the anti-IL8 antibody and the BSC1-Protein A fusion protein (bottom row 3). It can be seen that co-expression of the antibody with the BSC1-Protein A fusion molecule significantly enhanced the level of expression of the antibody secreted into the culture medium (bottom row 3) as compared to the level of the antibody expressed in the absence of the BSC1-Protein A fusion molecule (row 2). No antibody was detected in medium alone (top row of FIG. 28A).

FIG. 28B shows the results of a densitometry analysis of the chemiluminescent signals in the dot blots in the rows of FIG. 28A using the NIH ImageJ image processing program. The bar graphs in FIG. 28B are numbered to correspond to the rows in FIG. 28A. The results indicate that co-expression of the antibody with the BSC1-Protein A fusion molecule (bar graph 3) significantly enhanced expression of the secreted antibody, providing an approximately four to five-fold greater enhancement in the level of expression as compared to that obtained when the antibody was expressed in the absence of the BSC1-Protein A fusion protein (bar graph 2).

FIG. 28C shows the results of an ELISA for IL8 binding. A 96-well plate was coated with recombinant purified human IL8 and incubated with the anti-IL8 antibody (target protein) secreted into the media of cultures stably expressing the anti-IL8 antibody alone (bar graph 2) or co-expressing the anti-IL8 antibody and the BSC1-Protein A fusion protein (bar graph 3). Cell culture medium was used as a negative control (bar graph 1, no anti-IL8 antibody). The results of this series of experiments clearly show that the secreted anti-IL8 antibody that was expressed at enhanced levels when co-expressed with the BSC1-Protein A fusion protein retained its binding activity for IL8.

The results indicate that a BSC1-Protein A fusion protein can be employed in an unmodified arrangement to significantly enhance the level of production of a target protein that is already stably expressed in an established production cell line.

Example 21. Enhancement of Expression of Secreted Alpha-1 Antitrvpsin Z Protein This experiment indicates that enhancement of protein expression according to the invention has the potential to treat a disease resulting from an improper conformation of a critical protein.

Alpha1 antitrypsin (AAT) deficiency is an autosomal genetic disorder that affects both genders. AAT is a 52-kDa serine protease inhibitor produced mainly in the liver. Over 90 genetic variants have been identified in the protease inhibitor 1 (PI) gene on chromosome 14 that are associated with AAT deficiency. The most common basis of AAT deficiency is the Z mutation, a single base pair substitution that changes a Glu to Lys at codon 342 (Glu342Lys). The mutant AAT protein with the Z mutation (AATZ protein) retains approximately 80% of the serine protease activity of the wild type AAT protein. The AATZ protein also cannot fold to establish a normal conformation and consequently accumulates in aggregates within the endoplasmic reticulum (ER). Accumulation of aggregated AATZ in liver cells leads to liver toxicity and liver cirrhosis.

For this experiment, the target proteins were an engineered AAT-Fc fusion protein and an engineered V5-tagged α1ATZ-Fc fusion protein. The amino acid sequence of the AAT-Fc fusion protein is the same as described in Example 4.3 above. The amino acid sequence for the AATZ-Fc fusion protein is shown in the table below.

TABLE 69

Amino Acid Sequence of a V5-Tagged α1AATZ-Fc Target Protein.

| Protein Region (N- to C-terminal) | Sequence Identifier | Amino Acid Sequence 123456789012345678901234567890 |
|---|---|---|
| V5-tagged α1AATZ-Fc fusion molecule | SEQ ID NO: 325 | MPSSVSWGILLLAGLCCLVPVSLAEDPQGD AAQKTDTSHHDQDHPTFNKITPNLAEFAFS LYRQLAHQSNSTNIFFSPVSIATAFAMLSL GTKADTHDEILEGLNFNLTEIPEAQIHEGF QELLRTLNQPDSQLQLTTGNGLFLSEGLKL VDKFLEDVKKLYHSEAFTVNFGDTEEAKKQ INDYVEKGTQGKIVDLVKELDRDTVFALVN YIFFKGKWERPFEVKDTEEEDFHVDQVTTV |

TABLE 69-continued Amino Acid Sequence of a V5-Tagged α1AATZ-Fc Target Protein.

| Protein Region (N- to C-terminal) | Sequence Identifier | Amino Acid Sequence<br>         1234567890123456789012345678 90 |
|---|---|---|
| | | KVPMMKRLGMFNIQHCKKLSSWVLLMKYLG<br>NATAIFFLPDEGKLQHLENELTHDIITKFL<br>ENEDRRSASLHLPKLSITGTYDLKSVLGQL<br>GITKVFSNGADLSGVTEEAPLKLSKAVHKA<br>VLTIDKKGTEAAGAMFLEAIPMSIPPEVKF<br>NKPFVFLMIEQNTKSPLFMGKVVNPTQKGT<br>GSEFDIAAALEGKPIPNPLLGLDSTSRPKS<br>CDKTHTCPPCPAPELLGGPSVFLFPPKPKD<br>TLMISRTPEVTCVVVDVSHEDPEVKFNWYV<br>DGVEVHNAKTKPREEQYNSTYRVVSVLTVL<br>HQDWLNGKEYKCKVSNKALPAPIEKTISKA<br>KGQPREPQVYTLPPSRDELTKNQVSLTCLV<br>KGFYPSDIAVEWESNGQPENNYKTTPPVLD<br>SDGSFFLYSKLTVDKSRWQQGNVFSCSVMH<br>EALHNHYTQKSLSLSPGK |
| α1AATZ | residues 1-418 of SEQ ID NO: 325 | MPSSVSWGILLLAGLCCLVPVSLAEDPQGD<br>AAQKTDTSHHDQDHPTFNKITPNLAEFAFS<br>LYRQLAHQSNSTNIFFSPVSIATAFAMLSL<br>GTKADTHDEILEGLNFNLTEIPEAQIHEGF<br>QELLRTLNQPDSQLQLTTGNGLFLSEGLKL<br>VDKFLEDVKKLYHSEAFTVNFGDTEEAKKQ<br>INDYVEKGTQGKIVDLVKELDRDTVFALVN<br>YIFFKGKWERPFEVKDTEEEDFHVDQVTTV<br>KVPMMKRLGMFNIQHCKKLSSWVLLMKYLG<br>NATAIFFLPDEGKLQHLENELTHDIITKFL<br>ENEDRRSASLHLPKLSITGTYDLKSVLGQL<br>GITKVFSNGADLSGVTEEAPLKLSKAVHKA<br>VLTIDKKGTEAAGAMFLEAIPMSIPPEVKF<br>NKPFVFLMIEQNTKSPLFMGKVVNPTQK |
| Linker 1 | residues 419-431 of SEQ ID NO: 325 | GTGSEFDIAAALE |
| V5 epitope domain | residues 432-445 of SEQ ID NO: 325 | GKPIPNPLLGLDST |
| Linker 2 | residues 446-447 of SEQ ID NO: 325 | SR |
| Fc domain | residues 448-678 of SEQ ID NO: 325 | PKSCDKTHTCPPCPAPELLGGPSVFLFPPK<br>PKDTLMISRTPEVTCVVVDVSHEDPEVKFN<br>WYVDGVEVHNAKTKPREEQYNSTYRVVSVL<br>TVLHQDWLNGKEYKCKVSNKALPAPIEKTI<br>SKAKGQPREPQVYTLPPSRDELTKNQVSLT<br>CLVKGFYPSDIAVEWESNGQPENNYKTTPP<br>VLDSDGSFFLYSKLTVDKSRWQQGNVFSCS<br>VMHEALHNHYTQKSLSLSPGK |

FIG. 29A shows images of chemiluminescent signals of a Western blot assay using anti-V5 antibody to detect expression of the V5-tagged AAT- and AATZ-Fc fusion proteins. Lane 1 in the top panel of FIG. 29A shows non-expressing cell culture medium as a control. Lane 2 of the top panel shows culture medium of cells expressing AAT-Fc alone. As expected for the wild type AAT protein, the AAT-Fc fusion was secreted into the culture medium. Lane 3 of the top panel of FIG. 29A shows that little if any of AATZ-Fc protein was secreted into the medium of a culture of transfected cells expressing the AATZ-Fc fusion protein alone. As expected for the AATZ protein, which is known to be retained in the endoplasmic reticulum, AATZ-Fc fusion protein was detected in cell lysates of the cells expressing AATZ-Fc protein alone. See, lane 3 of the middle panel (cell lysates). Surprisingly, as shown in lane 4 of the top panel of FIG. 29A, co-expression of the AATZ-Fc protein and the BSC1-Protein A fusion protein resulted in a dramatic increase in the level of expression of AATZ-Fc protein secreted into the cultures medium. Moreover, little if any of AATZ-Fc fusion protein was detected in cell lysate (lane 4, middle panel of FIG. 29A). The same membrane was blotted with anti-tubulin antibody for a loading control.

The results clearly show that co-expression of the BSC1-Protein A fusion protein significantly elevated the level of expression of the AATZ-Fc target protein secreted into the culture medium as compared to the level of expression of the target protein in the absence of the BSC1-Protein A fusion protein. Moreover, little if any of the AATZ-Fc proteins was detected in cell lysates, indicating that the AATZ-Fc protein was not retained in the endoplasmic reticulum. Accordingly, these data suggest for the first time that a gene therapy that would provide a fusion protein comprising an AATZ-binding domain and a protein expression enhancing polypeptide of this invention would be effective in treating an individual for AAT deficiency due to the Z mutation by enhancing expression of secreted AATZ protein from cells of the individual, eliminating or reducing liver toxicity due to retention of AATZ in the endoplasmic reticulum, and restoring required levels of extracellular AAT serine protease activity to individual.

All patents, applications, and publications cited in the above text are incorporated herein by reference.

Other variations and embodiments of the invention described herein will now be apparent to those of skill in the art without departing from the disclosure of the invention or the claims below.

What is claimed is:

1. A fusion protein comprising:
   (1) a protein expression enhancing polypeptide (PEEP) domain linked to (2) a target protein binding domain, wherein said protein expression enhancing polypeptide (1) is selected from the group consisting of:
   (a) an isolated J domain of a J protein;
   (b) a J domain analog polypeptide comprising the amino acid sequence of formula I:

X1-X2-X3-X4-X5-X6-X7-X8-X9 (SEQ ID NO:47), (I)
   wherein:
   X1 is isoleucine (I), leucine (L), valine (V), alanine (A), or methionine (M);
   X2 and X3 are each independently any amino acid with the proviso that one or both are K or R;
   X4 is any amino acid or X4 may be absent when X1 through X3 are present and X5 through X9 are present;
   X5 is tyrosine (Y), tryptophan (W), or phenylalanine (F);
   X6 and X7 are each independently any amino acid with the proviso that one or both are lysine (K) or arginine (R); or either one of X6 and X7 may be absent when the other is K or R and when X1 through X5 are present and X8 and X9 are present; and
   X8 and X9 are any amino acid with the proviso that one or both are leucine (L) or alanine (A); or one of X8 and X9 may be absent when the other is L or A and when X1 through X7 are present; and
   (c) a decapeptide selected from the group consisting of:
   IKKAYKLALQ (SEQ ID NO:49),
   IKKAYRLALQ (SEQ ID NO:50),
   IKKAYRKALQ (SEQ ID NO:51), and
   IKKAYRKLLQ (SEQ ID NO:52);
   wherein said target protein binding domain (2) is a protein or binding domain thereof that specifically binds a target protein of interest; and
   wherein co-expression of said fusion protein with said target protein of interest that is bound by said target protein binding domain of said fusion protein results in an enhanced level of expression of said target protein of interest compared to the level of expression in the absence of said fusion protein.

2. The fusion protein according to claim 1, wherein the protein expression enhancing polypeptide (1) consists of an isolated J domain of a J protein.

3. The fusion protein according to claim 2, wherein the isolated J domain is an isolated J domain of an ERdj protein, a large T antigen of SV40, or a mammalian cysteine string protein alpha (CSP-α).

4. The fusion protein according to claim 2, wherein the isolated J domain is an isolated J domain of an Erdj protein selected from Erdj1, Erdj2, Erdj3, Erdj4, Erdj5, Erdj6 and Erdj7.

5. The fusion protein according to claim 4, wherein the isolated J domain is an isolated J domain of Erdj3.

6. The fusion protein according to claim 1, wherein the protein expression enhancing polypeptide is selected from the group consisting of:
I-K-K-A-Y-R-K-L-A (SEQ ID NO:48),
I-R-K-A-Y-R-K-L-S-L-T-L (SEQ ID NO:83),
I-K-K-Q-Y-R-L-L-S-L-K-Y (SEQ ID NO:84),
I-K-K-A-F-H-K-L-A-M-K-Y (SEQ ID NO:85),
I-R-Q-A-F-K-K-L-A-L-K-L (SEQ ID NO:86),
I-I-K-A-Y-R-K-L-A-L-Q-W (SEQ ID NO:87),
I-A-R-A-Y-R-Q-L-A-R-R-Y (SEQ ID NO:88),
I-K-R-A-Y-R-R-Q-A-L-R-Y (SEQ ID NO:89),
I-K-K-S-Y-R-K-L-A-L-K-Y (SEQ ID NO:90), and
I-K-K-A-Y-K-R-L-A-M-K-Y (SEQ ID NO:91).

7. The fusion protein according to claim 1, wherein the protein expression enhancing polypeptide is a J domain analog polypeptide, wherein said J domain analog polypeptide comprises the amino acid sequence of formula I.

8. The fusion protein according to claim 7, wherein said J domain analog polypeptide comprises the amino acid sequence (SEQ ID NO:326) wherein:
X1 is I, L, V, A, or M;
the dipeptide X2-X3 is selected from the group consisting of: KR, KK, RK, RR, AK, AR, KA, IK, NK, KQ, RQ, and RD;
X4 is A, S, T, R, Q, E, F, C, or I;
X5 is Y or F;
the dipeptide X6-X7 is selected from the group consisting of: KR, KK, RK, RR, RQ, FR, RL, KL, HK, LK, QK, and KV; and
the dipeptide X8-X9 is selected from the group consisting of: LA, LL, AL, AA, LC, LV, QA, KA, LS, LI, LY, and RA.

9. The fusion protein according to claim 1, wherein said protein expression enhancing polypeptide (1) comprises one of the following amino acid sequences:

| Sequence Identifier | Amino Acid Sequence 123456789012345 |
|---|---|
| SEQ ID NO: 48 | IKKAYRKLA |
| SEQ ID NO: 49 | IKKAYKLALQ |
| SEQ ID NO: 50 | IKKAYRLALQ |
| SEQ ID NO: 51 | IKKAYRKALQ |
| SEQ ID NO: 52 | IKKAYRKLLQ |
| SEQ ID NO: 53 | IKKYRKLA |
| SEQ ID NO: 54 | IKKAYKLA |
| SEQ ID NO: 55 | IKKAYRLA |
| SEQ ID NO: 56 | IKKAYRKA |
| SEQ ID NO: 57 | LKKAYRKLA |
| SEQ ID NO: 58 | VKKAYRKLA |
| SEQ ID NO: 59 | MKKAYRKLA |
| SEQ ID NO: 60 | AKKAYRKLA |
| SEQ ID NO: 61 | IAKAYRKLA |
| SEQ ID NO: 62 | IKAAYRKLA |
| SEQ ID NO: 63 | IKKRYRKLA |
| SEQ ID NO: 64 | IKKSYRKLA |
| SEQ ID NO: 65 | IKKQYRKLA |
| SEQ ID NO: 66 | IKKEYRKLA |
| SEQ ID NO: 67 | IKKFYRKLA |
| SEQ ID NO: 68 | IKKCYRKLA |
| SEQ ID NO: 69 | IKKAFRKLA |
| SEQ ID NO: 70 | IKKAWRKLA |
| SEQ ID NO: 71 | IKKAYRKQA |
| SEQ ID NO: 72 | IKKAYRKMA |
| SEQ ID NO: 73 | IKKAYRKIA |
| SEQ ID NO: 74 | IKKAYRKAA |
| SEQ ID NO: 75 | IKKAYRKVA |
| SEQ ID NO: 76 | IKKAYRKRA |
| SEQ ID NO: 77 | IKKAYRKLM |
| SEQ ID NO: 78 | IKKAYRKLI |
| SEQ ID NO: 79 | IKKAYRKLV |
| SEQ ID NO: 80 | IKKAYRKLC |
| SEQ ID NO: 81 | IKKAYRKLS |
| SEQ ID NO: 82 | IKKAYRKLY |
| SEQ ID NO: 83 | IRKAYRKLSLTL |
| SEQ ID NO: 84 | IKKQYRLLSLKY |
| SEQ ID NO: 85 | IKKAFHKLAMKY |
| SEQ ID NO: 86 | IRQAFKKLALKL |
| SEQ ID NO: 87 | IIKAYRKLALQW |
| SEQ ID NO: 88 | IARAYRQLARRY |
| SEQ ID NO: 89 | IKRAYRRQALRY |
| SEQ ID NO: 90 | IKKSYRKLALKY |
| SEQ ID NO: 91 | IKKAYKRLAMKY. |

10. The fusion protein according to claim 1, wherein the target protein binding domain (2) is an antibody or an antigen-binding fragment thereof, an antibody binding protein, a ligand binding domain of a receptor protein, a protein ligand of a receptor protein, a protein antigen that is bound by an antibody or an antigen-binding fragment thereof, or a PDZ domain.

11. The fusion protein according to claim 10, wherein the target protein binding domain (2) is an antibody binding protein.

12. The fusion protein according to claim 11, wherein the antibody binding protein is an Fc binding protein.

13. The fusion protein according to claim 12, wherein the Fc binding protein is Protein A, Protein G, or a viral gE protein.

14. The fusion protein according to claim 11, wherein the antibody binding protein is Protein L.

15. The fusion protein according to claim 10, wherein said target protein binding domain (2) is a ligand binding domain of a receptor protein, wherein the receptor protein is a cytokine receptor.

16. The fusion protein according to claim 10, wherein said target protein binding domain (2) is a protein ligand of a receptor protein, wherein the protein ligand is a cytokine.

17. An isolated nucleic acid molecule comprising a nucleic acid sequence encoding a fusion protein according to claim 1 or claim 9.

18. A nucleic acid vector molecule comprising the isolated nucleic acid molecule according to claim 17.

19. A host cell comprising the nucleic acid vector molecule according to claim 18.

20. A method of expressing a fusion protein comprising culturing a host cell according to claim 19 under conditions sufficient to produce the fusion protein.

21. A method of enhancing the expression of a target protein of interest expressed by a host cell comprising transfecting the host cell with an expression vector comprising a structural gene encoding a fusion protein according to claim 1, and culturing said transfected host cell under conditions causing the co-expression of said fusion protein encoded by said structural gene and of said target protein of interest.

22. A method of enhancing the expression of a target protein of interest comprising the steps of:
 1) constructing a recombinant gene encoding a fusion protein according to claim 1 wherein the target protein binding domain (2) of the fusion protein binds said target protein of interest;
 2) inserting the recombinant gene into an expression vector to form a recombinant expression vector wherein said recombinant gene sequence is operably linked to a transcriptional promoter sequence;
 3) transfecting said recombinant expression vector into host cells that are compatible with said promoter sequence; and
 4) culturing said transfected host cells under conditions that permit co-expression of said fusion protein encoded by said recombinant gene and of said target protein of interest.

23. A method of restoring a secreted protein function in cells of a mammalian subject that are deficient in the secretion of a native secreted protein that provides said secreted protein function comprising inserting into cells of the subject an exogenous nucleic acid molecule encoding a fusion protein according to claim 1 wherein the target protein binding domain (2) of the fusion protein binds the native secreted protein, wherein expression of the fusion protein and the native secreted protein in the cells enhances secretion of said native protein to provide said protein function to the cells of the subject.

24. The method according to claim 23, wherein the subject has a disease associated with the deficient secretion of the native protein in the subject.

25. The method according to claim 24, wherein said disease is selected from the group consisting of a prion-associated disease, Alzheimer's disease, Parkinson's disease, Huntington's disease, cystic fibrosis (CF), and α1-antitrypsin (AAT) deficiency.

26. The method according to claim 25, wherein the subject is a human subject deficient in the secretion of cystic fibrosis transmembrane conductance regulator protein and the disease is cystic fibrosis.

27. The method according to claim 25, wherein the subject is a human subject deficient in secretion of AAT and the disease is AAT deficiency.

* * * * *

SEQUENCE LISTING

```
<160> NUMBER OF SEQ ID NOS: 329

<210> SEQ ID NO 1
<211> LENGTH: 58
<212> TYPE: PRT
<213> ORGANISM: Homo sapiens

<400> SEQUENCE: 1

Lys Asp Tyr Tyr Gln Thr Leu Gly Leu Ala Arg Gly Ala Ser Asp Glu
1               5                   10                  15

Glu Ile Lys Arg Ala Tyr Arg Arg Gln Ala Leu Arg Tyr His Pro Asp
            20                  25                  30

Lys Asn Lys Glu Pro Gly Ala Glu Glu Lys Phe Lys Glu Ile Ala Glu
        35                  40                  45

Ala Tyr Asp Val Leu Ser Asp Pro Arg Lys
    50                  55

<210> SEQ ID NO 2
<211> LENGTH: 58
<212> TYPE: PRT
<213> ORGANISM: Homo sapiens

<400> SEQUENCE: 2

Leu Asn Phe Tyr Gln Phe Leu Gly Val Gln Gln Asp Ala Ser Ser Ala
1               5                   10                  15

Asp Ile Arg Lys Ala Tyr Arg Lys Leu Ser Leu Thr Leu His Pro Asp
            20                  25                  30

Lys Asn Lys Asp Glu Asn Ala Glu Thr Gln Phe Arg Gln Leu Val Ala
        35                  40                  45

Ile Tyr Glu Val Leu Lys Asp Asp Glu Arg
    50                  55

<210> SEQ ID NO 3
<211> LENGTH: 55
<212> TYPE: PRT
<213> ORGANISM: Homo sapiens

<400> SEQUENCE: 3

Tyr Asn Pro Tyr Glu Val Leu Asn Leu Asp Pro Gly Ala Thr Val Ala
1               5                   10                  15

Glu Ile Lys Lys Gln Tyr Arg Leu Leu Ser Leu Lys Tyr His Pro Asp
            20                  25                  30

Lys Gly Gly Asp Glu Val Met Phe Met Arg Ile Ala Lys Ala Tyr Ala
        35                  40                  45

Ala Leu Thr Asp Glu Glu Ser
    50                  55

<210> SEQ ID NO 4
<211> LENGTH: 59
<212> TYPE: PRT
<213> ORGANISM: Homo sapiens

<400> SEQUENCE: 4
```

```
Arg Asp Phe Tyr Lys Ile Leu Gly Val Pro Arg Ser Ala Ser Ile Lys
1               5                   10                  15

Asp Ile Lys Lys Ala Tyr Arg Lys Leu Ala Leu Gln Leu His Pro Asp
            20                  25                  30

Arg Asn Pro Asp Asp Pro Gln Ala Gln Glu Lys Phe Gln Asp Leu Gly
        35                  40                  45

Ala Ala Tyr Glu Val Leu Ser Asp Ser Glu Lys
    50                  55
```

<210> SEQ ID NO 5
<211> LENGTH: 58
<212> TYPE: PRT
<213> ORGANISM: Homo sapiens

<400> SEQUENCE: 5

```
Lys Ser Tyr Tyr Asp Ile Leu Gly Val Pro Lys Ser Ala Ser Glu Arg
1               5                   10                  15

Gln Ile Lys Lys Ala Phe His Lys Leu Ala Met Lys Tyr His Pro Asp
            20                  25                  30

Lys Asn Lys Ser Pro Asp Ala Glu Ala Lys Phe Arg Glu Ile Ala Glu
        35                  40                  45

Ala Tyr Glu Thr Leu Ser Asp Ala Asn Arg
    50                  55
```

<210> SEQ ID NO 6
<211> LENGTH: 59
<212> TYPE: PRT
<213> ORGANISM: Homo sapiens

<400> SEQUENCE: 6

```
Gln Asp Phe Tyr Ser Leu Leu Gly Val Ser Lys Thr Ala Ser Ser Arg
1               5                   10                  15

Glu Ile Arg Gln Ala Phe Lys Lys Leu Ala Leu Lys Leu His Pro Asp
            20                  25                  30

Lys Asn Pro Asn Asn Pro Asn Ala His Gly Asp Phe Leu Lys Ile Asn
        35                  40                  45

Arg Ala Tyr Glu Val Leu Lys Asp Glu Asp Leu
    50                  55
```

<210> SEQ ID NO 7
<211> LENGTH: 62
<212> TYPE: PRT
<213> ORGANISM: Homo sapiens

<400> SEQUENCE: 7

```
Arg Asp Tyr Tyr Lys Ile Leu Gly Val Lys Arg Asn Ala Lys Lys Gln
1               5                   10                  15

Glu Ile Ile Lys Ala Tyr Arg Lys Leu Ala Leu Gln Trp His Pro Asp
            20                  25                  30

Asn Phe Gln Asn Glu Glu Glu Lys Lys Lys Ala Glu Lys Lys Phe Ile
        35                  40                  45

Asp Ile Ala Ala Ala Lys Glu Val Leu Ser Asp Pro Glu Met
    50                  55                  60
```

<210> SEQ ID NO 8
<211> LENGTH: 59
<212> TYPE: PRT
<213> ORGANISM: Homo sapiens

<400> SEQUENCE: 8

```
Glu Ser Leu Tyr His Val Leu Gly Leu Asp Lys Asn Ala Thr Ser Asp
1               5                   10                  15

Asp Ile Lys Lys Ser Tyr Arg Lys Leu Ala Leu Lys Tyr His Pro Asp
                20                  25                  30

Lys Asn Pro Asp Asn Pro Glu Ala Ala Asp Lys Phe Lys Glu Ile Asn
            35                  40                  45

Asn Ala His Ala Ile Leu Thr Asp Ala Thr Lys
            50                  55
```

<210> SEQ ID NO 9
<211> LENGTH: 57
<212> TYPE: PRT
<213> ORGANISM: Simian virus 40

<400> SEQUENCE: 9

```
Leu Gln Leu Met Asp Leu Leu Gly Leu Glu Arg Ser Ala Trp Gly Asn
1               5                   10                  15

Ile Pro Leu Met Arg Lys Ala Tyr Leu Lys Lys Cys Lys Glu Phe His
                20                  25                  30

Pro Asp Lys Gly Gly Asp Glu Glu Lys Met Lys Lys Met Asn Thr Leu
            35                  40                  45

Tyr Lys Lys Met Glu Asp Gly Val Lys
            50                  55
```

<210> SEQ ID NO 10
<211> LENGTH: 59
<212> TYPE: PRT
<213> ORGANISM: Homo sapiens

<400> SEQUENCE: 10

```
Gln Asp Tyr Tyr Glu Ile Leu Gly Val Ser Lys Thr Ala Glu Glu Arg
1               5                   10                  15

Glu Ile Lys Lys Ala Tyr Lys Arg Leu Ala Met Lys Tyr His Pro Asp
                20                  25                  30

Arg Asn Gln Gly Asp Lys Glu Ala Glu Ala Lys Phe Lys Glu Ile Lys
            35                  40                  45

Glu Ala Tyr Glu Val Leu Thr Asp Ser Gln Lys
            50                  55
```

<210> SEQ ID NO 11
<211> LENGTH: 68
<212> TYPE: PRT
<213> ORGANISM: Homo sapiens

<400> SEQUENCE: 11

```
Asn Pro Phe Glu Val Leu Gln Ile Asp Pro Glu Val Thr Asp Glu Glu
1               5                   10                  15

Ile Lys Lys Arg Phe Arg Gln Leu Ser Ile Leu Val His Pro Asp Lys
                20                  25                  30

Asn Gln Asp Asp Ala Asp Arg Ala Gln Lys Ala Phe Glu Ala Val Asp
            35                  40                  45

Lys Ala Tyr Lys Leu Leu Leu Asp Gln Glu Lys Lys Arg Ala Leu
            50                  55                  60

Asp Val Ile Gln
65
```

<210> SEQ ID NO 12
<211> LENGTH: 59

<212> TYPE: PRT
<213> ORGANISM: Homo sapiens

<400> SEQUENCE: 12

Glu Ala Leu Tyr Glu Ile Leu Gly Leu His Lys Gly Ala Ser Asn Glu
1               5                   10                  15

Glu Ile Lys Lys Thr Tyr Arg Lys Leu Ala Leu Lys His His Pro Asp
                20                  25                  30

Lys Asn Pro Asp Asp Pro Ala Ala Thr Glu Lys Phe Lys Glu Ile Asn
            35                  40                  45

Asn Ala His Ala Ile Leu Thr Asp Ile Ser Lys
        50                  55

<210> SEQ ID NO 13
<211> LENGTH: 58
<212> TYPE: PRT
<213> ORGANISM: Homo sapiens

<400> SEQUENCE: 13

Leu Asn Pro Phe His Val Leu Gly Val Glu Ala Thr Ala Ser Asp Val
1               5                   10                  15

Glu Leu Lys Lys Ala Tyr Arg Gln Leu Ala Val Met Val His Pro Asp
                20                  25                  30

Lys Asn His His Pro Arg Ala Glu Glu Ala Phe Lys Val Leu Arg Ala
            35                  40                  45

Ala Trp Asp Ile Val Ser Asn Ala Glu Lys
        50                  55

<210> SEQ ID NO 14
<211> LENGTH: 69
<212> TYPE: PRT
<213> ORGANISM: Homo sapiens

<400> SEQUENCE: 14

Arg Asp Cys Tyr Glu Val Leu Gly Val Ser Arg Ser Ala Gly Lys Ala
1               5                   10                  15

Glu Ile Ala Arg Ala Tyr Arg Gln Leu Ala Arg Arg Tyr His Pro Asp
                20                  25                  30

Arg Tyr Arg Pro Gln Pro Gly Asp Glu Gly Pro Gly Arg Thr Pro Gln
            35                  40                  45

Ser Ala Glu Glu Ala Phe Leu Leu Val Ala Thr Ala Tyr Glu Thr Leu
        50                  55                  60

Lys Asp Glu Glu Thr
65

<210> SEQ ID NO 15
<211> LENGTH: 60
<212> TYPE: PRT
<213> ORGANISM: Homo sapiens

<400> SEQUENCE: 15

Ala Ser Tyr Tyr Glu Ile Leu Asp Val Pro Arg Ser Ala Ser Ala Asp
1               5                   10                  15

Asp Ile Lys Lys Ala Tyr Arg Arg Lys Ala Leu Gln Trp His Pro Asp
                20                  25                  30

Lys Asn Pro Asp Asn Lys Glu Phe Ala Glu Lys Phe Lys Glu Val
            35                  40                  45

Ala Glu Ala Tyr Glu Val Leu Ser Asp Lys His Lys
        50                  55                  60

```
<210> SEQ ID NO 16
<211> LENGTH: 60
<212> TYPE: PRT
<213> ORGANISM: Homo sapiens

<400> SEQUENCE: 16

Ala Ser Tyr Tyr Glu Ile Leu Asp Val Pro Arg Ser Ala Ser Ala Asp
1               5                   10                  15

Asp Ile Lys Lys Ala Tyr Arg Arg Lys Ala Leu Gln Trp His Pro Asp
            20                  25                  30

Lys Asn Pro Asp Asn Lys Glu Phe Ala Glu Lys Phe Lys Glu Val
        35                  40                  45

Ala Glu Ala Tyr Glu Val Leu Ser Asp Lys His Lys
    50                  55                  60

<210> SEQ ID NO 17
<211> LENGTH: 56
<212> TYPE: PRT
<213> ORGANISM: Homo sapiens

<400> SEQUENCE: 17

Thr Thr Tyr Tyr Asp Val Leu Gly Val Lys Pro Asn Ala Thr Gln Glu
1               5                   10                  15

Glu Leu Lys Lys Ala Tyr Arg Lys Leu Ala Leu Lys Tyr His Pro Asp
            20                  25                  30

Lys Asn Pro Asn Glu Gly Glu Lys Phe Lys Gln Ile Ser Gln Ala Tyr
        35                  40                  45

Glu Val Leu Ser Asp Ala Lys Lys
    50                  55

<210> SEQ ID NO 18
<211> LENGTH: 60
<212> TYPE: PRT
<213> ORGANISM: Homo sapiens

<400> SEQUENCE: 18

Ala Ser Tyr Tyr Glu Ile Leu Asp Val Pro Arg Ser Ala Ser Ala Asp
1               5                   10                  15

Asp Ile Lys Lys Ala Tyr Arg Arg Lys Ala Leu Gln Trp His Pro Asp
            20                  25                  30

Lys Asn Pro Asp Asn Lys Glu Phe Ala Glu Lys Phe Lys Glu Val
        35                  40                  45

Ala Glu Ala Tyr Glu Val Leu Ser Asp Lys His Lys
    50                  55                  60

<210> SEQ ID NO 19
<211> LENGTH: 58
<212> TYPE: PRT
<213> ORGANISM: Homo sapiens

<400> SEQUENCE: 19

Lys Asp Ser Trp Asp Met Leu Gly Val Lys Pro Gly Ala Ser Arg Asp
1               5                   10                  15

Glu Val Asn Lys Ala Tyr Arg Lys Leu Ala Val Leu Leu His Pro Asp
            20                  25                  30

Lys Cys Val Ala Pro Gly Ser Glu Asp Ala Phe Lys Ala Val Val Asn
        35                  40                  45

Ala Arg Thr Ala Leu Leu Lys Asn Ile Lys
```

```
                50                  55

<210> SEQ ID NO 20
<211> LENGTH: 60
<212> TYPE: PRT
<213> ORGANISM: Homo sapiens

<400> SEQUENCE: 20

Val Asp Tyr Tyr Glu Val Leu Asp Val Pro Arg Gln Ala Ser Ser Glu
1               5                   10                  15

Ala Ile Lys Lys Ala Tyr Arg Lys Leu Ala Leu Lys Trp His Pro Asp
            20                  25                  30

Lys Asn Pro Glu Asn Lys Glu Ala Glu Arg Arg Phe Lys Gln Val
        35                  40                  45

Ala Glu Ala Tyr Glu Val Leu Ser Asp Ala Lys Lys
    50                  55                  60

<210> SEQ ID NO 21
<211> LENGTH: 59
<212> TYPE: PRT
<213> ORGANISM: Homo sapiens

<400> SEQUENCE: 21

Gly Asp Tyr Tyr Gln Ile Leu Gly Val Pro Arg Asn Ala Ser Gln Lys
1               5                   10                  15

Glu Ile Lys Lys Ala Tyr Tyr Gln Leu Ala Lys Lys Tyr His Pro Asp
            20                  25                  30

Thr Asn Lys Asp Asp Pro Lys Ala Lys Glu Lys Phe Ser Gln Leu Ala
        35                  40                  45

Glu Ala Tyr Glu Val Leu Ser Asp Glu Val Lys
    50                  55

<210> SEQ ID NO 22
<211> LENGTH: 58
<212> TYPE: PRT
<213> ORGANISM: Homo sapiens

<400> SEQUENCE: 22

Gly Ser Tyr Tyr Asp Ile Leu Gly Val Pro Lys Ser Ala Ser Glu Arg
1               5                   10                  15

Gln Ile Lys Lys Ala Phe His Lys Leu Ala Met Lys Tyr His Pro Asp
            20                  25                  30

Lys Asn Lys Ser Pro Asp Ala Glu Ala Lys Phe Arg Glu Ile Ala Glu
        35                  40                  45

Ala Tyr Glu Thr Leu Ser Asp Ala Asn Arg
    50                  55

<210> SEQ ID NO 23
<211> LENGTH: 58
<212> TYPE: PRT
<213> ORGANISM: Homo sapiens

<400> SEQUENCE: 23

Gly Asp Tyr Tyr Glu Ile Leu Gly Val Ser Arg Gly Ala Ser Asp Glu
1               5                   10                  15

Asp Leu Lys Lys Ala Tyr Arg Arg Leu Ala Leu Lys Phe His Pro Asp
            20                  25                  30

Lys Asn His Ala Pro Gly Ala Thr Glu Ala Phe Lys Ala Ile Gly Thr
        35                  40                  45
```

Ala Tyr Ala Val Leu Ser Asn Pro Glu Lys
          50                  55

<210> SEQ ID NO 24
<211> LENGTH: 58
<212> TYPE: PRT
<213> ORGANISM: Homo sapiens

<400> SEQUENCE: 24

Lys Asp Tyr Tyr Gln Thr Leu Gly Leu Ala Arg Gly Ala Ser Asp Glu
1               5                   10                  15

Glu Ile Lys Arg Ala Tyr Arg Arg Gln Ala Leu Arg Tyr His Pro Asp
            20                  25                  30

Lys Asn Lys Glu Pro Gly Ala Glu Glu Lys Phe Lys Glu Ile Ala Glu
        35                  40                  45

Ala Tyr Asp Val Leu Ser Asp Pro Arg Lys
         50                  55

<210> SEQ ID NO 25
<211> LENGTH: 59
<212> TYPE: PRT
<213> ORGANISM: Homo sapiens

<400> SEQUENCE: 25

Thr Ala Leu Tyr Asp Leu Leu Gly Val Pro Ser Thr Ala Thr Gln Ala
1               5                   10                  15

Gln Ile Lys Ala Ala Tyr Tyr Arg Gln Cys Phe Leu Tyr His Pro Asp
            20                  25                  30

Arg Asn Ser Gly Ser Ala Glu Ala Glu Arg Phe Thr Arg Ile Ser
        35                  40                  45

Gln Ala Tyr Val Val Leu Gly Ser Ala Thr Leu
         50                  55

<210> SEQ ID NO 26
<211> LENGTH: 60
<212> TYPE: PRT
<213> ORGANISM: Homo sapiens

<400> SEQUENCE: 26

Ala Asn Tyr Tyr Glu Val Leu Gly Val Gln Ala Ser Ala Ser Pro Glu
1               5                   10                  15

Asp Ile Lys Lys Ala Tyr Arg Lys Leu Ala Leu Arg Trp His Pro Asp
            20                  25                  30

Lys Asn Pro Asp Asn Lys Glu Glu Ala Glu Lys Lys Phe Lys Leu Val
        35                  40                  45

Ser Glu Ala Tyr Glu Val Leu Ser Asp Ser Lys Lys
         50                  55                  60

<210> SEQ ID NO 27
<211> LENGTH: 59
<212> TYPE: PRT
<213> ORGANISM: Homo sapiens

<400> SEQUENCE: 27

Glu Asp Tyr Tyr Thr Leu Leu Gly Cys Asp Glu Leu Ser Ser Val Glu
1               5                   10                  15

Gln Ile Leu Ala Glu Phe Lys Val Arg Ala Leu Glu Cys His Pro Asp
            20                  25                  30

Lys His Pro Glu Asn Pro Lys Ala Val Glu Thr Phe Gln Lys Leu Gln
        35                  40                  45

```
Lys Ala Lys Glu Ile Leu Thr Asn Glu Glu Ser
    50                  55

<210> SEQ ID NO 28
<211> LENGTH: 57
<212> TYPE: PRT
<213> ORGANISM: Homo sapiens

<400> SEQUENCE: 28

Ser Ile Leu Lys Glu Val Thr Ser Val Val Glu Gln Ala Trp Lys Leu
1               5                   10                  15

Pro Glu Ser Glu Arg Lys Lys Ile Ile Arg Arg Leu Tyr Leu Lys Trp
                20                  25                  30

His Pro Asp Lys Asn Pro Glu Asn His Asp Ile Ala Asn Glu Val Phe
            35                  40                  45

Lys His Leu Gln Asn Glu Ile Asn Arg
    50                  55

<210> SEQ ID NO 29
<211> LENGTH: 60
<212> TYPE: PRT
<213> ORGANISM: Homo sapiens

<400> SEQUENCE: 29

Val Asp Tyr Tyr Glu Val Leu Gly Val Gln Arg His Ala Ser Pro Glu
1               5                   10                  15

Asp Ile Lys Lys Ala Tyr Arg Lys Leu Ala Leu Lys Trp His Pro Asp
                20                  25                  30

Lys Asn Pro Glu Asn Lys Glu Glu Ala Glu Arg Lys Phe Lys Gln Val
            35                  40                  45

Ala Glu Ala Tyr Glu Val Leu Ser Asp Ala Lys Lys
    50                  55                  60

<210> SEQ ID NO 30
<211> LENGTH: 60
<212> TYPE: PRT
<213> ORGANISM: Homo sapiens

<400> SEQUENCE: 30

Val Asp Tyr Tyr Glu Val Leu Gly Val Gln Arg His Ala Ser Pro Glu
1               5                   10                  15

Asp Ile Lys Lys Ala Tyr Arg Lys Leu Ala Leu Lys Trp His Pro Asp
                20                  25                  30

Lys Asn Pro Glu Asn Lys Glu Glu Ala Glu Arg Lys Phe Lys Gln Val
            35                  40                  45

Ala Glu Ala Tyr Glu Val Leu Ser Asp Ala Lys Lys
    50                  55                  60

<210> SEQ ID NO 31
<211> LENGTH: 58
<212> TYPE: PRT
<213> ORGANISM: Homo sapiens

<400> SEQUENCE: 31

Lys Ser Tyr Tyr Asp Ile Leu Gly Val Pro Lys Ser Ala Ser Glu Arg
1               5                   10                  15

Gln Ile Lys Lys Ala Phe His Lys Leu Ala Met Lys Tyr His Pro Asp
                20                  25                  30

Lys Asn Lys Ser Pro Asp Ala Glu Ala Lys Phe Arg Glu Ile Ala Glu
```

35                  40                  45
Ala Tyr Glu Thr Leu Ser Asp Ala Asn Arg
    50                  55

<210> SEQ ID NO 32
<211> LENGTH: 60
<212> TYPE: PRT
<213> ORGANISM: Homo sapiens

<400> SEQUENCE: 32

Leu Asn Pro Phe Glu Val Leu Gln Ile Asp Pro Glu Val Thr Asp Glu
1               5                   10                  15

Glu Ile Lys Lys Arg Phe Arg Gln Leu Ser Ile Leu Val His Pro Asp
            20                  25                  30

Lys Asn Gln Asp Asp Ala Asp Arg Ala Gln Lys Ala Phe Glu Ala Val
        35                  40                  45

Asp Lys Ala Tyr Lys Leu Leu Leu Asp Gln Glu Gln
    50                  55                  60

<210> SEQ ID NO 33
<211> LENGTH: 59
<212> TYPE: PRT
<213> ORGANISM: Homo sapiens

<400> SEQUENCE: 33

Asp Asp Ala Tyr Glu Val Leu Asn Leu Pro Gln Gly Gln Gly Pro His
1               5                   10                  15

Asp Glu Ser Lys Ile Arg Lys Ala Tyr Phe Arg Leu Ala Gln Lys Tyr
            20                  25                  30

His Pro Asp Lys Asn Pro Glu Gly Arg Asp Met Phe Glu Lys Val Asn
        35                  40                  45

Lys Ala Tyr Glu Phe Leu Cys Thr Lys Ser Ala
    50                  55

<210> SEQ ID NO 34
<211> LENGTH: 35
<212> TYPE: PRT
<213> ORGANISM: Homo sapiens

<400> SEQUENCE: 34

Arg Glu Ala Ala Leu Ile Leu Gly Val Ser Pro Thr Ala Asn Lys Gly
1               5                   10                  15

Lys Ile Arg Asp Ala His Arg Arg Ile Met Leu Leu Asn His Pro Asp
            20                  25                  30

Lys Gly Lys
        35

<210> SEQ ID NO 35
<211> LENGTH: 59
<212> TYPE: PRT
<213> ORGANISM: Homo sapiens

<400> SEQUENCE: 35

Glu Ser Leu Tyr His Val Leu Gly Leu Asp Lys Asn Ala Thr Ser Asp
1               5                   10                  15

Asp Ile Lys Lys Ser Tyr Arg Lys Leu Ala Leu Lys Tyr His Pro Asp
            20                  25                  30

Lys Asn Pro Asp Asn Pro Glu Ala Ala Asp Lys Phe Lys Glu Ile Asn
        35                  40                  45

```
Asn Ala His Ala Ile Leu Thr Asp Ala Thr Lys
    50                  55
```

<210> SEQ ID NO 36
<211> LENGTH: 59
<212> TYPE: PRT
<213> ORGANISM: Homo sapiens

<400> SEQUENCE: 36

```
Ser Thr Tyr Tyr Glu Leu Leu Gly Val His Pro Gly Ala Ser Thr Glu
1               5                   10                  15

Glu Val Lys Arg Ala Phe Phe Ser Lys Ser Lys Glu Leu His Pro Asp
            20                  25                  30

Arg Asp Pro Gly Asn Pro Ser Leu His Ser Arg Phe Val Glu Leu Ser
        35                  40                  45

Glu Ala Tyr Arg Val Leu Ser Arg Glu Gln Ser
    50                  55
```

<210> SEQ ID NO 37
<211> LENGTH: 65
<212> TYPE: PRT
<213> ORGANISM: Homo sapiens

<400> SEQUENCE: 37

```
Lys Asp Trp Tyr Ser Ile Leu Gly Ala Asp Pro Ser Ala Asn Ile Ser
1               5                   10                  15

Asp Leu Lys Gln Lys Tyr Gln Lys Leu Ile Leu Met Tyr His Pro Asp
            20                  25                  30

Lys Gln Ser Thr Asp Val Pro Ala Gly Thr Val Glu Cys Val Gln
        35                  40                  45

Lys Phe Ile Glu Ile Asp Gln Ala Trp Lys Ile Leu Gly Asn Glu Glu
    50                  55                  60

Thr
65
```

<210> SEQ ID NO 38
<211> LENGTH: 59
<212> TYPE: PRT
<213> ORGANISM: Homo sapiens

<400> SEQUENCE: 38

```
Met Asp Leu Tyr Ala Leu Leu Gly Ile Glu Glu Lys Ala Ala Asp Lys
1               5                   10                  15

Glu Val Lys Lys Ala Tyr Arg Gln Lys Ala Leu Ser Cys His Pro Asp
            20                  25                  30

Lys Asn Pro Asp Asn Pro Arg Ala Ala Glu Leu Phe His Gln Leu Ser
        35                  40                  45

Gln Ala Leu Glu Val Leu Thr Asp Ala Ala Ala
    50                  55
```

<210> SEQ ID NO 39
<211> LENGTH: 58
<212> TYPE: PRT
<213> ORGANISM: Homo sapiens

<400> SEQUENCE: 39

```
Lys Ser Tyr Tyr Asp Ile Leu Gly Val Pro Lys Ser Ala Ser Glu Arg
1               5                   10                  15

Gln Ile Lys Lys Ala Phe His Lys Leu Ala Met Lys Tyr His Pro Asp
            20                  25                  30
```

```
Lys Asn Lys Ser Pro Asp Ala Glu Ala Lys Phe Arg Glu Ile Ala Glu
            35                  40                  45

Gly Ala Ser Val Pro Ala Ala Ser Ser Phe
    50                  55

<210> SEQ ID NO 40
<211> LENGTH: 59
<212> TYPE: PRT
<213> ORGANISM: Homo sapiens

<400> SEQUENCE: 40

Ser Thr Tyr Tyr Glu Leu Leu Gly Val His Pro Gly Ala Ser Thr Glu
1               5                   10                  15

Glu Val Lys Arg Ala Phe Phe Ser Lys Ser Lys Glu Leu His Pro Asp
            20                  25                  30

Arg Asp Pro Gly Asn Pro Ser Leu His Ser Arg Phe Val Glu Leu Ser
        35                  40                  45

Glu Ala Tyr Arg Val Leu Ser Arg Glu Gln Ser
    50                  55

<210> SEQ ID NO 41
<211> LENGTH: 59
<212> TYPE: PRT
<213> ORGANISM: Homo sapiens

<400> SEQUENCE: 41

Ser Thr Tyr Tyr Glu Leu Leu Gly Val His Pro Gly Ala Ser Thr Glu
1               5                   10                  15

Glu Val Lys Arg Ala Phe Phe Ser Lys Ser Lys Glu Leu His Pro Asp
            20                  25                  30

Arg Asp Pro Gly Asn Pro Ser Leu His Ser Arg Phe Val Glu Leu Ser
        35                  40                  45

Glu Ala Tyr Arg Val Leu Ser Arg Glu Gln Ser
    50                  55

<210> SEQ ID NO 42
<211> LENGTH: 62
<212> TYPE: PRT
<213> ORGANISM: Homo sapiens

<400> SEQUENCE: 42

Glu Asp Tyr Tyr Ser Leu Leu Asn Val Arg Arg Glu Ala Ser Ser Glu
1               5                   10                  15

Glu Leu Lys Ala Ala Tyr Arg Arg Leu Cys Met Leu Tyr His Pro Asp
            20                  25                  30

Lys His Arg Asp Pro Glu Leu Lys Ser Gln Ala Glu Arg Leu Phe Asn
        35                  40                  45

Leu Val His Gln Ala Tyr Glu Val Leu Ser Asp Pro Gln Thr
    50                  55                  60

<210> SEQ ID NO 43
<211> LENGTH: 65
<212> TYPE: PRT
<213> ORGANISM: Homo sapiens

<400> SEQUENCE: 43

Lys Asp Trp Tyr Ser Ile Leu Gly Ala Asp Pro Ser Ala Asn Ile Ser
1               5                   10                  15

Asp Leu Lys Gln Lys Tyr Gln Lys Leu Ile Leu Met Tyr His Pro Asp
```

-continued

```
                    20                  25                  30

Lys Gln Ser Thr Asp Val Pro Ala Gly Thr Val Glu Glu Cys Val Gln
            35                  40                  45

Lys Phe Ile Glu Ile Asp Gln Ala Trp Lys Ile Leu Gly Asn Glu Glu
        50                  55                  60

Thr
 65

<210> SEQ ID NO 44
<211> LENGTH: 66
<212> TYPE: PRT
<213> ORGANISM: Homo sapiens

<400> SEQUENCE: 44

Arg Asp Tyr Phe Ser Leu Met Asp Cys Asn Arg Ser Phe Arg Val Asp
 1               5                  10                  15

Thr Ala Lys Leu Gln His Arg Tyr Gln Gln Leu Gln Arg Leu Val His
            20                  25                  30

Pro Asp Phe Phe Ser Gln Arg Ser Gln Thr Glu Lys Asp Phe Ser Glu
        35                  40                  45

Lys His Ser Thr Leu Val Asn Asp Ala Tyr Lys Thr Leu Leu Ala Pro
    50                  55                  60

Leu Ser
 65

<210> SEQ ID NO 45
<211> LENGTH: 69
<212> TYPE: PRT
<213> ORGANISM: Homo sapiens

<400> SEQUENCE: 45

Arg Asp Cys Tyr Glu Val Leu Gly Val Ser Arg Ser Ala Gly Lys Ala
 1               5                  10                  15

Glu Ile Ala Arg Ala Tyr Arg Gln Leu Ala Arg Arg Tyr His Pro Asp
            20                  25                  30

Arg Tyr Arg Pro Gln Pro Gly Asp Glu Gly Pro Gly Arg Thr Pro Gln
        35                  40                  45

Ser Ala Glu Glu Ala Phe Leu Leu Val Ala Thr Ala Tyr Glu Thr Leu
    50                  55                  60

Lys Asp Glu Glu Thr
 65

<210> SEQ ID NO 46
<211> LENGTH: 49
<212> TYPE: PRT
<213> ORGANISM: Homo sapiens

<400> SEQUENCE: 46

Thr Thr Tyr Tyr Asp Val Leu Gly Val Lys Pro Asn Ala Thr Gln Glu
 1               5                  10                  15

Glu Leu Lys Lys Ala Tyr Arg Lys Leu Ala Leu Lys Tyr His Pro Asp
            20                  25                  30

Lys Asn Pro Asn Glu Gly Glu Lys Val Lys Met Leu Tyr Ile Ser Ser
        35                  40                  45

Gln

<210> SEQ ID NO 47
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile, Leu, Val, Ala or Met
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: Any amino acid or absent
<220> FEATURE:
<221> NAME/KEY: MOD_RES
<222> LOCATION: (5)..(5)
<223> OTHER INFORMATION: Tyr, Trp or Phe
<220> FEATURE:
<221> NAME/KEY: MOD_RES
<222> LOCATION: (6)..(9)
<223> OTHER INFORMATION: Any amino acid or absent
<220> FEATURE:
<223> OTHER INFORMATION: See specification as filed for detailed
      description of substitutions and preferred embodiments

<400> SEQUENCE: 47

Xaa Xaa Xaa Xaa Xaa Xaa Xaa Xaa Xaa
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ile Lys Lys Ala Tyr Arg Lys Leu Ala
1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Lys Lys Ala Tyr Lys Leu Ala Leu Gln
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ile Lys Lys Ala Tyr Arg Leu Ala Leu Gln
1               5                   10

<210> SEQ ID NO 51
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Lys Lys Ala Tyr Arg Lys Ala Leu Gln
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Lys Lys Ala Tyr Arg Lys Leu Leu Gln
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ile Lys Lys Tyr Arg Lys Leu Ala
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Lys Lys Ala Tyr Lys Leu Ala
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Lys Lys Ala Tyr Arg Leu Ala
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Lys Lys Ala Tyr Arg Lys Ala
```

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Leu Lys Lys Ala Tyr Arg Lys Leu Ala
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Val Lys Lys Ala Tyr Arg Lys Leu Ala
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Met Lys Lys Ala Tyr Arg Lys Leu Ala
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Lys Lys Ala Tyr Arg Lys Leu Ala
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Ala Lys Ala Tyr Arg Lys Leu Ala
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 62

Ile Lys Ala Ala Tyr Arg Lys Leu Ala
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Lys Lys Arg Tyr Arg Lys Leu Ala
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Lys Lys Ser Tyr Arg Lys Leu Ala
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ile Lys Lys Gln Tyr Arg Lys Leu Ala
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Lys Lys Glu Tyr Arg Lys Leu Ala
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ile Lys Lys Phe Tyr Arg Lys Leu Ala
1               5

<210> SEQ ID NO 68

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Lys Lys Cys Tyr Arg Lys Leu Ala
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ile Lys Lys Ala Phe Arg Lys Leu Ala
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Lys Lys Ala Trp Arg Lys Leu Ala
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Lys Lys Ala Tyr Arg Lys Gln Ala
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Lys Lys Ala Tyr Arg Lys Met Ala
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73
```

```
Ile Lys Lys Ala Tyr Arg Lys Ile Ala
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Lys Lys Ala Tyr Arg Lys Ala Ala
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ile Lys Lys Ala Tyr Arg Lys Val Ala
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Lys Lys Ala Tyr Arg Lys Arg Ala
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ile Lys Lys Ala Tyr Arg Lys Leu Met
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Lys Lys Ala Tyr Arg Lys Leu Ile
1               5

<210> SEQ ID NO 79
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 79

Ile Lys Lys Ala Tyr Arg Lys Leu Val
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Lys Lys Ala Tyr Arg Lys Leu Cys
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ile Lys Lys Ala Tyr Arg Lys Leu Ser
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Lys Lys Ala Tyr Arg Lys Leu Tyr
1               5

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ile Arg Lys Ala Tyr Arg Lys Leu Ser Leu Thr Leu
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ile Lys Lys Gln Tyr Arg Leu Leu Ser Leu Lys Tyr
1               5                   10

```
<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ile Lys Lys Ala Phe His Lys Leu Ala Met Lys Tyr
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ile Arg Gln Ala Phe Lys Lys Leu Ala Leu Lys Leu
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ile Ile Lys Ala Tyr Arg Lys Leu Ala Leu Gln Trp
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ile Ala Arg Ala Tyr Arg Gln Leu Ala Arg Arg Tyr
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ile Lys Arg Ala Tyr Arg Arg Gln Ala Leu Arg Tyr
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90
```

```
Ile Lys Lys Ser Tyr Arg Lys Leu Ala Leu Lys Tyr
1               5                   10
```

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

```
Ile Lys Lys Ala Tyr Lys Arg Leu Ala Met Lys Tyr
1               5                   10
```

<210> SEQ ID NO 92
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Gly Arg Asp Phe Tyr Lys Ile Leu Gly Val Pro Arg Ser Ala Ser Ile
1               5                   10                  15

Lys Asp Ile Lys Lys Ala Tyr Arg Lys Leu Ala Leu Gln Leu His Pro
            20                  25                  30

Asp Arg Asn Pro Asp Asp Pro Gln Ala Gln Glu Lys Phe Gln Asp Leu
        35                  40                  45

Gly Ala Ala Tyr Glu Val Leu Ser Asp Ser Glu Lys Arg
    50                  55                  60
```

<210> SEQ ID NO 93
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

```
Ile Leu Gly Val Pro Arg Ser Ala Ser Ile Lys Asp Ile Lys Lys Ala
1               5                   10                  15

Tyr Arg Lys Leu Ala Leu Gln Leu His Pro Asp Arg Asn Pro Asp Asp
            20                  25                  30

Pro Gln Ala Gln Glu Lys Phe Gln Asp Leu Gly Ala Ala Tyr Glu Val
        35                  40                  45

Leu Ser Asp Ser Glu Lys Arg
    50                  55
```

<210> SEQ ID NO 94
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Ser Ala Ser Ile Lys Asp Ile Lys Lys Ala Tyr Arg Lys Leu Ala Leu
1               5                   10                  15

Gln Leu His Pro Asp Arg Asn Pro Asp Asp Pro Gln Ala Gln Glu Lys
```

```
                20                  25                  30
Phe Gln Asp Leu Gly Ala Ala Tyr Glu Val Leu Ser Asp Ser Glu Lys
        35                  40                  45
Arg

<210> SEQ ID NO 95
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gly Arg Asp Phe Tyr Lys Ile Leu Gly Val Pro Arg Ser Ala Ser Ile
1               5                   10                  15

Lys Asp Ile Lys Lys Ala Tyr Arg Lys Leu Ala Leu Gln Leu His Pro
            20                  25                  30

Asp Arg Asn Pro Asp Asp Pro Gln Ala Gln Glu Lys Phe Gln Asp Leu
        35                  40                  45

Gly

<210> SEQ ID NO 96
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ile Leu Gly Val Pro Arg Ser Ala Ser Ile Lys Asp Ile Lys Lys Ala
1               5                   10                  15

Tyr Arg Lys Leu Ala Leu Gln Leu His Pro Asp Arg Asn Pro Asp Asp
            20                  25                  30

Pro Gln Ala Gln Glu Lys Phe Gln Asp Leu Gly
        35                  40

<210> SEQ ID NO 97
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ser Ala Ser Ile Lys Asp Ile Lys Lys Ala Tyr Arg Lys Leu Ala Leu
1               5                   10                  15

Gln Leu His Pro Asp Arg Asn Pro Asp Asp Pro Gln Ala Gln Glu Lys
            20                  25                  30

Phe Gln Asp Leu Gly
        35

<210> SEQ ID NO 98
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98
```

-continued

```
Lys Ala Tyr Arg Lys Leu Ala Leu Gln Leu His Pro Asp Arg Asn Pro
1               5                   10                  15

Asp Asp Pro Gln Ala Gln Glu Lys Phe Gln Asp Leu Gly
            20                  25

<210> SEQ ID NO 99
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Lys Ala Tyr Arg Lys Leu Ala Leu Gln Leu His Pro Asp Arg Asn Pro
1               5                   10                  15

Asp Asp Pro Gln Ala Gln Glu Lys Phe Gln Asp Leu Gly Ala Ala Tyr
            20                  25                  30

Glu Val Leu Ser Asp Ser Glu Lys Arg
        35                  40

<210> SEQ ID NO 100
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Leu Gln Leu His Pro Asp Arg Asn Pro Asp Asp Pro Gln Ala Gln Glu
1               5                   10                  15

Lys Phe Gln Asp Leu Gly
            20

<210> SEQ ID NO 101
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Leu Gln Leu His Pro Asp Arg Asn Pro Asp Asp Pro Gln Ala Gln Glu
1               5                   10                  15

Lys Phe Gln Asp Leu Gly Ala Ala Tyr Glu Val Leu Ser Asp Ser Glu
            20                  25                  30

Lys Arg

<210> SEQ ID NO 102
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Ile Lys Asp Ile Lys Lys Ala Tyr Arg Lys Leu Ala Leu Gln Leu His
1               5                   10                  15

Pro Asp Arg Asn Pro Asp Asp Pro Gln Ala Gln Glu Lys Phe Gln Asp
            20                  25                  30
```

Leu Gly

<210> SEQ ID NO 103
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ser Ala Ser Ile Lys Asp Ile Lys Lys Ala Tyr Arg Lys Leu Ala Leu
1               5                   10                  15

Gln Leu His Pro Asp Arg Asn Pro Asp Asp Pro Gln Ala Gln Glu
            20                  25                  30

<210> SEQ ID NO 104
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ala Ser Ile Lys Asp Ile Lys Lys Ala Tyr Arg Lys Leu Ala Leu
1               5                   10                  15

Gln Leu His Pro Asp Arg Asn
            20

<210> SEQ ID NO 105
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Lys Asp Ile Lys Lys Ala Tyr Arg Lys Leu Ala Leu Gln Leu His
1               5                   10                  15

Pro Asp Arg Asn Pro Asp Asp Pro Gln Ala Gln Glu
            20                  25

<210> SEQ ID NO 106
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ile Lys Asp Ile Lys Lys Ala Tyr Arg Lys Leu Ala Leu Gln Leu His
1               5                   10                  15

Pro Asp Arg Asn
            20

<210> SEQ ID NO 107
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 107

Asp Ile Lys Lys Ala Tyr Arg Lys Leu Ala Leu Gln Leu His Pro Asp
1               5                   10                  15

Arg Asn Pro Asp Asp Pro Gln Ala Gln Glu
            20                  25

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Lys Asp Ile Lys Lys Ala Tyr Arg Lys Leu Ala Leu Gln Leu His
1               5                   10                  15

Pro Asp

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ile Lys Asp Ile Lys Lys Ala Tyr Arg Lys Leu Ala Leu Gln Leu
1               5                   10                  15

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Lys Pro Ile Pro Asn Pro Leu Leu Gly Leu Asp Ser Thr
1               5                   10

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Asp Tyr Lys Asp Asp Asp Asp Lys
1               5

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 112

His His His His His His
```

```
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Tyr Pro Tyr Asp Val Pro Asp Tyr Ala
1               5

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Glu Gln Lys Leu Ile Ser Glu Glu Asp Leu
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Tyr Thr Asp Ile Glu Met Asn Arg Leu Gly Lys
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Pro Glu Leu Ala Pro Glu Asp Pro Glu Asp
1               5                   10

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Ile Ala Ala Ala
1               5

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                             -continued
        peptide

<400> SEQUENCE: 118

Asp Ile Ala Ala Ala Leu Glu
1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Thr Gly Ser Glu Phe
1               5

<210> SEQ ID NO 120
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Ser Thr Lys
1

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Gly Gly Ser Gly Gly Ser Gly Gly Ser Gly Gly
1               5                   10

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Asp Ile Gly Gly Gly Ser Gly Gly Ser Gly Gly Ser Gly Gly Ala Ala
1               5                   10                  15

Ala

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Lys Thr Thr Pro Lys Leu Glu Glu Gly Glu Phe Ser Glu Ala Arg
1               5                   10                  15
```

```
<210> SEQ ID NO 124
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ala Lys Thr Thr Pro Lys Leu Glu Glu Gly Glu Phe Ser Glu Ala Arg
1               5                   10                  15

Val

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ala Lys Thr Thr Pro Lys Leu Gly Gly
1               5

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ser Ala Lys Thr Thr Pro Lys Leu Gly Gly
1               5                   10

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ser Ala Lys Thr Thr Pro
1               5

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Ala Asp Ala Ala Pro
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 129

Arg Ala Asp Ala Ala Pro Thr Val Ser
1               5

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Arg Ala Asp Ala Ala Ala Ala Gly Gly Pro Gly Ser
1               5                   10

<210> SEQ ID NO 131
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Arg Ala Asp Ala Ala Ala Ala Gly Gly Gly Gly Ser Gly Gly Gly Gly
1               5                   10                  15

Ser Gly Gly Gly Gly Ser Gly Gly Gly Gly Ser
            20                  25

<210> SEQ ID NO 132
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ser Ala Lys Thr Thr Pro Lys Leu Glu Glu Gly Glu Phe Ser Glu Ala
1               5                   10                  15

Arg Val

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Asp Ala Ala Pro
1               5

<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

```
Ala Asp Ala Ala Pro Thr Val Ser Ile Phe Pro Pro
1               5                   10
```

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

```
Thr Val Ala Ala Pro
1               5
```

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

```
Thr Val Ala Ala Pro Ser Val Phe Ile Phe Pro Pro
1               5                   10
```

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

```
Gln Pro Lys Ala Ala Pro
1               5
```

<210> SEQ ID NO 138
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

```
Gln Pro Lys Ala Ala Pro Ser Val Thr Leu Phe Pro Pro
1               5                   10
```

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

```
Ala Lys Thr Thr Pro Pro
1               5
```

<210> SEQ ID NO 140
<211> LENGTH: 13
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 140

Ala Lys Thr Thr Pro Pro Ser Val Thr Pro Leu Ala Pro
1               5                  10

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Lys Thr Thr Ala Pro
1               5

<210> SEQ ID NO 142
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Lys Thr Thr Ala Pro Ser Val Tyr Pro Leu Ala Pro
1               5                  10

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ala Ser Thr Lys Gly Pro
1               5

<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ala Ser Thr Lys Gly Pro Ser Val Phe Pro Leu Ala Pro
1               5                  10

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gly Gly Gly Ser Gly Gly Gly Ser Gly Gly Gly Gly Ser
1               5                  10                  15
```

```
<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Glu Asn Lys Val Glu Tyr Ala Pro Ala Leu Met Ala Leu Ser
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Pro Ala Lys Glu Leu Thr Pro Leu Lys Glu Ala Lys Val Ser
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly His Glu Ala Ala Ala Val Met Gln Val Gln Tyr Pro Ala Ser
1               5                   10                  15

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Gly Gly Gly Gly Gly Gly Pro
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Gly Gly Gly Gly Gly Gly Gly Pro
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151
```

```
Pro Ala Pro Asn Leu Leu Gly Gly Pro
1               5

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Pro Asn Leu Leu Gly Gly Pro
1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Gly Gly Gly Gly Gly Pro
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Pro Ala Pro Glu Leu Leu Gly Gly Pro
1               5

<210> SEQ ID NO 155
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Pro Thr Ile Ser Pro Ala Pro Asn Leu Leu Gly Gly Pro
1               5                   10

<210> SEQ ID NO 156
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Thr Val Ala Ala Asp Asp Asp Asp Lys Ser Val Phe Ile Val Pro Pro
1               5                   10                  15

<210> SEQ ID NO 157
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 157

Thr Val Asp Asp Asp Lys Ala Ala Pro
1               5                   10

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Leu Val Pro Arg Gly Ser Ala Ala Pro
1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Ser Thr Lys Gly Pro Ser Val
1               5

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Ser Thr Lys Gly Pro Ser Val Phe Pro
1               5                   10

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Thr Val Ala Ala Pro Ser Val
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Thr Val Ala Ala Pro Ser Val Phe Ile
1               5
```

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Asp Tyr Lys Asp Asp Asp Asp Lys
1               5

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ala Ser Asp Asp Asp Asp Lys Gly Gly Pro
1               5                   10

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ala Leu Val Pro Arg Gly Ser Gly Pro
1               5

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ala Ser Thr Asp Asp Asp Asp Lys Ser Val Phe Pro Leu Ala Pro
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Thr Val Ala Leu Val Pro Arg Gly Ser Val Phe Ile Phe Pro Pro
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 168

Ala Ser Thr Leu Val Pro Arg Gly Ser Val Phe Pro Leu Ala Pro
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Thr Val Ala Ala Asp Asp Asp Lys Ser Val Phe Ile Val Pro Pro
1               5                   10                  15

<210> SEQ ID NO 170
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Ser Thr Asp Asp Asp Lys Ser Val Phe Pro Leu Ala Pro
1               5                   10

<210> SEQ ID NO 171
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Leu Glu Val Leu Phe Gln Gly Pro
1               5

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Thr Val Ala Ala Leu Glu Val Leu Phe Gln Gly Pro Ala Pro
1               5                   10

<210> SEQ ID NO 173
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Ser Thr Leu Glu Val Leu Phe Gln Gly Pro Leu Ala Pro
1               5                   10

<210> SEQ ID NO 174
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 174

Pro Ala Pro Leu Glu Val Leu Phe Gln Gly Pro
1               5                   10

<210> SEQ ID NO 175
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Thr Ala Glu Asn Leu Tyr Phe Gln Gly Ala Pro
1               5                   10

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Glu Asn Leu Tyr Phe Gln Gly Ala
1               5

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Pro Gly Pro Phe Gly Arg Ser Ala Gly Gly Pro
1               5                   10

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Pro Gly Pro Phe Gly Arg Ser Ala Gly Gly
1               5                   10

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Pro Gln Arg Gly Arg Ser Ala Gly
1               5
```

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Pro His Tyr Gly Arg Ser Gly Gly
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Pro Phe Gly Arg Ser Ala Gly Pro
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Asp Asp Asp Asp Lys Gly Gly Pro
1               5

<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Gly Asp Asp Asp Asp Lys Gly Gly Pro
1               5                   10

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Gly Asp Asp Asp Asp Lys Gly Gly Pro
1               5                   10

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Glu Asn Leu Tyr Phe Gln Gly
1               5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Glu Asn Leu Tyr Phe Gln Ser
1               5

<210> SEQ ID NO 187
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
agcttggtac cggatccgaa ttcgatatcg cggccgctct cgagtctaga gggcc        55

<210> SEQ ID NO 188
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ctctagactc gagagcggcc gcgatatcga attcggatcc ggtacca              47

<210> SEQ ID NO 189
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
atgggtaagc ctatccctaa ccctctcctc ggtctcgatt ctacg                45

<210> SEQ ID NO 190
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
gattacaagg atgacgatga caag                                      24

<210> SEQ ID NO 191
<211> LENGTH: 36
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 191
ggaggcggaa gtggtgggag cggtggaagc ggaggc         36

<210> SEQ ID NO 192
<211> LENGTH: 419
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

```
Ser Lys Lys Thr Leu Leu Arg Phe Trp Leu Pro Phe Gly Phe Ile Leu
            340                 345                 350

Ile Leu Val Ile Phe Val Thr Gly Leu Leu Arg Lys Pro Asn Thr
            355                 360                 365

Tyr Pro Lys Met Ile Pro Glu Phe Phe Cys Asp Thr Gly Thr Gly Ser
            370                 375                 380

Glu Phe Asp Ile Ala Ala Ala Leu Glu Gly Lys Pro Ile Pro Asn Pro
385                 390                 395                 400

Leu Leu Gly Leu Asp Ser Thr Ser Arg Gly Pro Tyr Ser Ile Val Ser
            405                 410                 415

Pro Lys Cys

<210> SEQ ID NO 193
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Met Ala Phe Val Cys Leu Ala Ile Gly Cys Leu Tyr Thr Phe Leu Ile
1               5                   10                  15

Ser Thr Thr Phe Gly Cys Thr Ser Ser Ser Asp Thr Glu Ile Lys Val
            20                  25                  30

Asn Pro Pro Gln Asp Phe Glu Ile Val Asp Pro Gly Tyr Leu Gly Tyr
            35                  40                  45

Leu Tyr Leu Gln Trp Gln Pro Pro Leu Ser Leu Asp His Phe Lys Glu
50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
            85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
            130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
            165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
            195                 200                 205

Asp Phe Tyr Ile Cys Val Asn Gly Ser Ser Glu Asn Lys Pro Ile Arg
            210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
            245                 250                 255

Lys Trp Ser Ile Pro Leu Gly Pro Ile Pro Ala Arg Cys Phe Asp Tyr
            260                 265                 270
```

```
Glu Ile Glu Ile Arg Glu Asp Asp Thr Thr Leu Val Thr Ala Thr Val
            275                 280                 285

Glu Asn Glu Thr Tyr Thr Leu Lys Thr Thr Asn Glu Thr Arg Gln Leu
        290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Arg Lys Pro Asn Thr
            355                 360                 365

Tyr Pro Lys Met Ile Pro Glu Phe Phe Cys Asp Thr Gly Thr Gly Ser
        370                 375                 380

Glu Phe His Pro Gly Val Leu Lys Val Glu Ala Ile Leu Glu Lys Val
385                 390                 395                 400

Gln Gly Leu Glu Gln Ala Val Asp Asn Phe Glu Gly Lys Lys Thr Asp
                405                 410                 415

Lys Lys Tyr Leu Met Ile Glu Glu Tyr Leu Thr Lys Glu Leu Leu Ala
            420                 425                 430

Leu Asp Ser Val Asp Pro Glu Gly Arg Ala Asp Val Arg Gln Ala Arg
        435                 440                 445

Arg Asp Gly Val Arg Lys Val Gln Thr Ile Leu Glu Lys Leu Glu Gln
        450                 455                 460

Lys Ala Ile Asp Asp Ile Ala Ala Ala Leu Glu Gly Lys Pro Ile Pro
465                 470                 475                 480

Asn Pro Leu Leu Gly Leu Asp Ser Thr Ser Arg Gly Pro Tyr Ser Ile
                485                 490                 495

Val Ser Pro Lys Cys
            500

<210> SEQ ID NO 194
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
```

```
                115                 120                 125
Trp Ile Ser Pro Gln Gly Ile Pro Glu Thr Lys Val Gln Asp Met Asp
            130                 135                 140
Cys Val Tyr Tyr Asn Trp Gln Tyr Leu Leu Cys Ser Trp Lys Pro Gly
145                 150                 155                 160
Ile Gly Val Leu Leu Asp Thr Asn Tyr Asn Leu Phe Tyr Trp Tyr Glu
                165                 170                 175
Gly Leu Asp His Ala Leu Gln Cys Val Asp Tyr Ile Lys Ala Asp Gly
            180                 185                 190
Gln Asn Ile Gly Cys Arg Phe Pro Tyr Leu Glu Ala Ser Asp Tyr Lys
        195                 200                 205
Asp Phe Tyr Ile Cys Val Asn Gly Ser Ser Glu Asn Lys Pro Ile Arg
        210                 215                 220
Ser Ser Tyr Phe Thr Phe Gln Leu Gln Asn Ile Val Lys Pro Leu Pro
225                 230                 235                 240
Pro Val Tyr Leu Thr Phe Thr Arg Glu Ser Ser Cys Glu Ile Lys Leu
                245                 250                 255
Lys Trp Ser Ile Pro Leu Gly Pro Ile Pro Ala Arg Cys Phe Asp Tyr
            260                 265                 270
Glu Ile Glu Ile Arg Glu Asp Asp Thr Thr Leu Val Thr Ala Thr Val
        275                 280                 285
Glu Asn Glu Thr Tyr Thr Leu Lys Thr Thr Asn Glu Thr Arg Gln Leu
        290                 295                 300
Cys Phe Val Val Arg Ser Lys Val Asn Ile Tyr Cys Ser Asp Asp Gly
305                 310                 315                 320
Ile Trp Ser Glu Trp Ser Asp Lys Gln Cys Trp Gly Glu Asp Leu
                325                 330                 335
Ser Lys Lys Thr Leu Leu Arg Phe Trp Leu Pro Phe Gly Phe Ile Leu
            340                 345                 350
Ile Leu Val Ile Phe Val Thr Gly Leu Leu Leu Arg Lys Pro Asn Thr
        355                 360                 365
Tyr Pro Lys Met Ile Pro Glu Phe Phe Cys Asp Thr Gly Thr Gly Ser
        370                 375                 380
Glu Phe Glu Ser Thr Pro Pro Ser Ile Lys Lys Ile Ile His Val Leu
385                 390                 395                 400
Glu Lys Val Gln Tyr Leu Glu Gln Glu Val Glu Phe Val Gly Lys
                405                 410                 415
Lys Thr Asp Lys Ala Tyr Trp Leu Leu Glu Glu Met Leu Thr Lys Glu
            420                 425                 430
Leu Leu Glu Leu Asp Ser Val Glu Thr Gly Gly Gln Asp Ser Val Arg
        435                 440                 445
Gln Ala Arg Lys Glu Ala Val Cys Lys Ile Gln Ala Ile Leu Glu Lys
        450                 455                 460
Leu Glu Lys Lys Gly Leu Asp Ile Ala Ala Leu Glu Gly Lys Pro
465                 470                 475                 480
Ile Pro Asn Pro Leu Leu Gly Leu Asp Ser Thr Ser Arg Gly Pro Tyr
                485                 490                 495
Ser Ile Val Ser Pro Lys Cys
            500

<210> SEQ ID NO 195
<211> LENGTH: 502
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 195

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
            35                  40                  45

Leu Tyr Leu Gln Trp Gln Pro Pro Leu Ser Leu Asp His Phe Lys Glu
        50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
        130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
        355                 360                 365

Tyr Pro Lys Met Ile Pro Glu Phe Phe Cys Asp Thr Gly Thr Gly Ser
    370                 375                 380

Glu Phe Glu His Pro Ser His Lys Ala Val Trp Asn Val Leu Gly Asn

-continued

```
                385                 390                 395                 400
Leu Ser Glu Ile Gln Gly Glu Val Leu Ser Phe Asp Gly Asn Arg Thr
                    405                 410                 415
Asp Lys Asn Tyr Ile Arg Leu Glu Glu Leu Leu Thr Lys Gln Leu Leu
                    420                 425                 430
Ala Leu Asp Ala Val Asp Pro Gln Gly Glu Lys Cys Lys Ala Ala
                    435                 440                 445
Arg Lys Gln Ala Val Arg Leu Ala Gln Asn Ile Leu Ser Tyr Leu Asp
                    450                 455                 460
Leu Lys Ser Asp Glu Asp Ile Ala Ala Ala Leu Glu Gly Lys Pro Ile
465                 470                 475                 480
Pro Asn Pro Leu Leu Gly Leu Asp Ser Thr Ser Arg Gly Pro Tyr Ser
                    485                 490                 495
Ile Val Ser Pro Lys Cys
                500

<210> SEQ ID NO 196
<211> LENGTH: 506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Met Ala Phe Val Cys Leu Ala Ile Gly Cys Leu Tyr Thr Phe Leu Ile
1               5                   10                  15
Ser Thr Thr Phe Gly Cys Thr Ser Ser Ser Asp Thr Glu Ile Lys Val
                    20                  25                  30
Asn Pro Pro Gln Asp Phe Glu Ile Val Asp Pro Gly Tyr Leu Gly Tyr
                35                  40                  45
Leu Tyr Leu Gln Trp Gln Pro Pro Leu Ser Leu Asp His Phe Lys Glu
    50                  55                  60
Cys Thr Val Glu Tyr Glu Leu Lys Tyr Arg Asn Ile Gly Ser Glu Thr
65                  70                  75                  80
Trp Lys Thr Ile Ile Thr Lys Asn Leu His Tyr Lys Asp Gly Phe Asp
                    85                  90                  95
Leu Asn Lys Gly Ile Glu Ala Lys Ile His Thr Leu Leu Pro Trp Gln
                100                 105                 110
Cys Thr Asn Gly Ser Glu Val Gln Ser Ser Trp Ala Glu Thr Thr Tyr
            115                 120                 125
Trp Ile Ser Pro Gln Gly Ile Pro Glu Thr Lys Val Gln Asp Met Asp
    130                 135                 140
Cys Val Tyr Tyr Asn Trp Gln Tyr Leu Leu Cys Ser Trp Lys Pro Gly
145                 150                 155                 160
Ile Gly Val Leu Leu Asp Thr Asn Tyr Asn Leu Phe Tyr Trp Tyr Glu
                165                 170                 175
Gly Leu Asp His Ala Leu Gln Cys Val Asp Tyr Ile Lys Ala Asp Gly
                180                 185                 190
Gln Asn Ile Gly Cys Arg Phe Pro Tyr Leu Glu Ala Ser Asp Tyr Lys
            195                 200                 205
Asp Phe Tyr Ile Cys Val Asn Gly Ser Ser Glu Asn Lys Pro Ile Arg
    210                 215                 220
Ser Ser Tyr Phe Thr Phe Gln Leu Gln Asn Ile Val Lys Pro Leu Pro
225                 230                 235                 240
```

```
Pro Val Tyr Leu Thr Phe Thr Arg Glu Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
        355                 360                 365

Tyr Pro Lys Met Ile Pro Glu Phe Phe Cys Asp Thr Gly Thr Gly Ser
    370                 375                 380

Glu Phe Met Pro Ala Lys Arg Arg Lys Thr Met Gln Gly Glu Gly Pro
385                 390                 395                 400

Gln Leu Leu Leu Ser Glu Ala Val Ser Arg Ala Ala Lys Ala Ala Gly
                405                 410                 415

Ala Arg Pro Leu Thr Ser Pro Glu Ser Leu Ser Arg Asp Leu Glu Ala
            420                 425                 430

Pro Glu Val Gln Glu Ser Tyr Arg Gln Leu Arg Ser Asp Ile Gln
        435                 440                 445

Lys Arg Leu Gln Glu Asp Pro Asn Tyr Ser Pro Gln Arg Phe Pro Asn
450                 455                 460

Ala Gln Arg Ala Phe Ala Asp Asp Pro Asp Ile Ala Ala Ala Leu Glu
465                 470                 475                 480

Gly Lys Pro Ile Pro Asn Pro Leu Leu Gly Leu Asp Ser Thr Ser Arg
                485                 490                 495

Gly Pro Tyr Ser Ile Val Ser Pro Lys Cys
            500                 505

<210> SEQ ID NO 197
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95
```

```
Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
            165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
            195                 200                 205

Asp Phe Tyr Ile Cys Val Asn Gly Ser Ser Glu Asn Lys Pro Ile Arg
            210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
            245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
            275                 280                 285

Glu Asn Glu Thr Tyr Thr Leu Lys Thr Thr Asn Glu Thr Arg Gln Leu
            290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
            325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
            355                 360                 365

Tyr Pro Lys Met Ile Pro Glu Phe Phe Cys Asp Thr Gly Thr Gly Ser
            370                 375                 380

Glu Phe Met Gly Lys Asp Tyr Tyr Gln Thr Leu Gly Leu Ala Arg Gly
385                 390                 395                 400

Ala Ser Asp Glu Glu Ile Lys Arg Ala Tyr Arg Arg Gln Ala Leu Arg
            405                 410                 415

Tyr His Pro Asp Lys Asn Lys Glu Pro Gly Ala Glu Glu Lys Phe Lys
            420                 425                 430

Glu Ile Ala Glu Ala Tyr Asp Val Leu Ser Asp Pro Arg Lys Arg Glu
            435                 440                 445

Ile Phe Asp Arg Tyr Asp Ile Ala Ala Ala Leu Glu Gly Lys Pro Ile
            450                 455                 460

Pro Asn Pro Leu Leu Gly Leu Asp Ser Thr Ser Arg Gly Pro Tyr Ser
465                 470                 475                 480

Ile Val Ser Pro Lys Cys
            485
```

<210> SEQ ID NO 198
<211> LENGTH: 499

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 198

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
            35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
                100                 105                 110

Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
            195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
                260                 265                 270

Glu Ile Glu Ile Arg Glu Asp Asp Thr Thr Leu Val Thr Ala Thr Val
    275                 280                 285

Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
            355                 360                 365

Tyr Pro Lys Met Ile Pro Glu Phe Phe Cys Asp Thr Gly Thr Gly Ser
            370                 375                 380

```
Glu Phe Met Asp Lys Val Leu Asn Arg Glu Glu Ser Leu Gln Leu Met
385                 390                 395                 400

Asp Leu Leu Gly Leu Glu Arg Ser Ala Trp Gly Asn Ile Pro Leu Met
            405                 410                 415

Arg Lys Ala Tyr Leu Lys Lys Cys Lys Glu Phe His Pro Asp Lys Gly
            420                 425                 430

Gly Asp Glu Glu Lys Met Lys Lys Met Asn Thr Leu Tyr Lys Lys Met
            435                 440                 445

Glu Asp Gly Val Lys Tyr Ala His Gln Pro Asp Phe Gly Gly Phe Trp
            450                 455                 460

Asp Ala Asp Ile Ala Ala Ala Leu Glu Gly Lys Pro Ile Pro Asn Pro
465                 470                 475                 480

Leu Leu Gly Leu Asp Ser Thr Ser Arg Gly Pro Tyr Ser Ile Val Ser
            485                 490                 495

Pro Lys Cys

<210> SEQ ID NO 199
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
                20                  25                  30

Asn Pro Pro Gln Asp Phe Glu Ile Val Asp Pro Gly Tyr Leu Gly Tyr
            35                  40                  45

Leu Tyr Leu Gln Trp Gln Pro Pro Leu Ser Leu Asp His Phe Lys Glu
50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
            195                 200                 205

Asp Phe Tyr Ile Cys Val Asn Gly Ser Ser Glu Asn Lys Pro Ile Arg
        210                 215                 220

Ser Ser Tyr Phe Thr Phe Gln Leu Gln Asn Ile Val Lys Pro Leu Pro
225                 230                 235                 240
```

```
Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
            340                 345                 350

Ile Leu Val Ile Phe Val Thr Gly Leu Leu Leu Arg Lys Pro Asn Thr
        355                 360                 365

Tyr Pro Lys Met Ile Pro Glu Phe Phe Cys Asp Thr Gly Thr Gly Ser
    370                 375                 380

Glu Phe Met Ala Asp Gln Arg Gln Arg Ser Leu Ser Thr Ser Gly Glu
385                 390                 395                 400

Ser Leu Tyr His Val Leu Gly Leu Asp Lys Asn Ala Thr Ser Asp Asp
                405                 410                 415

Ile Lys Lys Ser Tyr Arg Lys Leu Ala Leu Lys Tyr His Pro Asp Lys
            420                 425                 430

Asn Pro Asp Asn Pro Glu Ala Ala Asp Lys Phe Lys Glu Ile Asn Asn
        435                 440                 445

Ala His Ala Ile Leu Thr Asp Ala Thr Lys Arg Asn Ile Tyr Asp Lys
    450                 455                 460

Tyr Gly Ser Leu Gly Leu Tyr Val Asp Ile Ala Ala Ala Leu Glu Gly
465                 470                 475                 480

Lys Pro Ile Pro Asn Pro Leu Leu Gly Leu Asp Ser Thr Ser Arg Gly
                485                 490                 495

Pro Tyr Ser Ile Val Ser Pro Lys Cys
            500                 505

<210> SEQ ID NO 200
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
```

85                  90                  95
Leu Asn Lys Gly Ile Glu Ala Lys Ile His Thr Leu Leu Pro Trp Gln
                100                 105                 110

Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
        130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
                180                 185                 190

Gln Asn Ile Gly Cys Arg Phe Pro Tyr Leu Glu Ala Ser Asp Tyr Lys
            195                 200                 205

Asp Phe Tyr Ile Cys Val Asn Gly Ser Ser Glu Asn Lys Pro Ile Arg
        210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
                260                 265                 270

Glu Ile Glu Ile Arg Glu Asp Asp Thr Thr Leu Val Thr Ala Thr Val
            275                 280                 285

Glu Asn Glu Thr Tyr Thr Leu Lys Thr Thr Asn Glu Thr Arg Gln Leu
        290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Gly Thr Gly Ser Glu Phe Asp Ile Ala Ala Ala Leu Glu
            340                 345                 350

Gly Lys Pro Ile Pro Asn Pro Leu Gly Leu Asp Ser Thr Ser Arg
        355                 360                 365

Gly Pro Tyr Ser Ile Val Ser Pro Lys Cys
        370                 375

<210> SEQ ID NO 201
<211> LENGTH: 430
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Asp Ile Ala Ala Ser Asp Thr Glu Ile Lys Val Asn
            85                  90                  95

Pro Pro Gln Asp Phe Glu Ile Val Asp Pro Gly Tyr Leu Gly Tyr Leu
            100                 105                 110

Tyr Leu Gln Trp Gln Pro Pro Leu Ser Leu Asp His Phe Lys Glu Cys
            115                 120                 125

Thr Val Glu Tyr Glu Leu Lys Tyr Arg Asn Ile Gly Ser Glu Thr Trp
130                 135                 140

Lys Thr Ile Ile Thr Lys Asn Leu His Tyr Lys Asp Gly Phe Asp Leu
145                 150                 155                 160

Asn Lys Gly Ile Glu Ala Lys Ile His Thr Leu Leu Pro Trp Gln Cys
            165                 170                 175

Thr Asn Gly Ser Glu Val Gln Ser Ser Trp Ala Glu Thr Thr Tyr Trp
            180                 185                 190

Ile Ser Pro Gln Gly Ile Pro Glu Thr Lys Val Gln Asp Met Asp Cys
            195                 200                 205

Val Tyr Tyr Asn Trp Gln Tyr Leu Leu Cys Ser Trp Lys Pro Gly Ile
210                 215                 220

Gly Val Leu Leu Asp Thr Asn Tyr Asn Leu Phe Tyr Trp Tyr Glu Gly
225                 230                 235                 240

Leu Asp His Ala Leu Gln Cys Val Asp Tyr Ile Lys Ala Asp Gly Gln
            245                 250                 255

Asn Ile Gly Cys Arg Phe Pro Tyr Leu Glu Ala Ser Asp Tyr Lys Asp
            260                 265                 270

Phe Tyr Ile Cys Val Asn Gly Ser Ser Glu Asn Lys Pro Ile Arg Ser
            275                 280                 285

Ser Tyr Phe Thr Phe Gln Leu Gln Asn Ile Val Lys Pro Leu Pro Pro
            290                 295                 300

Val Tyr Leu Thr Phe Thr Arg Glu Ser Ser Cys Glu Ile Lys Leu Lys
305                 310                 315                 320

Trp Ser Ile Pro Leu Gly Pro Ile Pro Ala Arg Cys Phe Asp Tyr Glu
            325                 330                 335

Ile Glu Ile Arg Glu Asp Asp Thr Thr Leu Val Thr Ala Thr Val Glu
            340                 345                 350

Asn Glu Thr Tyr Thr Leu Lys Thr Thr Asn Glu Thr Arg Gln Leu Cys
            355                 360                 365

Phe Val Val Arg Ser Lys Val Asn Ile Tyr Cys Ser Asp Asp Gly Ile
370                 375                 380

Trp Ser Glu Trp Ser Asp Lys Gln Cys Trp Glu Gly Glu Asp Leu Ser
385                 390                 395                 400

Lys Lys Leu Glu Gly Lys Pro Ile Pro Asn Pro Leu Leu Gly Leu Asp
            405                 410                 415

Ser Thr Ser Arg Gly Pro Tyr Ser Ile Val Ser Pro Lys Cys
            420                 425                 430

<210> SEQ ID NO 202
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

```
Met Gly Val Lys Val Leu Phe Ala Leu Ile Cys Ile Ala Val Ala Glu
1               5                   10                  15

Ala Gly Thr Gly Ser Glu Phe His Pro Gly Val Leu Lys Val Glu Ala
            20                  25                  30

Ile Leu Glu Lys Val Gln Gly Leu Glu Gln Ala Val Asp Asn Phe Glu
            35                  40                  45

Gly Lys Lys Thr Asp Lys Lys Tyr Leu Met Ile Glu Glu Tyr Leu Thr
50                  55                  60

Lys Glu Leu Leu Ala Leu Asp Ser Val Asp Pro Gly Gly Arg Ala Asp
65                  70                  75                  80

Val Arg Gln Ala Arg Arg Asp Gly Val Arg Lys Val Gln Thr Ile Leu
                85                  90                  95

Glu Lys Leu Glu Gln Lys Ala Ile Asp Asp Ile Ala Ala Ala Ser Asp
            100                 105                 110

Thr Glu Ile Lys Val Asn Pro Pro Gln Asp Phe Glu Ile Val Asp Pro
            115                 120                 125

Gly Tyr Leu Gly Tyr Leu Tyr Leu Gln Trp Gln Pro Pro Leu Ser Leu
130                 135                 140

Asp His Phe Lys Glu Cys Thr Val Glu Tyr Glu Leu Lys Tyr Arg Asn
145                 150                 155                 160

Ile Gly Ser Glu Thr Trp Lys Thr Ile Ile Thr Lys Asn Leu His Tyr
                165                 170                 175

Lys Asp Gly Phe Asp Leu Asn Lys Gly Ile Glu Ala Lys Ile His Thr
                180                 185                 190

Leu Leu Pro Trp Gln Cys Thr Asn Gly Ser Glu Val Gln Ser Ser Trp
            195                 200                 205

Ala Glu Thr Thr Tyr Trp Ile Ser Pro Gln Gly Ile Pro Glu Thr Lys
210                 215                 220

Val Gln Asp Met Asp Cys Val Tyr Tyr Asn Trp Gln Tyr Leu Leu Cys
225                 230                 235                 240

Ser Trp Lys Pro Gly Ile Gly Val Leu Leu Asp Thr Asn Tyr Asn Leu
                245                 250                 255

Phe Tyr Trp Tyr Glu Gly Leu Asp His Ala Leu Gln Cys Val Asp Tyr
            260                 265                 270

Ile Lys Ala Asp Gly Gln Asn Ile Gly Cys Arg Phe Pro Tyr Leu Glu
            275                 280                 285

Ala Ser Asp Tyr Lys Asp Phe Tyr Ile Cys Val Asn Gly Ser Ser Glu
290                 295                 300

Asn Lys Pro Ile Arg Ser Ser Tyr Phe Thr Phe Gln Leu Gln Asn Ile
305                 310                 315                 320

Val Lys Pro Leu Pro Pro Val Tyr Leu Thr Phe Thr Arg Glu Ser Ser
                325                 330                 335

Cys Glu Ile Lys Leu Lys Trp Ser Ile Pro Leu Gly Pro Ile Pro Ala
            340                 345                 350

Arg Cys Phe Asp Tyr Glu Ile Glu Ile Arg Glu Asp Thr Thr Leu
            355                 360                 365

Val Thr Ala Thr Val Glu Asn Glu Thr Tyr Thr Leu Lys Thr Asn
370                 375                 380

Glu Thr Arg Gln Leu Cys Phe Val Val Arg Ser Lys Val Asn Ile Tyr
385                 390                 395                 400

Cys Ser Asp Asp Gly Ile Trp Ser Glu Trp Ser Asp Lys Gln Cys Trp
                405                 410                 415
```

```
Glu Gly Glu Asp Leu Ser Lys Lys Leu Gly Lys Pro Ile Pro Asn
            420                 425                 430

Pro Leu Leu Gly Leu Asp Ser Thr Ser Arg Gly Pro Tyr Ser Ile Val
        435                 440                 445

Ser Pro Lys Cys
    450

<210> SEQ ID NO 203
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320
```

```
Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Gly Thr Gly Ser Glu Phe Asp Ile Ala Ala Ala Leu Glu Gly
            420                 425                 430

Lys Pro Ile Pro Asn Pro Leu Leu Gly Leu Asp Ser Thr Ser Arg Gly
        435                 440                 445

Pro Tyr Ser Ile Val Ser Pro Lys Cys
    450                 455

<210> SEQ ID NO 204
<211> LENGTH: 539
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
        115                 120                 125

Gln Pro Asp Ser Gln Leu Gln Leu Thr Thr Gly Asn Gly Leu Phe Leu
    130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
```

```
            210                 215                 220
Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
        290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Gly Thr Gly Ser Glu Phe His Pro Gly Val Leu Lys Val Glu
            420                 425                 430

Ala Ile Leu Glu Lys Val Gln Gly Leu Glu Gln Ala Val Asp Asn Phe
        435                 440                 445

Glu Gly Lys Lys Thr Asp Lys Lys Tyr Leu Met Ile Glu Glu Tyr Leu
450                 455                 460

Thr Lys Glu Leu Leu Ala Leu Asp Ser Val Asp Pro Glu Gly Arg Ala
465                 470                 475                 480

Asp Val Arg Gln Ala Arg Arg Asp Gly Val Arg Lys Val Gln Thr Ile
                485                 490                 495

Leu Glu Lys Leu Glu Gln Lys Ala Ile Asp Asp Ile Ala Ala Ala Leu
            500                 505                 510

Glu Gly Lys Pro Ile Pro Asn Pro Leu Leu Gly Leu Asp Ser Thr Ser
        515                 520                 525

Arg Gly Pro Tyr Ser Ile Val Ser Pro Lys Cys
530                 535

<210> SEQ ID NO 205
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30
```

```
Gln Lys Thr Asp Thr Ser His His Asp Gln Asp His Pro Thr Phe Asn
             35                  40                  45

Lys Ile Thr Pro Asn Leu Ala Glu Phe Ala Phe Ser Leu Tyr Arg Gln
 50                  55                  60

Leu Ala His Gln Ser Asn Ser Thr Asn Ile Phe Phe Ser Pro Val Ser
 65                  70                  75                  80

Ile Ala Thr Ala Phe Ala Met Leu Ser Leu Gly Thr Lys Ala Asp Thr
                 85                  90                  95

His Asp Glu Ile Leu Glu Gly Leu Asn Phe Asn Leu Thr Glu Ile Pro
                100                 105                 110

Glu Ala Gln Ile His Glu Gly Phe Gln Glu Leu Leu Arg Thr Leu Asn
                115                 120                 125

Gln Pro Asp Ser Gln Leu Gln Leu Thr Thr Gly Asn Gly Leu Phe Leu
130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
                180                 185                 190

Ile Val Asp Leu Val Lys Glu Leu Asp Arg Asp Thr Val Phe Ala Leu
                195                 200                 205

Val Asn Tyr Ile Phe Phe Lys Gly Lys Trp Glu Arg Pro Phe Glu Val
                210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
                275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Glu Lys Gly
                355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Gly Thr Gly Ser Glu Phe Gly Arg Asp Phe Tyr Lys Ile Leu
                420                 425                 430

Gly Val Pro Arg Ser Ala Ser Ile Lys Asp Ile Lys Lys Ala Tyr Arg
                435                 440                 445

Lys Leu Ala Leu Gln Leu His Pro Asp Arg Asn Pro Asp Asp Pro Gln
```

```
                450                 455                 460
Ala Gln Glu Lys Phe Gln Asp Leu Gly Ala Ala Tyr Glu Val Leu Ser
465                 470                 475                 480

Asp Ser Glu Lys Arg Asp Ile Ala Ala Ala Leu Glu Gly Lys Pro Ile
                485                 490                 495

Pro Asn Pro Leu Leu Gly Leu Asp Ser Thr Ser Arg Gly Pro Tyr Ser
                500                 505                 510

Ile Val Ser Pro Lys Cys
            515

<210> SEQ ID NO 206
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Gly Thr Gly Ser Glu Phe Asp Ile Ala Ala Ala Leu Glu
210                 215                 220

Gly Lys Pro Ile Pro Asn Pro Leu Leu Gly Leu Asp Ser Thr Ser Arg
225                 230                 235                 240

Gly Pro Tyr Ser Ile Val Ser Pro Lys Cys
                245                 250

<210> SEQ ID NO 207
<211> LENGTH: 311
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 207

Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Gly Thr Gly Ser Glu Phe Gly Arg Asp Phe Tyr Lys Ile
    210                 215                 220

Leu Gly Val Pro Arg Ser Ala Ser Ile Lys Asp Ile Lys Lys Ala Tyr
225                 230                 235                 240

Arg Lys Leu Ala Leu Gln Leu His Pro Asp Arg Asn Pro Asp Asp Pro
                245                 250                 255

Gln Ala Gln Glu Lys Phe Gln Asp Leu Gly Ala Ala Tyr Glu Val Leu
            260                 265                 270

Ser Asp Ser Glu Lys Arg Asp Ile Ala Ala Leu Glu Gly Lys Pro
        275                 280                 285

Ile Pro Asn Pro Leu Leu Gly Leu Asp Ser Thr Ser Arg Gly Pro Tyr
    290                 295                 300

Ser Ile Val Ser Pro Lys Cys
305                 310

<210> SEQ ID NO 208
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Met Gly Leu Ser Thr Val Pro Asp Leu Leu Pro Leu Val Leu Leu
1               5                   10                  15

-continued

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Gly Thr Gly Ser Glu Phe Asp Ile Ala Ala Ala Leu Glu
210                 215                 220

Gly Lys Pro Ile Pro Asn Pro Leu Leu Gly Leu Asp Ser Thr Ser Arg
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser

```
               435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 209
<211> LENGTH: 532
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Met Gly Leu Ser Thr Val Pro Asp Leu Leu Pro Leu Val Leu Leu
1               5                  10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Gly Thr Gly Ser Glu Phe Gly Arg Asp Phe Tyr Lys Ile
210                 215                 220

Leu Gly Val Pro Arg Ser Ala Ser Ile Lys Asp Ile Lys Lys Ala Tyr
225                 230                 235                 240

Arg Lys Leu Ala Leu Gln Leu His Pro Asp Arg Asn Pro Asp Asp Pro
                245                 250                 255

Gln Ala Gln Glu Lys Phe Gln Asp Leu Gly Ala Ala Tyr Glu Val Leu
            260                 265                 270

Ser Asp Ser Glu Lys Arg Asp Ile Ala Ala Leu Glu Gly Lys Pro
        275                 280                 285

Ile Pro Asn Pro Leu Leu Gly Leu Asp Ser Thr Ser Arg Pro Lys Ser
        290                 295                 300

Cys Asp Lys Thr His Thr Cys Pro Pro Cys Pro Ala Pro Glu Leu Leu
305                 310                 315                 320
```

Gly Gly Pro Ser Val Phe Leu Phe Pro Pro Lys Pro Lys Asp Thr Leu
            325                 330                 335

Met Ile Ser Arg Thr Pro Glu Val Thr Cys Val Val Val Asp Val Ser
            340                 345                 350

His Glu Asp Pro Glu Val Lys Phe Asn Trp Tyr Val Asp Gly Val Glu
            355                 360                 365

Val His Asn Ala Lys Thr Lys Pro Arg Glu Glu Gln Tyr Asn Ser Thr
        370                 375                 380

Tyr Arg Val Val Ser Val Leu Thr Val Leu His Gln Asp Trp Leu Asn
385                 390                 395                 400

Gly Lys Glu Tyr Lys Cys Lys Val Ser Asn Lys Ala Leu Pro Ala Pro
                405                 410                 415

Ile Glu Lys Thr Ile Ser Lys Ala Lys Gly Gln Pro Arg Glu Pro Gln
            420                 425                 430

Val Tyr Thr Leu Pro Pro Ser Arg Asp Glu Leu Thr Lys Asn Gln Val
        435                 440                 445

Ser Leu Thr Cys Leu Val Lys Gly Phe Tyr Pro Ser Asp Ile Ala Val
    450                 455                 460

Glu Trp Glu Ser Asn Gly Gln Pro Glu Asn Asn Tyr Lys Thr Thr Pro
465                 470                 475                 480

Pro Val Leu Asp Ser Asp Gly Ser Phe Phe Leu Tyr Ser Lys Leu Thr
                485                 490                 495

Val Asp Lys Ser Arg Trp Gln Gln Gly Asn Val Phe Ser Cys Ser Val
            500                 505                 510

Met His Glu Ala Leu His Asn His Tyr Thr Gln Lys Ser Leu Ser Leu
        515                 520                 525

Ser Pro Gly Lys
    530

<210> SEQ ID NO 210
<211> LENGTH: 599
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Met Ala Phe Val Cys Leu Ala Ile Gly Cys Leu Tyr Thr Phe Leu Ile
1               5                   10                  15

Ser Thr Thr Phe Gly Cys Thr Ser Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

```
Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Gly Glu Asp Leu
                325                 330                 335

Ser Lys Lys Gly Thr Gly Ser Glu Phe Asp Ile Ala Ala Ala Leu Glu
            340                 345                 350

Gly Lys Pro Ile Pro Asn Pro Leu Leu Gly Leu Asp Ser Thr Ser Arg
        355                 360                 365

Pro Lys Ser Cys Asp Lys Thr His Thr Cys Pro Pro Cys Pro Ala Pro
370                 375                 380

Glu Leu Leu Gly Gly Pro Ser Val Phe Leu Phe Pro Pro Lys Pro Lys
385                 390                 395                 400

Asp Thr Leu Met Ile Ser Arg Thr Pro Glu Val Thr Cys Val Val Val
                405                 410                 415

Asp Val Ser His Glu Asp Pro Glu Val Lys Phe Asn Trp Tyr Val Asp
            420                 425                 430

Gly Val Glu Val His Asn Ala Lys Thr Lys Pro Arg Glu Glu Gln Tyr
        435                 440                 445

Asn Ser Thr Tyr Arg Val Val Ser Val Leu Thr Val Leu His Gln Asp
    450                 455                 460

Trp Leu Asn Gly Lys Glu Tyr Lys Cys Lys Val Ser Asn Lys Ala Leu
465                 470                 475                 480

Pro Ala Pro Ile Glu Lys Thr Ile Ser Lys Ala Lys Gly Gln Pro Arg
                485                 490                 495

Glu Pro Gln Val Tyr Thr Leu Pro Pro Ser Arg Asp Glu Leu Thr Lys
            500                 505                 510

Asn Gln Val Ser Leu Thr Cys Leu Val Lys Gly Phe Tyr Pro Ser Asp
        515                 520                 525

Ile Ala Val Glu Trp Glu Ser Asn Gly Gln Pro Glu Asn Asn Tyr Lys
    530                 535                 540

Thr Thr Pro Pro Val Leu Asp Ser Asp Gly Ser Phe Phe Leu Tyr Ser
545                 550                 555                 560
```

```
Lys Leu Thr Val Asp Lys Ser Arg Trp Gln Gln Gly Asn Val Phe Ser
                565                 570                 575

Cys Ser Val Met His Glu Ala Leu His Asn His Tyr Thr Gln Lys Ser
            580                 585                 590

Leu Ser Leu Ser Pro Gly Lys
        595

<210> SEQ ID NO 211
<211> LENGTH: 660
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320
```

```
Ile Trp Ser Glu Trp Ser Asp Lys Gln Cys Trp Glu Gly Glu Asp Leu
            325                 330                 335

Ser Lys Lys Gly Thr Gly Ser Glu Phe Gly Arg Asp Phe Tyr Lys Ile
            340                 345                 350

Leu Gly Val Pro Arg Ser Ala Ser Ile Lys Asp Ile Lys Lys Ala Tyr
            355                 360                 365

Arg Lys Leu Ala Leu Gln Leu His Pro Asp Arg Asn Pro Asp Asp Pro
            370                 375                 380

Gln Ala Gln Glu Lys Phe Gln Asp Leu Gly Ala Ala Tyr Glu Val Leu
385                 390                 395                 400

Ser Asp Ser Glu Lys Arg Asp Ile Ala Ala Leu Glu Gly Lys Pro
            405                 410                 415

Ile Pro Asn Pro Leu Leu Gly Leu Asp Ser Thr Ser Arg Pro Lys Ser
            420                 425                 430

Cys Asp Lys Thr His Thr Cys Pro Pro Cys Pro Ala Pro Glu Leu Leu
            435                 440                 445

Gly Gly Pro Ser Val Phe Leu Phe Pro Pro Lys Pro Lys Asp Thr Leu
            450                 455                 460

Met Ile Ser Arg Thr Pro Glu Val Thr Cys Val Val Val Asp Val Ser
465                 470                 475                 480

His Glu Asp Pro Glu Val Lys Phe Asn Trp Tyr Val Asp Gly Val Glu
            485                 490                 495

Val His Asn Ala Lys Thr Lys Pro Arg Glu Glu Gln Tyr Asn Ser Thr
            500                 505                 510

Tyr Arg Val Val Ser Val Leu Thr Val Leu His Gln Asp Trp Leu Asn
            515                 520                 525

Gly Lys Glu Tyr Lys Cys Lys Val Ser Asn Lys Ala Leu Pro Ala Pro
            530                 535                 540

Ile Glu Lys Thr Ile Ser Lys Ala Lys Gly Gln Pro Arg Glu Pro Gln
545                 550                 555                 560

Val Tyr Thr Leu Pro Pro Ser Arg Asp Glu Leu Thr Lys Asn Gln Val
            565                 570                 575

Ser Leu Thr Cys Leu Val Lys Gly Phe Tyr Pro Ser Asp Ile Ala Val
            580                 585                 590

Glu Trp Glu Ser Asn Gly Gln Pro Glu Asn Asn Tyr Lys Thr Thr Pro
            595                 600                 605

Pro Val Leu Asp Ser Asp Gly Ser Phe Phe Leu Tyr Ser Lys Leu Thr
            610                 615                 620

Val Asp Lys Ser Arg Trp Gln Gln Gly Asn Val Phe Ser Cys Ser Val
625                 630                 635                 640

Met His Glu Ala Leu His Asn His Tyr Thr Gln Lys Ser Leu Ser Leu
            645                 650                 655

Ser Pro Gly Lys
            660

<210> SEQ ID NO 212
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Met Pro Ser Ser Val Ser Trp Gly Ile Leu Leu Leu Ala Gly Leu Cys
```

-continued

```
1               5                   10                  15
Cys Leu Val Pro Val Ser Leu Ala Glu Asp Pro Gln Gly Asp Ala Ala
            20                  25                  30
Gln Lys Thr Asp Thr Ser His His Asp Gln Asp His Pro Thr Phe Asn
            35                  40                  45
Lys Ile Thr Pro Asn Leu Ala Glu Phe Ala Phe Ser Leu Tyr Arg Gln
            50                  55                  60
Leu Ala His Gln Ser Asn Ser Thr Asn Ile Phe Phe Ser Pro Val Ser
65                  70                  75                  80
Ile Ala Thr Ala Phe Ala Met Leu Ser Leu Gly Thr Lys Ala Asp Thr
                85                  90                  95
His Asp Glu Ile Leu Glu Gly Leu Asn Phe Asn Leu Thr Glu Ile Pro
                100                 105                 110
Glu Ala Gln Ile His Glu Gly Phe Gln Glu Leu Leu Arg Thr Leu Asn
                115                 120                 125
Gln Pro Asp Ser Gln Leu Gln Leu Thr Thr Gly Asn Gly Leu Phe Leu
                130                 135                 140
Ser Glu Gly Leu Lys Leu Val Asp Lys Phe Leu Glu Asp Val Lys Lys
145                 150                 155                 160
Leu Tyr His Ser Glu Ala Phe Thr Val Asn Phe Gly Asp Thr Glu Glu
                165                 170                 175
Ala Lys Lys Gln Ile Asn Asp Tyr Val Glu Lys Gly Thr Gln Gly Lys
                180                 185                 190
Ile Val Asp Leu Val Lys Glu Leu Asp Arg Asp Thr Val Phe Ala Leu
                195                 200                 205
Val Asn Tyr Ile Phe Phe Lys Gly Lys Trp Glu Arg Pro Phe Glu Val
                210                 215                 220
Lys Asp Thr Glu Glu Asp Phe His Val Asp Gln Val Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
                260                 265                 270
Thr Ala Ile Phe Phe Leu Pro Asp Glu Gly Lys Leu Gln His Leu Glu
                275                 280                 285
Asn Glu Leu Thr His Asp Ile Ile Thr Lys Phe Leu Glu Asn Glu Asp
                290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
                340                 345                 350
Leu Ser Lys Ala Val His Lys Ala Val Leu Thr Ile Asp Glu Lys Gly
                355                 360                 365
Thr Glu Ala Ala Gly Ala Met Phe Leu Glu Ala Ile Pro Met Ser Ile
                370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys Gly Thr Gly Ser Glu Phe Asp Ile Ala Ala Ala Leu Glu Gly
                420                 425                 430
```

-continued

```
Lys Pro Ile Pro Asn Pro Leu Leu Gly Leu Asp Ser Thr Ser Arg Pro
            435                 440                 445

Lys Ser Cys Asp Lys Thr His Thr Cys Pro Pro Cys Pro Ala Pro Glu
        450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Asn
        515                 520                 525

Ser Thr Tyr Arg Val Val Ser Val Leu Thr Val Leu His Gln Asp Trp
    530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Asp Glu Leu Thr Lys Asn
            580                 585                 590

Gln Val Ser Leu Thr Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
        675

<210> SEQ ID NO 213
<211> LENGTH: 739
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
```

```
                100                 105                 110
Glu Ala Gln Ile His Glu Gly Phe Gln Glu Leu Leu Arg Thr Leu Asn
            115                 120                 125
Gln Pro Asp Ser Gln Leu Gln Leu Thr Thr Gly Asn Gly Leu Phe Leu
130                 135                 140
Ser Glu Gly Leu Lys Leu Val Asp Lys Phe Leu Glu Asp Val Lys Lys
145                 150                 155                 160
Leu Tyr His Ser Glu Ala Phe Thr Val Asn Phe Gly Asp Thr Glu Glu
                165                 170                 175
Ala Lys Lys Gln Ile Asn Asp Tyr Val Glu Lys Gly Thr Gln Gly Lys
            180                 185                 190
Ile Val Asp Leu Val Lys Glu Leu Asp Arg Asp Thr Val Phe Ala Leu
            195                 200                 205
Val Asn Tyr Ile Phe Phe Lys Gly Lys Trp Glu Arg Pro Phe Glu Val
        210                 215                 220
Lys Asp Thr Glu Glu Glu Asp Phe His Val Asp Gln Val Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
            260                 265                 270
Thr Ala Ile Phe Phe Leu Pro Asp Glu Gly Lys Leu Gln His Leu Glu
            275                 280                 285
Asn Glu Leu Thr His Asp Ile Ile Thr Lys Phe Leu Glu Asn Glu Asp
    290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
            340                 345                 350
Leu Ser Lys Ala Val His Lys Ala Val Leu Thr Ile Asp Glu Lys Gly
            355                 360                 365
Thr Glu Ala Ala Gly Ala Met Phe Leu Glu Ala Ile Pro Met Ser Ile
    370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys Gly Thr Gly Ser Glu Phe Gly Arg Asp Phe Tyr Lys Ile Leu
            420                 425                 430
Gly Val Pro Arg Ser Ala Ser Ile Lys Asp Ile Lys Lys Ala Tyr Arg
            435                 440                 445
Lys Leu Ala Leu Gln Leu His Pro Asp Arg Asn Pro Asp Asp Pro Gln
    450                 455                 460
Ala Gln Glu Lys Phe Gln Asp Leu Gly Ala Ala Tyr Glu Val Leu Ser
465                 470                 475                 480
Asp Ser Glu Lys Arg Asp Ile Ala Ala Ala Leu Glu Gly Lys Pro Ile
                485                 490                 495
Pro Asn Pro Leu Leu Gly Leu Asp Ser Thr Ser Arg Pro Lys Ser Cys
            500                 505                 510
Asp Lys Thr His Thr Cys Pro Pro Cys Pro Ala Pro Glu Leu Leu Gly
            515                 520                 525
```

Gly Pro Ser Val Phe Leu Phe Pro Lys Pro Lys Asp Thr Leu Met
        530                 535                 540

Ile Ser Arg Thr Pro Glu Val Thr Cys Val Val Val Asp Val Ser His
545                 550                 555                 560

Glu Asp Pro Glu Val Lys Phe Asn Trp Tyr Val Asp Gly Val Glu Val
                565                 570                 575

His Asn Ala Lys Thr Lys Pro Arg Glu Glu Gln Tyr Asn Ser Thr Tyr
            580                 585                 590

Arg Val Val Ser Val Leu Thr Val Leu His Gln Asp Trp Leu Asn Gly
        595                 600                 605

Lys Glu Tyr Lys Cys Lys Val Ser Asn Lys Ala Leu Pro Ala Pro Ile
    610                 615                 620

Glu Lys Thr Ile Ser Lys Ala Lys Gly Gln Pro Arg Glu Pro Gln Val
625                 630                 635                 640

Tyr Thr Leu Pro Pro Ser Arg Asp Glu Leu Thr Lys Asn Gln Val Ser
                645                 650                 655

Leu Thr Cys Leu Val Lys Gly Phe Tyr Pro Ser Asp Ile Ala Val Glu
            660                 665                 670

Trp Glu Ser Asn Gly Gln Pro Glu Asn Asn Tyr Lys Thr Thr Pro Pro
        675                 680                 685

Val Leu Asp Ser Asp Gly Ser Phe Phe Leu Tyr Ser Lys Leu Thr Val
    690                 695                 700

Asp Lys Ser Arg Trp Gln Gln Gly Asn Val Phe Ser Cys Ser Val Met
705                 710                 715                 720

His Glu Ala Leu His Asn His Tyr Thr Gln Lys Ser Leu Ser Leu Ser
                725                 730                 735

Pro Gly Lys

<210> SEQ ID NO 214
<211> LENGTH: 436
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Met Gly Lys Pro Ile Pro Asn Pro Leu Leu Gly Leu Asp Ser Thr Gly
1               5                   10                  15

Thr Gly Ser Glu Phe Asp Ile Ala Ala Ala Met Glu Glu Pro Gln Ser
            20                  25                  30

Asp Pro Ser Val Glu Pro Pro Leu Ser Gln Glu Thr Phe Ser Asp Leu
        35                  40                  45

Trp Lys Leu Leu Pro Glu Asn Asn Val Leu Ser Pro Leu Pro Ser Gln
    50                  55                  60

Ala Met Asp Asp Leu Met Leu Ser Pro Asp Asp Ile Glu Gln Trp Phe
65                  70                  75                  80

Thr Glu Asp Pro Gly Pro Asp Glu Ala Pro Arg Met Pro Glu Ala Ala
                85                  90                  95

Pro Pro Val Ala Pro Ala Pro Ala Ala Pro Thr Pro Ala Ala Pro Ala
            100                 105                 110

Pro Ala Pro Ser Trp Pro Leu Ser Ser Ser Val Pro Ser Gln Lys Thr
        115                 120                 125

Tyr Gln Gly Ser Tyr Gly Phe Arg Leu Gly Phe Leu His Ser Gly Thr
    130                 135                 140

Ala Lys Ser Val Thr Cys Thr Tyr Ser Pro Ala Leu Asn Lys Met Phe
145                 150                 155                 160

Cys Gln Leu Ala Lys Thr Cys Pro Val Gln Leu Trp Val Asp Ser Thr
            165                 170                 175

Pro Pro Pro Gly Thr Arg Val Arg Ala Met Ala Ile Tyr Lys Gln Ser
        180                 185                 190

Gln His Met Thr Glu Val Val Arg Arg Cys Pro His His Glu Arg Cys
    195                 200                 205

Ser Asp Ser Asp Gly Leu Ala Pro Pro Gln His Leu Ile Arg Val Glu
210                 215                 220

Gly Asn Leu Arg Val Glu Tyr Leu Asp Asp Arg Asn Thr Phe Arg His
225                 230                 235                 240

Ser Val Val Val Pro Tyr Glu Pro Pro Glu Val Gly Ser Asp Cys Thr
                245                 250                 255

Thr Ile His Tyr Asn Tyr Met Cys Asn Ser Ser Cys Met Gly Gly Met
            260                 265                 270

Asn Arg Arg Pro Ile Leu Thr Ile Ile Thr Leu Glu Asp Ser Ser Gly
        275                 280                 285

Asn Leu Leu Gly Arg Asn Ser Phe Glu Val Arg Val Cys Ala Cys Pro
    290                 295                 300

Gly Arg Asp Arg Arg Thr Glu Glu Asn Leu Arg Lys Lys Gly Glu
305                 310                 315                 320

Pro His His Glu Leu Pro Pro Gly Ser Thr Lys Arg Ala Leu Pro Asn
            325                 330                 335

Asn Thr Ser Ser Ser Pro Gln Pro Lys Lys Lys Pro Leu Asp Gly Glu
        340                 345                 350

Tyr Phe Thr Leu Gln Ile Arg Gly Arg Glu Arg Phe Glu Met Phe Arg
    355                 360                 365

Glu Leu Asn Glu Ala Leu Glu Leu Lys Asp Ala Gln Ala Gly Lys Glu
370                 375                 380

Pro Gly Gly Ser Arg Ala His Ser Ser His Leu Lys Ser Lys Lys Gly
385                 390                 395                 400

Gln Ser Thr Ser Arg His Lys Lys Leu Met Phe Lys Thr Glu Gly Pro
                405                 410                 415

Asp Ser Asp Ala Ala Ala Leu Glu Ser Arg Gly Pro Tyr Ser Ile Val
            420                 425                 430

Ser Pro Lys Cys
        435

<210> SEQ ID NO 215
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Met Gly Lys Pro Ile Pro Asn Pro Leu Leu Gly Leu Asp Ser Thr Gly
1               5                   10                  15

Thr Gly Ser Glu Phe Met Asp Lys Val Leu Asn Arg Glu Glu Ser Leu
            20                  25                  30

Gln Leu Met Asp Leu Leu Gly Leu Glu Arg Ser Ala Trp Gly Asn Ile
        35                  40                  45

Pro Leu Met Arg Lys Ala Tyr Leu Lys Lys Cys Lys Glu Phe His Pro

```
        50                  55                  60
Asp Lys Gly Gly Asp Glu Lys Met Lys Met Asn Thr Leu Tyr
 65                  70                  75                  80
Lys Lys Met Glu Asp Gly Val Lys Tyr Ala His Gln Pro Asp Phe Gly
                 85                  90                  95
Gly Phe Trp Asp Ala Asp Ile Ala Ala Met Glu Glu Pro Gln Ser
            100                 105                 110
Asp Pro Ser Val Glu Pro Pro Leu Ser Gln Glu Thr Phe Ser Asp Leu
            115                 120                 125
Trp Lys Leu Leu Pro Glu Asn Asn Val Leu Ser Pro Leu Pro Ser Gln
130                 135                 140
Ala Met Asp Asp Leu Met Leu Ser Pro Asp Asp Ile Glu Gln Trp Phe
145                 150                 155                 160
Thr Glu Asp Pro Gly Pro Asp Glu Ala Pro Arg Met Pro Glu Ala Ala
            165                 170                 175
Pro Pro Val Ala Pro Ala Pro Ala Ala Pro Thr Pro Ala Ala Pro Ala
            180                 185                 190
Pro Ala Pro Ser Trp Pro Leu Ser Ser Ser Val Pro Ser Gln Lys Thr
            195                 200                 205
Tyr Gln Gly Ser Tyr Gly Phe Arg Leu Gly Phe Leu His Ser Gly Thr
210                 215                 220
Ala Lys Ser Val Thr Cys Thr Tyr Ser Pro Ala Leu Asn Lys Met Phe
225                 230                 235                 240
Cys Gln Leu Ala Lys Thr Cys Pro Val Gln Leu Trp Val Asp Ser Thr
            245                 250                 255
Pro Pro Pro Gly Thr Arg Val Arg Ala Met Ala Ile Tyr Lys Gln Ser
            260                 265                 270
Gln His Met Thr Glu Val Val Arg Arg Cys Pro His His Glu Arg Cys
            275                 280                 285
Ser Asp Ser Asp Gly Leu Ala Pro Pro Gln His Leu Ile Arg Val Glu
            290                 295                 300
Gly Asn Leu Arg Val Glu Tyr Leu Asp Asp Arg Asn Thr Phe Arg His
305                 310                 315                 320
Ser Val Val Val Pro Tyr Glu Pro Pro Glu Val Gly Ser Asp Cys Thr
            325                 330                 335
Thr Ile His Tyr Asn Tyr Met Cys Asn Ser Ser Cys Met Gly Gly Met
            340                 345                 350
Asn Arg Arg Pro Ile Leu Thr Ile Ile Thr Leu Glu Asp Ser Ser Gly
            355                 360                 365
Asn Leu Leu Gly Arg Asn Ser Phe Glu Val Arg Val Cys Ala Cys Pro
370                 375                 380
Gly Arg Asp Arg Arg Thr Glu Glu Glu Asn Leu Arg Lys Lys Gly Glu
385                 390                 395                 400
Pro His His Glu Leu Pro Pro Gly Ser Thr Lys Arg Ala Leu Pro Asn
            405                 410                 415
Asn Thr Ser Ser Ser Pro Gln Pro Lys Lys Lys Pro Leu Asp Gly Glu
            420                 425                 430
Tyr Phe Thr Leu Gln Ile Arg Gly Arg Glu Arg Phe Glu Met Phe Arg
            435                 440                 445
Glu Leu Asn Glu Ala Leu Glu Leu Lys Asp Ala Gln Ala Gly Lys Glu
            450                 455                 460
Pro Gly Gly Ser Arg Ala His Ser Ser His Leu Lys Ser Lys Lys Gly
465                 470                 475                 480
```

Gln Ser Thr Ser Arg His Lys Lys Leu Met Phe Lys Thr Glu Gly Pro
            485                 490                 495

Asp Ser Asp Ala Ala Ala Leu Glu Ser Arg Gly Pro Tyr Ser Ile Val
        500                 505                 510

Ser Pro Lys Cys
        515

<210> SEQ ID NO 216
<211> LENGTH: 1506
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Met Gly Lys Pro Ile Pro Asn Pro Leu Leu Gly Leu Asp Ser Thr Gly
1               5                   10                  15

Thr Gly Ser Glu Phe Asp Ile Ala Ala Met Gln Arg Ser Pro Leu
            20                  25                  30

Glu Lys Ala Ser Val Val Ser Lys Leu Phe Phe Ser Trp Thr Arg Pro
        35                  40                  45

Ile Leu Arg Lys Gly Tyr Arg Gln Arg Leu Glu Leu Ser Asp Ile Tyr
50                  55                  60

Gln Ile Pro Ser Val Asp Ser Ala Asp Asn Leu Ser Glu Lys Leu Glu
65                  70                  75                  80

Arg Glu Trp Asp Arg Glu Leu Ala Ser Lys Lys Asn Pro Lys Leu Ile
                85                  90                  95

Asn Ala Leu Arg Arg Cys Phe Phe Trp Arg Phe Met Phe Tyr Gly Ile
            100                 105                 110

Phe Leu Tyr Leu Gly Glu Val Thr Lys Ala Val Gln Pro Leu Leu Leu
        115                 120                 125

Gly Arg Ile Ile Ala Ser Tyr Asp Pro Asp Asn Lys Glu Glu Arg Ser
    130                 135                 140

Ile Ala Ile Tyr Leu Gly Ile Gly Leu Cys Leu Leu Phe Ile Val Arg
145                 150                 155                 160

Thr Leu Leu Leu His Pro Ala Ile Phe Gly Leu His His Ile Gly Met
                165                 170                 175

Gln Met Arg Ile Ala Met Phe Ser Leu Ile Tyr Lys Lys Thr Leu Lys
            180                 185                 190

Leu Ser Ser Arg Val Leu Asp Lys Ile Ser Ile Gly Gln Leu Val Ser
        195                 200                 205

Leu Leu Ser Asn Asn Leu Asn Lys Phe Asp Glu Gly Leu Ala Leu Ala
    210                 215                 220

His Phe Val Trp Ile Ala Pro Leu Gln Val Ala Leu Leu Met Gly Leu
225                 230                 235                 240

Ile Trp Glu Leu Leu Gln Ala Ser Ala Phe Cys Gly Leu Gly Phe Leu
                245                 250                 255

Ile Val Leu Ala Leu Phe Gln Ala Gly Leu Gly Arg Met Met Met Lys
            260                 265                 270

Tyr Arg Asp Gln Arg Ala Gly Lys Ile Ser Glu Arg Leu Val Ile Thr
        275                 280                 285

Ser Glu Met Ile Glu Asn Ile Gln Ser Val Lys Ala Tyr Cys Trp Glu
    290                 295                 300

Glu Ala Met Glu Lys Met Ile Glu Asn Leu Arg Gln Thr Glu Leu Lys

```
305                 310                 315                 320
Leu Thr Arg Lys Ala Ala Tyr Val Arg Tyr Phe Asn Ser Ser Ala Phe
                325                 330                 335

Phe Phe Ser Gly Phe Val Val Phe Leu Ser Val Leu Pro Tyr Ala
                340                 345                 350

Leu Ile Lys Gly Ile Ile Leu Arg Lys Ile Phe Thr Thr Ile Ser Phe
                355                 360                 365

Cys Ile Val Leu Arg Met Ala Val Thr Arg Gln Phe Pro Trp Ala Val
                370                 375                 380

Gln Thr Trp Tyr Asp Ser Leu Gly Ala Ile Asn Lys Ile Gln Asp Phe
385                 390                 395                 400

Leu Gln Lys Gln Glu Tyr Lys Thr Leu Glu Tyr Asn Leu Thr Thr Thr
                405                 410                 415

Glu Val Val Met Glu Asn Val Thr Ala Phe Trp Glu Glu Gly Phe Gly
                420                 425                 430

Glu Leu Phe Glu Lys Ala Lys Gln Asn Asn Asn Arg Lys Thr Ser
                435                 440                 445

Asn Gly Asp Asp Ser Leu Phe Phe Ser Asn Phe Ser Leu Leu Gly Thr
                450                 455                 460

Pro Val Leu Lys Asp Ile Asn Phe Lys Ile Glu Arg Gly Gln Leu Leu
465                 470                 475                 480

Ala Val Ala Gly Ser Thr Gly Ala Gly Lys Thr Ser Leu Leu Met Val
                485                 490                 495

Ile Met Gly Glu Leu Glu Pro Ser Glu Gly Lys Ile Lys His Ser Gly
                500                 505                 510

Arg Ile Ser Phe Cys Ser Gln Phe Ser Trp Ile Met Pro Gly Thr Ile
                515                 520                 525

Lys Glu Asn Ile Ile Phe Gly Val Ser Tyr Asp Glu Tyr Arg Tyr Arg
                530                 535                 540

Ser Val Ile Lys Ala Cys Gln Leu Glu Glu Asp Ile Ser Lys Phe Ala
545                 550                 555                 560

Glu Lys Asp Asn Ile Val Leu Gly Glu Gly Gly Ile Thr Leu Ser Gly
                565                 570                 575

Gly Gln Arg Ala Arg Ile Ser Leu Ala Arg Ala Val Tyr Lys Asp Ala
                580                 585                 590

Asp Leu Tyr Leu Leu Asp Ser Pro Phe Gly Tyr Leu Asp Val Leu Thr
                595                 600                 605

Glu Lys Glu Ile Phe Glu Ser Cys Val Cys Lys Leu Met Ala Asn Lys
                610                 615                 620

Thr Arg Ile Leu Val Thr Ser Lys Met Glu His Leu Lys Lys Ala Asp
625                 630                 635                 640

Lys Ile Leu Ile Leu His Glu Gly Ser Ser Tyr Phe Tyr Gly Thr Phe
                645                 650                 655

Ser Glu Leu Gln Asn Leu Gln Pro Asp Phe Ser Ser Lys Leu Met Gly
                660                 665                 670

Cys Asp Ser Phe Asp Gln Phe Ser Ala Glu Arg Arg Asn Ser Ile Leu
                675                 680                 685

Thr Glu Thr Leu His Arg Phe Ser Leu Glu Gly Asp Ala Pro Val Ser
                690                 695                 700

Trp Thr Glu Thr Lys Lys Gln Ser Phe Lys Gln Thr Gly Glu Phe Gly
705                 710                 715                 720

Glu Lys Arg Lys Asn Ser Ile Leu Asn Pro Ile Asn Ser Ile Arg Lys
                725                 730                 735
```

```
Phe Ser Ile Val Gln Lys Thr Pro Leu Gln Met Asn Gly Ile Glu Glu
            740                 745                 750

Asp Ser Asp Glu Pro Leu Glu Arg Arg Leu Ser Leu Val Pro Asp Ser
            755                 760                 765

Glu Gln Gly Glu Ala Ile Leu Pro Arg Ile Ser Val Ile Ser Thr Gly
            770                 775                 780

Pro Thr Leu Gln Ala Arg Arg Arg Gln Ser Val Leu Asn Leu Met Thr
785                 790                 795                 800

His Ser Val Asn Gln Gly Gln Asn Ile His Arg Lys Thr Thr Ala Ser
            805                 810                 815

Thr Arg Lys Val Ser Leu Ala Pro Gln Ala Asn Leu Thr Glu Leu Asp
            820                 825                 830

Ile Tyr Ser Arg Arg Leu Ser Gln Glu Thr Gly Leu Glu Ile Ser Glu
            835                 840                 845

Glu Ile Asn Glu Glu Asp Leu Lys Glu Cys Phe Phe Asp Asp Met Glu
            850                 855                 860

Ser Ile Pro Ala Val Thr Thr Trp Asn Thr Tyr Leu Arg Tyr Ile Thr
865                 870                 875                 880

Val His Lys Ser Leu Ile Phe Val Leu Ile Trp Cys Leu Val Ile Phe
            885                 890                 895

Leu Ala Glu Val Ala Ala Ser Leu Val Val Leu Trp Leu Leu Gly Asn
            900                 905                 910

Thr Pro Leu Gln Asp Lys Gly Asn Ser Thr His Ser Arg Asn Asn Ser
            915                 920                 925

Tyr Ala Val Ile Ile Thr Ser Thr Ser Ser Tyr Tyr Val Phe Tyr Ile
            930                 935                 940

Tyr Val Gly Val Ala Asp Thr Leu Leu Ala Met Gly Phe Phe Arg Gly
945                 950                 955                 960

Leu Pro Leu Val His Thr Leu Ile Thr Val Ser Lys Ile Leu His His
            965                 970                 975

Lys Met Leu His Ser Val Leu Gln Ala Pro Met Ser Thr Leu Asn Thr
            980                 985                 990

Leu Lys Ala Gly Gly Ile Leu Asn Arg Phe Ser Lys Asp Ile Ala Ile
            995                1000                1005

Leu Asp Asp Leu Leu Pro Leu Thr Ile Phe Asp Phe Ile Gln Leu
    1010                1015                1020

Leu Leu Ile Val Ile Gly Ala Ile Ala Val Val Ala Val Leu Gln
    1025                1030                1035

Pro Tyr Ile Phe Val Ala Thr Val Pro Val Ile Val Ala Phe Ile
    1040                1045                1050

Met Leu Arg Ala Tyr Phe Leu Gln Thr Ser Gln Gln Leu Lys Gln
    1055                1060                1065

Leu Glu Ser Glu Gly Arg Ser Pro Ile Phe Thr His Leu Val Thr
    1070                1075                1080

Ser Leu Lys Gly Leu Trp Thr Leu Arg Ala Phe Gly Arg Gln Pro
    1085                1090                1095

Tyr Phe Glu Thr Leu Phe His Lys Ala Leu Asn Leu His Thr Ala
    1100                1105                1110

Asn Trp Phe Leu Tyr Leu Ser Thr Leu Arg Trp Phe Gln Met Arg
    1115                1120                1125

Ile Glu Met Ile Phe Val Ile Phe Phe Ile Ala Val Thr Phe Ile
    1130                1135                1140
```

Ser Ile Leu Thr Thr Gly Glu Gly Glu Gly Arg Val Gly Ile Ile
1145                     1150                1155

Leu Thr Leu Ala Met Asn Ile Met Ser Thr Leu Gln Trp Ala Val
1160                1165                1170

Asn Ser Ser Ile Asp Val Asp Ser Leu Met Arg Ser Val Ser Arg
1175                1180                1185

Val Phe Lys Phe Ile Asp Met Pro Thr Glu Gly Lys Pro Thr Lys
1190                1195                1200

Ser Thr Lys Pro Tyr Lys Asn Gly Gln Leu Ser Lys Val Met Ile
1205                1210                1215

Ile Glu Asn Ser His Val Lys Lys Asp Asp Ile Trp Pro Ser Gly
1220                1225                1230

Gly Gln Met Thr Val Lys Asp Leu Thr Ala Lys Tyr Thr Glu Gly
1235                1240                1245

Gly Asn Ala Ile Leu Glu Asn Ile Ser Phe Ser Ile Ser Pro Gly
1250                1255                1260

Gln Arg Val Gly Leu Leu Gly Arg Thr Gly Ser Gly Lys Ser Thr
1265                1270                1275

Leu Leu Ser Ala Phe Leu Arg Leu Leu Asn Thr Glu Gly Glu Ile
1280                1285                1290

Gln Ile Asp Gly Val Ser Trp Asp Ser Ile Thr Leu Gln Gln Trp
1295                1300                1305

Arg Lys Ala Phe Gly Val Ile Pro Gln Lys Val Phe Ile Phe Ser
1310                1315                1320

Gly Thr Phe Arg Lys Asn Leu Asp Pro Tyr Glu Gln Trp Ser Asp
1325                1330                1335

Gln Glu Ile Trp Lys Val Ala Asp Glu Val Gly Leu Arg Ser Val
1340                1345                1350

Ile Glu Gln Phe Pro Gly Lys Leu Asp Phe Val Leu Val Asp Gly
1355                1360                1365

Gly Cys Val Leu Ser His Gly His Lys Gln Leu Met Cys Leu Ala
1370                1375                1380

Arg Ser Val Leu Ser Lys Ala Lys Ile Leu Leu Leu Asp Glu Pro
1385                1390                1395

Ser Ala His Leu Asp Pro Val Thr Tyr Gln Ile Ile Arg Arg Thr
1400                1405                1410

Leu Lys Gln Ala Phe Ala Asp Cys Thr Val Ile Leu Cys Glu His
1415                1420                1425

Arg Ile Glu Ala Met Leu Glu Cys Gln Gln Phe Leu Val Ile Glu
1430                1435                1440

Glu Asn Lys Val Arg Gln Tyr Asp Ser Ile Gln Lys Leu Leu Asn
1445                1450                1455

Glu Arg Ser Leu Phe Arg Gln Ala Ile Ser Pro Ser Asp Arg Val
1460                1465                1470

Lys Leu Phe Pro His Arg Asn Ser Ser Lys Cys Lys Ser Lys Pro
1475                1480                1485

Gln Ile Ala Ala Leu Lys Glu Glu Thr Glu Glu Glu Val Gln Asp
1490                1495                1500

Thr Arg Leu
1505

<210> SEQ ID NO 217
<211> LENGTH: 1588
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 217

Met Gly Lys Pro Ile Pro Asn Pro Leu Leu Gly Leu Asp Ser Thr Gly
1               5                   10                  15

Thr Gly Ser Glu Phe His Pro Gly Val Leu Lys Val Glu Ala Ile Leu
            20                  25                  30

Glu Lys Val Gln Gly Leu Glu Gln Ala Val Asp Asn Phe Glu Gly Lys
        35                  40                  45

Lys Thr Asp Lys Lys Tyr Leu Met Ile Glu Glu Tyr Leu Thr Lys Glu
50                  55                  60

Leu Leu Ala Leu Asp Ser Val Asp Pro Glu Gly Arg Ala Asp Val Arg
65                  70                  75                  80

Gln Ala Arg Arg Asp Gly Val Arg Lys Val Gln Thr Ile Leu Glu Lys
                85                  90                  95

Leu Glu Gln Lys Ala Ile Asp Asp Ile Ala Ala Met Gln Arg Ser
            100                 105                 110

Pro Leu Glu Lys Ala Ser Val Val Ser Lys Leu Phe Phe Ser Trp Thr
            115                 120                 125

Arg Pro Ile Leu Arg Lys Gly Tyr Arg Gln Arg Leu Glu Leu Ser Asp
        130                 135                 140

Ile Tyr Gln Ile Pro Ser Val Asp Ser Ala Asp Asn Leu Ser Glu Lys
145                 150                 155                 160

Leu Glu Arg Glu Trp Asp Arg Glu Leu Ala Ser Lys Lys Asn Pro Lys
                165                 170                 175

Leu Ile Asn Ala Leu Arg Arg Cys Phe Phe Trp Arg Phe Met Phe Tyr
            180                 185                 190

Gly Ile Phe Leu Tyr Leu Gly Glu Val Thr Lys Ala Val Gln Pro Leu
        195                 200                 205

Leu Leu Gly Arg Ile Ile Ala Ser Tyr Asp Pro Asp Asn Lys Glu Glu
    210                 215                 220

Arg Ser Ile Ala Ile Tyr Leu Gly Ile Gly Leu Cys Leu Leu Phe Ile
225                 230                 235                 240

Val Arg Thr Leu Leu Leu His Pro Ala Ile Phe Gly Leu His Ile
                245                 250                 255

Gly Met Gln Met Arg Ile Ala Met Phe Ser Leu Ile Tyr Lys Lys Thr
            260                 265                 270

Leu Lys Leu Ser Ser Arg Val Leu Asp Lys Ile Ser Ile Gly Gln Leu
        275                 280                 285

Val Ser Leu Leu Ser Asn Asn Leu Asn Lys Phe Asp Glu Gly Leu Ala
    290                 295                 300

Leu Ala His Phe Val Trp Ile Ala Pro Leu Gln Val Ala Leu Leu Met
305                 310                 315                 320

Gly Leu Ile Trp Glu Leu Leu Gln Ala Ser Ala Phe Cys Gly Leu Gly
                325                 330                 335

Phe Leu Ile Val Leu Ala Leu Phe Gln Ala Gly Leu Gly Arg Met Met
            340                 345                 350

Met Lys Tyr Arg Asp Gln Arg Ala Gly Lys Ile Ser Glu Arg Leu Val
        355                 360                 365

Ile Thr Ser Glu Met Ile Glu Asn Ile Gln Ser Val Lys Ala Tyr Cys
370                 375                 380

```
Trp Glu Glu Ala Met Glu Lys Met Ile Glu Asn Leu Arg Gln Thr Glu
385                 390                 395                 400

Leu Lys Leu Thr Arg Lys Ala Ala Tyr Val Arg Tyr Phe Asn Ser Ser
            405                 410                 415

Ala Phe Phe Phe Ser Gly Phe Val Val Phe Leu Ser Val Leu Pro
        420                 425                 430

Tyr Ala Leu Ile Lys Gly Ile Ile Leu Arg Lys Ile Phe Thr Thr Ile
            435                 440                 445

Ser Phe Cys Ile Val Leu Arg Met Ala Val Thr Arg Gln Phe Pro Trp
    450                 455                 460

Ala Val Gln Thr Trp Tyr Asp Ser Leu Gly Ala Ile Asn Lys Ile Gln
465                 470                 475                 480

Asp Phe Leu Gln Lys Gln Glu Tyr Lys Thr Leu Glu Tyr Asn Leu Thr
            485                 490                 495

Thr Thr Glu Val Val Met Glu Asn Val Thr Ala Phe Trp Glu Glu Gly
            500                 505                 510

Phe Gly Glu Leu Phe Glu Lys Ala Lys Gln Asn Asn Asn Asn Arg Lys
        515                 520                 525

Thr Ser Asn Gly Asp Asp Ser Leu Phe Phe Ser Asn Phe Ser Leu Leu
    530                 535                 540

Gly Thr Pro Val Leu Lys Asp Ile Asn Phe Lys Ile Glu Arg Gly Gln
545                 550                 555                 560

Leu Leu Ala Val Ala Gly Ser Thr Gly Ala Gly Lys Thr Ser Leu Leu
            565                 570                 575

Met Val Ile Met Gly Glu Leu Glu Pro Ser Glu Gly Lys Ile Lys His
            580                 585                 590

Ser Gly Arg Ile Ser Phe Cys Ser Gln Phe Ser Trp Ile Met Pro Gly
    595                 600                 605

Thr Ile Lys Glu Asn Ile Ile Phe Gly Val Ser Tyr Asp Glu Tyr Arg
610                 615                 620

Tyr Arg Ser Val Ile Lys Ala Cys Gln Leu Glu Glu Asp Ile Ser Lys
625                 630                 635                 640

Phe Ala Glu Lys Asp Asn Ile Val Leu Gly Glu Gly Gly Ile Thr Leu
            645                 650                 655

Ser Gly Gly Gln Arg Ala Arg Ile Ser Leu Ala Arg Ala Val Tyr Lys
            660                 665                 670

Asp Ala Asp Leu Tyr Leu Leu Asp Ser Pro Phe Gly Tyr Leu Asp Val
            675                 680                 685

Leu Thr Glu Lys Glu Ile Phe Glu Ser Cys Val Cys Lys Leu Met Ala
    690                 695                 700

Asn Lys Thr Arg Ile Leu Val Thr Ser Lys Met Glu His Leu Lys Lys
705                 710                 715                 720

Ala Asp Lys Ile Leu Ile Leu His Glu Gly Ser Ser Tyr Phe Tyr Gly
            725                 730                 735

Thr Phe Ser Glu Leu Gln Asn Leu Gln Pro Asp Phe Ser Ser Lys Leu
            740                 745                 750

Met Gly Cys Asp Ser Phe Asp Gln Phe Ser Ala Glu Arg Arg Asn Ser
        755                 760                 765

Ile Leu Thr Glu Thr Leu His Arg Phe Ser Leu Glu Gly Asp Ala Pro
    770                 775                 780

Val Ser Trp Thr Glu Thr Lys Lys Gln Ser Phe Lys Gln Thr Gly Glu
785                 790                 795                 800

Phe Gly Glu Lys Arg Lys Asn Ser Ile Leu Asn Pro Ile Asn Ser Ile
```

```
                805                 810                 815
Arg Lys Phe Ser Ile Val Gln Lys Thr Pro Leu Gln Met Asn Gly Ile
                820                 825                 830
Glu Glu Asp Ser Asp Glu Pro Leu Glu Arg Arg Leu Ser Leu Val Pro
                835                 840                 845
Asp Ser Glu Gln Gly Glu Ala Ile Leu Pro Arg Ile Ser Val Ile Ser
                850                 855                 860
Thr Gly Pro Thr Leu Gln Ala Arg Arg Gln Ser Val Leu Asn Leu
865                 870                 875                 880
Met Thr His Ser Val Asn Gln Gly Gln Asn Ile His Arg Lys Thr Thr
                885                 890                 895
Ala Ser Thr Arg Lys Val Ser Leu Ala Pro Gln Ala Asn Leu Thr Glu
                900                 905                 910
Leu Asp Ile Tyr Ser Arg Arg Leu Ser Gln Glu Thr Gly Leu Glu Ile
                915                 920                 925
Ser Glu Glu Ile Asn Glu Glu Asp Leu Lys Glu Cys Phe Phe Asp Asp
                930                 935                 940
Met Glu Ser Ile Pro Ala Val Thr Thr Trp Asn Thr Tyr Leu Arg Tyr
945                 950                 955                 960
Ile Thr Val His Lys Ser Leu Ile Phe Val Leu Ile Trp Cys Leu Val
                965                 970                 975
Ile Phe Leu Ala Glu Val Ala Ala Ser Leu Val Val Leu Trp Leu Leu
                980                 985                 990
Gly Asn Thr Pro Leu Gln Asp Lys Gly Asn Ser Thr His Ser Arg Asn
                995                1000                1005
Asn Ser Tyr Ala Val Ile Ile Thr Ser Thr Ser Ser Tyr Tyr Val
                1010                1015                1020
Phe Tyr Ile Tyr Val Gly Val Ala Asp Thr Leu Leu Ala Met Gly
                1025                1030                1035
Phe Phe Arg Gly Leu Pro Leu Val His Thr Leu Ile Thr Val Ser
                1040                1045                1050
Lys Ile Leu His His Lys Met Leu His Ser Val Leu Gln Ala Pro
                1055                1060                1065
Met Ser Thr Leu Asn Thr Leu Lys Ala Gly Gly Ile Leu Asn Arg
                1070                1075                1080
Phe Ser Lys Asp Ile Ala Ile Leu Asp Asp Leu Leu Pro Leu Thr
                1085                1090                1095
Ile Phe Asp Phe Ile Gln Leu Leu Leu Ile Val Ile Gly Ala Ile
                1100                1105                1110
Ala Val Val Ala Val Leu Gln Pro Tyr Ile Phe Val Ala Thr Val
                1115                1120                1125
Pro Val Ile Val Ala Phe Ile Met Leu Arg Ala Tyr Phe Leu Gln
                1130                1135                1140
Thr Ser Gln Gln Leu Lys Gln Leu Glu Ser Glu Gly Arg Ser Pro
                1145                1150                1155
Ile Phe Thr His Leu Val Thr Ser Leu Lys Gly Leu Trp Thr Leu
                1160                1165                1170
Arg Ala Phe Gly Arg Gln Pro Tyr Phe Glu Thr Leu Phe His Lys
                1175                1180                1185
Ala Leu Asn Leu His Thr Ala Asn Trp Phe Leu Tyr Leu Ser Thr
                1190                1195                1200
Leu Arg Trp Phe Gln Met Arg Ile Glu Met Ile Phe Val Ile Phe
                1205                1210                1215
```

```
Phe Ile Ala Val Thr Phe Ile Ser Ile Leu Thr Thr Gly Glu Gly
    1220                1225                1230

Glu Gly Arg Val Gly Ile Ile Leu Thr Leu Ala Met Asn Ile Met
    1235                1240                1245

Ser Thr Leu Gln Trp Ala Val Asn Ser Ser Ile Asp Val Asp Ser
    1250                1255                1260

Leu Met Arg Ser Val Ser Arg Val Phe Lys Phe Ile Asp Met Pro
    1265                1270                1275

Thr Glu Gly Lys Pro Thr Lys Ser Thr Lys Pro Tyr Lys Asn Gly
    1280                1285                1290

Gln Leu Ser Lys Val Met Ile Ile Glu Asn Ser His Val Lys Lys
    1295                1300                1305

Asp Asp Ile Trp Pro Ser Gly Gly Gln Met Thr Val Lys Asp Leu
    1310                1315                1320

Thr Ala Lys Tyr Thr Glu Gly Gly Asn Ala Ile Leu Glu Asn Ile
    1325                1330                1335

Ser Phe Ser Ile Ser Pro Gly Gln Arg Val Gly Leu Leu Gly Arg
    1340                1345                1350

Thr Gly Ser Gly Lys Ser Thr Leu Leu Ser Ala Phe Leu Arg Leu
    1355                1360                1365

Leu Asn Thr Glu Gly Glu Ile Gln Ile Asp Gly Val Ser Trp Asp
    1370                1375                1380

Ser Ile Thr Leu Gln Gln Trp Arg Lys Ala Phe Gly Val Ile Pro
    1385                1390                1395

Gln Lys Val Phe Ile Phe Ser Gly Thr Phe Arg Lys Asn Leu Asp
    1400                1405                1410

Pro Tyr Glu Gln Trp Ser Asp Gln Glu Ile Trp Lys Val Ala Asp
    1415                1420                1425

Glu Val Gly Leu Arg Ser Val Ile Glu Gln Phe Pro Gly Lys Leu
    1430                1435                1440

Asp Phe Val Leu Val Asp Gly Gly Cys Val Leu Ser His Gly His
    1445                1450                1455

Lys Gln Leu Met Cys Leu Ala Arg Ser Val Leu Ser Lys Ala Lys
    1460                1465                1470

Ile Leu Leu Leu Asp Glu Pro Ser Ala His Leu Asp Pro Val Thr
    1475                1480                1485

Tyr Gln Ile Ile Arg Arg Thr Leu Lys Gln Ala Phe Ala Asp Cys
    1490                1495                1500

Thr Val Ile Leu Cys Glu His Arg Ile Glu Ala Met Leu Glu Cys
    1505                1510                1515

Gln Gln Phe Leu Val Ile Glu Glu Asn Lys Val Arg Gln Tyr Asp
    1520                1525                1530

Ser Ile Gln Lys Leu Leu Asn Glu Arg Ser Leu Phe Arg Gln Ala
    1535                1540                1545

Ile Ser Pro Ser Asp Arg Val Lys Leu Phe Pro His Arg Asn Ser
    1550                1555                1560

Ser Lys Cys Lys Ser Lys Pro Gln Ile Ala Ala Leu Lys Glu Glu
    1565                1570                1575

Thr Glu Glu Glu Val Gln Asp Thr Arg Leu
    1580                1585
```

<210> SEQ ID NO 218
<211> LENGTH: 1586

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 218

```
Met Gly Lys Pro Ile Pro Asn Pro Leu Leu Gly Leu Asp Ser Thr Gly
1               5                   10                  15

Thr Gly Ser Glu Phe Met Asp Lys Val Leu Asn Arg Glu Glu Ser Leu
            20                  25                  30

Gln Leu Met Asp Leu Leu Gly Leu Glu Arg Ser Ala Trp Gly Asn Ile
        35                  40                  45

Pro Leu Met Arg Lys Ala Tyr Leu Lys Lys Cys Lys Glu Phe His Pro
    50                  55                  60

Asp Lys Gly Gly Asp Glu Glu Lys Met Lys Met Asn Thr Leu Tyr
65                  70                  75                  80

Lys Lys Met Glu Asp Gly Val Lys Tyr Ala His Gln Pro Asp Phe Gly
                85                  90                  95

Gly Phe Trp Asp Ala Asp Ile Ala Ala Met Gln Arg Ser Pro Leu
            100                 105                 110

Glu Lys Ala Ser Val Val Ser Lys Leu Phe Phe Ser Trp Thr Arg Pro
        115                 120                 125

Ile Leu Arg Lys Gly Tyr Arg Gln Arg Leu Glu Leu Ser Asp Ile Tyr
130                 135                 140

Gln Ile Pro Ser Val Asp Ser Ala Asp Asn Leu Ser Glu Lys Leu Glu
145                 150                 155                 160

Arg Glu Trp Asp Arg Glu Leu Ala Ser Lys Lys Asn Pro Lys Leu Ile
                165                 170                 175

Asn Ala Leu Arg Arg Cys Phe Phe Trp Arg Phe Met Phe Tyr Gly Ile
            180                 185                 190

Phe Leu Tyr Leu Gly Glu Val Thr Lys Ala Val Gln Pro Leu Leu Leu
        195                 200                 205

Gly Arg Ile Ile Ala Ser Tyr Asp Pro Asp Asn Lys Glu Glu Arg Ser
    210                 215                 220

Ile Ala Ile Tyr Leu Gly Ile Gly Leu Cys Leu Leu Phe Ile Val Arg
225                 230                 235                 240

Thr Leu Leu Leu His Pro Ala Ile Phe Gly Leu His His Ile Gly Met
                245                 250                 255

Gln Met Arg Ile Ala Met Phe Ser Leu Ile Tyr Lys Lys Thr Leu Lys
            260                 265                 270

Leu Ser Ser Arg Val Leu Asp Lys Ile Ser Ile Gly Gln Leu Val Ser
        275                 280                 285

Leu Leu Ser Asn Asn Leu Asn Lys Phe Asp Glu Gly Leu Ala Leu Ala
    290                 295                 300

His Phe Val Trp Ile Ala Pro Leu Gln Val Ala Leu Leu Met Gly Leu
305                 310                 315                 320

Ile Trp Glu Leu Leu Gln Ala Ser Ala Phe Cys Gly Leu Gly Phe Leu
                325                 330                 335

Ile Val Leu Ala Leu Phe Gln Ala Gly Leu Gly Arg Met Met Met Lys
            340                 345                 350

Tyr Arg Asp Gln Arg Ala Gly Lys Ile Ser Glu Arg Leu Val Ile Thr
        355                 360                 365

Ser Glu Met Ile Glu Asn Ile Gln Ser Val Lys Ala Tyr Cys Trp Glu
    370                 375                 380
```

```
Glu Ala Met Glu Lys Met Ile Glu Asn Leu Arg Gln Thr Glu Leu Lys
385                 390                 395                 400

Leu Thr Arg Lys Ala Ala Tyr Val Arg Tyr Phe Asn Ser Ser Ala Phe
            405                 410                 415

Phe Phe Ser Gly Phe Phe Val Val Phe Leu Ser Val Leu Pro Tyr Ala
            420                 425                 430

Leu Ile Lys Gly Ile Ile Leu Arg Lys Ile Phe Thr Thr Ile Ser Phe
            435                 440                 445

Cys Ile Val Leu Arg Met Ala Val Thr Arg Gln Phe Pro Trp Ala Val
450                 455                 460

Gln Thr Trp Tyr Asp Ser Leu Gly Ala Ile Asn Lys Ile Gln Asp Phe
465                 470                 475                 480

Leu Gln Lys Gln Glu Tyr Lys Thr Leu Glu Tyr Asn Leu Thr Thr Thr
                485                 490                 495

Glu Val Val Met Glu Asn Val Thr Ala Phe Trp Glu Gly Phe Gly
                500                 505                 510

Glu Leu Phe Glu Lys Ala Lys Gln Asn Asn Asn Asn Arg Lys Thr Ser
            515                 520                 525

Asn Gly Asp Asp Ser Leu Phe Phe Ser Asn Phe Ser Leu Leu Gly Thr
530                 535                 540

Pro Val Leu Lys Asp Ile Asn Phe Lys Ile Glu Arg Gly Gln Leu Leu
545                 550                 555                 560

Ala Val Ala Gly Ser Thr Gly Ala Gly Lys Thr Ser Leu Leu Met Val
            565                 570                 575

Ile Met Gly Glu Leu Glu Pro Ser Glu Gly Lys Ile Lys His Ser Gly
            580                 585                 590

Arg Ile Ser Phe Cys Ser Gln Phe Ser Trp Ile Met Pro Gly Thr Ile
            595                 600                 605

Lys Glu Asn Ile Ile Phe Gly Val Ser Tyr Asp Glu Tyr Arg Tyr Arg
610                 615                 620

Ser Val Ile Lys Ala Cys Gln Leu Glu Glu Asp Ile Ser Lys Phe Ala
625                 630                 635                 640

Glu Lys Asp Asn Ile Val Leu Gly Glu Gly Gly Ile Thr Leu Ser Gly
            645                 650                 655

Gly Gln Arg Ala Arg Ile Ser Leu Ala Arg Ala Val Tyr Lys Asp Ala
            660                 665                 670

Asp Leu Tyr Leu Leu Asp Ser Pro Phe Gly Tyr Leu Asp Val Leu Thr
            675                 680                 685

Glu Lys Glu Ile Phe Glu Ser Cys Val Cys Lys Leu Met Ala Asn Lys
            690                 695                 700

Thr Arg Ile Leu Val Thr Ser Lys Met Glu His Leu Lys Lys Ala Asp
705                 710                 715                 720

Lys Ile Leu Ile Leu His Glu Gly Ser Ser Tyr Phe Tyr Gly Thr Phe
            725                 730                 735

Ser Glu Leu Gln Asn Leu Gln Pro Asp Phe Ser Ser Lys Leu Met Gly
            740                 745                 750

Cys Asp Ser Phe Asp Gln Phe Ser Ala Glu Arg Arg Asn Ser Ile Leu
            755                 760                 765

Thr Glu Thr Leu His Arg Phe Ser Leu Glu Gly Asp Ala Pro Val Ser
            770                 775                 780

Trp Thr Glu Thr Lys Lys Gln Ser Phe Lys Gln Thr Gly Glu Phe Gly
785                 790                 795                 800
```

```
Glu Lys Arg Lys Asn Ser Ile Leu Asn Pro Ile Asn Ser Ile Arg Lys
                805                 810                 815

Phe Ser Ile Val Gln Lys Thr Pro Leu Gln Met Asn Gly Ile Glu Glu
        820                 825                 830

Asp Ser Asp Glu Pro Leu Glu Arg Arg Leu Ser Leu Val Pro Asp Ser
    835                 840                 845

Glu Gln Gly Glu Ala Ile Leu Pro Arg Ile Ser Val Ile Ser Thr Gly
850                 855                 860

Pro Thr Leu Gln Ala Arg Arg Gln Ser Val Leu Asn Leu Met Thr
865                 870                 875                 880

His Ser Val Asn Gln Gly Gln Asn Ile His Arg Lys Thr Thr Ala Ser
            885                 890                 895

Thr Arg Lys Val Ser Leu Ala Pro Gln Ala Asn Leu Thr Glu Leu Asp
        900                 905                 910

Ile Tyr Ser Arg Arg Leu Ser Gln Glu Thr Gly Leu Glu Ile Ser Glu
    915                 920                 925

Glu Ile Asn Glu Glu Asp Leu Lys Glu Cys Phe Phe Asp Asp Met Glu
930                 935                 940

Ser Ile Pro Ala Val Thr Thr Trp Asn Thr Tyr Leu Arg Tyr Ile Thr
945                 950                 955                 960

Val His Lys Ser Leu Ile Phe Val Leu Ile Trp Cys Leu Val Ile Phe
            965                 970                 975

Leu Ala Glu Val Ala Ala Ser Leu Val Val Leu Trp Leu Leu Gly Asn
            980                 985                 990

Thr Pro Leu Gln Asp Lys Gly Asn Ser Thr His Ser Arg Asn Asn Ser
        995                 1000                1005

Tyr Ala Val Ile Ile Thr Ser Thr Ser Ser Tyr Tyr Val Phe Tyr
    1010                1015                1020

Ile Tyr Val Gly Val Ala Asp Thr Leu Leu Ala Met Gly Phe Phe
    1025                1030                1035

Arg Gly Leu Pro Leu Val His Thr Leu Ile Thr Val Ser Lys Ile
    1040                1045                1050

Leu His His Lys Met Leu His Ser Val Leu Gln Ala Pro Met Ser
    1055                1060                1065

Thr Leu Asn Thr Leu Lys Ala Gly Gly Ile Leu Asn Arg Phe Ser
    1070                1075                1080

Lys Asp Ile Ala Ile Leu Asp Asp Leu Leu Pro Leu Thr Ile Phe
    1085                1090                1095

Asp Phe Ile Gln Leu Leu Leu Ile Val Ile Gly Ala Ile Ala Val
    1100                1105                1110

Val Ala Val Leu Gln Pro Tyr Ile Phe Val Ala Thr Val Pro Val
    1115                1120                1125

Ile Val Ala Phe Ile Met Leu Arg Ala Tyr Phe Leu Gln Thr Ser
    1130                1135                1140

Gln Gln Leu Lys Gln Leu Glu Ser Glu Gly Arg Ser Pro Ile Phe
    1145                1150                1155

Thr His Leu Val Thr Ser Leu Lys Gly Leu Trp Thr Leu Arg Ala
    1160                1165                1170

Phe Gly Arg Gln Pro Tyr Phe Glu Thr Leu Phe His Lys Ala Leu
    1175                1180                1185

Asn Leu His Thr Ala Asn Trp Phe Leu Tyr Leu Ser Thr Leu Arg
    1190                1195                1200

Trp Phe Gln Met Arg Ile Glu Met Ile Phe Val Ile Phe Phe Ile
```

```
            1205                1210                1215
Ala Val Thr Phe Ile Ser Ile Leu Thr Thr Gly Glu Gly Glu Gly
            1220                1225                1230
Arg Val Gly Ile Ile Leu Thr Leu Ala Met Asn Ile Met Ser Thr
            1235                1240                1245
Leu Gln Trp Ala Val Asn Ser Ser Ile Asp Val Asp Ser Leu Met
            1250                1255                1260
Arg Ser Val Ser Arg Val Phe Lys Phe Ile Asp Met Pro Thr Glu
            1265                1270                1275
Gly Lys Pro Thr Lys Ser Thr Lys Pro Tyr Lys Asn Gly Gln Leu
            1280                1285                1290
Ser Lys Val Met Ile Ile Glu Asn Ser His Val Lys Lys Asp Asp
            1295                1300                1305
Ile Trp Pro Ser Gly Gly Gln Met Thr Val Lys Asp Leu Thr Ala
            1310                1315                1320
Lys Tyr Thr Glu Gly Gly Asn Ala Ile Leu Glu Asn Ile Ser Phe
            1325                1330                1335
Ser Ile Ser Pro Gly Gln Arg Val Gly Leu Leu Gly Arg Thr Gly
            1340                1345                1350
Ser Gly Lys Ser Thr Leu Leu Ser Ala Phe Leu Arg Leu Leu Asn
            1355                1360                1365
Thr Glu Gly Glu Ile Gln Ile Asp Gly Val Ser Trp Asp Ser Ile
            1370                1375                1380
Thr Leu Gln Gln Trp Arg Lys Ala Phe Gly Val Ile Pro Gln Lys
            1385                1390                1395
Val Phe Ile Phe Ser Gly Thr Phe Arg Lys Asn Leu Asp Pro Tyr
            1400                1405                1410
Glu Gln Trp Ser Asp Gln Glu Ile Trp Lys Val Ala Asp Glu Val
            1415                1420                1425
Gly Leu Arg Ser Val Ile Glu Gln Phe Pro Gly Lys Leu Asp Phe
            1430                1435                1440
Val Leu Val Asp Gly Gly Cys Val Leu Ser His Gly His Lys Gln
            1445                1450                1455
Leu Met Cys Leu Ala Arg Ser Val Leu Ser Lys Ala Lys Ile Leu
            1460                1465                1470
Leu Leu Asp Glu Pro Ser Ala His Leu Asp Pro Val Thr Tyr Gln
            1475                1480                1485
Ile Ile Arg Arg Thr Leu Lys Gln Ala Phe Ala Asp Cys Thr Val
            1490                1495                1500
Ile Leu Cys Glu His Arg Ile Glu Ala Met Leu Glu Cys Gln Gln
            1505                1510                1515
Phe Leu Val Ile Glu Glu Asn Lys Val Arg Gln Tyr Asp Ser Ile
            1520                1525                1530
Gln Lys Leu Leu Asn Glu Arg Ser Leu Phe Arg Gln Ala Ile Ser
            1535                1540                1545
Pro Ser Asp Arg Val Lys Leu Phe Pro His Arg Asn Ser Ser Lys
            1550                1555                1560
Cys Lys Ser Lys Pro Gln Ile Ala Ala Leu Lys Glu Glu Thr Glu
            1565                1570                1575
Glu Glu Val Gln Asp Thr Arg Leu
            1580                1585

<210> SEQ ID NO 219
```

<211> LENGTH: 1505
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 219

```
Met Gly Lys Pro Ile Pro Asn Pro Leu Leu Gly Leu Asp Ser Thr Gly
1               5                   10                  15

Thr Gly Ser Glu Phe Asp Ile Ala Ala Met Gln Arg Ser Pro Leu
            20                  25                  30

Glu Lys Ala Ser Val Val Ser Lys Leu Phe Phe Ser Trp Thr Arg Pro
        35                  40                  45

Ile Leu Arg Lys Gly Tyr Arg Gln Arg Leu Glu Leu Ser Asp Ile Tyr
50                  55                  60

Gln Ile Pro Ser Val Asp Ser Ala Asp Asn Leu Ser Glu Lys Leu Glu
65                  70                  75                  80

Arg Glu Trp Asp Arg Glu Leu Ala Ser Lys Lys Asn Pro Lys Leu Ile
                85                  90                  95

Asn Ala Leu Arg Arg Cys Phe Phe Trp Arg Phe Met Phe Tyr Gly Ile
            100                 105                 110

Phe Leu Tyr Leu Gly Glu Val Thr Lys Ala Val Gln Pro Leu Leu Leu
        115                 120                 125

Gly Arg Ile Ile Ala Ser Tyr Asp Pro Asp Asn Lys Glu Glu Arg Ser
130                 135                 140

Ile Ala Ile Tyr Leu Gly Ile Gly Leu Cys Leu Leu Phe Ile Val Arg
145                 150                 155                 160

Thr Leu Leu Leu His Pro Ala Ile Phe Gly Leu His His Ile Gly Met
                165                 170                 175

Gln Met Arg Ile Ala Met Phe Ser Leu Ile Tyr Lys Lys Thr Leu Lys
            180                 185                 190

Leu Ser Ser Arg Val Leu Asp Lys Ile Ser Ile Gly Gln Leu Val Ser
        195                 200                 205

Leu Leu Ser Asn Asn Leu Asn Lys Phe Asp Glu Gly Leu Ala Leu Ala
210                 215                 220

His Phe Val Trp Ile Ala Pro Leu Gln Val Ala Leu Leu Met Gly Leu
225                 230                 235                 240

Ile Trp Glu Leu Leu Gln Ala Ser Ala Phe Cys Gly Leu Gly Phe Leu
                245                 250                 255

Ile Val Leu Ala Leu Phe Gln Ala Gly Leu Gly Arg Met Met Met Lys
            260                 265                 270

Tyr Arg Asp Gln Arg Ala Gly Lys Ile Ser Glu Arg Leu Val Ile Thr
        275                 280                 285

Ser Glu Met Ile Glu Asn Ile Gln Ser Val Lys Ala Tyr Cys Trp Glu
290                 295                 300

Glu Ala Met Glu Lys Met Ile Glu Asn Leu Arg Gln Thr Glu Leu Lys
305                 310                 315                 320

Leu Thr Arg Lys Ala Ala Tyr Val Arg Tyr Phe Asn Ser Ser Ala Phe
                325                 330                 335

Phe Phe Ser Gly Phe Phe Val Val Phe Leu Ser Val Leu Pro Tyr Ala
            340                 345                 350

Leu Ile Lys Gly Ile Ile Leu Arg Lys Ile Phe Thr Thr Ile Ser Phe
        355                 360                 365

Cys Ile Val Leu Arg Met Ala Val Thr Arg Gln Phe Pro Trp Ala Val
```

```
            370                 375                 380
Gln Thr Trp Tyr Asp Ser Leu Gly Ala Ile Asn Lys Ile Gln Asp Phe
385                 390                 395                 400

Leu Gln Lys Gln Glu Tyr Lys Thr Leu Glu Tyr Asn Leu Thr Thr Thr
                405                 410                 415

Glu Val Val Met Glu Asn Val Thr Ala Phe Trp Glu Gly Phe Gly
            420                 425                 430

Glu Leu Phe Glu Lys Ala Lys Gln Asn Asn Asn Arg Lys Thr Ser
            435                 440                 445

Asn Gly Asp Asp Ser Leu Phe Phe Ser Asn Phe Ser Leu Leu Gly Thr
            450                 455                 460

Pro Val Leu Lys Asp Ile Asn Phe Lys Ile Glu Arg Gly Gln Leu Leu
465                 470                 475                 480

Ala Val Ala Gly Ser Thr Gly Ala Gly Lys Thr Ser Leu Leu Met Val
            485                 490                 495

Ile Met Gly Glu Leu Glu Pro Ser Glu Gly Lys Ile Lys His Ser Gly
            500                 505                 510

Arg Ile Ser Phe Cys Ser Gln Phe Ser Trp Ile Met Pro Gly Thr Ile
            515                 520                 525

Lys Glu Asn Ile Ile Gly Val Ser Tyr Asp Glu Tyr Arg Tyr Arg Ser
            530                 535                 540

Val Ile Lys Ala Cys Gln Leu Glu Glu Asp Ile Ser Lys Phe Ala Glu
545                 550                 555                 560

Lys Asp Asn Ile Val Leu Gly Glu Gly Gly Ile Thr Leu Ser Gly Gly
            565                 570                 575

Gln Arg Ala Arg Ile Ser Leu Ala Arg Ala Val Tyr Lys Asp Ala Asp
            580                 585                 590

Leu Tyr Leu Leu Asp Ser Pro Phe Gly Tyr Leu Asp Val Leu Thr Glu
            595                 600                 605

Lys Glu Ile Phe Glu Ser Cys Val Cys Lys Leu Met Ala Asn Lys Thr
            610                 615                 620

Arg Ile Leu Val Thr Ser Lys Met Glu His Leu Lys Lys Ala Asp Lys
625                 630                 635                 640

Ile Leu Ile Leu His Glu Gly Ser Ser Tyr Phe Tyr Gly Thr Phe Ser
            645                 650                 655

Glu Leu Gln Asn Leu Gln Pro Asp Phe Ser Ser Lys Leu Met Gly Cys
            660                 665                 670

Asp Ser Phe Asp Gln Phe Ser Ala Glu Arg Arg Asn Ser Ile Leu Thr
            675                 680                 685

Glu Thr Leu His Arg Phe Ser Leu Glu Gly Asp Ala Pro Val Ser Trp
            690                 695                 700

Thr Glu Thr Lys Lys Gln Ser Phe Lys Gln Thr Gly Glu Phe Gly Glu
705                 710                 715                 720

Lys Arg Lys Asn Ser Ile Leu Asn Pro Ile Asn Ser Ile Arg Lys Phe
            725                 730                 735

Ser Ile Val Gln Lys Thr Pro Leu Gln Met Asn Gly Ile Glu Glu Asp
            740                 745                 750

Ser Asp Glu Pro Leu Glu Arg Arg Leu Ser Leu Val Pro Asp Ser Glu
            755                 760                 765

Gln Gly Glu Ala Ile Leu Pro Arg Ile Ser Val Ile Ser Thr Gly Pro
            770                 775                 780

Thr Leu Gln Ala Arg Arg Arg Gln Ser Val Leu Asn Leu Met Thr His
785                 790                 795                 800
```

-continued

Ser Val Asn Gln Gly Gln Asn Ile His Arg Lys Thr Thr Ala Ser Thr
              805                 810                 815

Arg Lys Val Ser Leu Ala Pro Gln Ala Asn Leu Thr Glu Leu Asp Ile
          820                 825                 830

Tyr Ser Arg Arg Leu Ser Gln Glu Thr Gly Leu Glu Ile Ser Glu Glu
          835                 840                 845

Ile Asn Glu Glu Asp Leu Lys Glu Cys Phe Phe Asp Asp Met Glu Ser
850                 855                 860

Ile Pro Ala Val Thr Thr Trp Asn Thr Tyr Leu Arg Tyr Ile Thr Val
865                 870                 875                 880

His Lys Ser Leu Ile Phe Val Leu Ile Trp Cys Leu Val Ile Phe Leu
              885                 890                 895

Ala Glu Val Ala Ala Ser Leu Val Val Leu Trp Leu Leu Gly Asn Thr
              900                 905                 910

Pro Leu Gln Asp Lys Gly Asn Ser Thr His Ser Arg Asn Asn Ser Tyr
              915                 920                 925

Ala Val Ile Ile Thr Ser Thr Ser Ser Tyr Tyr Val Phe Tyr Ile Tyr
          930                 935                 940

Val Gly Val Ala Asp Thr Leu Leu Ala Met Gly Phe Phe Arg Gly Leu
945                 950                 955                 960

Pro Leu Val His Thr Leu Ile Thr Val Ser Lys Ile Leu His His Lys
              965                 970                 975

Met Leu His Ser Val Leu Gln Ala Pro Met Ser Thr Leu Asn Thr Leu
              980                 985                 990

Lys Ala Gly Gly Ile Leu Asn Arg Phe Ser Lys Asp Ile Ala Ile Leu
          995                 1000                1005

Asp Asp Leu Leu Pro Leu Thr Ile Phe Asp Phe Ile Gln Leu Leu
    1010                1015                1020

Leu Ile Val Ile Gly Ala Ile Ala Val Val Ala Val Leu Gln Pro
    1025                1030                1035

Tyr Ile Phe Val Ala Thr Val Pro Val Ile Val Ala Phe Ile Met
    1040                1045                1050

Leu Arg Ala Tyr Phe Leu Gln Thr Ser Gln Gln Leu Lys Gln Leu
    1055                1060                1065

Glu Ser Glu Gly Arg Ser Pro Ile Phe Thr His Leu Val Thr Ser
    1070                1075                1080

Leu Lys Gly Leu Trp Thr Leu Arg Ala Phe Gly Arg Gln Pro Tyr
    1085                1090                1095

Phe Glu Thr Leu Phe His Lys Ala Leu Asn Leu His Thr Ala Asn
    1100                1105                1110

Trp Phe Leu Tyr Leu Ser Thr Leu Arg Trp Phe Gln Met Arg Ile
    1115                1120                1125

Glu Met Ile Phe Val Ile Phe Ile Ala Val Thr Phe Ile Ser
    1130                1135                1140

Ile Leu Thr Thr Gly Glu Gly Glu Gly Arg Val Gly Ile Ile Leu
    1145                1150                1155

Thr Leu Ala Met Asn Ile Met Ser Thr Leu Gln Trp Ala Val Asn
    1160                1165                1170

Ser Ser Ile Asp Val Asp Ser Leu Met Arg Ser Val Ser Arg Val
    1175                1180                1185

Phe Lys Phe Ile Asp Met Pro Thr Glu Gly Lys Pro Thr Lys Ser
    1190                1195                1200

-continued

```
Thr Lys Pro Tyr Lys Asn Gly Gln Leu Ser Lys Val Met Ile Ile
    1205                1210                1215

Glu Asn Ser His Val Lys Lys Asp Asp Ile Trp Pro Ser Gly Gly
    1220                1225                1230

Gln Met Thr Val Lys Asp Leu Thr Ala Lys Tyr Thr Glu Gly Gly
    1235                1240                1245

Asn Ala Ile Leu Glu Asn Ile Ser Phe Ser Ile Ser Pro Gly Gln
    1250                1255                1260

Arg Val Gly Leu Leu Gly Arg Thr Gly Ser Gly Lys Ser Thr Leu
    1265                1270                1275

Leu Ser Ala Phe Leu Arg Leu Leu Asn Thr Glu Gly Glu Ile Gln
    1280                1285                1290

Ile Asp Gly Val Ser Trp Asp Ser Ile Thr Leu Gln Gln Trp Arg
    1295                1300                1305

Lys Ala Phe Gly Val Ile Pro Gln Lys Val Phe Ile Phe Ser Gly
    1310                1315                1320

Thr Phe Arg Lys Asn Leu Asp Pro Tyr Glu Gln Trp Ser Asp Gln
    1325                1330                1335

Glu Ile Trp Lys Val Ala Asp Glu Val Gly Leu Arg Ser Val Ile
    1340                1345                1350

Glu Gln Phe Pro Gly Lys Leu Asp Phe Val Leu Val Asp Gly Gly
    1355                1360                1365

Cys Val Leu Ser His Gly His Lys Gln Leu Met Cys Leu Ala Arg
    1370                1375                1380

Ser Val Leu Ser Lys Ala Lys Ile Leu Leu Leu Asp Glu Pro Ser
    1385                1390                1395

Ala His Leu Asp Pro Val Thr Tyr Gln Ile Ile Arg Arg Thr Leu
    1400                1405                1410

Lys Gln Ala Phe Ala Asp Cys Thr Val Ile Leu Cys Glu His Arg
    1415                1420                1425

Ile Glu Ala Met Leu Glu Cys Gln Gln Phe Leu Val Ile Glu Glu
    1430                1435                1440

Asn Lys Val Arg Gln Tyr Asp Ser Ile Gln Lys Leu Leu Asn Glu
    1445                1450                1455

Arg Ser Leu Phe Arg Gln Ala Ile Ser Pro Ser Asp Arg Val Lys
    1460                1465                1470

Leu Phe Pro His Arg Asn Ser Ser Lys Cys Lys Ser Lys Pro Gln
    1475                1480                1485

Ile Ala Ala Leu Lys Glu Glu Thr Glu Glu Val Gln Asp Thr
    1490                1495                1500

Arg Leu
    1505
```

<210> SEQ ID NO 220
<211> LENGTH: 1587
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 220

```
Met Gly Lys Pro Ile Pro Asn Pro Leu Leu Gly Leu Asp Ser Thr Gly
1               5                   10                  15

Thr Gly Ser Glu Phe His Pro Gly Val Leu Lys Val Glu Ala Ile Leu
            20                  25                  30
```

```
Glu Lys Val Gln Gly Leu Glu Gln Ala Val Asp Asn Phe Glu Gly Lys
            35                  40                  45

Lys Thr Asp Lys Lys Tyr Leu Met Ile Glu Glu Tyr Leu Thr Lys Glu
    50                  55                  60

Leu Leu Ala Leu Asp Ser Val Asp Pro Glu Gly Arg Ala Asp Val Arg
65                  70                  75                  80

Gln Ala Arg Arg Asp Gly Val Arg Lys Val Gln Thr Ile Leu Glu Lys
                85                  90                  95

Leu Glu Gln Lys Ala Ile Asp Asp Ile Ala Ala Met Gln Arg Ser
            100                 105                 110

Pro Leu Glu Lys Ala Ser Val Val Ser Lys Leu Phe Phe Ser Trp Thr
            115                 120                 125

Arg Pro Ile Leu Arg Lys Gly Tyr Arg Gln Arg Leu Glu Leu Ser Asp
130                 135                 140

Ile Tyr Gln Ile Pro Ser Val Asp Ser Ala Asp Asn Leu Ser Glu Lys
145                 150                 155                 160

Leu Glu Arg Glu Trp Asp Arg Glu Leu Ala Ser Lys Lys Asn Pro Lys
                165                 170                 175

Leu Ile Asn Ala Leu Arg Arg Cys Phe Phe Trp Arg Phe Met Phe Tyr
            180                 185                 190

Gly Ile Phe Leu Tyr Leu Gly Glu Val Thr Lys Ala Val Gln Pro Leu
            195                 200                 205

Leu Leu Gly Arg Ile Ile Ala Ser Tyr Asp Pro Asp Asn Lys Glu Glu
            210                 215                 220

Arg Ser Ile Ala Ile Tyr Leu Gly Ile Gly Leu Cys Leu Leu Phe Ile
225                 230                 235                 240

Val Arg Thr Leu Leu Leu His Pro Ala Ile Phe Gly Leu His His Ile
                245                 250                 255

Gly Met Gln Met Arg Ile Ala Met Phe Ser Leu Ile Tyr Lys Lys Thr
            260                 265                 270

Leu Lys Leu Ser Ser Arg Val Leu Asp Lys Ile Ser Ile Gly Gln Leu
            275                 280                 285

Val Ser Leu Leu Ser Asn Asn Leu Asn Lys Phe Asp Glu Gly Leu Ala
            290                 295                 300

Leu Ala His Phe Val Trp Ile Ala Pro Leu Gln Val Ala Leu Leu Met
305                 310                 315                 320

Gly Leu Ile Trp Glu Leu Leu Gln Ala Ser Ala Phe Cys Gly Leu Gly
                325                 330                 335

Phe Leu Ile Val Leu Ala Leu Phe Gln Ala Gly Leu Gly Arg Met Met
            340                 345                 350

Met Lys Tyr Arg Asp Gln Arg Ala Gly Lys Ile Ser Glu Arg Leu Val
            355                 360                 365

Ile Thr Ser Glu Met Ile Glu Asn Ile Gln Ser Val Lys Ala Tyr Cys
370                 375                 380

Trp Glu Glu Ala Met Glu Lys Met Ile Glu Asn Leu Arg Gln Thr Glu
385                 390                 395                 400

Leu Lys Leu Thr Arg Lys Ala Ala Tyr Val Arg Tyr Phe Asn Ser Ser
                405                 410                 415

Ala Phe Phe Phe Ser Gly Phe Phe Val Val Phe Leu Ser Val Leu Pro
            420                 425                 430

Tyr Ala Leu Ile Lys Gly Ile Ile Leu Arg Lys Ile Phe Thr Thr Ile
            435                 440                 445
```

```
Ser Phe Cys Ile Val Leu Arg Met Ala Val Thr Arg Gln Phe Pro Trp
    450                 455                 460

Ala Val Gln Thr Trp Tyr Asp Ser Leu Gly Ala Ile Asn Lys Ile Gln
465                 470                 475                 480

Asp Phe Leu Gln Lys Gln Glu Tyr Lys Thr Leu Glu Tyr Asn Leu Thr
                485                 490                 495

Thr Thr Glu Val Val Met Glu Asn Val Thr Ala Phe Trp Glu Glu Gly
            500                 505                 510

Phe Gly Glu Leu Phe Glu Lys Ala Lys Gln Asn Asn Asn Asn Arg Lys
        515                 520                 525

Thr Ser Asn Gly Asp Asp Ser Leu Phe Phe Ser Asn Phe Ser Leu Leu
    530                 535                 540

Gly Thr Pro Val Leu Lys Asp Ile Asn Phe Lys Ile Glu Arg Gly Gln
545                 550                 555                 560

Leu Leu Ala Val Ala Gly Ser Thr Gly Ala Gly Lys Thr Ser Leu Leu
                565                 570                 575

Met Val Ile Met Gly Glu Leu Glu Pro Ser Gly Lys Ile Lys His
            580                 585                 590

Ser Gly Arg Ile Ser Phe Cys Ser Gln Phe Ser Trp Ile Met Pro Gly
    595                 600                 605

Thr Ile Lys Glu Asn Ile Ile Gly Val Ser Tyr Asp Glu Tyr Arg Tyr
    610                 615                 620

Arg Ser Val Ile Lys Ala Cys Gln Leu Glu Glu Asp Ile Ser Lys Phe
625                 630                 635                 640

Ala Glu Lys Asp Asn Ile Val Leu Gly Glu Gly Gly Ile Thr Leu Ser
                645                 650                 655

Gly Gly Gln Arg Ala Arg Ile Ser Leu Ala Arg Ala Val Tyr Lys Asp
                660                 665                 670

Ala Asp Leu Tyr Leu Leu Asp Ser Pro Phe Gly Tyr Leu Asp Val Leu
                675                 680                 685

Thr Glu Lys Glu Ile Phe Glu Ser Cys Val Cys Lys Leu Met Ala Asn
            690                 695                 700

Lys Thr Arg Ile Leu Val Thr Ser Lys Met Glu His Leu Lys Lys Ala
705                 710                 715                 720

Asp Lys Ile Leu Ile Leu His Glu Gly Ser Ser Tyr Phe Tyr Gly Thr
                725                 730                 735

Phe Ser Glu Leu Gln Asn Leu Gln Pro Asp Phe Ser Ser Lys Leu Met
            740                 745                 750

Gly Cys Asp Ser Phe Asp Gln Phe Ser Ala Glu Arg Arg Asn Ser Ile
        755                 760                 765

Leu Thr Glu Thr Leu His Arg Phe Ser Leu Glu Gly Asp Ala Pro Val
    770                 775                 780

Ser Trp Thr Glu Thr Lys Lys Gln Ser Phe Lys Gln Thr Gly Glu Phe
785                 790                 795                 800

Gly Glu Lys Arg Lys Asn Ser Ile Leu Asn Pro Ile Asn Ser Ile Arg
                805                 810                 815

Lys Phe Ser Ile Val Gln Lys Thr Pro Leu Gln Met Asn Gly Ile Glu
                820                 825                 830

Glu Asp Ser Asp Glu Pro Leu Glu Arg Arg Leu Ser Leu Val Pro Asp
            835                 840                 845

Ser Glu Gln Gly Glu Ala Ile Leu Pro Arg Ile Ser Val Ile Ser Thr
    850                 855                 860

Gly Pro Thr Leu Gln Ala Arg Arg Arg Gln Ser Val Leu Asn Leu Met
```

```
                865                 870                 875                 880
Thr His Ser Val Asn Gly Gln Asn Ile His Arg Lys Thr Thr Ala
                    885                 890                 895
Ser Thr Arg Lys Val Ser Leu Ala Pro Gln Ala Asn Leu Thr Glu Leu
                    900                 905                 910
Asp Ile Tyr Ser Arg Arg Leu Ser Gln Glu Thr Gly Leu Glu Ile Ser
                    915                 920                 925
Glu Glu Ile Asn Glu Glu Asp Leu Lys Glu Cys Phe Phe Asp Asp Met
                    930                 935                 940
Glu Ser Ile Pro Ala Val Thr Thr Trp Asn Thr Tyr Leu Arg Tyr Ile
945                 950                 955                 960
Thr Val His Lys Ser Leu Ile Phe Val Leu Ile Trp Cys Leu Val Ile
                    965                 970                 975
Phe Leu Ala Glu Val Ala Ala Ser Leu Val Val Leu Trp Leu Leu Gly
                    980                 985                 990
Asn Thr Pro Leu Gln Asp Lys Gly Asn Ser Thr His Ser Arg Asn Asn
                    995                 1000                1005
Ser Tyr Ala Val Ile Ile Thr Ser Thr Ser Ser Tyr Tyr Val Phe
    1010                1015                1020
Tyr Ile Tyr Val Gly Val Ala Asp Thr Leu Leu Ala Met Gly Phe
    1025                1030                1035
Phe Arg Gly Leu Pro Leu Val His Thr Leu Ile Thr Val Ser Lys
    1040                1045                1050
Ile Leu His His Lys Met Leu His Ser Val Leu Gln Ala Pro Met
    1055                1060                1065
Ser Thr Leu Asn Thr Leu Lys Ala Gly Gly Ile Leu Asn Arg Phe
    1070                1075                1080
Ser Lys Asp Ile Ala Ile Leu Asp Asp Leu Leu Pro Leu Thr Ile
    1085                1090                1095
Phe Asp Phe Ile Gln Leu Leu Leu Ile Val Ile Gly Ala Ile Ala
    1100                1105                1110
Val Val Ala Val Leu Gln Pro Tyr Ile Phe Val Ala Thr Val Pro
    1115                1120                1125
Val Ile Val Ala Phe Ile Met Leu Arg Ala Tyr Phe Leu Gln Thr
    1130                1135                1140
Ser Gln Gln Leu Lys Gln Leu Glu Ser Glu Gly Arg Ser Pro Ile
    1145                1150                1155
Phe Thr His Leu Val Thr Ser Leu Lys Gly Leu Trp Thr Leu Arg
    1160                1165                1170
Ala Phe Gly Arg Gln Pro Tyr Phe Glu Thr Leu Phe His Lys Ala
    1175                1180                1185
Leu Asn Leu His Thr Ala Asn Trp Phe Leu Tyr Leu Ser Thr Leu
    1190                1195                1200
Arg Trp Phe Gln Met Arg Ile Glu Met Ile Phe Val Ile Phe Phe
    1205                1210                1215
Ile Ala Val Thr Phe Ile Ser Ile Leu Thr Thr Gly Glu Gly Glu
    1220                1225                1230
Gly Arg Val Gly Ile Ile Leu Thr Leu Ala Met Asn Ile Met Ser
    1235                1240                1245
Thr Leu Gln Trp Ala Val Asn Ser Ser Ile Asp Val Asp Ser Leu
    1250                1255                1260
Met Arg Ser Val Ser Arg Val Phe Lys Phe Ile Asp Met Pro Thr
    1265                1270                1275
```

```
Glu Gly Lys Pro Thr Lys Ser Thr Lys Pro Tyr Lys Asn Gly Gln
    1280            1285                1290

Leu Ser Lys Val Met Ile Ile Glu Asn Ser His Val Lys Lys Asp
    1295            1300                1305

Asp Ile Trp Pro Ser Gly Gly Gln Met Thr Val Lys Asp Leu Thr
    1310            1315                1320

Ala Lys Tyr Thr Glu Gly Gly Asn Ala Ile Leu Glu Asn Ile Ser
    1325            1330                1335

Phe Ser Ile Ser Pro Gly Gln Arg Val Gly Leu Leu Gly Arg Thr
    1340            1345                1350

Gly Ser Gly Lys Ser Thr Leu Leu Ser Ala Phe Leu Arg Leu Leu
    1355            1360                1365

Asn Thr Glu Gly Glu Ile Gln Ile Asp Gly Val Ser Trp Asp Ser
    1370            1375                1380

Ile Thr Leu Gln Gln Trp Arg Lys Ala Phe Gly Val Ile Pro Gln
    1385            1390                1395

Lys Val Phe Ile Phe Ser Gly Thr Phe Arg Lys Asn Leu Asp Pro
    1400            1405                1410

Tyr Glu Gln Trp Ser Asp Gln Glu Ile Trp Lys Val Ala Asp Glu
    1415            1420                1425

Val Gly Leu Arg Ser Val Ile Glu Gln Phe Pro Gly Lys Leu Asp
    1430            1435                1440

Phe Val Leu Val Asp Gly Gly Cys Val Leu Ser His Gly His Lys
    1445            1450                1455

Gln Leu Met Cys Leu Ala Arg Ser Val Leu Ser Lys Ala Lys Ile
    1460            1465                1470

Leu Leu Leu Asp Glu Pro Ser Ala His Leu Asp Pro Val Thr Tyr
    1475            1480                1485

Gln Ile Ile Arg Arg Thr Leu Lys Gln Ala Phe Ala Asp Cys Thr
    1490            1495                1500

Val Ile Leu Cys Glu His Arg Ile Glu Ala Met Leu Glu Cys Gln
    1505            1510                1515

Gln Phe Leu Val Ile Glu Glu Asn Lys Val Arg Gln Tyr Asp Ser
    1520            1525                1530

Ile Gln Lys Leu Leu Asn Glu Arg Ser Leu Phe Arg Gln Ala Ile
    1535            1540                1545

Ser Pro Ser Asp Arg Val Lys Leu Phe Pro His Arg Asn Ser Ser
    1550            1555                1560

Lys Cys Lys Ser Lys Pro Gln Ile Ala Ala Leu Lys Glu Glu Thr
    1565            1570                1575

Glu Glu Glu Val Gln Asp Thr Arg Leu
    1580            1585

<210> SEQ ID NO 221
<211> LENGTH: 1585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Met Gly Lys Pro Ile Pro Asn Pro Leu Leu Gly Leu Asp Ser Thr Gly
1               5                   10                  15

Thr Gly Ser Glu Phe Met Asp Lys Val Leu Asn Arg Glu Glu Ser Leu
```

-continued

```
                 20                  25                  30
Gln Leu Met Asp Leu Leu Gly Leu Glu Arg Ser Ala Trp Gly Asn Ile
             35                  40                  45
Pro Leu Met Arg Lys Ala Tyr Leu Lys Lys Cys Lys Glu Phe His Pro
         50                  55                  60
Asp Lys Gly Gly Asp Glu Lys Met Lys Met Asn Thr Leu Tyr
 65                  70                  75                  80
Lys Lys Met Glu Asp Gly Val Lys Tyr Ala His Gln Pro Asp Phe Gly
                 85                  90                  95
Gly Phe Trp Asp Ala Asp Ile Ala Ala Met Gln Arg Ser Pro Leu
                100                 105                 110
Glu Lys Ala Ser Val Val Ser Lys Leu Phe Phe Ser Trp Thr Arg Pro
            115                 120                 125
Ile Leu Arg Lys Gly Tyr Arg Gln Arg Leu Glu Leu Ser Asp Ile Tyr
            130                 135                 140
Gln Ile Pro Ser Val Asp Ser Ala Asp Asn Leu Ser Glu Lys Leu Glu
145                 150                 155                 160
Arg Glu Trp Asp Arg Glu Leu Ala Ser Lys Lys Asn Pro Lys Leu Ile
                165                 170                 175
Asn Ala Leu Arg Arg Cys Phe Phe Trp Arg Phe Met Phe Tyr Gly Ile
                180                 185                 190
Phe Leu Tyr Leu Gly Glu Val Thr Lys Ala Val Gln Pro Leu Leu Leu
                195                 200                 205
Gly Arg Ile Ile Ala Ser Tyr Asp Pro Asp Asn Lys Glu Glu Arg Ser
            210                 215                 220
Ile Ala Ile Tyr Leu Gly Ile Gly Leu Cys Leu Leu Phe Ile Val Arg
225                 230                 235                 240
Thr Leu Leu Leu His Pro Ala Ile Phe Gly Leu His His Ile Gly Met
                245                 250                 255
Gln Met Arg Ile Ala Met Phe Ser Leu Ile Tyr Lys Lys Thr Leu Lys
            260                 265                 270
Leu Ser Ser Arg Val Leu Asp Lys Ile Ser Ile Gly Gln Leu Val Ser
            275                 280                 285
Leu Leu Ser Asn Asn Leu Asn Lys Phe Asp Glu Gly Leu Ala Leu Ala
            290                 295                 300
His Phe Val Trp Ile Ala Pro Leu Gln Val Ala Leu Leu Met Gly Leu
305                 310                 315                 320
Ile Trp Glu Leu Leu Gln Ala Ser Ala Phe Cys Gly Leu Gly Phe Leu
                325                 330                 335
Ile Val Leu Ala Leu Phe Gln Ala Gly Leu Gly Arg Met Met Met Lys
            340                 345                 350
Tyr Arg Asp Gln Arg Ala Gly Lys Ile Ser Glu Arg Leu Val Ile Thr
            355                 360                 365
Ser Glu Met Ile Glu Asn Ile Gln Ser Val Lys Ala Tyr Cys Trp Glu
            370                 375                 380
Glu Ala Met Glu Lys Met Ile Glu Asn Leu Arg Gln Thr Glu Leu Lys
385                 390                 395                 400
Leu Thr Arg Lys Ala Ala Tyr Val Arg Tyr Phe Asn Ser Ser Ala Phe
                405                 410                 415
Phe Phe Ser Gly Phe Phe Val Val Phe Leu Ser Val Leu Pro Tyr Ala
            420                 425                 430
Leu Ile Lys Gly Ile Ile Leu Arg Lys Ile Phe Thr Thr Ile Ser Phe
            435                 440                 445
```

```
Cys Ile Val Leu Arg Met Ala Val Thr Arg Gln Phe Pro Trp Ala Val
450                 455                 460

Gln Thr Trp Tyr Asp Ser Leu Gly Ala Ile Asn Lys Ile Gln Asp Phe
465                 470                 475                 480

Leu Gln Lys Gln Glu Tyr Lys Thr Leu Glu Tyr Asn Leu Thr Thr Thr
                485                 490                 495

Glu Val Val Met Glu Asn Val Thr Ala Phe Trp Glu Glu Gly Phe Gly
                500                 505                 510

Glu Leu Phe Glu Lys Ala Lys Gln Asn Asn Asn Arg Lys Thr Ser
515                 520                 525

Asn Gly Asp Asp Ser Leu Phe Phe Ser Asn Phe Ser Leu Leu Gly Thr
530                 535                 540

Pro Val Leu Lys Asp Ile Asn Phe Lys Ile Glu Arg Gly Gln Leu Leu
545                 550                 555                 560

Ala Val Ala Gly Ser Thr Gly Ala Gly Lys Thr Ser Leu Leu Met Val
                565                 570                 575

Ile Met Gly Glu Leu Glu Pro Ser Glu Gly Lys Ile Lys His Ser Gly
                580                 585                 590

Arg Ile Ser Phe Cys Ser Gln Phe Ser Trp Ile Met Pro Gly Thr Ile
                595                 600                 605

Lys Glu Asn Ile Ile Gly Val Ser Tyr Asp Glu Tyr Arg Tyr Arg Ser
610                 615                 620

Val Ile Lys Ala Cys Gln Leu Glu Glu Asp Ile Ser Lys Phe Ala Glu
625                 630                 635                 640

Lys Asp Asn Ile Val Leu Gly Glu Gly Gly Ile Thr Leu Ser Gly Gly
                645                 650                 655

Gln Arg Ala Arg Ile Ser Leu Ala Arg Ala Val Tyr Lys Asp Ala Asp
                660                 665                 670

Leu Tyr Leu Leu Asp Ser Pro Phe Gly Tyr Leu Asp Val Leu Thr Glu
                675                 680                 685

Lys Glu Ile Phe Glu Ser Cys Val Cys Lys Leu Met Ala Asn Lys Thr
690                 695                 700

Arg Ile Leu Val Thr Ser Lys Met Glu His Leu Lys Lys Ala Asp Lys
705                 710                 715                 720

Ile Leu Ile Leu His Glu Gly Ser Ser Tyr Phe Tyr Gly Thr Phe Ser
                725                 730                 735

Glu Leu Gln Asn Leu Gln Pro Asp Phe Ser Ser Lys Leu Met Gly Cys
                740                 745                 750

Asp Ser Phe Asp Gln Phe Ser Ala Glu Arg Arg Asn Ser Ile Leu Thr
                755                 760                 765

Glu Thr Leu His Arg Phe Ser Leu Glu Gly Asp Ala Pro Val Ser Trp
770                 775                 780

Thr Glu Thr Lys Lys Gln Ser Phe Lys Gln Thr Gly Glu Phe Gly Glu
785                 790                 795                 800

Lys Arg Lys Asn Ser Ile Leu Asn Pro Ile Asn Ser Ile Arg Lys Phe
                805                 810                 815

Ser Ile Val Gln Lys Thr Pro Leu Gln Met Asn Gly Ile Glu Glu Asp
                820                 825                 830

Ser Asp Glu Pro Leu Glu Arg Arg Leu Ser Leu Val Pro Asp Ser Glu
                835                 840                 845

Gln Gly Glu Ala Ile Leu Pro Arg Ile Ser Val Ile Ser Thr Gly Pro
850                 855                 860
```

```
Thr Leu Gln Ala Arg Arg Gln Ser Val Leu Asn Leu Met Thr His
865                 870                 875                 880

Ser Val Asn Gln Gly Gln Asn Ile His Arg Lys Thr Thr Ala Ser Thr
                    885                 890                 895

Arg Lys Val Ser Leu Ala Pro Gln Ala Asn Leu Thr Glu Leu Asp Ile
            900                 905                 910

Tyr Ser Arg Arg Leu Ser Gln Glu Thr Gly Leu Glu Ile Ser Glu Glu
        915                 920                 925

Ile Asn Glu Glu Asp Leu Lys Glu Cys Phe Phe Asp Asp Met Glu Ser
930                 935                 940

Ile Pro Ala Val Thr Thr Trp Asn Thr Tyr Leu Arg Tyr Ile Thr Val
945                 950                 955                 960

His Lys Ser Leu Ile Phe Val Leu Ile Trp Cys Leu Val Ile Phe Leu
                965                 970                 975

Ala Glu Val Ala Ala Ser Leu Val Val Leu Trp Leu Leu Gly Asn Thr
            980                 985                 990

Pro Leu Gln Asp Lys Gly Asn Ser Thr His Ser Arg Asn Asn Ser Tyr
        995                 1000                1005

Ala Val Ile Ile Thr Ser Thr Ser Ser Tyr Tyr Val Phe Tyr Ile
    1010                1015                1020

Tyr Val Gly Val Ala Asp Thr Leu Leu Ala Met Gly Phe Phe Arg
    1025                1030                1035

Gly Leu Pro Leu Val His Thr Leu Ile Thr Val Ser Lys Ile Leu
    1040                1045                1050

His His Lys Met Leu His Ser Val Leu Gln Ala Pro Met Ser Thr
    1055                1060                1065

Leu Asn Thr Leu Lys Ala Gly Gly Ile Leu Asn Arg Phe Ser Lys
    1070                1075                1080

Asp Ile Ala Ile Leu Asp Asp Leu Leu Pro Leu Thr Ile Phe Asp
    1085                1090                1095

Phe Ile Gln Leu Leu Leu Ile Val Ile Gly Ala Ile Ala Val Val
    1100                1105                1110

Ala Val Leu Gln Pro Tyr Ile Phe Val Ala Thr Val Pro Val Ile
    1115                1120                1125

Val Ala Phe Ile Met Leu Arg Ala Tyr Phe Leu Gln Thr Ser Gln
    1130                1135                1140

Gln Leu Lys Gln Leu Glu Ser Glu Gly Arg Ser Pro Ile Phe Thr
    1145                1150                1155

His Leu Val Thr Ser Leu Lys Gly Leu Trp Thr Leu Arg Ala Phe
    1160                1165                1170

Gly Arg Gln Pro Tyr Phe Glu Thr Leu Phe His Lys Ala Leu Asn
    1175                1180                1185

Leu His Thr Ala Asn Trp Phe Leu Tyr Leu Ser Thr Leu Arg Trp
    1190                1195                1200

Phe Gln Met Arg Ile Glu Met Ile Phe Val Ile Phe Phe Ile Ala
    1205                1210                1215

Val Thr Phe Ile Ser Ile Leu Thr Thr Gly Glu Gly Glu Gly Arg
    1220                1225                1230

Val Gly Ile Ile Leu Thr Leu Ala Met Asn Ile Met Ser Thr Leu
    1235                1240                1245

Gln Trp Ala Val Asn Ser Ser Ile Asp Val Asp Ser Leu Met Arg
    1250                1255                1260

Ser Val Ser Arg Val Phe Lys Phe Ile Asp Met Pro Thr Glu Gly
```

```
                    1265                1270                1275

Lys Pro Thr Lys Ser Thr Lys Pro Tyr Lys Asn Gly Gln Leu Ser
            1280                1285                1290

Lys Val Met Ile Ile Glu Asn Ser His Val Lys Lys Asp Asp Ile
        1295                1300                1305

Trp Pro Ser Gly Gly Gln Met Thr Val Lys Asp Leu Thr Ala Lys
    1310                1315                1320

Tyr Thr Glu Gly Gly Asn Ala Ile Leu Glu Asn Ile Ser Phe Ser
1325                1330                1335

Ile Ser Pro Gly Gln Arg Val Gly Leu Leu Gly Arg Thr Gly Ser
    1340                1345                1350

Gly Lys Ser Thr Leu Leu Ser Ala Phe Leu Arg Leu Leu Asn Thr
    1355                1360                1365

Glu Gly Glu Ile Gln Ile Asp Gly Val Ser Trp Asp Ser Ile Thr
    1370                1375                1380

Leu Gln Gln Trp Arg Lys Ala Phe Gly Val Ile Pro Gln Lys Val
    1385                1390                1395

Phe Ile Phe Ser Gly Thr Phe Arg Lys Asn Leu Asp Pro Tyr Glu
    1400                1405                1410

Gln Trp Ser Asp Gln Glu Ile Trp Lys Val Ala Asp Glu Val Gly
    1415                1420                1425

Leu Arg Ser Val Ile Glu Gln Phe Pro Gly Lys Leu Asp Phe Val
    1430                1435                1440

Leu Val Asp Gly Gly Cys Val Leu Ser His Gly His Lys Gln Leu
    1445                1450                1455

Met Cys Leu Ala Arg Ser Val Leu Ser Lys Ala Lys Ile Leu Leu
    1460                1465                1470

Leu Asp Glu Pro Ser Ala His Leu Asp Pro Val Thr Tyr Gln Ile
    1475                1480                1485

Ile Arg Arg Thr Leu Lys Gln Ala Phe Ala Asp Cys Thr Val Ile
    1490                1495                1500

Leu Cys Glu His Arg Ile Glu Ala Met Leu Glu Cys Gln Gln Phe
    1505                1510                1515

Leu Val Ile Glu Glu Asn Lys Val Arg Gln Tyr Asp Ser Ile Gln
    1520                1525                1530

Lys Leu Leu Asn Glu Arg Ser Leu Phe Arg Gln Ala Ile Ser Pro
    1535                1540                1545

Ser Asp Arg Val Lys Leu Phe Pro His Arg Asn Ser Ser Lys Cys
    1550                1555                1560

Lys Ser Lys Pro Gln Ile Ala Ala Leu Lys Glu Glu Thr Glu Glu
    1565                1570                1575

Glu Val Gln Asp Thr Arg Leu
    1580                1585

<210> SEQ ID NO 222
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Met Ala Phe Val Cys Leu Ala Ile Gly Cys Leu Tyr Thr Phe Leu Ile
1               5                   10                  15
```

Ser Thr Thr Phe Gly Cys Thr Ser Ser Asp Thr Glu Ile Lys Val
                20                  25                  30

Asn Pro Pro Gln Asp Phe Glu Ile Val Asp Pro Gly Tyr Leu Gly Tyr
         35                  40                  45

Leu Tyr Leu Gln Trp Gln Pro Pro Leu Ser Leu Asp His Phe Lys Glu
 50                  55                  60

Cys Thr Val Glu Tyr Glu Leu Lys Tyr Arg Asn Ile Gly Ser Glu Thr
 65                  70                  75                  80

Trp Lys Thr Ile Ile Thr Lys Asn Leu His Tyr Lys Asp Gly Phe Asp
                 85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
            115                 120                 125

Trp Ile Ser Pro Gln Gly Ile Pro Glu Thr Lys Val Gln Asp Met Asp
        130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Gly Thr Gly Ser Glu Phe Asp Ile Ala Ala Ala Leu Glu
            340                 345                 350

Gly Lys Pro Ile Pro Asn Pro Leu Leu Gly Leu Asp Ser Thr Ser Arg
        355                 360                 365

Gly Pro Tyr Ser Ile Val Ser Pro Lys Cys
370                 375

<210> SEQ ID NO 223
<211> LENGTH: 174
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

```
Met Gly Val Lys Val Leu Phe Ala Leu Ile Cys Ile Ala Val Ala Glu
1               5                   10                  15

Ala Gly Thr Gly Ser Glu Phe Asp Ile Ala Ala Ala Leu Thr Cys Leu
                20                  25                  30

Gly Gly Phe Ala Ser Pro Gly Pro Val Pro Pro Ser Thr Ala Leu Arg
            35                  40                  45

Glu Leu Ile Glu Glu Leu Val Asn Ile Thr Gln Asn Gln Lys Ala Pro
50                  55                  60

Leu Cys Asn Gly Ser Met Val Trp Ser Ile Asn Leu Thr Ala Gly Met
65                  70                  75                  80

Tyr Cys Ala Ala Leu Glu Ser Leu Ile Asn Val Ser Gly Cys Ser Ala
                85                  90                  95

Ile Glu Lys Thr Gln Arg Met Leu Ser Gly Phe Cys Pro His Lys Val
            100                 105                 110

Ser Ala Gly Gln Phe Ser Ser Leu His Val Arg Asp Thr Lys Ile Glu
        115                 120                 125

Val Ala Gln Phe Val Lys Asp Leu Leu Leu His Leu Lys Lys Leu Phe
130                 135                 140

Arg Glu Gly Gln Phe Asn Leu Glu Gly Asp Tyr Lys Asp Asp Asp Asp
145                 150                 155                 160

Lys Gly Ser Arg Gly Pro Tyr Ser Ile Val Ser Pro Lys Cys
                165                 170
```

<210> SEQ ID NO 224
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

```
Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
                20                  25                  30

Pro Arg Ser Ala Ser Ile Lys Asp Ile Lys Lys Ala Tyr Arg Lys Leu
            35                  40                  45

Ala Leu Gln Leu His Pro Asp Arg Asn Pro Asp Asp Pro Gln Ala Gln
50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Ser Gly Gly Ser Gly Gly Ser Gly
            85                  90                  95

Gly Ala Ala Ala Leu Thr Cys Leu Gly Gly Phe Ala Ser Pro Gly Pro
            100                 105                 110

Val Pro Pro Ser Thr Ala Leu Arg Glu Leu Ile Glu Glu Leu Val Asn
        115                 120                 125

Ile Thr Gln Asn Gln Lys Ala Pro Leu Cys Asn Gly Ser Met Val Trp
130                 135                 140

Ser Ile Asn Leu Thr Ala Gly Met Tyr Cys Ala Ala Leu Glu Ser Leu
145                 150                 155                 160

Ile Asn Val Ser Gly Cys Ser Ala Ile Glu Lys Thr Gln Arg Met Leu
                165                 170                 175

Ser Gly Phe Cys Pro His Lys Val Ser Ala Gly Gln Phe Ser Ser Leu
```

180                 185                 190
His Val Arg Asp Thr Lys Ile Glu Val Ala Gln Phe Val Lys Asp Leu
            195                 200                 205

Leu Leu His Leu Lys Lys Leu Phe Arg Glu Gly Gln Phe Asn Leu Glu
    210                 215                 220

Gly Asp Tyr Lys Asp Asp Asp Lys Gly Ser Arg Gly Pro Tyr Ser
225                 230                 235                 240

Ile Val Ser Pro Lys Cys
                245

<210> SEQ ID NO 225
<211> LENGTH: 599
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
                35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

-continued

```
Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Gly Thr Gly Ser Glu Phe Asp Ile Ala Ala Ala Leu Glu
            340                 345                 350

Gly Lys Pro Ile Pro Asn Pro Leu Gly Leu Asp Ser Thr Ser Arg
        355                 360                 365

Pro Lys Ser Cys Asp Lys Thr His Thr Cys Pro Pro Cys Pro Ala Pro
    370                 375                 380

Glu Leu Leu Gly Gly Pro Ser Val Phe Leu Phe Pro Pro Lys Pro Lys
385                 390                 395                 400

Asp Thr Leu Met Ile Ser Arg Thr Pro Glu Val Thr Cys Val Val Val
                405                 410                 415

Asp Val Ser His Glu Asp Pro Glu Val Lys Phe Asn Trp Tyr Val Asp
            420                 425                 430

Gly Val Glu Val His Asn Ala Lys Thr Lys Pro Arg Glu Glu Gln Tyr
        435                 440                 445

Asn Ser Thr Tyr Arg Val Val Ser Val Leu Thr Val Leu His Gln Asp
    450                 455                 460

Trp Leu Asn Gly Lys Glu Tyr Lys Cys Lys Val Ser Asn Lys Ala Leu
465                 470                 475                 480

Pro Ala Pro Ile Glu Lys Thr Ile Ser Lys Ala Lys Gly Gln Pro Arg
                485                 490                 495

Glu Pro Gln Val Tyr Thr Leu Pro Pro Ser Arg Asp Glu Leu Thr Lys
            500                 505                 510

Asn Gln Val Ser Leu Thr Cys Leu Val Lys Gly Phe Tyr Pro Ser Asp
        515                 520                 525

Ile Ala Val Glu Trp Glu Ser Asn Gly Gln Pro Glu Asn Asn Tyr Lys
    530                 535                 540

Thr Thr Pro Pro Val Leu Asp Ser Asp Gly Ser Phe Phe Leu Tyr Ser
545                 550                 555                 560

Lys Leu Thr Val Asp Lys Ser Arg Trp Gln Gln Gly Asn Val Phe Ser
                565                 570                 575

Cys Ser Val Met His Glu Ala Leu His Asn His Tyr Thr Gln Lys Ser
            580                 585                 590

Leu Ser Leu Ser Pro Gly Lys
        595

<210> SEQ ID NO 226
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Met Gly Val Lys Val Leu Phe Ala Leu Ile Cys Ile Ala Val Ala Glu
1               5                   10                  15

Ala Gly Thr Gly Ser Glu Phe Asp Ile Ala Ala Ala Asp Asn Lys
            20                  25                  30

Phe Asn Lys Glu Gln Gln Asn Ala Phe Tyr Glu Ile Leu Asn Met Pro
        35                  40                  45
```

-continued

Asn Leu Asn Glu Glu Gln Arg Asn Gly Phe Ile Gln Ser Leu Lys Asp
            50                  55                  60

Asp Pro Ser Gln Ser Ala Asn Val Leu Gly Glu Ala Lys Lys Leu Asn
 65                  70                  75                  80

Asp Ser Gln Ala Pro Lys Leu Glu Gly Asp Tyr Lys Asp Asp Asp
                85                  90                  95

Lys Gly Ser Arg Gly Pro Tyr Ser Ile Val Ser Pro Lys Cys
                100                 105                 110

<210> SEQ ID NO 227
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Met Ala Pro Gln Asn Leu Ser Thr Phe Cys Leu Leu Leu Leu Tyr Leu
 1               5                  10                  15

Ile Gly Ala Val Ile Ala Gly Arg Asp Phe Tyr Lys Ile Leu Gly Val
                20                  25                  30

Pro Arg Ser Ala Ser Ile Lys Asp Ile Lys Lys Ala Tyr Arg Lys Leu
            35                  40                  45

Ala Leu Gln Leu His Pro Asp Arg Asn Pro Asp Pro Gln Ala Gln
 50                  55                  60

Glu Lys Phe Gln Asp Leu Gly Ala Ala Tyr Glu Val Leu Ser Asp Ser
 65                  70                  75                  80

Glu Lys Arg Asp Ile Gly Gly Gly Ser Gly Gly Ser Gly Gly Ser Gly
                85                  90                  95

Gly Ala Ala Ala Ala Asp Asn Lys Phe Asn Lys Glu Gln Gln Asn Ala
                100                 105                 110

Phe Tyr Glu Ile Leu Asn Met Pro Asn Leu Asn Glu Glu Gln Arg Asn
            115                 120                 125

Gly Phe Ile Gln Ser Leu Lys Asp Asp Pro Ser Gln Ser Ala Asn Val
        130                 135                 140

Leu Gly Glu Ala Lys Lys Leu Asn Asp Ser Gln Ala Pro Lys Leu Glu
145                 150                 155                 160

Gly Asp Tyr Lys Asp Asp Asp Lys Gly Ser Arg Gly Pro Tyr Ser
                165                 170                 175

Ile Val Ser Pro Lys Cys
            180

<210> SEQ ID NO 228
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Met Gly Val Trp Leu Asn Lys Asp Asp Tyr Ile Arg Asp Leu Lys Arg
 1               5                  10                  15

Ile Ile Leu Cys Phe Leu Ile Val Tyr Met Ala Ile Leu Val Gly Thr
                20                  25                  30

Asp Gln Asp Phe Tyr Ser Leu Leu Gly Val Ser Lys Thr Ala Ser Ser
            35                  40                  45

```
Arg Glu Ile Arg Gln Ala Phe Lys Lys Leu Ala Leu Lys Leu His Pro
         50                  55                  60

Asp Lys Asn Pro Asn Pro Asn Ala His Gly Asp Phe Leu Lys Ile
 65              70                  75                  80

Asn Arg Ala Tyr Glu Val Leu Lys Asp Glu Asp Gly Ser Glu Phe Asp
                 85                  90                  95

Ile Gly Gly Gly Ser Gly Gly Ser Gly Gly Ser Gly Gly Ala Ala Ala
            100                 105                 110

Ala Asp Asn Lys Phe Asn Lys Glu Gln Gln Asn Ala Phe Tyr Glu Ile
            115                 120                 125

Leu Asn Met Pro Asn Leu Asn Glu Glu Gln Arg Asn Gly Phe Ile Gln
    130                 135                 140

Ser Leu Lys Asp Asp Pro Ser Gln Ser Ala Asn Val Leu Gly Glu Ala
145                 150                 155                 160

Lys Lys Leu Asn Asp Ser Gln Ala Pro Lys Leu Glu Gly Asp Tyr Lys
                165                 170                 175

Asp Asp Asp Asp Lys Gly Ser Arg Gly Pro Tyr Ser Ile Val Ser Pro
            180                 185                 190

Lys Cys

<210> SEQ ID NO 229
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Met Gly Leu Ser Thr Val Pro Asp Leu Leu Leu Pro Leu Val Leu Leu
 1               5                  10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
 50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
            115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
            195                 200                 205
```

-continued

Gly Thr Thr Gly Thr Gly Ser Glu Phe Asp Ile Ala Ala Ala Leu Glu
        210                 215                 220

Gly Lys Pro Ile Pro Asn Pro Leu Leu Gly Leu Asp Ser Thr Ser Arg
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Asp Glu Leu Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
        450                 455                 460

Leu Ser Leu Ser Pro Gly Lys
465                 470

<210> SEQ ID NO 230
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr

```
                     85                  90                  95
His Asp Glu Ile Leu Glu Gly Leu Asn Phe Asn Leu Thr Glu Ile Pro
                100                 105                 110

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
        130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Gly Thr Gly Ser Glu Phe Asp Ile Ala Ala Leu Glu Gly
            420                 425                 430

Lys Pro Ile Pro Asn Pro Leu Leu Gly Leu Asp Ser Thr Ser Arg Pro
        435                 440                 445

Lys Ser Cys Asp Lys Thr His Thr Cys Pro Pro Cys Pro Ala Pro Glu
450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510
```

-continued

```
Val Glu Val His Asn Ala Lys Thr Lys Pro Arg Glu Glu Gln Tyr Asn
            515                 520                 525

Ser Thr Tyr Arg Val Val Ser Val Leu Thr Val Leu His Gln Asp Trp
        530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Asp Glu Leu Thr Lys Asn
            580                 585                 590

Gln Val Ser Leu Thr Cys Leu Val Lys Gly Phe Tyr Pro Ser Asp Ile
        595                 600                 605

Ala Val Glu Trp Glu Ser Asn Gly Gln Pro Glu Asn Asn Tyr Lys Thr
    610                 615                 620

Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
                645                 650                 655

Ser Val Met His Glu Ala Leu His Asn His Tyr Thr Gln Lys Ser Leu
            660                 665                 670

Ser Leu Ser Pro Gly Lys
            675

<210> SEQ ID NO 231
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Met Gly Val Lys Val Leu Phe Ala Leu Ile Cys Ile Ala Val Ala Glu
1               5                   10                  15

Ala Gly Thr Gly Ser Glu Phe Asp Ile Ala Ala Ala Val Thr Ile Lys
            20                  25                  30

Ala Asn Leu Ile Phe Ala Asp Gly Lys Thr Gln Thr Ala Glu Phe Lys
        35                  40                  45

Gly Thr Phe Glu Glu Ala Thr Ala Glu Ala Tyr Arg Tyr Ala Asp Leu
    50                  55                  60

Leu Ala Lys Glu Asn Gly Glu Tyr Thr Ala Asp Leu Glu Asp Gly Gly
65                  70                  75                  80

Tyr Thr Ile Asn Ile Lys Phe Ala Lys Glu Thr Pro Glu Thr Pro Glu
                85                  90                  95

Glu Pro Lys Glu Glu Leu Glu Gly Asp Tyr Lys Asp Asp Asp Asp Lys
            100                 105                 110

Gly Ser Arg Gly Pro Tyr Ser Ile Val Ser Pro Lys Cys
        115                 120                 125

<210> SEQ ID NO 232
<211> LENGTH: 197
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232
```

```
Met Ala Pro Gln Asn Leu Ser Thr Phe Cys Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Pro Gln Ala Gln
50                  55                  60

Glu Lys Phe Gln Asp Leu Gly Ala Ala Tyr Glu Val Leu Ser Asp Ser
65              70                  75                  80

Glu Lys Arg Asp Ile Gly Gly Gly Ser Gly Ser Gly Gly Ser Gly
                85                  90                  95

Gly Ala Ala Val Thr Ile Lys Ala Asn Leu Ile Phe Ala Asp Gly
            100                 105                 110

Lys Thr Gln Thr Ala Glu Phe Lys Gly Thr Phe Glu Glu Ala Thr Ala
            115                 120                 125

Glu Ala Tyr Arg Tyr Ala Asp Leu Leu Ala Lys Glu Asn Gly Glu Tyr
            130                 135                 140

Thr Ala Asp Leu Glu Asp Gly Tyr Thr Ile Asn Ile Lys Phe Ala
145                 150                 155                 160

Lys Glu Thr Pro Glu Thr Pro Glu Glu Pro Lys Glu Glu Leu Glu Gly
                165                 170                 175

Asp Tyr Lys Asp Asp Asp Asp Lys Gly Ser Arg Gly Pro Tyr Ser Ile
                180                 185                 190

Val Ser Pro Lys Cys
        195

<210> SEQ ID NO 233
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Met Gly Val Lys Val Leu Phe Ala Leu Ile Cys Ile Ala Val Ala Glu
1               5                   10                  15

Ala Gly Thr Gly Ser Glu Phe Asp Ile Ala Ala Ser Ala Lys Glu
            20                  25                  30

Leu Arg Cys Gln Cys Ile Lys Thr Tyr Ser Lys Pro Phe His Pro Lys
        35                  40                  45

Phe Ile Lys Glu Leu Arg Val Ile Glu Ser Gly Pro His Cys Ala Asn
50                  55                  60

Thr Glu Ile Ile Val Lys Leu Ser Asp Gly Arg Glu Leu Cys Leu Asp
65              70                  75                  80

Pro Lys Glu Asn Trp Val Gln Arg Val Val Glu Lys Phe Leu Lys Arg
                85                  90                  95

Ala Glu Asn Ser Leu Glu Gly Asp Tyr Lys Asp Asp Asp Lys Gly
            100                 105                 110

Ser Arg Gly Pro Tyr Ser Ile Val Ser Pro Lys Cys
            115                 120

<210> SEQ ID NO 234
<211> LENGTH: 196
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 234

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Gly Ser Gly Gly Ser Gly Gly Ser Gly
                85                  90                  95

Gly Ala Ala Ala Ser Ala Lys Glu Leu Arg Cys Gln Cys Ile Lys Thr
            100                 105                 110

Tyr Ser Lys Pro Phe His Pro Lys Phe Ile Lys Glu Leu Arg Val Ile
        115                 120                 125

Glu Ser Gly Pro His Cys Ala Asn Thr Glu Ile Ile Val Lys Leu Ser
    130                 135                 140

Asp Gly Arg Glu Leu Cys Leu Asp Pro Lys Glu Asn Trp Val Gln Arg
145                 150                 155                 160

Val Val Glu Lys Phe Leu Lys Arg Ala Glu Asn Ser Leu Glu Gly Asp
                165                 170                 175

Tyr Lys Asp Asp Asp Asp Lys Gly Ser Arg Gly Pro Tyr Ser Ile Val
            180                 185                 190

Ser Pro Lys Cys
        195

<210> SEQ ID NO 235
<211> LENGTH: 194
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 235

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Gly Ser Gly Gly Ser Gly Gly Ser Gly
                85                  90                  95

Gly Ala Ala Ala Thr Tyr Lys Leu Val Ile Asn Gly Lys Thr Leu Lys
            100                 105                 110

Gly Glu Thr Thr Thr Glu Ala Val Asp Ala Ala Thr Ala Glu Lys Val

```
            115                 120                 125
Phe Lys Gln Tyr Ala Asn Asp Asn Gly Val Asp Gly Glu Trp Thr Tyr
        130                 135                 140
Asp Asp Ala Thr Lys Thr Phe Thr Val Thr Glu Lys Pro Glu Val Ile
145                 150                 155                 160
Asp Ala Ser Glu Leu Thr Pro Ala Val Thr Leu Glu Gly Asp Tyr Lys
                165                 170                 175
Asp Asp Asp Asp Lys Gly Ser Arg Gly Pro Tyr Ser Ile Val Ser Pro
            180                 185                 190
Lys Cys

<210> SEQ ID NO 236
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Met Ala Pro Gln Asn Leu Ser Thr Phe Cys Leu Leu Leu Leu Tyr Leu
1               5                   10                  15
Ile Gly Ala Val Ile Ala Gly Arg Asp Phe Tyr Lys Ile Leu Gly Val
            20                  25                  30
Pro Arg Ser Ala Ser Ile Lys Asp Ile Lys Lys Ala Tyr Arg Lys Leu
        35                  40                  45
Ala Leu Gln Leu His Pro Asp Arg Asn Pro Asp Pro Gln Ala Gln
50                  55                  60
Glu Lys Phe Gln Asp Leu Gly Ala Ala Tyr Glu Val Leu Ser Asp Ser
65                  70                  75                  80
Glu Lys Arg Asp Ile Gly Gly Ser Gly Gly Ser Gly Gly Ser Gly
            85                  90                  95
Gly Ala Ala Ala Val Ile Thr Leu Gln Pro Pro Trp Val Ser Val
        100                 105                 110
Phe Gln Glu Glu Thr Val Thr Leu His Cys Glu Val Leu His Leu Pro
            115                 120                 125
Gly Ser Ser Ser Thr Gln Trp Phe Leu Asn Gly Thr Ala Thr Gln Thr
        130                 135                 140
Ser Thr Pro Ser Tyr Arg Ile Thr Ser Ala Ser Val Asn Asp Ser Gly
145                 150                 155                 160
Glu Tyr Arg Cys Gln Arg Gly Leu Ser Gly Arg Ser Asp Pro Ile Gln
                165                 170                 175
Leu Glu Ile His Arg Gly Trp Leu Leu Leu Gln Val Ser Ser Arg Val
            180                 185                 190
Phe Thr Glu Gly Glu Pro Leu Ala Leu Arg Cys His Ala Trp Lys Asp
        195                 200                 205
Lys Leu Val Tyr Asn Val Leu Tyr Tyr Arg Asn Gly Lys Ala Phe Lys
    210                 215                 220
Phe Phe His Trp Asn Ser Asn Leu Thr Ile Leu Lys Thr Asn Ile Ser
225                 230                 235                 240
His Asn Gly Thr Tyr His Cys Ser Gly Met Gly Lys Leu Glu Gly Asp
                245                 250                 255
Tyr Lys Asp Asp Asp Asp Lys Gly Ser Arg Gly Pro Tyr Ser Ile Val
            260                 265                 270
Ser Pro Lys Cys
```

<210> SEQ ID NO 237
<211> LENGTH: 279
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 237

```
Met Ala Pro Gln Asn Leu Ser Thr Phe Cys Leu Leu Leu Leu Tyr Leu
1               5                   10                  15
Ile Gly Ala Val Ile Ala Gly Arg Asp Phe Tyr Lys Ile Leu Gly Val
            20                  25                  30
Pro Arg Ser Ala Ser Ile Lys Asp Ile Lys Lys Ala Tyr Arg Lys Leu
        35                  40                  45
Ala Leu Gln Leu His Pro Asp Arg Asn Pro Asp Asp Pro Gln Ala Gln
    50                  55                  60
Glu Lys Phe Gln Asp Leu Gly Ala Ala Tyr Glu Val Leu Ser Asp Ser
65                  70                  75                  80
Glu Lys Arg Asp Ile Gly Gly Gly Ser Gly Gly Ser Gly Ser Gly
                85                  90                  95
Gly Ala Ala Ala Lys Leu Thr Ser Val Pro Thr Trp Cys Pro Pro
            100                 105                 110
His Pro Gly Asp Thr Tyr Leu Leu Thr Cys Arg Gly Thr Ser Thr Ala
            115                 120                 125
Arg Asp Gln Arg Ser Thr Gln Trp Phe Arg Asn Asn Thr Leu Met Arg
    130                 135                 140
Gly Ser Asn Phe Tyr Gly Arg Leu Val Ser Val Thr Pro Asn Ala Thr
145                 150                 155                 160
Ile Ser Asp Arg Tyr Ala Cys Gln Thr Lys Thr Thr Thr Arg Ser Asn
                165                 170                 175
Asn Ile Asp Phe Arg Val Ser Ser Arg Leu Thr Leu Gln Glu Arg
            180                 185                 190
Cys Ser Ser Tyr Gly Tyr Thr Tyr Ala Asn Asn Thr Arg Val Leu Arg
        195                 200                 205
Cys Tyr Ser Gly Gly Asn Val Thr Leu Arg Asn Val Val Phe His Leu
    210                 215                 220
Asn Gly Thr Ala Val Ile Asn Gly Thr Thr Thr Asn Ile His Thr Phe
225                 230                 235                 240
Val Leu Thr Glu Lys Thr Gly Gly Thr Tyr Phe Cys Ser Ala Phe Leu
                245                 250                 255
Glu Gly Asp Tyr Lys Asp Asp Asp Lys Gly Ser Arg Gly Pro Tyr
            260                 265                 270
Ser Ile Val Ser Pro Lys Cys
        275
```

<210> SEQ ID NO 238
<211> LENGTH: 336
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 238

```
Met Ala Pro Gln Asn Leu Ser Thr Phe Cys Leu Leu Leu Leu Tyr Leu
```

```
              1               5                  10                 15
            Ile Gly Ala Val Ile Ala Gly Arg Asp Phe Tyr Lys Ile Leu Gly Val
                            20                 25                 30
            Pro Arg Ser Ala Ser Ile Lys Asp Ile Lys Lys Ala Tyr Arg Lys Leu
                            35                 40                 45
            Ala Leu Gln Leu His Pro Asp Arg Asn Pro Asp Pro Gln Ala Gln
            50                              55                 60
            Glu Lys Phe Gln Asp Leu Gly Ala Ala Tyr Glu Val Leu Ser Asp Ser
            65                          70                 75                 80
            Glu Lys Arg Asp Ile Gly Gly Ser Gly Gly Ser Gly Gly Ser Gly
                                    85                 90                 95
            Gly Ala Ala Ala Leu Val Val Arg Gly Pro Thr Val Ser Leu Val Ser
                                100                105                110
            Asn Ser Phe Val Asp Ala Gly Ala Leu Gly Pro Asp Gly Val Val Glu
                                115                120                125
            Glu Asp Leu Leu Ile Leu Gly Glu Leu Arg Phe Val Gly Asp Gln Val
                            130                135                140
            Pro His Thr Thr Tyr Tyr Asp Gly Val Val Glu Leu Trp His Tyr Pro
            145                         150                155                160
            Met Gly His Lys Cys Pro Arg Val Val His Val Val Thr Val Thr Ala
                                165                170                175
            Cys Pro Arg Arg Pro Ala Val Ala Phe Ala Leu Cys Arg Ala Thr Asp
                                180                185                190
            Ser Thr His Ser Pro Ala Tyr Pro Thr Leu Glu Leu Asn Leu Ala Gln
                            195                200                205
            Gln Pro Leu Leu Arg Val Arg Arg Ala Thr Arg Asp Tyr Ala Gly Val
                            210                215                220
            Tyr Val Leu Arg Val Trp Val Gly Asp Ala Pro Asn Ala Ser Leu Phe
            225                         230                235                240
            Val Leu Gly Met Ala Ile Ala Ala Glu Gly Thr Leu Ala Tyr Asn Gly
                                245                250                255
            Ser Ala His Gly Ser Cys Asp Pro Lys Leu Leu Pro Tyr Ser Ala Pro
                                260                265                270
            Arg Leu Ala Pro Ala Ser Val Tyr Gln Pro Ala Pro Asn Pro Ala Ser
                            275                280                285
            Thr Pro Ser Thr Thr Ile Pro Ala Pro Gln Ala Ser Thr Thr Pro Phe
                        290                295                300
            Pro Thr Gly Asp Pro Lys Pro Gln Leu Glu Gly Asp Tyr Lys Asp Asp
            305                         310                315                320
            Asp Asp Lys Gly Ser Arg Gly Pro Tyr Ser Ile Val Ser Pro Lys Cys
                                325                330                335

<210> SEQ ID NO 239
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Met Ala Pro Gln Asn Leu Ser Thr Phe Cys Leu Leu Leu Leu Tyr Leu
1               5                  10                 15
Ile Gly Ala Val Ile Ala Gly Arg Asp Phe Tyr Lys Ile Leu Gly Val
                20                 25                 30
```

```
Pro Arg Ser Ala Ser Ile Lys Asp Ile Lys Lys Ala Tyr Arg Lys Leu
            35                  40                  45

Ala Leu Gln Leu His Pro Asp Arg Asn Pro Asp Pro Gln Ala Gln
    50                  55                  60

Glu Lys Phe Gln Asp Leu Gly Ala Ala Tyr Glu Val Leu Ser Asp Ser
65              70                  75                  80

Glu Lys Arg Asp Ile Gly Gly Ser Gly Gly Ser Gly Gly Ser Gly
                85              90                  95

Gly Ala Ala Ala Gly Thr Pro Lys Thr Ser Trp Arg Val Ser Val
        100                 105                 110

Gly Glu Asp Val Ser Leu Leu Pro Ala Pro Gly Pro Thr Gly Arg Gly
        115                 120                 125

Pro Thr Gln Lys Leu Leu Trp Ala Val Glu Pro Leu Asp Gly Cys Gly
        130                 135                 140

Pro Leu His Pro Ser Trp Val Ser Leu Met Pro Pro Lys Gln Val Pro
145                 150                 155                 160

Glu Thr Val Val Asp Ala Ala Cys Met Arg Pro Val Pro Leu Ala
                165                 170                 175

Met Ala Tyr Ala Pro Pro Ala Pro Ser Ala Thr Gly Gly Leu Arg Thr
            180                 185                 190

Asp Phe Val Trp Gln Glu Arg Ala Ala Val Val Asn Arg Ser Leu Val
        195                 200                 205

Ile His Gly Val Arg Glu Thr Asp Ser Gly Leu Tyr Thr Leu Ser Val
        210                 215                 220

Gly Asp Ile Lys Asp Pro Ala Arg Gln Val Ala Ser Val Val Leu Val
225                 230                 235                 240

Val Gln Pro Ala Pro Val Pro Thr Pro Pro Thr Pro Ala Asp Tyr
                245                 250                 255

Asp Glu Asp Asp Asn Asp Glu Gly Glu Asp Glu Ser Leu Ala Gly Thr
            260                 265                 270

Pro Ala Ser Gly Thr Pro Arg Leu Pro Pro Pro Ala Pro Pro Arg
            275                 280                 285

Ser Trp Pro Ser Ala Pro Glu Val Ser His Val Arg Gly Val Thr Val
    290                 295                 300

Arg Met Glu Thr Pro Glu Ala Ile Leu Phe Ser Pro Gly Glu Thr Phe
305                 310                 315                 320

Ser Thr Asn Val Ser Ile His Ala Ile Ala His Asp Gln Thr Tyr
                325                 330                 335

Ser Met Asp Val Val Trp Leu Arg Phe Asp Val Pro Thr Ser Cys Ala
            340                 345                 350

Glu Met Arg Ile Tyr Glu Ser Cys Leu Tyr His Pro Gln Leu Pro Glu
            355                 360                 365

Cys Leu Ser Pro Ala Asp Ala Pro Cys Ala Ala Ser Thr Trp Thr Ser
    370                 375                 380

Arg Leu Ala Val Arg Ser Tyr Ala Gly Cys Ser Arg Thr Asn Pro Pro
385                 390                 395                 400

Pro Arg Cys Ser Ala Glu Ala His Met Glu Pro Val Pro Gly Leu Ala
                405                 410                 415

Trp Gln Ala Ala Ser Val Asn Leu Glu Phe Arg Asp Ala Ser Pro Gln
                420                 425                 430

His Ser Gly Leu Tyr Leu Cys Val Val Tyr Val Asn Asp His Ile His
            435                 440                 445

Ala Trp Gly His Ile Thr Ile Ser Thr Ala Ala Gln Tyr Arg Asn Ala
```

```
            450                 455                 460
Val Val Glu Gln Pro Leu Pro Gln Arg Gly Ala Asp Leu Ala Glu Leu
465                 470                 475                 480

Glu Gly Asp Tyr Lys Asp Asp Asp Lys Gly Ser Arg Gly Pro Tyr
            485                 490                 495

Ser Ile Val Ser Pro Lys Cys
            500

<210> SEQ ID NO 240
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Asp Cys Ala Trp His Leu Gly Glu Leu Val Trp Cys Thr
1               5                   10

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

His Trp Arg Gly Trp Val
1               5

<210> SEQ ID NO 242
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

His Val His Tyr Tyr Trp
1               5

<210> SEQ ID NO 243
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Tyr Tyr Trp Leu His His
1               5

<210> SEQ ID NO 244
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

His Val His Tyr Tyr
```

```
1               5

<210> SEQ ID NO 245
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Tyr Tyr Trp Leu
1

<210> SEQ ID NO 246
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
                20                  25                  30

Pro Arg Ser Ala Ser Ile Lys Asp Ile Lys Lys Ala Tyr Arg Lys Leu
            35                  40                  45

Ala Leu Gln Leu His Pro Asp Arg Asn Pro Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Ser Gly Gly Ser Gly Gly Ser Gly
                85                  90                  95

Gly Ala Ala Ala Asp Cys Ala Trp His Leu Gly Glu Leu Val Trp Cys
            100                 105                 110

Thr Leu Glu Gly Asp Tyr Lys Asp Asp Asp Asp Lys Gly Ser Arg Gly
            115                 120                 125

Pro Tyr Ser Ile Val Ser Pro Lys Cys
    130                 135

<210> SEQ ID NO 247
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
                20                  25                  30

Pro Arg Ser Ala Ser Ile Lys Asp Ile Lys Lys Ala Tyr Arg Lys Leu
            35                  40                  45

Ala Leu Gln Leu His Pro Asp Arg Asn Pro Asp Pro Gln Ala Gln
    50                  55                  60

Glu Lys Phe Gln Asp Leu Gly Ala Ala Tyr Glu Val Leu Ser Asp Ser
65                  70                  75                  80
```

```
Glu Lys Arg Asp Ile Gly Gly Gly Ser Gly Gly Ser Gly Ser Gly
                85                  90                  95

Gly Ala Ala Ala His Trp Arg Gly Trp Val Leu Glu Gly Asp Tyr Lys
                100                 105                 110

Asp Asp Asp Asp Lys Gly Ser Arg Gly Pro Tyr Ser Ile Val Ser Pro
            115                 120                 125

Lys Cys
    130

<210> SEQ ID NO 248
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
                20                  25                  30

Pro Arg Ser Ala Ser Ile Lys Asp Ile Lys Lys Ala Tyr Arg Lys Leu
            35                  40                  45

Ala Leu Gln Leu His Pro Asp Arg Asn Pro Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Gly Ser Gly Gly Ser Gly Gly Ser Gly
                85                  90                  95

Gly Ala Ala Ala His Val His Tyr Tyr Trp Leu Glu Gly Asp Tyr Lys
                100                 105                 110

Asp Asp Asp Asp Lys Gly Ser Arg Gly Pro Tyr Ser Ile Val Ser Pro
            115                 120                 125

Lys Cys
    130

<210> SEQ ID NO 249
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
                20                  25                  30

Pro Arg Ser Ala Ser Ile Lys Asp Ile Lys Lys Ala Tyr Arg Lys Leu
            35                  40                  45

Ala Leu Gln Leu His Pro Asp Arg Asn Pro Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Gly Ser Gly Gly Ser Gly Gly Ser Gly
                85                  90                  95
```

Gly Ala Ala Ala Tyr Tyr Trp Leu His His Leu Glu Gly Asp Tyr Lys
                100                 105                 110

Asp Asp Asp Asp Lys Gly Ser Arg Gly Pro Tyr Ser Ile Val Ser Pro
            115                 120                 125

Lys Cys
    130

<210> SEQ ID NO 250
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Gly Ser Gly Gly Ser Gly Gly Ser Gly
                85                  90                  95

Gly Ala Ala Ala His Val His Tyr Tyr Leu Glu Gly Asp Tyr Lys Asp
                100                 105                 110

Asp Asp Asp Lys Gly Ser Arg Gly Pro Tyr Ser Ile Val Ser Pro Lys
            115                 120                 125

Cys

<210> SEQ ID NO 251
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Met Ala Pro Gln Asn Leu Ser Thr Phe Cys Leu Leu Leu Leu Tyr Leu
1               5                   10                  15

Ile Gly Ala Val Ile Ala Gly Arg Asp Phe Tyr Lys Ile Leu Gly Val
            20                  25                  30

Pro Arg Ser Ala Ser Ile Lys Asp Ile Lys Lys Ala Tyr Arg Lys Leu
        35                  40                  45

Ala Leu Gln Leu His Pro Asp Arg Asn Pro Asp Pro Gln Ala Gln
    50                  55                  60

Glu Lys Phe Gln Asp Leu Gly Ala Ala Tyr Glu Val Leu Ser Asp Ser
65                  70                  75                  80

Glu Lys Arg Asp Ile Gly Gly Gly Ser Gly Gly Ser Gly Gly Ser Gly
                85                  90                  95

Gly Ala Ala Ala Tyr Tyr Trp Leu Leu Glu Gly Asp Tyr Lys Asp Asp
                100                 105                 110

Asp Asp Lys Gly Ser Arg Gly Pro Tyr Ser Ile Val Ser Pro Lys Cys
            115                 120                 125

<210> SEQ ID NO 252
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Thr Gly Ser Gly Glu Phe
1               5

<210> SEQ ID NO 253
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Met Gly Val Lys Val Leu Phe Ala Leu Ile Cys Ile Ala Val Ala Glu
1               5                   10                  15

Ala

<210> SEQ ID NO 254
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Ala Asp Asn Lys Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Val Leu Gly Glu Ala
        35                  40                  45

Lys Lys Leu Asn Asp Ser Gln Ala Pro Lys
    50                  55

<210> SEQ ID NO 255
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Leu Glu Gly
1

<210> SEQ ID NO 256
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 256

Gly Arg Asp Phe Tyr Lys Ile Leu Gly Val Pro Arg Ser Ala Ser Ile
1               5                   10                  15

Lys Asp Ile Lys Lys Ala Tyr Arg Lys Leu Ala Leu Gln Leu His Pro
            20                  25                  30

Asp Arg Asn Pro Asp Asp Pro Gln Ala Gln Glu Lys Phe Gln Asp Leu
        35                  40                  45

Gly Ala Ala Tyr Glu Val Leu Ser Asp Ser Glu Lys Arg
50                  55                  60

<210> SEQ ID NO 257
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Ile Leu Gly Val Pro Arg Ser Ala Ser Ile Lys Asp Ile Lys Lys Ala
1               5                   10                  15

Tyr Arg Lys Leu Ala Leu Gln Leu His Pro Asp Arg Asn Pro Asp Asp
            20                  25                  30

Pro Gln Ala Gln Glu Lys Phe Gln Asp Leu Gly Ala Ala Tyr Glu Val
        35                  40                  45

Leu Ser Asp Ser Glu Lys Arg
    50                  55

<210> SEQ ID NO 258
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Ser Ala Ser Ile Lys Asp Ile Lys Lys Ala Tyr Arg Lys Leu Ala Leu
1               5                   10                  15

Gln Leu His Pro Asp Arg Asn Pro Asp Asp Pro Gln Ala Gln Glu Lys
            20                  25                  30

Phe Gln Asp Leu Gly Ala Ala Tyr Glu Val Leu Ser Asp Ser Glu Lys
        35                  40                  45

Arg

<210> SEQ ID NO 259
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gly Arg Asp Phe Tyr Lys Ile Leu Gly Val Pro Arg Ser Ala Ser Ile
1               5                   10                  15

Lys Asp Ile Lys Lys Ala Tyr Arg Lys Leu Ala Leu Gln Leu His Pro
            20                  25                  30

Asp Arg Asn Pro Asp Asp Pro Gln Ala Gln Glu Lys Phe Gln Asp Leu
        35                  40                  45
```

Gly

<210> SEQ ID NO 260
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Ile Leu Gly Val Pro Arg Ser Ala Ser Ile Lys Asp Ile Lys Lys Ala
1               5                   10                  15

Tyr Arg Lys Leu Ala Leu Gln Leu His Pro Asp Arg Asn Pro Asp Asp
            20                  25                  30

Pro Gln Ala Gln Glu Lys Phe Gln Asp Leu Gly
        35                  40

<210> SEQ ID NO 261
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Ser Ala Ser Ile Lys Asp Ile Lys Lys Ala Tyr Arg Lys Leu Ala Leu
1               5                   10                  15

Gln Leu His Pro Asp Arg Asn Pro Asp Asp Pro Gln Ala Gln Glu Lys
            20                  25                  30

Phe Gln Asp Leu Gly
        35

<210> SEQ ID NO 262
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Lys Ala Tyr Arg Lys Leu Ala Leu Gln Leu His Pro Asp Arg Asn Pro
1               5                   10                  15

Asp Asp Pro Gln Ala Gln Glu Lys Phe Gln Asp Leu Gly
            20                  25

<210> SEQ ID NO 263
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Lys Ala Tyr Arg Lys Leu Ala Leu Gln Leu His Pro Asp Arg Asn Pro
1               5                   10                  15

Asp Asp Pro Gln Ala Gln Glu Lys Phe Gln Asp Leu Gly Ala Ala Tyr
            20                  25                  30

Glu Val Leu Ser Asp Ser Glu Lys Arg
        35                  40

<210> SEQ ID NO 264
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Leu Gln Leu His Pro Asp Arg Asn Pro Asp Asp Pro Gln Ala Gln Glu
1               5                   10                  15

Lys Phe Gln Asp Leu Gly
            20

<210> SEQ ID NO 265
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Leu Gln Leu His Pro Asp Arg Asn Pro Asp Asp Pro Gln Ala Gln Glu
1               5                   10                  15

Lys Phe Gln Asp Leu Gly Ala Ala Tyr Glu Val Leu Ser Asp Ser Glu
            20                  25                  30

Lys Arg

<210> SEQ ID NO 266
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Ile Lys Asp Ile Lys Lys Ala Tyr Arg Lys Leu Ala Leu Gln Leu His
1               5                   10                  15

Pro Asp Arg Asn Pro Asp Asp Pro Gln Ala Gln Glu Lys Phe Gln Asp
            20                  25                  30

Leu Gly

<210> SEQ ID NO 267
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Ser Ala Ser Ile Lys Asp Ile Lys Lys Ala Tyr Arg Lys Leu Ala Leu
1               5                   10                  15

Gln Leu His Pro Asp Arg Asn Pro Asp Asp Pro Gln Ala Gln Glu
            20                  25                  30

<210> SEQ ID NO 268
<211> LENGTH: 20
<212> TYPE: PRT
<213> ORGANISM: Artificial Sequence
<220> FEATURE:
<223> OTHER INFORMATION: Description of Artificial Sequence: Synthetic

```
                            peptide

<400> SEQUENCE: 268

Ser Ala Ser Ile Lys Asp Ile Lys Lys Ala Tyr Arg Lys Leu Ala Leu
1               5                   10                  15

Gln Leu His Pro
            20

<210> SEQ ID NO 269
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ile Lys Asp Ile Lys Lys Ala Tyr Arg Lys Leu Ala Leu Gln Leu His
1               5                   10                  15

Pro Asp Arg Asn Pro Asp Pro Gln Ala Gln Glu
            20                  25

<210> SEQ ID NO 270
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ile Lys Asp Ile Lys Lys Ala Tyr Arg Lys Leu Ala Leu Gln Leu His
1               5                   10                  15

Pro Asp Arg Asn
            20

<210> SEQ ID NO 271
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Asp Ile Lys Lys Ala Tyr Arg Lys Leu Ala Leu Gln Leu His Pro Asp
1               5                   10                  15

Arg Asn Pro Asp Pro Gln Ala Gln Glu
            20                  25

<210> SEQ ID NO 272
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ile Lys Asp Ile Lys Lys Ala Tyr Arg Lys Leu Ala Leu Gln Leu His
1               5                   10                  15

Pro Asp

<210> SEQ ID NO 273
```

<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ile Lys Asp Ile Lys Lys Ala Tyr Arg Lys Leu Ala Leu Gln Leu
1               5                   10                  15

<210> SEQ ID NO 274
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Asp Ile Lys Lys Ala Tyr Arg Lys Leu Ala Leu Gln Leu
1               5                   10

<210> SEQ ID NO 275
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Asp Ile Lys Lys Ala Tyr Arg Lys Leu Ala Leu Gln
1               5                   10

<210> SEQ ID NO 276
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Asp Ile Lys Lys Ala Tyr Arg Lys Leu Ala Leu
1               5                   10

<210> SEQ ID NO 277
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Asp Ile Lys Lys Ala Tyr Arg Lys Leu Ala
1               5                   10

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Asp Ile Lys Lys Ala Tyr Arg Lys Leu
1               5

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Asp Ile Lys Lys Ala Tyr Arg Lys
1               5

<210> SEQ ID NO 280
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Asp Ile Lys Lys Ala Tyr Arg
1               5

<210> SEQ ID NO 281
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Ile Lys Lys Ala Tyr Arg Lys Leu Ala Leu Gln Leu
1               5                   10

<210> SEQ ID NO 282
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Lys Lys Ala Tyr Arg Lys Leu Ala Leu Gln Leu
1               5                   10

<210> SEQ ID NO 283
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ile Lys Lys Ala Tyr Arg Lys Leu Ala Leu Gln
1               5                   10

<210> SEQ ID NO 284
<211> LENGTH: 10
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 284

Ile Lys Lys Ala Tyr Arg Lys Leu Ala Leu
1               5                   10

<210> SEQ ID NO 285
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ile Lys Lys Ala Tyr Arg Lys Leu
1               5

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Lys Lys Ala Tyr Arg Lys Leu Ala Leu Gln
1               5                   10

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Lys Lys Ala Tyr Arg Lys Leu Ala Leu
1               5

<210> SEQ ID NO 288
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Lys Lys Ala Tyr Arg Lys Leu Ala
1               5

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Lys Ala Tyr Arg Lys Leu Ala Leu Gln
1               5
```

```
<210> SEQ ID NO 290
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ile Lys Lys Ala Tyr Arg Lys
1               5

<210> SEQ ID NO 291
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ile Lys Lys Ala Tyr Arg
1               5

<210> SEQ ID NO 292
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ile Lys Ala Tyr Arg Lys Leu Ala Leu Gln
1               5                   10

<210> SEQ ID NO 293
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ile Lys Lys Tyr Arg Lys Leu Ala Leu Gln
1               5                   10

<210> SEQ ID NO 294
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ile Lys Lys Ala Arg Lys Leu Ala Leu Gln
1               5                   10

<210> SEQ ID NO 295
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295
```

```
Ile Lys Ala Tyr Arg Lys Leu Ala
1               5

<210> SEQ ID NO 296
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ser Lys Lys Ala Tyr Arg Lys Leu Ala
1               5

<210> SEQ ID NO 297
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Phe Lys Lys Ala Tyr Arg Lys Leu Ala
1               5

<210> SEQ ID NO 298
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Ile Ala Gln Ala Tyr Arg Lys Leu Ala
1               5

<210> SEQ ID NO 299
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ile Leu Ala Ala Tyr Arg Lys Leu Ala
1               5

<210> SEQ ID NO 300
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Ile Lys Lys Ala His Arg Lys Leu Ala
1               5

<210> SEQ ID NO 301
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 301

Ile Lys Lys Ala Ile Arg Lys Leu Ala
1               5

<210> SEQ ID NO 302
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Ile Lys Lys Ala Ala Arg Lys Leu Ala
1               5

<210> SEQ ID NO 303
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Ile Lys Lys Ala Ser Arg Lys Leu Ala
1               5

<210> SEQ ID NO 304
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ile Lys Lys Ala Tyr His Gln Leu Ala
1               5

<210> SEQ ID NO 305
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ile Lys Lys Ala Tyr Tyr Gln Leu Ala
1               5

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ile Lys Lys Ala Tyr Phe Ser Leu Ala
1               5
```

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ile Lys Lys Ala Tyr Arg Lys Gln Ser
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ile Lys Lys Ala Tyr Arg Lys Gln Cys
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ile Lys Lys Ala Tyr Arg Lys Asp Ile
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Met Arg Lys Ala Tyr Leu Lys Lys Cys
1               5

<210> SEQ ID NO 311
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ile Leu Ala Glu Phe Lys Val Arg Ala Leu
1               5                   10

<210> SEQ ID NO 312
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Ile Lys Lys Ala Arg Lys Leu Ala
1               5

<210> SEQ ID NO 313
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Ile Lys Lys Ala Tyr Lys Leu Ala
1               5

<210> SEQ ID NO 314
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ile Lys Lys Ala Tyr Arg Leu Ala
1               5

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Ile Lys Lys Ala Tyr Arg Lys Leu
1               5

<210> SEQ ID NO 316
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Met Ala Phe Val Cys Leu Ala Ile Gly Cys Leu Tyr Thr Phe Leu Ile
1               5                   10                  15

Ser Thr Thr Phe Gly Cys Thr Ser Ser Ser Asp Thr Glu Ile Lys Val
                20                  25                  30

Asn Pro Pro Gln Asp Phe Glu Ile Val Asp Pro Gly Tyr Leu Gly Tyr
            35                  40                  45

Leu Tyr Leu Gln Trp Gln Pro Pro Leu Ser Leu Asp His Phe Lys Glu
        50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
             115                 120                 125

Trp Ile Ser Pro Gln Gly Ile Pro Glu Thr Lys Val Gln Asp Met Asp
130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Gly Thr Gly Ser Glu Phe Ile Lys Lys Ala Tyr Arg Lys
            340                 345                 350

Leu Ala Asp Ile Gly Gly Gly Ser Gly Gly Ser Gly Ser Gly Gly
        355                 360                 365

Ala Ala Ala Leu Glu Gly Lys Pro Ile Pro Asn Pro Leu Leu Gly Leu
370                 375                 380

Asp Ser Thr
385

<210> SEQ ID NO 317
<211> LENGTH: 387
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Met Ala Phe Val Cys Leu Ala Ile Gly Cys Leu Tyr Thr Phe Leu Ile
1               5                   10                  15

Ser Thr Thr Phe Gly Cys Thr Ser Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

```
Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300

Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Gly Glu Asp Leu
                325                 330                 335

Ser Lys Lys Gly Thr Gly Ser Glu Phe Ile Ala Gln Ala Tyr Arg Lys
            340                 345                 350

Leu Ala Asp Ile Gly Gly Gly Ser Gly Gly Ser Gly Gly Ser Gly Gly
        355                 360                 365

Ala Ala Ala Leu Glu Gly Lys Pro Ile Pro Asn Pro Leu Leu Gly Leu
    370                 375                 380

Asp Ser Thr
385

<210> SEQ ID NO 318
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Met Gly Val Lys Val Leu Phe Ala Leu Ile Cys Ile Ala Val Ala Glu
1               5                   10                  15

Ala Gly Thr Gly Ser Gly Glu Phe Ile Lys Lys Ala Tyr Arg Lys Leu
            20                  25                  30

Ala Asp Ile Gly Gly Gly Ser Gly Gly Ser Gly Gly Ser Gly Gly Ala
```

```
                35                  40                  45
Ala Ala Ala Asp Asn Lys Phe Asn Lys Glu Gln Gln Asn Ala Phe Tyr
 50                  55                  60

Glu Ile Leu Asn Met Pro Asn Leu Asn Glu Glu Gln Arg Asn Gly Phe
 65                  70                  75                  80

Ile Gln Ser Leu Lys Asp Asp Pro Ser Gln Ser Ala Asn Val Leu Gly
                 85                  90                  95

Glu Ala Lys Lys Leu Asn Asp Ser Gln Ala Pro Lys Leu Glu Gly Asp
                100                 105                 110

Tyr Lys Asp Asp Asp Asp Lys
            115

<210> SEQ ID NO 319
<211> LENGTH: 715
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Met Val Ser Gln Ala Leu Arg Leu Leu Cys Leu Leu Leu Gly Leu Gln
 1               5                  10                  15

Gly Cys Leu Ala Ala Gly Gly Val Ala Lys Ala Ser Gly Gly Glu Thr
                20                  25                  30

Arg Asp Met Pro Trp Lys Pro Gly Pro His Arg Val Phe Val Thr Gln
                35                  40                  45

Glu Glu Ala His Gly Val Leu His Arg Arg Arg Arg Ala Asn Ala Phe
 50                  55                  60

Leu Glu Glu Leu Arg Pro Gly Ser Leu Glu Arg Glu Cys Lys Glu Glu
 65                  70                  75                  80

Gln Cys Ser Phe Glu Glu Ala Arg Glu Ile Phe Lys Asp Ala Glu Arg
                 85                  90                  95

Thr Lys Leu Phe Trp Ile Ser Tyr Ser Asp Gly Asp Gln Cys Ala Ser
                100                 105                 110

Ser Pro Cys Gln Asn Gly Gly Ser Cys Lys Asp Gln Leu Gln Ser Tyr
                115                 120                 125

Ile Cys Phe Cys Leu Pro Ala Phe Glu Gly Arg Asn Cys Glu Thr His
                130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

Gly Tyr Ser Leu Leu Ala Asp Gly Val Ser Cys Thr Pro Thr Val Glu
                180                 185                 190

Tyr Pro Cys Gly Lys Ile Pro Ile Leu Glu Lys Arg Asn Ala Ser Lys
                195                 200                 205

Pro Gln Gly Arg Ile Val Gly Gly Lys Val Cys Pro Lys Gly Glu Cys
                210                 215                 220

Pro Trp Gln Val Leu Leu Leu Val Asn Gly Ala Gln Leu Cys Gly Gly
225                 230                 235                 240

Thr Leu Ile Asn Thr Ile Trp Val Val Ser Ala Ala His Cys Phe Asp
                245                 250                 255

Lys Ile Lys Asn Trp Arg Asn Leu Ile Ala Val Leu Gly Glu His Asp
                260                 265                 270
```

```
Leu Ser Glu His Asp Gly Asp Glu Gln Ser Arg Arg Val Ala Gln Val
            275                 280                 285

Ile Ile Pro Ser Thr Tyr Val Pro Gly Thr Thr Asn His Asp Ile Ala
        290                 295                 300

Leu Leu Arg Leu His Gln Pro Val Val Leu Thr Asp His Val Val Pro
305                 310                 315                 320

Leu Cys Leu Pro Glu Arg Thr Phe Ser Glu Arg Thr Leu Ala Phe Val
                325                 330                 335

Arg Phe Ser Leu Val Ser Gly Trp Gly Gln Leu Leu Asp Arg Gly Ala
            340                 345                 350

Thr Ala Leu Glu Leu Met Val Leu Asn Val Pro Arg Leu Met Thr Gln
        355                 360                 365

Asp Cys Leu Gln Gln Ser Arg Lys Val Gly Asp Ser Pro Asn Ile Thr
370                 375                 380

Glu Tyr Met Phe Cys Ala Gly Tyr Ser Asp Gly Ser Lys Asp Ser Cys
385                 390                 395                 400

Lys Gly Asp Ser Gly Gly Pro His Ala Thr His Tyr Arg Gly Thr Trp
                405                 410                 415

Tyr Leu Thr Gly Ile Val Ser Trp Gly Gln Gly Cys Ala Thr Val Gly
            420                 425                 430

His Phe Gly Val Tyr Thr Arg Val Ser Gln Tyr Ile Glu Trp Leu Gln
        435                 440                 445

Lys Leu Met Arg Ser Glu Pro Arg Pro Gly Val Leu Leu Arg Ala Pro
450                 455                 460

Phe Pro Leu Glu Gly Lys Pro Ile Pro Asn Pro Leu Leu Gly Leu Asp
465                 470                 475                 480

Ser Thr Ser Arg Pro Lys Ser Cys Asp Lys Thr His Thr Cys Pro Pro
                485                 490                 495

Cys Pro Ala Pro Glu Leu Leu Gly Gly Pro Ser Val Phe Leu Phe Pro
            500                 505                 510

Pro Lys Pro Lys Asp Thr Leu Met Ile Ser Arg Thr Pro Glu Val Thr
        515                 520                 525

Cys Val Val Val Asp Val Ser His Glu Asp Pro Glu Val Lys Phe Asn
530                 535                 540

Trp Tyr Val Asp Gly Val Glu Val His Asn Ala Lys Thr Lys Pro Arg
545                 550                 555                 560

Glu Glu Gln Tyr Asn Ser Thr Tyr Arg Val Val Ser Val Leu Thr Val
                565                 570                 575

Leu His Gln Asp Trp Leu Asn Gly Lys Glu Tyr Lys Cys Lys Val Ser
            580                 585                 590

Asn Lys Ala Leu Pro Ala Pro Ile Glu Lys Thr Ile Ser Lys Ala Lys
        595                 600                 605

Gly Gln Pro Arg Glu Pro Gln Val Tyr Thr Leu Pro Pro Ser Arg Asp
610                 615                 620

Glu Leu Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
            660                 665                 670

Phe Leu Tyr Ser Lys Leu Thr Val Asp Lys Ser Arg Trp Gln Gln Gly
        675                 680                 685

Asn Val Phe Ser Cys Ser Val Met His Glu Ala Leu His Asn His Tyr
```

```
                690                 695                 700
Thr Gln Lys Ser Leu Ser Leu Ser Pro Gly Lys
705                 710                 715

<210> SEQ ID NO 320
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Met Gly Val Lys Val Leu Phe Ala Leu Ile Cys Ile Ala Val Ala Glu
1               5                   10                  15

Ala Gly Thr Gly Ser Gly Glu Phe Ile Lys Lys Ala Tyr Arg Lys Leu
            20                  25                  30

Ala Asp Ile Gly Gly Gly Ser Gly Gly Ser Gly Gly Ser Gly Gly Ala
        35                  40                  45

Ala Ala Ala Thr Tyr Lys Leu Val Ile Asn Gly Lys Thr Leu Lys Gly
    50                  55                  60

Glu Thr Thr Thr Glu Ala Val Asp Ala Ala Thr Ala Glu Lys Val Phe
65                  70                  75                  80

Lys Gln Tyr Ala Asn Asp Asn Gly Val Asp Gly Glu Trp Thr Tyr Asp
                85                  90                  95

Asp Ala Thr Lys Thr Phe Thr Val Thr Glu Lys Pro Glu Val Ile Asp
            100                 105                 110

Ala Ser Glu Leu Thr Pro Ala Val Thr Leu Glu Gly Asp Tyr Lys Asp
        115                 120                 125

Asp Asp Asp Lys
    130

<210> SEQ ID NO 321
<211> LENGTH: 710
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
```

```
                130               135               140
Cys Lys Asn Ser Ala Asp Asn Lys Val Val Cys Ser Cys Thr Glu Gly
145                 150               155                 160

Tyr Arg Leu Ala Glu Asn Gln Lys Ser Cys Glu Pro Ala Val Pro Phe
                165               170               175

Pro Cys Gly Arg Val Ser Val Ser Gln Thr Ser Lys Leu Thr Arg Ala
                180               185               190

Glu Thr Val Phe Pro Asp Val Asp Tyr Val Asn Ser Thr Glu Ala Glu
                195               200               205

Thr Ile Leu Asp Asn Ile Thr Gln Ser Thr Gln Ser Phe Asn Asp Phe
210                 215               220

Thr Arg Val Val Gly Gly Glu Asp Ala Lys Pro Gly Gln Phe Pro Trp
225                 230               235               240

Gln Val Val Leu Asn Gly Lys Val Asp Ala Phe Cys Gly Gly Ser Ile
                245               250               255

Val Asn Glu Lys Trp Ile Val Thr Ala Ala His Cys Val Glu Thr Gly
                260               265               270

Val Lys Ile Thr Val Val Ala Gly Glu His Asn Ile Glu Glu Thr Glu
                275               280               285

His Thr Glu Gln Lys Arg Asn Val Ile Arg Ile Ile Pro His His Asn
                290               295               300

Tyr Asn Ala Ala Ile Asn Lys Tyr Asn His Asp Ile Ala Leu Leu Glu
305                 310               315                 320

Leu Asp Glu Pro Leu Val Leu Asn Ser Tyr Val Thr Pro Ile Cys Ile
                325               330               335

Ala Asp Lys Glu Tyr Thr Asn Ile Phe Leu Lys Phe Gly Ser Gly Tyr
                340               345               350

Val Ser Gly Trp Gly Arg Val Phe His Lys Gly Arg Ser Ala Leu Val
                355               360               365

Leu Gln Tyr Leu Arg Val Pro Leu Val Asp Arg Ala Thr Cys Leu Arg
370                 375               380

Ser Thr Lys Phe Thr Ile Tyr Asn Asn Met Phe Cys Ala Gly Phe His
385                 390               395                 400

Glu Gly Gly Arg Asp Ser Cys Gln Gly Asp Ser Gly Gly Pro His Val
                405               410               415

Thr Glu Val Glu Gly Thr Ser Phe Leu Thr Gly Ile Ile Ser Trp Gly
                420               425               430

Glu Glu Cys Ala Met Lys Gly Lys Tyr Gly Ile Tyr Thr Lys Val Ser
                435               440               445

Arg Tyr Val Asn Trp Ile Lys Glu Lys Thr Lys Leu Thr Leu Glu Gly
                450               455               460

Lys Pro Ile Pro Asn Pro Leu Leu Gly Leu Asp Ser Thr Ser Arg Pro
465                 470               475                 480

Lys Ser Cys Asp Lys Thr His Thr Cys Pro Pro Cys Pro Ala Pro Glu
                485               490               495

Leu Leu Gly Gly Pro Ser Val Phe Leu Phe Pro Pro Lys Pro Lys Asp
                500               505               510

Thr Leu Met Ile Ser Arg Thr Pro Glu Val Thr Cys Val Val Val Asp
                515               520               525

Val Ser His Glu Asp Pro Glu Val Lys Phe Asn Trp Tyr Val Asp Gly
                530               535               540

Val Glu Val His Asn Ala Lys Thr Lys Pro Arg Glu Glu Gln Tyr Asn
545                 550               555                 560
```

-continued

```
Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Pro
            580                 585                 590

Ala Pro Ile Glu Lys Thr Ile Ser Lys Ala Lys Gly Gln Pro Arg Glu
        595                 600                 605

Pro Gln Val Tyr Thr Leu Pro Pro Ser Arg Asp Glu Leu Thr Lys Asn
    610                 615                 620

Gln Val Ser Leu Thr Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
        675                 680                 685

Ser Val Met His Glu Ala Leu His Asn His Tyr Thr Gln Lys Ser Leu
    690                 695                 700

Ser Leu Ser Pro Gly Lys
705                 710

<210> SEQ ID NO 322
<211> LENGTH: 2600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
```

```
            195                 200                 205
Gln Thr Leu His Lys Phe Ile Leu Leu Phe Ala Val Phe Asp Glu Gly
210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
                275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
                355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
                435                 440                 445

Ala Tyr Thr Asp Glu Thr Phe Lys Thr Arg Glu Ala Ile Gln His Glu
                450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
                530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
                610                 615                 620
```

```
Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035
```

-continued

Leu Leu Ile Glu Asn Ser Pro Ser Val Trp Gln Asn Ile Leu Glu
1040                    1045                1050

Ser Asp Thr Glu Phe Lys Lys Val Thr Pro Leu Ile His Asp Arg
1055                    1060                1065

Met Leu Met Asp Lys Asn Ala Thr Ala Leu Arg Leu Asn His Met
1070                    1075                1080

Ser Asn Lys Thr Thr Ser Ser Lys Asn Met Glu Met Val Gln Gln
1085                    1090                1095

Lys Lys Glu Gly Pro Ile Pro Pro Asp Ala Gln Asn Pro Asp Met
1100                    1105                1110

Ser Phe Phe Lys Met Leu Phe Leu Pro Glu Ser Ala Arg Trp Ile
1115                    1120                1125

Gln Arg Thr His Gly Lys Asn Ser Leu Asn Ser Gly Gln Gly Pro
1130                    1135                1140

Ser Pro Lys Gln Leu Val Ser Leu Gly Pro Glu Lys Ser Val Glu
1145                    1150                1155

Gly Gln Asn Phe Leu Ser Glu Lys Asn Lys Val Val Val Gly Lys
1160                    1165                1170

Gly Glu Phe Thr Lys Asp Val Gly Leu Lys Glu Met Val Phe Pro
1175                    1180                1185

Ser Ser Arg Asn Leu Phe Leu Thr Asn Leu Asp Asn Leu His Glu
1190                    1195                1200

Asn Asn Thr His Asn Gln Glu Lys Lys Ile Gln Glu Glu Ile Glu
1205                    1210                1215

Lys Lys Glu Thr Leu Ile Gln Glu Asn Val Val Leu Pro Gln Ile
1220                    1225                1230

His Thr Val Thr Gly Thr Lys Asn Phe Met Lys Asn Leu Phe Leu
1235                    1240                1245

Leu Ser Thr Arg Gln Asn Val Glu Gly Ser Tyr Asp Gly Ala Tyr
1250                    1255                1260

Ala Pro Val Leu Gln Asp Phe Arg Ser Leu Asn Asp Ser Thr Asn
1265                    1270                1275

Arg Thr Lys Lys His Thr Ala His Phe Ser Lys Lys Gly Glu Glu
1280                    1285                1290

Glu Asn Leu Glu Gly Leu Gly Asn Gln Thr Lys Gln Ile Val Glu
1295                    1300                1305

Lys Tyr Ala Cys Thr Thr Arg Ile Ser Pro Asn Thr Ser Gln Gln
1310                    1315                1320

Asn Phe Val Thr Gln Arg Ser Lys Arg Ala Leu Lys Gln Phe Arg
1325                    1330                1335

Leu Pro Leu Glu Glu Thr Glu Leu Glu Lys Arg Ile Ile Val Asp
1340                    1345                1350

Asp Thr Ser Thr Gln Trp Ser Lys Asn Met Lys His Leu Thr Pro
1355                    1360                1365

Ser Thr Leu Thr Gln Ile Asp Tyr Asn Glu Lys Glu Lys Gly Ala
1370                    1375                1380

Ile Thr Gln Ser Pro Leu Ser Asp Cys Leu Thr Arg Ser His Ser
1385                    1390                1395

Ile Pro Gln Ala Asn Arg Ser Pro Leu Pro Ile Ala Lys Val Ser
1400                    1405                1410

Ser Phe Pro Ser Ile Arg Pro Ile Tyr Leu Thr Arg Val Leu Phe
1415                    1420                1425

Gln Asp Asn Ser Ser His Leu Pro Ala Ala Ser Tyr Arg Lys Lys

```
                1430                1435                1440

Asp  Ser  Gly  Val  Gln  Glu  Ser  His  Phe  Leu  Gln  Gly  Ala  Lys
     1445                1450                1455

Lys  Asn  Asn  Leu  Ser  Leu  Ala  Ile  Leu  Thr  Leu  Glu  Met  Thr  Gly
     1460                1465                1470

Asp  Gln  Arg  Glu  Val  Gly  Ser  Leu  Gly  Thr  Ser  Ala  Thr  Asn  Ser
     1475                1480                1485

Val  Thr  Tyr  Lys  Lys  Val  Glu  Asn  Thr  Val  Leu  Pro  Lys  Pro  Asp
     1490                1495                1500

Leu  Pro  Lys  Thr  Ser  Gly  Lys  Val  Glu  Leu  Leu  Pro  Lys  Val  His
     1505                1510                1515

Ile  Tyr  Gln  Lys  Asp  Leu  Phe  Pro  Thr  Glu  Thr  Ser  Asn  Gly  Ser
     1520                1525                1530

Pro  Gly  His  Leu  Asp  Leu  Val  Glu  Gly  Ser  Leu  Leu  Gln  Gly  Thr
     1535                1540                1545

Glu  Gly  Ala  Ile  Lys  Trp  Asn  Glu  Ala  Asn  Arg  Pro  Gly  Lys  Val
     1550                1555                1560

Pro  Phe  Leu  Arg  Val  Ala  Thr  Glu  Ser  Ser  Ala  Lys  Thr  Pro  Ser
     1565                1570                1575

Lys  Leu  Leu  Asp  Pro  Leu  Ala  Trp  Asp  Asn  His  Tyr  Gly  Thr  Gln
     1580                1585                1590

Ile  Pro  Lys  Glu  Glu  Trp  Lys  Ser  Gln  Glu  Lys  Ser  Pro  Glu  Lys
     1595                1600                1605

Thr  Ala  Phe  Lys  Lys  Lys  Asp  Thr  Ile  Leu  Ser  Leu  Asn  Ala  Cys
     1610                1615                1620

Glu  Ser  Asn  His  Ala  Ile  Ala  Ala  Ile  Asn  Glu  Gly  Gln  Asn  Lys
     1625                1630                1635

Pro  Glu  Ile  Glu  Val  Thr  Trp  Ala  Lys  Gln  Gly  Arg  Thr  Glu  Arg
     1640                1645                1650

Leu  Cys  Ser  Gln  Asn  Pro  Pro  Val  Leu  Lys  Arg  His  Gln  Arg  Glu
     1655                1660                1665

Ile  Thr  Arg  Thr  Thr  Leu  Gln  Ser  Asp  Gln  Glu  Glu  Ile  Asp  Tyr
     1670                1675                1680

Asp  Asp  Thr  Ile  Ser  Val  Glu  Met  Lys  Lys  Glu  Asp  Phe  Asp  Ile
     1685                1690                1695

Tyr  Asp  Glu  Asp  Glu  Asn  Gln  Ser  Pro  Arg  Ser  Phe  Gln  Lys  Lys
     1700                1705                1710

Thr  Arg  His  Tyr  Phe  Ile  Ala  Ala  Val  Glu  Arg  Leu  Trp  Asp  Tyr
     1715                1720                1725

Gly  Met  Ser  Ser  Ser  Pro  His  Val  Leu  Arg  Asn  Arg  Ala  Gln  Ser
     1730                1735                1740

Gly  Ser  Val  Pro  Gln  Phe  Lys  Lys  Val  Val  Phe  Gln  Glu  Phe  Thr
     1745                1750                1755

Asp  Gly  Ser  Phe  Thr  Gln  Pro  Leu  Tyr  Arg  Gly  Glu  Leu  Asn  Glu
     1760                1765                1770

His  Leu  Gly  Leu  Leu  Gly  Pro  Tyr  Ile  Arg  Ala  Glu  Val  Glu  Asp
     1775                1780                1785

Asn  Ile  Met  Val  Thr  Phe  Arg  Asn  Gln  Ala  Ser  Arg  Pro  Tyr  Ser
     1790                1795                1800

Phe  Tyr  Ser  Ser  Leu  Ile  Ser  Tyr  Glu  Glu  Asp  Gln  Arg  Gln  Gly
     1805                1810                1815

Ala  Glu  Pro  Arg  Lys  Asn  Phe  Val  Lys  Pro  Asn  Glu  Thr  Lys  Thr
     1820                1825                1830
```

-continued

| | | | | | | | | | | | |
|---|---|---|---|---|---|---|---|---|---|---|---|
| Tyr | Phe | Trp | Lys | Val | Gln | His | His | Met | Ala | Pro | Thr | Lys | Asp | Glu |
| 1835 | | | | | 1840 | | | | | 1845 | | | | |
| Phe | Asp | Cys | Lys | Ala | Trp | Ala | Tyr | Phe | Ser | Asp | Val | Asp | Leu | Glu |
| 1850 | | | | | 1855 | | | | | 1860 | | | | |
| Lys | Asp | Val | His | Ser | Gly | Leu | Ile | Gly | Pro | Leu | Leu | Val | Cys | His |
| 1865 | | | | | 1870 | | | | | 1875 | | | | |
| Thr | Asn | Thr | Leu | Asn | Pro | Ala | His | Gly | Arg | Gln | Val | Thr | Val | Gln |
| 1880 | | | | | 1885 | | | | | 1890 | | | | |
| Glu | Phe | Ala | Leu | Phe | Phe | Thr | Ile | Phe | Asp | Glu | Thr | Lys | Ser | Trp |
| 1895 | | | | | 1900 | | | | | 1905 | | | | |
| Tyr | Phe | Thr | Glu | Asn | Met | Glu | Arg | Asn | Cys | Arg | Ala | Pro | Cys | Asn |
| 1910 | | | | | 1915 | | | | | 1920 | | | | |
| Ile | Gln | Met | Glu | Asp | Pro | Thr | Phe | Lys | Glu | Asn | Tyr | Arg | Phe | His |
| 1925 | | | | | 1930 | | | | | 1935 | | | | |
| Ala | Ile | Asn | Gly | Tyr | Ile | Met | Asp | Thr | Leu | Pro | Gly | Leu | Val | Met |
| 1940 | | | | | 1945 | | | | | 1950 | | | | |
| Ala | Gln | Asp | Gln | Arg | Ile | Arg | Trp | Tyr | Leu | Leu | Ser | Met | Gly | Ser |
| 1955 | | | | | 1960 | | | | | 1965 | | | | |
| Asn | Glu | Asn | Ile | His | Ser | Ile | His | Phe | Ser | Gly | His | Val | Phe | Thr |
| 1970 | | | | | 1975 | | | | | 1980 | | | | |
| Val | Arg | Lys | Lys | Glu | Glu | Tyr | Lys | Met | Ala | Leu | Tyr | Asn | Leu | Tyr |
| 1985 | | | | | 1990 | | | | | 1995 | | | | |
| Pro | Gly | Val | Phe | Glu | Thr | Val | Glu | Met | Leu | Pro | Ser | Lys | Ala | Gly |
| 2000 | | | | | 2005 | | | | | 2010 | | | | |
| Ile | Trp | Arg | Val | Glu | Cys | Leu | Ile | Gly | Glu | His | Leu | His | Ala | Gly |
| 2015 | | | | | 2020 | | | | | 2025 | | | | |
| Met | Ser | Thr | Leu | Phe | Leu | Val | Tyr | Ser | Asn | Lys | Cys | Gln | Thr | Pro |
| 2030 | | | | | 2035 | | | | | 2040 | | | | |
| Leu | Gly | Met | Ala | Ser | Gly | His | Ile | Arg | Asp | Phe | Gln | Ile | Thr | Ala |
| 2045 | | | | | 2050 | | | | | 2055 | | | | |
| Ser | Gly | Gln | Tyr | Gly | Gln | Trp | Ala | Pro | Lys | Leu | Ala | Arg | Leu | His |
| 2060 | | | | | 2065 | | | | | 2070 | | | | |
| Tyr | Ser | Gly | Ser | Ile | Asn | Ala | Trp | Ser | Thr | Lys | Glu | Pro | Phe | Ser |
| 2075 | | | | | 2080 | | | | | 2085 | | | | |
| Trp | Ile | Lys | Val | Asp | Leu | Leu | Ala | Pro | Met | Ile | Ile | His | Gly | Ile |
| 2090 | | | | | 2095 | | | | | 2100 | | | | |
| Lys | Thr | Gln | Gly | Ala | Arg | Gln | Lys | Phe | Ser | Ser | Leu | Tyr | Ile | Ser |
| 2105 | | | | | 2110 | | | | | 2115 | | | | |
| Gln | Phe | Ile | Ile | Met | Tyr | Ser | Leu | Asp | Gly | Lys | Lys | Trp | Gln | Thr |
| 2120 | | | | | 2125 | | | | | 2130 | | | | |
| Tyr | Arg | Gly | Asn | Ser | Thr | Gly | Thr | Leu | Met | Val | Phe | Phe | Gly | Asn |
| 2135 | | | | | 2140 | | | | | 2145 | | | | |
| Val | Asp | Ser | Ser | Gly | Ile | Lys | His | Asn | Ile | Phe | Asn | Pro | Pro | Ile |
| 2150 | | | | | 2155 | | | | | 2160 | | | | |
| Ile | Ala | Arg | Tyr | Ile | Arg | Leu | His | Pro | Thr | His | Tyr | Ser | Ile | Arg |
| 2165 | | | | | 2170 | | | | | 2175 | | | | |
| Ser | Thr | Leu | Arg | Met | Glu | Leu | Met | Gly | Cys | Asp | Leu | Asn | Ser | Cys |
| 2180 | | | | | 2185 | | | | | 2190 | | | | |
| Ser | Met | Pro | Leu | Gly | Met | Glu | Ser | Lys | Ala | Ile | Ser | Asp | Ala | Gln |
| 2195 | | | | | 2200 | | | | | 2205 | | | | |
| Ile | Thr | Ala | Ser | Ser | Tyr | Phe | Thr | Asn | Met | Phe | Ala | Thr | Trp | Ser |
| 2210 | | | | | 2215 | | | | | 2220 | | | | |

```
Pro Ser Lys Ala Arg Leu His Leu Gln Gly Arg Ser Asn Ala Trp
2225                2230                2235

Arg Pro Gln Val Asn Asn Pro Lys Glu Trp Leu Gln Val Asp Phe
2240                2245                2250

Gln Lys Thr Met Lys Val Thr Gly Val Thr Thr Gln Gly Val Lys
2255                2260                2265

Ser Leu Leu Thr Ser Met Tyr Val Lys Glu Phe Leu Ile Ser Ser
2270                2275                2280

Ser Gln Asp Gly His Gln Trp Thr Leu Phe Phe Gln Asn Gly Lys
2285                2290                2295

Val Lys Val Phe Gln Gly Asn Gln Asp Ser Phe Thr Pro Val Val
2300                2305                2310

Asn Ser Leu Asp Pro Pro Leu Leu Thr Arg Tyr Leu Arg Ile His
2315                2320                2325

Pro Gln Ser Trp Val His Gln Ile Ala Leu Arg Met Glu Val Leu
2330                2335                2340

Gly Cys Glu Ala Gln Asp Leu Tyr Leu Glu Gly Lys Pro Ile Pro
2345                2350                2355

Asn Pro Leu Leu Gly Leu Asp Ser Thr Ser Arg Pro Lys Ser Cys
2360                2365                2370

Asp Lys Thr His Thr Cys Pro Pro Cys Pro Ala Pro Glu Leu Leu
2375                2380                2385

Gly Gly Pro Ser Val Phe Leu Phe Pro Pro Lys Pro Lys Asp Thr
2390                2395                2400

Leu Met Ile Ser Arg Thr Pro Glu Val Thr Cys Val Val Val Asp
2405                2410                2415

Val Ser His Glu Asp Pro Glu Val Lys Phe Asn Trp Tyr Val Asp
2420                2425                2430

Gly Val Glu Val His Asn Ala Lys Thr Lys Pro Arg Glu Glu Gln
2435                2440                2445

Tyr Asn Ser Thr Tyr Arg Val Val Ser Val Leu Thr Val Leu His
2450                2455                2460

Gln Asp Trp Leu Asn Gly Lys Glu Tyr Lys Cys Lys Val Ser Asn
2465                2470                2475

Lys Ala Leu Pro Ala Pro Ile Glu Lys Thr Ile Ser Lys Ala Lys
2480                2485                2490

Gly Gln Pro Arg Glu Pro Gln Val Tyr Thr Leu Pro Pro Ser Arg
2495                2500                2505

Asp Glu Leu Thr Lys Asn Gln Val Ser Leu Thr Cys Leu Val Lys
2510                2515                2520

Gly Phe Tyr Pro Ser Asp Ile Ala Val Glu Trp Glu Ser Asn Gly
2525                2530                2535

Gln Pro Glu Asn Asn Tyr Lys Thr Thr Pro Pro Val Leu Asp Ser
2540                2545                2550

Asp Gly Ser Phe Phe Leu Tyr Ser Lys Leu Thr Val Asp Lys Ser
2555                2560                2565

Arg Trp Gln Gln Gly Asn Val Phe Ser Cys Ser Val Met His Glu
2570                2575                2580

Ala Leu His Asn His Tyr Thr Gln Lys Ser Leu Ser Leu Ser Pro
2585                2590                2595

Gly Lys
2600
```

```
<210> SEQ ID NO 323
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Ser Ala Ser Gln Asp Ile
        35                  40                  45

Ser Asn Tyr Leu Asn Trp Tyr Gln Gln Lys Pro Gly Lys Ala Pro Lys
    50                  55                  60

Val Leu Ile Tyr Phe Thr Ser Ser Leu His Ser Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Gln Gln Tyr Ser Thr
            100                 105                 110

Val Pro Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 324
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ser Ser Gln Gly Ile
        35                  40                  45

Arg Asn Tyr Leu His Trp Tyr Gln Gln Lys Pro Gly Lys Ala Pro Lys
    50                  55                  60

Leu Leu Ile Tyr Ala Ala Ser Thr Leu Gln Ser Gly Val Pro Ser Arg
```

```
                65                  70                  75                  80
        Phe Ser Gly Ser Gly Ser Gly Thr Asp Phe Thr Leu Thr Ile Ser Ser
                        85                  90                  95

Leu Gln Pro Glu Asp Val Ala Thr Tyr Tyr Cys Gln Arg Tyr Asn Arg
                        100                 105                 110

Ala Pro Tyr Thr Phe Gly Gln Gly Thr Lys Val Glu Ile Lys Arg Thr
                        115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
        145                 150                 155                 160

Arg Glu Ala Lys Val Gln Trp Lys Val Asp Asn Ala Leu Gln Ser Gly
                        165                 170                 175

Asn Ser Gln Glu Ser Val Thr Glu Gln Asp Ser Lys Asp Ser Thr Tyr
                        180                 185                 190

Ser Leu Ser Ser Thr Leu Thr Leu Ser Lys Ala Asp Tyr Glu Lys His
                        195                 200                 205

Lys Val Tyr Ala Cys Glu Val Thr His Gln Gly Leu Ser Ser Pro Val
        210                 215                 220

Thr Lys Ser Phe Asn Arg Gly Glu Cys
        225                 230

<210> SEQ ID NO 325
<211> LENGTH: 678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Met Pro Ser Ser Val Ser Trp Gly Ile Leu Leu Leu Ala Gly Leu Cys
        1               5                   10                  15

Cys Leu Val Pro Val Ser Leu Ala Glu Asp Pro Gln Gly Asp Ala Ala
                        20                  25                  30

Gln Lys Thr Asp Thr Ser His His Asp Gln Asp His Pro Thr Phe Asn
                        35                  40                  45

Lys Ile Thr Pro Asn Leu Ala Glu Phe Ala Phe Ser Leu Tyr Arg Gln
                        50                  55                  60

Leu Ala His Gln Ser Asn Ser Thr Asn Ile Phe Phe Ser Pro Val Ser
        65                  70                  75                  80

Ile Ala Thr Ala Phe Ala Met Leu Ser Leu Gly Thr Lys Ala Asp Thr
                        85                  90                  95

His Asp Glu Ile Leu Glu Gly Leu Asn Phe Asn Leu Thr Glu Ile Pro
                        100                 105                 110

Glu Ala Gln Ile His Glu Gly Phe Gln Glu Leu Leu Arg Thr Leu Asn
                        115                 120                 125

Gln Pro Asp Ser Gln Leu Gln Leu Thr Thr Gly Asn Gly Leu Phe Leu
        130                 135                 140

Ser Glu Gly Leu Lys Leu Val Asp Lys Phe Leu Glu Asp Val Lys Lys
        145                 150                 155                 160

Leu Tyr His Ser Glu Ala Phe Thr Val Asn Phe Gly Asp Thr Glu Glu
                        165                 170                 175

Ala Lys Lys Gln Ile Asn Asp Tyr Val Glu Lys Gly Thr Gln Gly Lys
                        180                 185                 190
```

```
Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
        210                 215                 220

Lys Asp Thr Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
                260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
        290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
                340                 345                 350

Leu Ser Lys Ala Val His Lys Ala Val Leu Thr Ile Asp Lys Lys Gly
            355                 360                 365

Thr Glu Ala Ala Gly Ala Met Phe Leu Glu Ala Ile Pro Met Ser Ile
        370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys Gly Thr Gly Ser Glu Phe Asp Ile Ala Ala Ala Leu Glu Gly
                420                 425                 430

Lys Pro Ile Pro Asn Pro Leu Leu Gly Leu Asp Ser Thr Ser Arg Pro
            435                 440                 445

Lys Ser Cys Asp Lys Thr His Thr Cys Pro Pro Cys Pro Ala Pro Glu
        450                 455                 460

Leu Leu Gly Gly Pro Ser Val Phe Leu Phe Pro Pro Lys Pro Lys Asp
465                 470                 475                 480

Thr Leu Met Ile Ser Arg Thr Pro Glu Val Thr Cys Val Val Val Asp
                485                 490                 495

Val Ser His Glu Asp Pro Glu Val Lys Phe Asn Trp Tyr Val Asp Gly
            500                 505                 510

Val Glu Val His Asn Ala Lys Thr Lys Pro Arg Glu Glu Gln Tyr Asn
        515                 520                 525

Ser Thr Tyr Arg Val Val Ser Val Leu Thr Val Leu His Gln Asp Trp
        530                 535                 540

Leu Asn Gly Lys Glu Tyr Lys Cys Lys Val Ser Asn Lys Ala Leu Pro
545                 550                 555                 560

Ala Pro Ile Glu Lys Thr Ile Ser Lys Ala Lys Gly Gln Pro Arg Glu
                565                 570                 575

Pro Gln Val Tyr Thr Leu Pro Pro Ser Arg Asp Glu Leu Thr Lys Asn
                580                 585                 590

Gln Val Ser Leu Thr Cys Leu Val Lys Gly Phe Tyr Pro Ser Asp Ile
            595                 600                 605

Ala Val Glu Trp Glu Ser Asn Gly Gln Pro Glu Asn Asn Tyr Lys Thr
```

```
            610                 615                 620
Thr Pro Pro Val Leu Asp Ser Asp Gly Ser Phe Phe Leu Tyr Ser Lys
625                 630                 635                 640

Leu Thr Val Asp Lys Ser Arg Trp Gln Gln Gly Asn Val Phe Ser Cys
            645                 650                 655

Ser Val Met His Glu Ala Leu His Asn His Tyr Thr Gln Lys Ser Leu
                660                 665                 670

Ser Leu Ser Pro Gly Lys
        675

<210> SEQ ID NO 326
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile, Leu, Val, Ala or Met
<220> FEATURE:
<221> NAME/KEY: MOD_RES
<222> LOCATION: (2)..(3)
<223> OTHER INFORMATION: This region may encompass "Lys Arg," "Lys Lys,"
      "Arg Lys," "Arg Arg," "Ala Lys," "Ala Arg," "Lys Ala," "Ile Lys,"
      "Asn Lys," "Lys Gln," "Arg Gln" or "Arg Asp"
<220> FEATURE:
<221> NAME/KEY: MOD_RES
<222> LOCATION: (4)..(4)
<223> OTHER INFORMATION: Ala, Ser, Thr, Arg, Gln, Glu, Phe, Cys or Ile
<220> FEATURE:
<221> NAME/KEY: MOD_RES
<222> LOCATION: (5)..(5)
<223> OTHER INFORMATION: Tyr or Phe
<220> FEATURE:
<221> NAME/KEY: MOD_RES
<222> LOCATION: (6)..(7)
<223> OTHER INFORMATION: This region may encompass "Lys Arg," "Lys Lys,"
      "Arg Lys," "Arg Arg," "Arg Gln," "Phe Arg," "Arg Leu," "Lys Leu,"
      "His Lys," "Leu Lys," "Gln Lys" or "Lys Val"
<220> FEATURE:
<221> NAME/KEY: MOD_RES
<222> LOCATION: (8)..(9)
<223> OTHER INFORMATION: This region may encompass "Leu Ala," "Leu Leu,"
      "Ala Leu," "Ala Ala," "Leu Cys," "Leu Val," "Gln Ala," "Lys Ala,"
      "Leu Ser," "Leu Ile," "Leu Tyr" or "Arg Ala"
<220> FEATURE:
<223> OTHER INFORMATION: See specification as filed for detailed
      description of substitutions and preferred embodiments

<400> SEQUENCE: 326

Xaa Xaa Xaa Xaa Xaa Xaa Xaa Xaa Xaa
1               5

<210> SEQ ID NO 327
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Met Gly Trp Ser Leu Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Tyr Thr Phe
```

```
            35                  40                  45
Thr Asn Tyr Gly Met Asn Trp Val Arg Gln Ala Pro Gly Lys Gly Leu
 50                  55                  60

Glu Trp Val Gly Trp Ile Asn Thr Tyr Thr Gly Glu Pro Thr Tyr Ala
 65                  70                  75                  80

Ala Asp Phe Lys Arg Arg Phe Thr Phe Ser Leu Asp Thr Ser Lys Ser
                 85                  90                  95

Thr Ala Tyr Leu Gln Met Asn Ser Leu Arg Ala Glu Asp Thr Ala Val
                100                 105                 110

Tyr Tyr Cys Ala Lys Tyr Pro His Tyr Tyr Gly Ser Ser His Trp Tyr
                115                 120                 125

Phe Asp Val Trp Gly Gln Gly Thr Leu Val Thr Val Ser Ser Ala Ser
                130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
                195                 200                 205

Ser Val Val Thr Val Pro Ser Ser Leu Gly Thr Gln Thr Tyr Ile
210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Leu Pro Pro Ser Arg Asp Glu Leu Thr
                370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
                435                 440                 445

Ser Cys Ser Val Met His Glu Ala Leu His Asn His Tyr Thr Gln Lys
                450                 455                 460
```

```
Ser Leu Ser Leu Ser Pro Gly Lys
465                 470

<210> SEQ ID NO 328
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Met Gly Trp Ser Leu Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Val Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
```

```
                      340               345               350
Ala Pro Ile Glu Lys Thr Ile Ser Lys Ala Lys Gly Gln Pro Arg Glu
                355               360               365

Pro Gln Val Tyr Thr Leu Pro Pro Ser Arg Asp Glu Leu Thr Lys Asn
        370               375               380

Gln Val Ser Leu Thr Cys Leu Val Lys Gly Phe Tyr Pro Ser Asp Ile
385               390               395               400

Ala Val Glu Trp Glu Ser Asn Gly Gln Pro Glu Asn Asn Tyr Lys Thr
                405               410               415

Thr Pro Pro Val Leu Asp Ser Asp Gly Ser Phe Phe Leu Tyr Ser Lys
                420               425               430

Leu Thr Val Asp Lys Ser Arg Trp Gln Gln Gly Asn Val Phe Ser Cys
            435               440               445

Ser Val Met His Glu Ala Leu His Asn His Tyr Thr Gln Lys Ser Leu
        450               455               460

Ser Leu Ser Pro Gly Lys
465               470

<210> SEQ ID NO 329
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Gly Arg Asp Phe Tyr Lys Ile Leu Gly Val Pro Arg Ser Ala Ser Ile
1               5                   10                  15

Lys Asp Ile Lys Lys Ala Tyr Arg Lys Leu Ala Leu Gln Leu His Pro
            20                  25                  30

Asp Arg Asn Pro Asp Asp Pro Gln Ala Gln Glu Lys Phe Gln Asp Leu
        35                  40                  45

Gly Ala Ala Tyr Glu Val Leu Ser Asp Ser Glu Lys Arg
    50                  55                  60
```